US008586039B2

(12) United States Patent
Tsuchiya et al.

(10) Patent No.: US 8,586,039 B2
(45) Date of Patent: *Nov. 19, 2013

(54) DEGRADED TPO AGONIST ANTIBODY

(75) Inventors: Masayuki Tsuchiya, Shizuoka-ken (JP); Toshihiko Ohtomo, Shizuoka-ken (JP); Naohiro Yabuta, Ibaraki (JP); Hiroyuki Tsunoda, Ibaraki (JP); Tetsuro Orita, Ibaraki (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/225,999

(22) Filed: Sep. 6, 2011

(65) Prior Publication Data
US 2012/0015436 A1 Jan. 19, 2012

Related U.S. Application Data

(60) Division of application No. 10/399,518, filed as application No. PCT/JP01/09259 on Oct. 22, 2001, now Pat. No. 8,034,903, which is a continuation of application No. PCT/JP01/03288, filed on Apr. 17, 2001.

(30) Foreign Application Priority Data

Oct. 20, 2000 (JP) ................................ 2000-321821
Sep. 12, 2001 (JP) ................................ 2001-277314

(51) Int. Cl.
*A61K 38/00* (2006.01)

(52) U.S. Cl.
USPC .................. 424/134.1; 424/136.1; 424/141.1; 424/146.1; 424/143.1; 435/69.1

(58) Field of Classification Search
None
See application file for complete search history.

(56) References Cited

U.S. PATENT DOCUMENTS

| 4,946,778 | A | 8/1990 | Ladner et al. |
|---|---|---|---|
| 5,618,920 | A | 4/1997 | Robinson et al. |
| 5,837,242 | A | 11/1998 | Holliger et al. |
| 5,837,821 | A | 11/1998 | Wu |
| 5,840,344 | A | 11/1998 | Fukushima |
| 5,877,291 | A | 3/1999 | Mezes et al. |
| 5,885,574 | A | 3/1999 | Elliott |
| 5,977,322 | A | 11/1999 | Marks et al. |
| 6,126,980 | A | 10/2000 | Smith et al. |
| 6,183,744 | B1 | 2/2001 | Goldenberg |
| 6,323,000 | B2 | 11/2001 | Briggs et al. |
| 6,342,220 | B1 | 1/2002 | Adams et al. |
| 6,368,596 | B1 | 4/2002 | Ghetie et al. |
| 6,579,692 | B1 | 6/2003 | Fukushima |
| 6,683,157 | B2 | 1/2004 | Briggs et al. |
| 6,699,686 | B1 | 3/2004 | Brocard et al. |
| 6,719,972 | B1 | 4/2004 | Gribben et al. |
| 6,759,043 | B2 | 7/2004 | Fukushima |
| 7,262,278 | B2 | 8/2007 | Tawara et al. |
| 8,034,903 | B2 * | 10/2011 | Tsuchiya et al. ........... 530/387.3 |
| 2001/0006796 | A1 | 7/2001 | Briggs et al. |
| 2002/0028178 | A1 | 3/2002 | Hanna et al. |
| 2002/0193571 | A1 | 12/2002 | Carter et al. |
| 2002/0197706 | A1 | 12/2002 | Nadkarni et al. |
| 2003/0073161 | A1 | 4/2003 | Briggs et al. |
| 2003/0082612 | A1 | 5/2003 | Snodgrass et al. |
| 2003/0147894 | A1 | 8/2003 | Fukushima et al. |
| 2003/0148409 | A1 | 8/2003 | Rossi et al. |
| 2003/0157100 | A1 | 8/2003 | Fukushima et al. |
| 2003/0157577 | A1 | 8/2003 | Fukushima et al. |
| 2003/0202975 | A1 | 10/2003 | Tedder |
| 2003/0211108 | A1 | 11/2003 | Fukushima et al. |
| 2004/0001828 | A1 | 1/2004 | Tuscano |
| 2004/0058393 | A1 | 3/2004 | Fukishima et al. |
| 2004/0073013 | A1 | 4/2004 | Fukushima et al. |
| 2004/0242847 | A1 | 12/2004 | Fukushima et al. |
| 2005/0130224 | A1 | 6/2005 | Saito et al. |
| 2006/0222643 | A1 | 10/2006 | Tsunoda et al. |
| 2006/0275301 | A1 | 12/2006 | Ozaki et al. |
| 2007/0003556 | A1 | 1/2007 | Tsuchiya et al. |
| 2007/0280951 | A1 | 12/2007 | Kimura et al. |
| 2007/0281327 | A1 | 12/2007 | Nakano et al. |
| 2008/0009038 | A1 | 1/2008 | Ohtomo et al. |
| 2008/0206229 | A1 | 8/2008 | Ono et al. |
| 2008/0274110 | A1 | 11/2008 | Ozaki et al. |
| 2009/0022687 | A1 | 1/2009 | Matsumoto et al. |
| 2009/0028854 | A1 | 1/2009 | Igawa et al. |
| 2009/0117097 | A1 | 5/2009 | Igawa et al. |

FOREIGN PATENT DOCUMENTS

| AU | 755822 | 3/1999 |
|---|---|---|
| EP | 0 721 015 A1 | 7/1996 |
| EP | 0 903 149 A1 | 3/1999 |
| EP | 1 035 132 A1 | 9/2000 |

(Continued)

OTHER PUBLICATIONS

Carter et al, (PNAS, 1992, 89:4285-4289).*
U.S. Appl. No. 12/497,131, filed Jul. 2, 2009, Fukushima et al.
Abe et al., "Surrogate thrombopoietin," Immunology Letters, 1998, 61:73-78.
Arndt et al., "Factors Influencing the Dimer to Monomer Transition of an Antibody Single-Chain Fv fragment," Biochemistry, 1998, 37:12918-12926.

(Continued)

*Primary Examiner* — Misook Yu
*Assistant Examiner* — Julie Wu
(74) *Attorney, Agent, or Firm* — Foley & Lardner LLP

(57) ABSTRACT

The invention relates to a modified antibody which contains two or more H chain V regions and two or more L chain V regions of monoclonal antibody and can transduce a signal into cells by crosslinking TPO receptor to thereby exert TPO agonist action. The modified antibody can be used as a TPO signal transduction agonist and, therefore, useful as a remedy for various diseases such as platelet-reduction-related blood diseases, thrombopenia following chemotherapy for cancer or leukemia, etc.

27 Claims, 50 Drawing Sheets

(56) References Cited

FOREIGN PATENT DOCUMENTS

| | | |
|---|---|---|
| EP | 1 327 680 | 7/2003 |
| EP | 1 369 431 | 12/2003 |
| EP | 1 396 500 | 3/2004 |
| EP | 1 561 759 | 8/2005 |
| EP | 1 712 565 | 10/2006 |
| EP | 1 757 686 A1 | 2/2007 |
| EP | 1 262 548 B1 | 10/2008 |
| JP | 7503622 | 4/1995 |
| JP | 7236475 A | 9/1995 |
| JP | 10-505231 | 5/1998 |
| JP | 11-500916 | 1/1999 |
| JP | 11-092500 A | 4/1999 |
| JP | 2001-506135 | 5/2001 |
| JP | 2001-513999 | 9/2001 |
| JP | 2001-518930 | 10/2001 |
| JP | 2002-544173 | 12/2002 |
| JP | 2004-086862 | 3/2004 |
| MX | 9905856 | 7/2000 |
| WO | WO 91/16928 A1 | 11/1991 |
| WO | WO 92/19759 A1 | 11/1992 |
| WO | WO 94/13806 A1 | 6/1994 |
| WO | WO 96/04925 | 2/1996 |
| WO | WO 96/26648 | 9/1996 |
| WO | WO 96/36360 A | 11/1996 |
| WO | WO 97/01633 | 1/1997 |
| WO | WO 97/31108 | 8/1997 |
| WO | WO 97/32601 A1 | 9/1997 |
| WO | WO 98/28331 | 7/1998 |
| WO | WO 98/41641 | 9/1998 |
| WO | WO 98/42378 | 10/1998 |
| WO | WO 98/44001 A1 | 10/1998 |
| WO | WO 99/02567 | 1/1999 |
| WO | WO 99/03495 A | 1/1999 |
| WO | WO 99/10494 A2 | 3/1999 |
| WO | WO 99/12973 A1 | 3/1999 |
| WO | WO9910494 A2 * | 8/1999 ................. 424/153.1 |
| WO | WO 00/23593 | 4/2000 |
| WO | WO 00/53634 A | 9/2000 |
| WO | WO 00/53634 A1 | 9/2000 |
| WO | WO 00/67795 | 11/2000 |
| WO | WO 00/75191 | 12/2000 |
| WO | WO 01/64713 | 9/2001 |
| WO | WO 01/66737 | 9/2001 |
| WO | WO 01/74388 | 10/2001 |
| WO | WO 01/77342 | 10/2001 |
| WO | WO 01/79494 | 10/2001 |
| WO | WO 01/87337 | 11/2001 |
| WO | WO 01/97858 | 12/2001 |
| WO | WO 02/04021 | 1/2002 |
| WO | WO 02/22212 | 3/2002 |
| WO | WO 02/33072 | 4/2002 |
| WO | WO 02/33073 | 4/2002 |
| WO | WO 02/078612 A | 10/2002 |
| WO | WO 02/094880 | 11/2002 |
| WO | WO 02/097033 | 12/2002 |
| WO | WO 03/033654 | 4/2003 |
| WO | WO 03/104425 | 12/2003 |
| WO | WO 03/107218 | 12/2003 |
| WO | WO 2004/033499 | 4/2004 |
| WO | WO 2004/087763 | 10/2004 |
| WO | WO 2005/056602 | 6/2005 |
| WO | WO 2005/056603 | 6/2005 |
| WO | WO 2005/056604 | 6/2005 |
| WO | WO 2005/056605 | 6/2005 |
| WO | WO 2005/056798 | 6/2005 |
| WO | WO 2005/100560 | 10/2005 |

OTHER PUBLICATIONS

Avent et al., "Monoclonal antibodies that recognize different membrane proteins that are deficient in $Rh_{null}$ human erythrocytes," Biochem. J., 1988, vol. 251, pp. 499-505.

Ballmaier et al., "c-mpl mutations are the cause of congenital amegakaryocytic thrombocytopenia," Blood, 2001, 97:139-146.

Bazil, V., et al., "Apoptosis of Human Hematopoietic Progenitor Cells Induced by Crosslinking of Surface CD43, the Major Sialoglycoprotein of Leukocytes," pp. 502-511 (1995).

Bazzoni et al., "Chimeric tumor necrosis factor receprors with constitutive signaling activity," Proc. Natl. Acad. Sci. USA (Jun. 6, 1995), vol. 92, No. 12, pp. 5376-5580.

Beresford et al., "Binding Characteristics and Tumor Targeting of a Covalently Linked Divalent CC49 Single-Chain Antibody," Int. J. Cancer, 1999, 81:911-917.

Berger, S. L., et al., "Inhibition of Intractable Nucleases with Ribonucleoside-Vanadyl Complexes: Isolation of Messenger Ribonucleic Acid From Resting Lymphocytes", Biochemistry, vol. 18, No. 23, pp. 5143-5149 (1979).

Bodmer et al,. "TRAIL Receptor-2 Signals Apoptosis Through FADD and Caspase-8," Nat. Cell. Biol., 2000, 2:241-243.

Boger et al., Bioorganic and Medicinal Chemistry, 2001, 9:557-562.

Bowie et al., "Deciphering the Message in Protein Sequences: Tolerance to Amino Acid Substitutions," Science, 1990, 247:1306-1310.

Brinkmann et al., "FTY720: targeting G-protein-couples receptors for sphingosine 1-phosphate in transplantation and autoimmunity," Curr. Opin. Immunol., 2002, 14:569-575.

Brooke et al., "Human Lymphocytes Interact Directly with CD47 through a Novel Member of the Signal Regulatory Protein (SIRP) Family," J. Immunol., 2004, 173:2562-2570.

Brown et al., "Integrin-associated protein (CD47) and its ligands," TRENDS in Cell Biology, Mar. 2001, 11(3), 130-135.

Brown et al., "Integrin-associated Protein: A 50-kD Plasma Membrane Antigen Physically and Functionally Associated with Integrins," J. Cell Biology, Dec. 1990, vol. 111, No. 6, pt. 1, pp. 2785-2794.

Bruenke et al., "A recombinant bispecific single-chain Fv antibody against HLA class II and FcγRIII (CD16) triggers effective lysis of lymphoma cells," Br. J. Maematol., 2004, 125:167-179.

Buchsbaum et al., "Antitumor Efficacy of TRA-8 Anti-DR5 Monoclolan Antibody Alone or in Combination with Chemotherapy and/or Radiation Therapy in a Human Breast Cancer Model," Clin. Cancer Res., 2003, 9:3731-3741.

Burgess et al., "Possible dissociation of the heparin-binding and mitogenic activities of heparin-binding (acidic fibroblast) growth factor-1 from its receptor-binding activities by site-directed mutagenesis of a single lysine residue," J. Cell. Biol., 1990, 111:2129-2138.

Burrone et al., "Stimulation of HLA-A,B,C by IFN-alpha. The derivation of Molt 4 variants and the differential expression of HLA-A,B,C subsets," The EMBO Journal, 1985, 4(11):2855-2860.

Burthem, et al., "Hairy Cell Interactions with Extracellular Matrix: Expression of Specific Integrin Receptors and Their Role in the Cell's Response to Specific Adhesive Proteins," Blood, vol. 84, No. 3, pp. 873-882 (1994).

Caldas, C., et al., Mol. Immunol., vol. 39, No. 15, pp. 941-952 (2003).

Cangemi et al,. "IFN-alpha mediates the up-regulation of HLA class I on melanoma cells without switching proteasome to immunoproteasome," International Immunology, 2005, 15(12):1415-1421.

CAPLUS Accession No. 2005:547624, 2 pages, 2008.

Caron et al. "Engineered Humanized Dimeric Forms of IgG are More Effective Antibodies," J. Exp. Med., 1992, 176:1191-1195.

Casset et al,. "A peptide mimetic of an anti-CD4 monoclonal antibody by rational design," Biochemical and Biophysical Research Communications, 2003, 307:198-205.

Chen et al., "Selection and analysis of an optimized anti-VEGF antibody: Crystal structure of an affinity-matured Fab in complex with antigen," Journal of Molecular Biology, 1999, 293:865-881.

Chien, N. C., et al., Proc. Natl. Acad. Sci. USA, vol. 84, No. 14, pp. 5532-5536 (1989).

Chirgwin, J. M., et al., "Isolation of Biologically Active Ribonucleic Acid from Sources Enriched in Ribonuclease", Biochemistry, vol. 18, No. 24, pp. 5294-5299 (1979).

Chuntharapai et al., "Isotype-Dependent Inhibition of Tumor Growth In Vivo by Monoclonal Antibodies to Death Receptor 4," J. Immunol., 2001, 166 4891-4898.

Clark, "CD22, a B Cell-Specific Receptor, Mediates Adhesion and Signal Transduction," J. Immunol., 1993, 150:4715-4718.

(56) References Cited

OTHER PUBLICATIONS

Co et al., "A humanized antibody specific for the platelet integrin gpllb/llla," J. Immunol., 1994, 152:2968-2976.
Cochlovius et al., "Cure of Burkitt's Lymphoma in Severe Combined Immunodeficiency Mice by T Cells, Tetravalent CD3 × CD 19 Tandem Diabody and CD28 Costimulation," Cancer Res., 2000, 60:4336-4341.
Cooper, D., et al., "Transendothelial migration of neutrophils involves integrin-associated protein (CD47)," Proc. Natl. Acad. Sci. USA, pp. 3978-3982 (1995).
Daniel et al., "Induction of Apoptosis in Human Lymphocytes by Human Anti-HLA Class I Antibodies," Transplantation, 2003, 75:1380-1386.
Daniel et al., "Pathway of apoptosis induced in Jurkat T Lymphoblasts by anti-HLA Class I antibotdies," Human Immunology, 2004, 65(3):189-199.
De Felice et al., "Differential regulatory role of monomorphic and polymorphic determinants of histocompatibility leukocyte antigen class I antigens in monoclonal antibody OKT3-induced T cell proliferation," J. Immunol., 1987, 139:2683-2689.
De Jonge et al., "In vivo retargeting of T cell effector function by recombinant bispecific single chain Fv (anti-DC3 × anti-idiottype) induces long term survival of the murine BCL1 lymphoma model," J. Immunol., 1998, 161(3):1454-1461.
De Leon et al., "High resolution human leukocyte antigen (HLA) class I and class II allele typing in Mexican mestizo women with sporadic breast cancer: case-control study," BMC Cancer, 2009, 9(48):1-9.
De Nardo et al., "Anti-HLA-DR/anti-DOTA Diabody Construction in a Modular Gene Design Platform: Bispecific Antibodies for Pretargeted Radioimmunotherapy," Cancer Biother. Radiopharm., 2001, 16:525-535.
De Pascalis et al., "Grafting of 'abbreviated' complementary-determining regions containing specificity-determining residues essentially for ligand contact to engineer a less immunogenic humanized monoclonal antibody," Journal of Immunology, 2002, 169:3076-3084.
de St. Groth, S. F., et al., "Production of Monoclonal Antibodies: Strategy and Tactics," Journal of Immunological Methods, vol. 35, pp. 1-21 (1980).
Degli-Esposti et al., "Cloning and Characterization of TRAIL-R3, a Novel Member of the Emerging TRAIL Receptor Family," J. Exp. Med., 1997, 186:1165-1170.
Deng et al., "An Agonist Murine Monoclonal Antibody to the Human c-Mpl Receptor Stimulates Magakaryocytopoiesis," Blood, Sep. 15, 1998, 92(6), 1981-1988.
Derossi D. et al., "The Third Helix of the Antennapedia Homeodomain Translocates Through Biological Membranes", *The Journal of Biological Chemistry*, (1994), pp. 10444-10450, vol. 269, No. 14, Centre National de la Recherche Scientifique Unite de Recherche Associee, The American Society for Biochemistry and Molecular Biology, Inc., USA.
Desplancq et al., "Multimerization behaviour of single chain Fv variants for the tumour-binding antibody B72.3," Protein Eng., Aug. 1994, vol. 7, No. 8, pp. 1027-1033 (Abstract).
Dillman, Robert O., "Monoclonal Antibodies for Treating Cancer," Annuals of Internal Medicine, Oct. 1, 1989, 11(7), 592-603.
Dorai et al., "Mammalian cell expression of single-chain Fv (sFv) antibody proteins and their C-terminal fusions with interleukin-2 and other effector domains," Biotechnology, Sep. 1994, vol. 12, No. 9, pp. 890-897 (Abstract).
Ebert et al., "Expression of Metallothionein II in Intestinal Metaplasia, Dysplasia, and Gastric Cancer," Cancer Res., 2000, 60:1995-2001.
Elliott et al., "Activation of the Erythropoietin (EPO) Receptor by Bivalent Anti-EPO Receptor Antibodies," J. Biol. Chem., 1996, 271:24691-24697.
Emery et al., "Osteoprotegrin is a Receptor for the Cytotoxic Ligand TRAIL," J. Biol. Chem., 1998, 273:14363-14367.

Fayen et al., "Negative signaling by anti-HLA class I antibodies is dependent upon two triggering events," Int. Immunol., 1998, 10:1347-1358.
Felgenhauer M. et al., "Nucleotide Sequences of the cDNAs Encoding the V-Regions of H- and L-Chains of a Human Monoclonal Antibody Specific to HIV-1—gp41", *Nucleic Acids Research*, (1990), p. 4927, vol. 18, No. 16, IRL Press, USA.
Fujimoto, T., et al., Blood, vol. 86, No. 6, pp. 2174-2182 (1995)
Fukushima et al., "Apoptosis of Bone Marrow Cells Via Integrin Associated Protein by the Novel Monoclonal Antibody," Blood, vol. 94, No. 10, Nov. 15, 1999, p. 479A.
Fukushima, N., et al., "Enhanced Hematopoiesis In Vivo and In Vitro by Splenic Stromal Cells Derived From the Mouse With Recombinant Granulocyte Colony-Stimulating Factor", Blood, vol. 80, No. 8, pp. 1914-1922 (1992).
Funaro et al,. "Monoclonal antibodies and therapy of human cancers," Biotechnol. Adv., 2000, 18:385-401.
Galfre, G., et al., "Preparation of Monoclonal Antibodies: Strategies and Procedures," Methods in Enzymology, vol. 73, pp. 3-46 (1981).
Galfre, G., et al., "Rat × rat hybrid myelomas and a monoclonal anti-Fd portion of mouse IgG," Nature, vol. 277, pp. 131-133 (1979).
Genestier et al., "Caspase-dependent Ceramide Production in Fas- and HLA Class I-mediated Peripheral T Cell Apoptosis," J. Biol. Chem., 1998, 273:5060-5066.
Genestier et al., "Fas-Independent Apoptosis of Activated T Cells Induced by Antibodies to the HLA Class I a1 Domain," Blood, 1997, 90:3629-3639.
Genestier et al., "T cell sensitivity to HLA class I-mediated apoptosis is dependent on interleukin-2 and interleukin-4," Eur. J. Immunol., 1997, 27:495-499.
Genestier, L., et al., "Antibodies to HLA Class I α 1 Domain Trigger Apoptosis of CD 40-Activated Human B Lymphocytes," Blood, vol. 90, No. 2, pp. 726-735 (1997).
Ghetie et al., "Homodimerization of tumor-reactive monoclonal antibodies markedly increases their ability to induce growth arrest or apoptosis of tumor cells," PNAS USA, 1997, 94:7509-7514.
Giusti, A. M., et al., Proc. Natl. Acad. Sci. USA, vol. 84, No. 9, pp. 2926-2930 (1987).
Goding, Monoclonal Antibodies: Principles and Practice, Academic Press, second Ed, pp. 125-129 (1986).
Goel et al. "$^{99m}$Tc-Labeled Divalent and Tetravalent CC49 Single-Chain Fv's: Novel Imaging Agents for Rapid In Vivo Localization of Human Colon Carcinoma," J. Nucl. Med., 2001, 42:1519-1527.
Goel et al., "Genetically Engineered Tetravalent Single-Chain Fv of the Pancarcinoma Monoclonal Antibody CC49: Improved Biodistribution and Potential for Therapeutic Application," Cancer Research, Dec. 15, 2000, 60:6964-6971.
Goto et al., "A Novel Membrane Antigen Selectively Expressed on terminally Differentiated Human B Cells," Blood, 1994, 84:1992-1930.
Greenspan et al., "Defining epitopes: It's not as easy as it seems," Nature Biotechnology, vol. 17, Oct. 1999, pp. 936-937.
Grell, M., et al., "TR50 and TR80 Tumor Necrosis Factor (TNF)-Receptors Can Independently Mediate Cytolysis", Lymphokine and Cytokine Research, vol. 12, No. 3, pp. 143-148 (Jun. 1993).
Griffith et al,. "Functional Analysis of TRAIL Receptors Using Monoclonal Antibodies," J. Immunol., 1999, 162:2597-2605.
Gussow, D., et al., Methods in Enzymology, vol. 203, pp. 99-121 (1991).
Holliger et al., "'Diabodies': Small bivalent and bispecific antibody fragments," PNAS USA, 1993, 90:6444-6448.
Holliger P. et al., "Specific Killing of Lymphoma Cells by Cytotoxic T-Cells Mediated by a Specific Diabody", *Protein Engineering*, (1996), pp. 299-305, vol. 9, No. 3, Oxford University Press.
Holm et al., "Functional mapping and single chain construction of the anti-cytokeratin 8 monoclonal antibody TS1," Molecular Immunology, 2007, 44:1075-1084.
Hopp T. et al., "A Short Polypeptide Marker Sequence Useful for Recombinant Protein Identification and Purification", *Biotechnology*, (1988), pp. 1204-1210, vol. 6, Nature Publishing Company, USA.

(56) References Cited

OTHER PUBLICATIONS

Horan et al., "Dimerization of the Extracellular Domain of Granulocyte-Colony Stimulating Factor Receptor by Ligand Binding: A Monovalent Ligand Induces 2:2 Complexes," Biochemistry, 1996, 35, 4886-4896.

Hu et al,. "Minibody: A Novel Engineerind Anti-Carcinoembryonic Antigen Antibody Fragment (Single-Chain Fv-CH3) which Exhibits Rapid, High-Level Targeting of Xenografts," Cancer Res., 1996, 56:3055-3061.

Hudson, P. J., et al., "High avidity scFv multimers; diabodies and triabodies" Journal of Immunological Methods, Elsevier Science Publishers, vol. 231, No. 1-2, pp. 177-189 (Dec. 10, 1999).

Huston J. et al., "Protein Engineering of Antibody Binding Sites: Recovery of Specific Activity in an Anti-Digoxin Single-Chain Fv Analogue Produced in *Escherichia Coli*", *Proc. Natl. Acad. Sci. USA*, (1988), pp. 5879-5883, vol. 85, USA.

Itoh, N., et al., "The Polypeptide Encoded by the cDNA for Human Cell Surface Antigen Fas Can Mediate Apoptosis," Cell, vol. 66, pp. 233-243 (1991).

Jiang et al., "A Novel Peptide Isolated from a Phage Display Peptide Library with Trastuzumab Can Mimic Antigen Epitope of HER-2," J. Biol. Chem., Feb. 11, 2005, vol. 280, No. 6, pp. 4656-4662.

Jones S.T. et al., "Rapid PCR-Cloning of Full-Length Mouse Immunoglobulin Variable Regions", *Biotechnology*, (1991), pp. 88-89, vol. 9, London, England.

Kearney, J. F., et al., "A New Mouse Myeloma Cell Line That Has Lost Immunoglobulin Expression But Permits the Construction of Antibody-Secreting Hybrid Cells Lines," The Journal of Immunology, vol. 123, No. 4, pp. 1548-1550 (1979).

Keen et al., "The use of serum-free medium for the production of functionally active humanized monoclonal antibody from NS0 mouse myeloma cells engineered using glutamine synthetase as a selectable marker," Cytotechnology, Jan. 1994, vol. 18, No. 3, pp. 207-217 (Abstract).

Kikuchi et al., "A bivalent single-chain Fv fragment against CD47 induces apoptosis for leukemic cells," Biochem. Biophys. Res. Commun., 2004, 315:912-918.

Kimura et al., "2D7 diabody bound to the a2 domain of HLA class I efficiently induces caspase-independent cell death against malignant and activated lymphoid cells," Biochem. Biophys. Res. Commun., 2004, 325:1201-1209.

Kipriyanov et al., "Effect of Domain Order on the Activity of Bacterially Produced Bispecific Single-chain Fv Antibodies," J. Mol. Biol., 2003, 330:99-111.

Kipriyanov S. et al., "Bispecific CD3×CD19 Diabody for T Cell-Mediated Lysis of Malignant Human B Cells", *Int. J. Cancer*, (1988), vol. 77, No. 5, pp. 763-772, Wiley-Liss, Inc., USA.

Kohler, G., et al., "Derivation of specific antibody-producing tissue culture and tumor lines by cell fusion," Eur. J. Immunol., vol. 6, pp. 511-519 (1976).

Kong et al., J. Biol. Chem., 1993, 268:23055-23058.

Kortt et al,. "Dimeric and trimeric antibodies: high avidity scFvs for cancer targeting," Biomol. Eng., 2001, 18:95-108.

Kortt et al., "Recombinant anti-sialidase single-chain variable fragment antibody: Characterization, formation of dimmer and higher-molecular-mass multimers and the solution of the crystal structure of the single-chain variable fragment/sialidase complex," Eur. J. Biochem., 1994, vol. 221, pp. 151-157.

Kortt et al., "Single-chain Fv fragments of anti-neuraminidase antibody NC10 containing five- and ten-residue linkers form dimmers and with zero-residue linker a trimer," Protein Engineering, 1997, vol. 10, No. 4, pp. 423-433.

Kozak M., "At Least Six Nucleotides Preceding the AUG Initiator Codon Enhance Translation in Mammalian Cells", *J. Mol. Biol.*, (1987) pp. 947-950, vol. 196, Academic Press Limited, USA.

Kreitman et al., "Cytotoxic Activity of Disulfide-stabilized Recombinant Immunotoxin RFB4(dsFv)-PE38 (BL22) toward Fresh Malignant Cells from Patients with B-cell Leukemias," Clin. Cancer Res., 2000, 6:1476-1487.

Kriangkum et al., "Bispecific and bifunctional single chain recombinant antibodies," Biomol. Eng., 2001, 18(2):31-40.

Kulkarni et al,. "Programmed Cell Death Signaling Via Cell-surface Expression of a Single-chain Antibody Transgene," Transplantation, 2000, 69:1209-1217.

Kulkarni et al., "Construction of a Single-Chain Antibody Derived from 5H7, A Monoclonal Antibody Specific for a Death Signaling Domain of Human Class I Major Histocompatibility Complex," Transplant Proc., 1998, 30:1081.

Kumar et al., "The second PDZ domain of INAD is a type I domain involved in binding to eye proteinkinase C. Mutational analysis and naturally occuring variants," J. Biol. Chem., 2001, 276(27):24971-24977.

Larrick, J. W., et al., "Polymerase Chain Reaction Using Mixed Primers: Cloning of Human Monoclonal Antibody Variable Region Genes From Single Hybridoma Cells", Bio/Technology, vol. 7, pp. 934-938 (1989.

Law, L. W., et al., "Observations on the Effect of a Folic-Acid Anatagonist on Transplantable Lymphoid Leukemias in Mice", Journal of the National Cancer Institute, vol. 10, pp. 179-193 (1949).

Lazar et al., "Transforming Growth Factor α: Mutation of Aspartic Acid 47 and Leucine 48 Results in Different Biological Activities," Molecular and Cellular Biology, Mar. 1988, 8(3):1247-1252.

Lebrun et al,. "Antibodies to the Extraellular Receptor Domain Restore the Hormone-insensitive Kinase and Conformation of the Mutant Insulin Receptor Valine 382," J. Biol. Chem., 1993, 268:11272-11277.

Ledbetter et al,. "Agonist activity of a CD40-specific single-chain Fv constructed regions of mAb G28-5," Critical Reviews in Immunology, 1997, 17:427-435.

Lei S. et al., "Characterization of the *Erwinia Carotovora pel*B Gene and Its Product Pectate Lyase", *Journal of Bacteriology*, (1987), pp. 4379-4383, vol. 169, No. 9, American Society for Microbiology, USA.

Li et al., "The Epitope Specificity and Tissue Reactivity of Four Murine Monoclonal Anti-CD22 Antibodies," Cell. Immunol., 1989, 118:85-99.

Lin et al., "Structure-function relationships in glucagon: properties of highly purified des-His-1-monoiodo-, and (des-Asn-28, Thr-29)(homoserine lactone-27)-glucagon," Biochemistry, 1975, 14:1559-1563.

Lindberg et al., "Molecular Cloning of Integrin-Associated Protein: An Immunoglobulin Family Member with Multiple Membrane-Spanning Domains Implicated in $\alpha_v\beta_3$-Dependent Ligand Binding," The Journal of Cell Biology, vol. 123, No. 2, The Rockefeller University Press, Oct. 1993, pp. 485-496.

Lindberg F. et al., "Molecular Cloning of Integrin-Associated Protein: An Immunoglobulin Family Member With Multiple Membrane-Spanning Domains Implicated in $\alpha_v\beta_3$-Dependent Ligand Binding", *The Journal of Cell Biology*, (1993), pp. 485-496, vol. 123, No. 2, The Rockefeller University Press, USA.

Lindberg, et al., "Rh-Related Antigen CD47 is the Signal-Transducer Integrin-Associated Protein," J. Biol. Chem., vol. 269, pp. 1567-1570 (1994).

Mac Callum et al., "Antibody-antigen interactions: Contact analysis and binding site topography," Journal of Molecular Biology, 1996, 262:732-745.

Mack et al., "A small bispecific antibody construct expressed as a functional single-chain molecule with high tumor cell cytotoxicity," PNAS USA, 1995, 92(15):7021-7025.

Mallender et al., "Construction, expression and activity of a bivalent bispecific single-chain antibody," J. Biol. Chem., 1994, 269(1):199-206.

Margulies, D. H., et al., "Somatic Cell Hybridization of Mouse Myeloma Cells," Cell, vol. 8, pp. 405-415 (1976).

Mariuzza, R. A., et al., Annu. Rev. Biophys. Biophys. Chem., vol. 16, pp. 139-159 (1987).

Marsters et al,. "A Novel Receptor for Apo2L/TRAIL Contains a Truncated Death Domain," Curr. Biol., 1997, 7:1003-1006.

Mateo et al., "CD47 ligation induces caspase-independent cell death in chronice lymphocytic leukemia," Nature Medicine, Nov. 1999, 5(11):1277-1284.

(56) References Cited

OTHER PUBLICATIONS

Mateo et al., "Induction of Apoptosis in B-Cells From Chronic Lymphocytic Leukemia (B-CLLs) by CD47," FASEB Journal, vol. 12, No. 5, Mar. 20, 1998, p. A1082.

Matsuoka et al., "A Monoclonal Antibody to the α2 Domain of Murine Major Histocompatibility Class I that Specifically Kills Activated Lymphocytes and Blocks Liver Damage in the Concanavalin A Hepatitis Model.," J. Exp. Med., 2003, 198:497-503.

Matsuoka et al., "A Novel Type of Cell Death of Lymphocytes Induced by a Monoclonal Antibody without Participation of Complement," J. Exp. Med., 1995, 181:2007-2015.

Mawby, W. J., et al., "Isolation and characterization of CD47 glycoprotein: a multispanning as integrin-associated protein (IAP) and the ovarian tumor marker OA3," Biochem. J., vol. 304, pp. 525-530 (1994).

McInnes et al., "Cytokines in the pathogenesis of rheumatoid arthritis," Nature Reviews/Immunology, 2007, 7:429-442.

Milili M. et al., "The VDJ Repertoire Expressed in Human PreB Cells Reflects the Selection of *Bona Fide* Heavy Chains", *Eur. J. Immunol.*, (1996), pp. 63-69, vol. 26, VCH Verlagsgesellschaft mbH.

Milligan, Mol. Pharm., 2004, 66:1-7.

Mizushima S. et al., pEF-BOS, "A Powerful Mammalian Expression Vector", *Nucleic Acids Research*, (1990), p. 5322, vol. 18, No. 17, Oxford University Press.

Moore et al., "Kinetics and thermodynamics of dimmer formation and dissociation for a recombinant humanized monoclonal antibody to vascular endothelial growth factor," Biochemistry, 1999, 38:13960-13967.

Mori et al., "Human normal hepatocytes are susceptible to apoptosis signal mediated by both TRAIL-R1 and TRAIL-R2," Cell Death and Differentiation, 2004, 11:203-207.

Mulligan R. et al., "Synthesis of Rabbit β-Globin in Cultured Monkey Kidney Cells Following Infection With a SV40 β-Globin Recombinant Genome", *Nature*, (1979), pp. 108-114, vol. 277, Macmillan Journals, Ltd, USA.

Nakayama et al., "Thrombocytosis in preterm infants: a possible involvement of thrombopoietin receptor gene expression," J. Mol. Med., 2005, 83:316-320.

Ngo et al., "Computational Complexity, Protein Structure Prediction, and the Levinthal Paradox," The Protein Folding Problem and Tertiary Structure Prediction, Merz, Jr. et al., Editors, Birkhauser Boston, 1994:433-506.

Nishii, "CD22 antibody Therapy", Current Therapy, 2001, 20:47-50, with English translation.

O'Brien et al., "Monoclonal antibodies for the human insulin receptor stimulate intrinsic receptor-kinase activity," *Biochim. Soc. Trans.* (1986), vol. 14, No. 6, pp. 1021-1023.

Ohtomo et al., "Molecular Cloning and Characterization of a Surface Antigen Preferentially on Multiple Myeloma Cells," Biochem. Biophys. Res. Commun., 1999, 258:583-591.

Ohtsuka et al,. "Synergistic induction of tumor cell apoptosis by death receptor antibody and chemotherapy agent through JNK/p38 and mitochondrial death pathway," Oncogene, 2003, 22:2034-2044.

Oka, "Development of Novel Immunotoxin Using Recombinant Alpha-Sarcin and its Application Treatment of Hematopoietic Tumor," Sankyo Seimei Kagaku Kenkyu Shinko Zaidan Kenkyu Hokokushu, 1998, 12:46-56, with concise English explanation.

Ono et al., "The humanized anti-NH1.24 antibody effecticely kills multiple myeloma cells by human effector cell-mediated cytotoxicity," Mol. Immunol., 1999, 36:387-395.

Orita et al., "A novel therapeutic approach for thrombocytopenia by minibody agonist of the thrombopoietin receptor," Blood, 2006, 105:562-566.

Ozaki et al., Humanized Anbi-HM1.24 Antibody Mediates Myeloma Cell Cytotoxicity that is Enhanced by Cytokine Stimulation of Effector Cells,' Blood, 1999, 93:3922-3930.

Ozaki et al., A Recombinant HLA Class I-Specific Single Chain Fv Diabody Induces Cell Death in Human Lymphoid Malignancies, Blood, 2003, 102:933a, Abstract No. 3474.

Palacios et al., "IL-3-dependent mouse clones that express B-220 surface antigen, contain IG genes in germ-line configuration, and generate B lymphocytes in vivo," Cell, 1985, 41:727-734.

Pan et al. "The Receptor for the Cytotoxic Ligand TRAIL," Science, 1997, 276:111-113.

Pan et al., "An Antagonist Decoy Receptor and a Death Domain-Containing Receptor for TRAIL," Science, 1997, 277:815-818.

Paul, Fundamental Immunology, Raven Press, NY, Chapter 8, p. 242 (1993).

Paul, Fundamental Immunology, Raven Press, NY, Chapter 8, p. 292-295 (1993).

Pettersen et al., "The TCR-Binding Region of HLA Class I a2 Domain Signals Rapid Fas-Independent Cell Death: A Direct Pathway for T Cell-Mediated Killing of Target Cells?" J. Immunol., 1998, 160:4343-4352.

Petterson et al., "CD47 Signals T Cell Death," J. Immunol., 1999, pp. 7031-7040.

Petterson, "CD47 and death signaling in the immune system," Apoptosis vol. 5, pp. 299-306 (2000).

Pietri-Rouxel et al., Eur. J. Biochem., 1997, 247:1174-1179.

Plückthun et al., "New protein engineering approaches to multivalent and bispecific antibody fragments," Immunotechnology, 1997, 3:83-105.

Reff et al., "A review of modifications to recombinant antibodies: attempt to increase efficacy in oncology applications," Critical Reviews in Oncology and Hematology, 2001, 40:25-35.

Reinholf et al., "In vivo expression of alternatively spliced forms of integrin-associated protein (CD47)," J. Cell Science, 1995, vol. 108, pp. 3419-3425.

Reinhold M. et al., "In vivo Expression of Alternatively Spliced Forms of Integrin-Associated Protein (CD47)", *Journal of Cell Science*, (1995), pp. 3419-3425, vol. 108, The Company of Biologists Limited, Great Britain.

Reiter et al., "Engineering interchain disulfide bonds into conserved framework regions of Fv fragments: improved biochemical characteristics of recombinant immunotoxins containing disulfide-stabelized Fv," Protein Engineering, 1994, vol. 7, No. 5, pp. 697-704.

Reiter et al., "Stabilization of the Fv Fragments in Recombinant Immunotoxins by Disulfide Bonds Engineered into Conserved Framework Regions," Biochemistry, 1994, vol. 33, pp. 5451-5459.

Reichmann L. et al., "Reshaping Human Antibodies for Therapy", *Nature*, (1988), pp. 323-327, vol. 332, Univ. of Cambridge, Cambridge, England.

Rossi et al., "Development of New Multivalent-bispecific Agents for Pretargeting Tumor Localization and Therapy," Clin. Cancer Res., 2003, 9:3886s-3896s.

Roue, G., et al., Biochimie, vol. 85, pp. 741-746 (2003).

Rozsnyay et al., "Phenylarsine oxide (PAO) blocks antigen receptor-induced calcium response and tyrosine phosphroylation of a distinct group of proteins," *Immunology Lett.* (Aug. 1993), vol. 37, Nos. 2-3, pp. 197-205.

Rudikoff et al,. "Single amino acid substitution altering antien-binding specificity," PNAS USA, 1982, 79:1979-1983.

Rudikoff, et al., Proc. Natl. Acad. Sci. USA vol. 79, p. 1979 (1982).

Sal-Man et al., "Arginine mutations within a transmembrane domain of Tar, as *Escherichia coli* aspartate receptor, can drive monodimer dissociation and heterodimer association in vivo," Biochem. J., 2005, 385(1):29-36.

Sato et al., "CD22 is Both a Posotive and Negative Regulator of B Lymphocyte Antigen Receptor Signal Transduction: Altered Signaling in CD22-Deficient Mice," Immunity, 1996, 5:551-562.

Sato K. et al., "Reshaping a Human Antibody to Inhibit the Interleukin 6-Dependent Tumor Cell Growth", *Cancer Research*, (1993), pp. 851-856, vol. 53.

Scheurle et al,. "Cancer Gene Discovery Using digital Differential Display," Cancer Res., 2000, 60:4037-4043.

Schickel, et al., "Gene for Integrin-Associated Protein (IAP, CD47): Physical Mapping, Genomic Structure, and Expression Studies in Skeletal Muscle," Biochem. Cell. Biol., vol. 80, No. 2, pp. 169-176 (2002).

Schmidt et al., "A bivalent single-chain antibody-toxin specific for ErbB-2 and the EFG receptor," Int. J. Cancer, 1996, 65(4):538-546.

(56) References Cited

OTHER PUBLICATIONS

Schwartz et al., "A superactive insulin: [B10-aspartic acid]insulin(human)," PNAS USA, 1987, 84:6408-6411.
Schwartz, M. A., et al., "A 50-kDa Integrin-associated Protein Is Required for Integrin-regulated Calcium Entry in endothelial Cells," J. Biol. Chem., vol. 268, No. 27, pp. 19931-19934 (1993).
Scott, "The Problem with Potency," Nature Biotechnology, 2005, 23(9):1037-1039.
Sekimoto et al. "A Single-Chain Fv Diabody Against Human Leukocyte Antigen-A Molecules Specifically Induces Myeloma Cell Death in the Bone Marrow Environment," Cancer Res., 2007, 67(3)1184-1192.
Sekimoto et al., "Eradication of Human Myeloma Cells by a Recombinant HLA Class I-Specific Single Chain Fv Diabody," Blood, 102:932a, XP009106629 (Abstract #3469) (Nov. 2003) [Abstract of the American Society of Hematology 45th Annual Meeting, Dec. 6-9, 2003, San Diego, California].
Sheridan et al., "Control of TRAIL-Induced Apoptosis by a Family of Signaling and Decoy Receptors," Science, 1997, 277:818-821.
Shigeta, M., et al., "Sperm-immobilizing monoclonal antibody to human seminal plasma antigens," Clin. Exp. Immunol., vol. 42, pp. 458-462 (1980).
Shulman, M., et al., "A better cell line for making hybridomas secreting specific antibodies," Nature, vol. 276, pp. 269-270 (1978).
Skolnick et al., "From genes to protein structure and function: novel applications of computational approaches in the genomic era," Trends in Biotechnology, 2000, 18:34-39.
Skolnick, et al., "From Genes to Protein Structure and Function: Novel Applications of Computational Approaches in the Genomic Era," Trends in Biotechnology, vol. 18, pp. 34-39 (2000).
Smith et al,. "Inhibition of T Cell Activation by a Monoclonal Antibody Reactive Against the α3 Domain of Human MHC Class I Molecules," J. Immunol., 1994, 153:1054-1067.
Souyri, Michele, "Mpl: From an Acute Myeloproliferative Virus to the Isolation of the Long Sought Thrombopoietin," Seminars in Hematology, Jul. 1998, 35(3):222-231.
Souyri, M., et al., "A Putative Truncated Cytokine Receptor Gene Transduced by the Myeloproliferative Leukemia Virus Immortalizes Hematopoietic Progenitors," Cell, vol. 63, Dec. 21, pp. 1137-1147 (1990).
Spaargaren, M., et aal., "Antibody-induced Dimerization Activates the Epidermal Growth Factor Receptor Tyrosine Kinase", The J. Boil. Chem., vol. 266, No. 3, pp. 1733-1739 (1981).
Stancovski et al., "Mechanistic aspects of the opposing effects of monoclonal antibodies to the ERBB2 receptor on tumor growth," Proc. Natl. Acad. Sci. USA, Oct. 1991, vol. 88, pp. 8691-8695.
Stein et al., "Characterization of humanized IgG4 anti-HLA-DR monoclonal antibody that lacks effector cell functions but retains direct antilymphoma activity and increases the potency of rituximab," Blood, 2006. 108(8):2736-2744.
Tahtis et al., "Biodistribution Properties of 111Indium-labeled C-Functionalized trans-Cyclohexyl Diethylenetriaminepentaacetic Acid Humanized 3S193 Diabody and F9ab')2 Constructs in a Breats arcinoma Xenograft Model," Clin. Cancer Res., 2001, 7:1061-1072.
Tedder et al., "CD22; a B Lymphocyte-Specific Adhesion Molecule that Regulates Antigen Receptor Signaling," Annu. Rev. Immunol., 1997, 15:481-504.
Thilenius et al,. "Agonist antibody and Fas ligand mediate different sensitivity to death in the signaling pathways of Fas and cytoplasmic mutants," Eur. J. Immunol., 1997, 27:1108-1114.
Trowbridge, I. S., "Interspecies Spleen-Myeloma Hybrid Producing Monoclonal Antibodies Against Mouse Lymphocyte Surface Glycoprotein, T200," J. Exp. Med., vol. 148, pp. 313-323 (1978).
U.S. Appl. No. 10/550,934, Final OA mailed Mar. 16, 2009, 13 pages.
U.S. Appl. No. 10/221,131, Final OA mailed Jun. 27, 2007, 6 pages.
U.S. Appl. No. 10/221,131, Final OA mailed Sep. 2, 2008, 11 pages.
U.S. Appl. No. 10/221,131, Non-Final OA mailed Apr. 18, 2006, 30 pages.
U.S. Appl. No. 10/221,131, Non-Final OA mailed Feb. 19, 2009, 11 pages.
U.S. Appl. No. 10/221,131, Non-Final OA mailed Feb. 28, 2008, 6 pages.
U.S. Appl. No. 10/221,131, Non-Final OA mailed Oct. 31, 2006, 12 pages.
U.S. Appl. No. 10/221,131, Notice of Allowance mailed Jan. 8, 2010, 19 pages.
U.S. Appl. No. 10/221,131, Notice of Allowance mailed Sep. 24, 2009, 6 pages.
U.S. Appl. No. 10/530,696, Final OA mailed Aug. 8, 2007, 11 pages.
U.S. Appl. No. 10/530,696, Final OA mailed Jun. 8, 2009, 7 pages.
U.S. Appl. No. 10/530,696, Non-Final OA mailed Dec. 21, 2006, 11 pages.
U.S. Appl. No. 10/530,696, Non-Final OA mailed Feb. 5, 2008, 8 pages.
U.S. Appl. No. 10/530,696, Non-Final OA mailed Nov. 17, 2008, 13 pages.
U.S. Appl. No. 10/548,727, Final OA mailed Apr. 29, 2008, 19 pages.
U.S. Appl. No. 10/548,727, Non-Final OA mailed Aug. 3, 2007, 14 pages.
U.S. Appl. No. 10/548,727, Non-Final OA mailed Jan. 28, 2009, 13 pages.
U.S. Appl. No. 10/550,934, Non-Final OA mailed Jun. 12, 2008, 16 pages.
U.S. Appl. No. 10/551,504, Non-Final OA mailed Apr. 15, 2009, 20 pages.
U.S. Appl. No. 10/582,304, Non-Final OA mailed Apr. 1, 2009, 20 pages.
U.S. Appl. No. 10/582,304, Non-Final OA mailed Sep. 15, 2009, 8 pages.
U.S. Appl. No. 10/582,413, Final OA mailed Jun. 25, 2009, 20 pages.
U.S. Appl. No. 10/582,413, Non-Final OA mailed Mar. 31, 2008, 8 pages.
U.S. Appl. No. 11/547,747, Non-Final OA mailed Jun. 1, 2009, 33 pages.
Vajdos et al. "Comprehensive functional maps of the antigen-binding site of an anti-ErbB2 antibody obtained with shotgun scanning mutagenesis," Journal of Molecular Biology, 2002, 320:415-428.
Van Geelen et al., et al., "Differential modulation of the TRAIL receptors and the CD95 receptor in colon carcinoma cell lines," Br. J. Cancer, 2003, 89(2):363-373.
Verma et al., "Antibody engineering: Comparison of bacterial, yeast, insect and mammalian expression systems," Journal of Immunological Methods, 1998, vol. 216, pp. 165-181.
Vernon-Wilson et al., CD47 is a ligand for rat macrophage membrane signal regulatory protein SIRP (OX41) and human SIRPα1, Eur. J. Immunol., 2000, 30:2130-2137.
Walczak et al., "TRAIL-R2: A Novel Apoptosis-Mediating Receptor for TRAIL," EMBO J., 1997, 16:5386-5397.
Wells, "Perspectives in Biochemistry," Biochemistry, 1990, 29(37):8509-8517.
Whitlow et al., "Multivilant Fvs: characterization of single-chain Fv oligomers and preparation of a bispecific Fv," Protein Engineering, 1994, 7(8):1017-1026.
Wiley et at "Identification and Characterization of a New Member of the TNF Family that Induces Apoptosis," Immunity, 1995, 3:673-682.
Winkler et al., "Changing the Antigen Binding Specificity by Single Point Mutations of an Anti-p24 (HIV-1) Antibody," J. Immunol., 2000, 265:4505-4514.
Woodle et al., "Anti-Human Class I a3 Domain-Specific Monoclonal Antibody Induces Programmed Cell Death in Murine Cells Expressing Human Class I MHC Transgenes," Transplant. Proc., 1998, 30:1059-1060.
Woodle et al., "Anti-Human Class I MHC Antibodies Induce Apoptosis by a Pathway that is Distinct from the Fas Antigen-Mediated Pathway," J. Immunol., 1997, 158:2156-2164.
Woodle et al., "Class I MHC Mediates Programmed Cell Death in Human Lymphoid Cells," Transplantation, 1997, 64:140-146.
Wu et al., "Humanization of a murine monoclonal antibody by simultaneous optimization of framework and CFR residues," Journal of Molecular Biology, 1999, 294:151-162.

(56) References Cited

OTHER PUBLICATIONS

Wu et al., "Tumor localization of anti-CEA single-chain Fvs: improved targeting by non-covalent dimmers," Immunotechnology, 1996, 2:21-36.

www.nlm.hih.gov/medlineplus/druginfo/medmaster/a682792.html, "Dexamethasone Oral," 4 pages, downloaded Jul. 19, 2007.

Xie M. et al., "Direct Demonstration of MuSK Involvement in Acetylcholine Receptor Clustering Through Identification of Agonist ScFv", *Nature Biotechnology*, (1997), pp. 768-771, vol. 15, No. 8, San Francisco, USA.

Xiong et al., "Efficient inhibition of human B-cell lymphoma xenografts with an anti-CD20 X anti-CD3 bispecific diabody," Cancer Lett., 2002, 177:29-39.

Xu et al., "Insight into hepatocellular carcinogenesis at transcriptome level by comparing gene expression profiles of hepatocellular carcinoma with those of corresponding noncancerous liver," PNAS USA, 2001, 98:15089-15094.

Yanabu et al, "Tyrosine phosphorylation and p72syk activation by an anti-glycoprotein lb monoclonal antibody," *Blood* (1997), vol. 89, No. 5, pp. 1590-1598.

Yarden et al, "Self-phosphorylation of epidermal growth factor receptor: evidence for a model of intermolecular allosteric activisation," *Biochemistry* (1987), vol. 26, No. 5, pp. 1434-1442.

Yelton, D. E., et al., "Fusion of Mouse Myeloma and Spleen Cells," Current Topics in Microbiology and Immunology, vol. 81, pp. 1-7 (1978).

\* cited by examiner

Fig. 21
SDS-PAGE analysis of MABL2-scFv
<CHO>
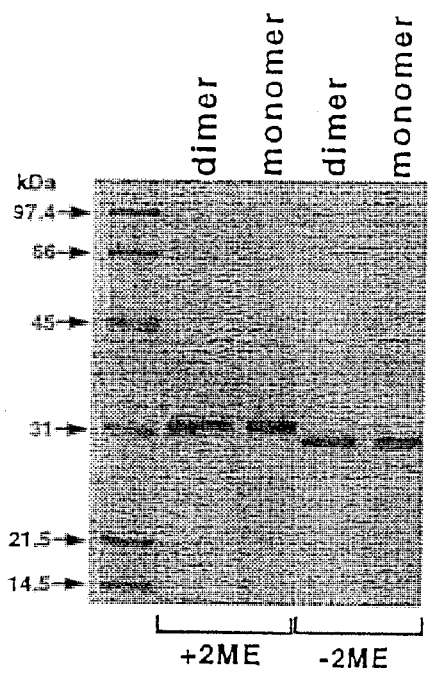
<E. coli>
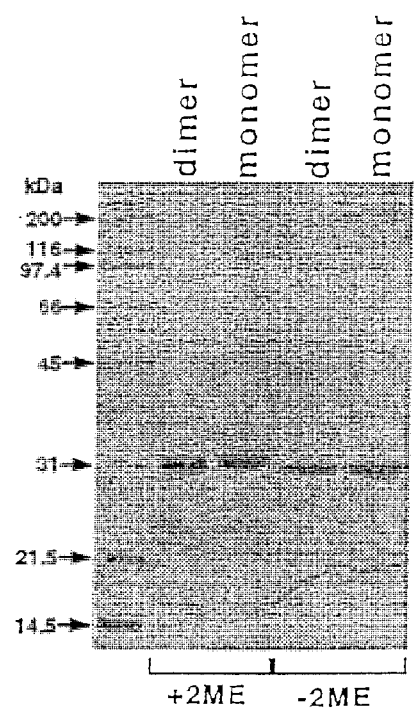

Figure 36

Base Sequence and Amino Acid Sequence of Linker for HL Type

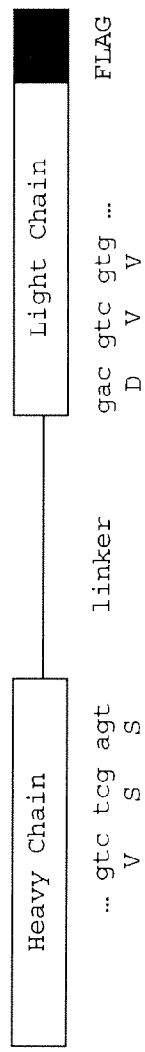

| Plasmid | Number of linker amino acid | | | | | | linker | | | | | | | | | | |
|---|---|---|---|---|---|---|---|---|---|---|---|---|---|---|---|---|---|
| CF2HL-0/pCOS1 | 0 | gtc<br>V | tcg<br>S | agt<br>S | | | | | | | | | | gac<br>D | gtc<br>V | gtg<br>V |
| CF2HL-3/pCOS1 | 3 | gtc<br>V | tcg<br>S | agt<br>S | ggt<br>G | ggt<br>G | tcc<br>S | | | | | | | gac<br>D | gtc<br>V | gtg<br>V |
| CF2HL-4/pCOS1 | 4 | gtc<br>V | tcg<br>S | agt<br>S | ggt<br>G | ggt<br>G | ggt<br>G | tcc<br>S | | | | | | gac<br>D | gtc<br>V | gtg<br>V |
| CF2HL-5/pCOS1 | 5 | gtc<br>V | tcg<br>S | agt<br>S | ggt<br>G | ggt<br>G | ggt<br>G | ggt<br>G | tcc<br>S | | | | | gac<br>D | gtc<br>V | gtg<br>V |
| CF2HL-6/pCOS1 | 6 | gtc<br>V | tcg<br>S | agt<br>S | ggt<br>G | ggt<br>G | ggt<br>G | ggt<br>G | ggt<br>G | tcc<br>S | | | | gac<br>D | gtc<br>V | gtg<br>V |
| CF2HL-7/pCOS1 | 7 | gtc<br>V | tcg<br>S | agt<br>S | ggt<br>G | ggt<br>G | ggt<br>G | ggt<br>G | ggt<br>G | ggt<br>G | tcc<br>S | | | gac<br>D | gtc<br>V | gtg<br>V |

Fig. 38

Base Sequence and Amino Acid Sequence of Linker for LH Type

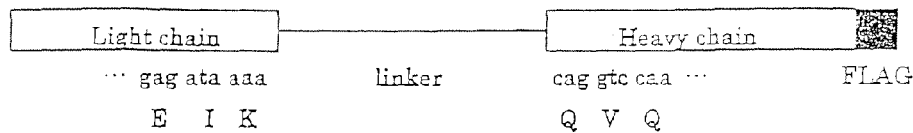

··· gag ata aaa     linker     cag gtc caa ···     FLAG
    E   I   K                Q   V   Q

| Plasmid | Number of linker amino acid | linker | |
|---|---|---|---|
| CF2LH-0/pCOS1 | 0 | gag ata aaa<br>E   I   K | cag gtc caa<br>Q   V   Q |
| CF2LH-3/pCOS1 | 3 | gag ata aaa tcc gga ggc<br>E   I   K   S   G   G | cag gtc caa<br>Q   V   Q |
| CF2LH-4/pCOS1 | 4 | gag ata aaa tcc gga ggt ggc<br>E   I   K   S   G   G   G | cag gtc caa<br>Q   V   Q |
| CF2LH-5/pCOS1 | 5 | gag ata aaa tcc gga ggt ggt ggc<br>E   I   K   S   G   G   G   G | cag gtc caa<br>Q   V   Q |
| CF2LH-6/pCOS1 | 6 | gag ata aaa tcc gga ggt ggt ggt ggc<br>E   I   K   S   G   G   G   G   G | cag gtc caa<br>Q   V   Q |
| CF2LH-7/pCOS1 | 7 | gag ata aaa tcc gga ggt ggt ggt ggt ggc cag gtc caa<br>E   I   K   S   G   G   G   G   G   Q   V   Q | |

M : MW marker
1 : sc12B5 fractionA
2 : sc12B5 fractionB

US 8,586,039 B2

DEGRADED TPO AGONIST ANTIBODY

CROSS-REFERENCE TO RELATED APPLICATIONS

This application is a Divisional of U.S. application Ser. No. 10/399,518, which is the U.S. National Stage application of PCT/JP01/09259 filed Oct. 22, 2001, which claims priority from Japanese application nos. JP 2000-321821, filed October 20, JP 2001-277314, filed Sep. 12, 2001, and is a Continuation of PCT/JP01/03288, filed Apr. 17, 2001.

TECHNICAL FIELD

This invention relates to modified antibodies containing two or more H chain V regions and two or more L chain V regions of an antibody which show TPO agonist activity by crosslinking TPO receptor. The modified antibodies have TPO agonist activity of transducing a signal into cells by crosslinking TPO receptor and are useful as a medicine for various purposes.

BACKGROUND ART

Thrombopoietin (TPO) is a platelet production regulation factor found in 1994 and is known to be composed of a glycoprotein having a molecular weight of 70-80 thousands produced mainly in liver. Thrombopoietin is a cytokine which in bone marrow promotes platelet precursor cells to survive, proliferate, differentiate and mature, namely promotes megakaryocytes to differentiate and proliferate. Thrombopoietin (TPO) receptor was identified earlier than TPO as c-Mpl, a receptor of a specific factor to regulate platelet production (M. Souyri et al., Cell 63: 1137 (1990)). It was reported that c-Mpl is distributed mainly in platelet precursor cells, megakayocytes and platelet cells and that the suppression of c-Mpl expression inhibits selectively megakaryocyte formation (M. Methia et al., Blood 82: 1395 (1993)). It was reported that the ligand to c-Mpl is TPO based on the results of proliferation assay of cells specific to c-Mpl ligand and purification of the ligand using c-Mpl (F. de Sauvage et al., Nature 369: 533 (1994); TD. Bartley et al., Cell 77: 1117 (1994)). At present Mpl is called TPO receptor. Therefore TPO and TPO receptor agonists have been expected to work as a therapeutic agent for thrombocytopenia, for example, as a medicine alleviating thrombocytopenia caused by bone marrow inhibition or bone marrow resection therapy for cancer patients.

On the other hand modified antibodies, especially antibodies with lowered molecular size, for example, single chain Fvs were developed to improve permeability into tissues and tumors by lowering molecular size and to produce by a recombinant method. Recently the dimers of single chain Fvs, especially bispecific-dimers have been used for crosslinking cells. Typical examples of such dimers are hetero-dimers of single chain Fvs recognizing antigens of cancer cells and antigens of host cells like NK cells and neutrophils (Kipriyanov et al., Int. J. Cancer, 77, 9763-9772, 1998). They were produced by construction technique of single chain Fv as modified antibodies, which are more effective in treating cancers by inducing intercellular crosslinking. It has been thought that the intercellular crosslinking is induced by antibodies and their fragments (e.g. Fab fragment), bispecific modified antibodies and even dimers of single chain Fvs, which are monospecific.

As antibodies capable of transducing a signal by crosslinking a cell surface molecule(s), there are known an antibody against EPO receptor involved in cell differentiation and proliferation (JP-A 2000-95800), an antibody against MuSK receptor (Xie et al., Nature Biotech. 15, 768-771, 1997) and others. There are also known an agonist antibody to TPO receptor, its fragments and single chain Fvs (WO99/17364). However there have been no reports on single chain Fv diners and modified antibodies such as single chain bivalent antibodies having agonist activity.

Noticing that single chain Fv monomers derived from monoclonal antibodies (antibody MABL-1 and antibody MABL-2 produced by the inventors) which induce apoptosis of LAP-containing cells do not induce apoptosis of cells and that dimers induce apoptosis, the inventors discovered that dimers crosslink (dimerize) LAP receptor on cell surface, thereby a signal is transduced into the cells and, as a result, apoptosis is induced. This suggests that monospecific single chain Fv dialers crosslink a cell surface molecule(s) (e.g. receptor) and transduce a signal like a ligand, thereby serving as an agonist.

Focusing on the intercellular crosslinking, it was discovered that the above-mentioned single chain Fv dimers do not cause hemagglutination while the above-mentioned monoclonal antibodies do. The same result was also observed with single chain bivalent antibodies (single chain polypeptides containing two H chain V regions and two L chain V regions). This suggests that monoclonal antibodies may form intercellular crosslinking while modified antibodies like single chain Fv dimers and single chain bivalent antibodies crosslink a cell surface molecule(s) but do not form intercellular crosslinking.

Based on those observations the inventors have newly discovered that modified antibodies such as single chain Fv dimers and single chain bivalent antibodies crosslink a cell surface molecule(s) or intracellular molecule(s) of the same cell, in addition to known intercellular crosslinking, and are suitable as a ligand to the molecule(s) (especially as a ligand which mimics the action of natural ligand).

Discovering further that an antibody molecule (whole IgG) can be modified into single chain Fv dimers, single chain bivalent antibodies and the like which crosslink a cell surface molecule(s), thereby reducing side effects caused by intercellular crosslinking and providing new medicines inducing only desired effect on the cell, the inventors completed the invention. The modified antibodies of the invention have remarkably high activity compared with whole antibodies (IgG) having the same V region as the modified antibodies. They have an improved permeability into tissues due to the lowered molecular size compared with antibody molecules and the lack of constant regions.

BRIEF DESCRIPTION OF THE DRAWINGS

FIG. 21 is the analysis on SDS-PAGE of the fractions obtained in the purification of the single chain Fv derived from the antibody MABL-2 produced by the CHO cells in Example 5.9.

FIG. 36 illustrates a structure of the HL-type nucleotide and amino acid sequences of peptide linkers (SEQ ID NOS: 148-159, respectively, in order of appearance).

FIG. 38 illustrates a structure of the LH-type nucleotide and amino acid sequences of peptide linkers (SEQ ID NOS: 162-173, respectively, in order of appearance).

DISCLOSURE OF INVENTION

Figure 1:
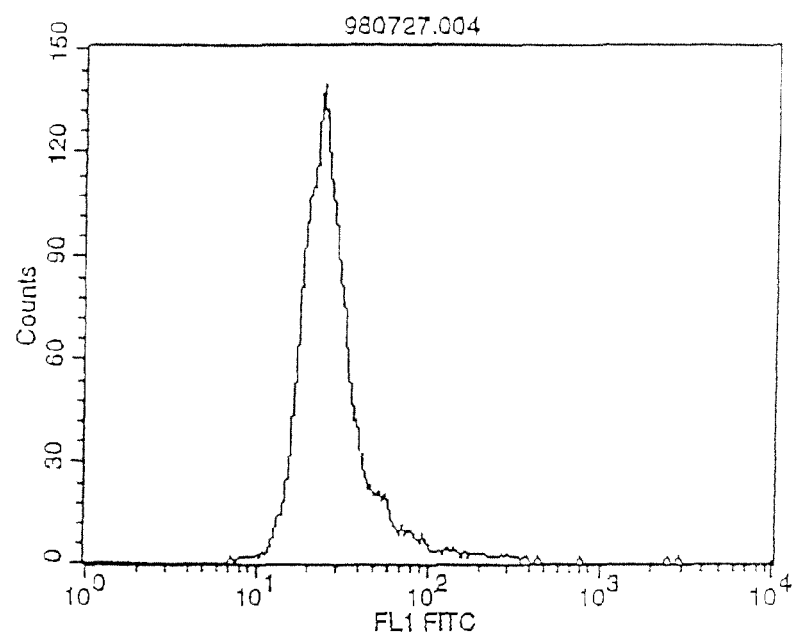
FIG. 1 shows the result of flow cytometry, illustrating that human IgG antibody does not bind to L1210 cells expressing human IAP (hIAP/L1210).

An object of this invention is to provide low molecular-sized agonistic modified antibodies which contain two or more H chain V regions and two or more L chain V regions of a monoclonal antibody and have TPO agonist action by crosslinking TPO receptor.

Therefore, this invention relates the modified antibodies which contain two or more H chain V regions and two or more L chain V regions, preferably 2 to 6 each, especially preferably 2 to 4 each, most preferably two each, and show TPO agonist activity by crosslinking TPO receptor.

The "modified antibodies" in the specification mean any substances which contain two or more H chain V regions and two or more L chain V regions, wherein said V regions are combined directly or via linker through covalent bond or non-covalent bond. For example, polypeptides and compounds produced by combining each V region of antibody through a peptide linker or a chemical crosslinking agent and the like. Two or more H chain V regions and two or more L chain V regions used in the invention can be derived from the same antibody or from different antibodies.

Modified antibodies of the invention can be any things as long as they specifically recognize and crosslink TPO receptor and thereby can transduce a signal into cells. They include modified antibodies produced by further modifying a part of the amino acid sequence of V region of the modified antibodies.

Preferable examples of the modified antibodies of the invention are multimers such as dimers, trimers or tetramers of single chain Fv containing an H chain V region and an L chain V region, or single chain polypeptides containing two or more H chain V regions and two or more L chain V regions. When the modified antibodies of the invention are multimers of single chain Fv such as dimers, trimers, tetramers and the like containing an H chain V region and an L chain V region, it is preferable that the H chain V region and L chain V region existing in the same chain are not associated to form an antigen-binding site.

More preferable examples are dimers of the single chain Fv which contains an H chain V region and an L chain V region, or a single chain polypeptide containing two H chain V regions and two L chain V regions. The H chain V region and L chain V region are connected preferably through a linker in the modified antibodies.

The above-mentioned single chain Fv multimer includes a multimer by non-covalent bond, a multimer by a covalent bond through a crosslinking radical and a multimer through a crosslinking reagent (an antibody, an antibody fragment, or bivalent modified antibody). Conventional crosslinking radicals used for crosslinking peptides can be used as the crosslinking radicals to form the multimers. Examples are disulfide crosslinking by cysteine residue, other crosslinking radicals such as $C_4$-$C_{10}$ alkylene (e.g. tetramethylene, pentamethylene, hexamethylene, heptamethylene and octamethylene, etc.) or $C_4$-$C_{10}$ alkenylene (cis/trans-3-butenylene, cis/trans-2-pentenylene, cis/trans-3-pentenylene, cis/trans-3-hexenylene, etc.).

Moreover, the crosslinking reagent which can combine with a single chain Fv is, for example, an amino acid sequence which can optionally be introduced into Fv, for example, an antibody against FLAG sequence and the like or a fragment thereof, or a modified antibody originated from the antibody, for example, single chain Fv.

"TPO agonist action" in the specification means a biological action occurring in the cell(s) into which a signal is transduced by crosslinking TPO receptor, for example, proliferation, differentiation or growth stimulation of megakaryocytes, or platelet production.

ED50 of the TPO agonist action in the invention is determined by known methods for measuring agonist action. Examples for measurement are cell proliferation assay using TPO sensitive cell lines such as BaF/mpl or UT7/TPO, measurement of phosphorylation of MPL protein, megakaryocyte colony assay by differentiation from bone marrow cells, in vivo mouse platelet recovery synthesis assay, measurement of expression induction of platelet antigen GPIIbIIIa (anti GPI-IbIIIa) using human leukemia megakaryoblastic cell line (CMK) or measurement of polyploidy induction of megakaryoblastic cell line (DAMI). ED50 is a dose needed for achieving 50% reaction of the maximum activity set as 100% in the dose-reaction curve.

Preferable modified antibodies of the invention have TPO agonist action (ED50) equivalent to or better than that of an antibody having the same antigen-binding region as the modified antibody, namely the whole antibody (hereinafter "parent antibody") like IgG having the same pair of H chain V region and L chain V region as the pair of H chain V region and L chain V region forming antigen-biding region of the modified antibody. More preferable are those having TPO agonist action (ED50) more than two times higher than that of parent antibody, further preferably more than 5 times, most preferably more than 10 times. The invention includes modified antibodies with TPO agonist action containing H chain V region and L chain V region forming the same antigen-binding region as the parent antibody which binds to TPO receptor but has no TPO agonist action to the molecule.

The compounds containing two or more H chain V regions and two or more L chain V regions of the invention can be any compounds which contain two or more H chain V regions and two or more L chain V regions of antibody and show TPO agonist action (ED50) equivalent to or better than that of thrombopoietin (TPO). Preferable are those having TPO agonist action (ED50) more than two times higher than that of TPO, more preferably more than 5 times, most preferably more than 10 times.

The "compounds" mentioned here include not only modified antibodies of the invention but also any compounds containing two or more, preferably from 2 to 6, more preferably from 2 to 4, most preferably 2 antigen-binding regions such as whole antibodies or F(ab')$_2$.

Preferable modified antibodies or compounds of the invention containing two or more H chain V regions and two or more L chain V regions of antibody have an intercellular adhesion action (ED50) not more than 1/10 compared with the parent antibody, more preferably have no substantial intercellular adhesion action.

ED50 of the intercellular adhesion action mentioned in the above is determined by known methods for measuring intercellular adhesion action, for example, by the measurement of agglomeration of cells expressing TPO receptor.

The invention relates to DNAs which code for the modified antibodies.

The invention relates to animal cells or microorganisms which produce the modified antibodies.

The invention relates to use of the modified antibody as TPO agonist.

The invention relates to a method of transducing a signal into cells by crosslinking TPO receptor using the modified antibody and thereby inducing TPO agonist action such as proliferation, differentiation-induction or growth stimulation of megakaryocytes, platelet production, phosphorylation of TPO receptor protein and the like.

The invention relates to a medicine for treating thrombocytopenia etc. containing the modified antibody as active component.

The invention relates to use of the modified antibody as a medicine.

The invention relates to a method of screening or measuring the modified antibody, which contains two or more H chain V regions and two or more L chain V regions of antibody and shows TPO agonist action by crosslinking TPO receptor, that comprises 1) to prepare a modified antibody containing two or more H chain V regions and two or more L chain V regions of antibody and binding specifically to TPO receptor, 2) to contact the modified antibody with cells expressing TPO receptor and 3) to measure TPO agonist action which occurs in the cells by crosslinking TPO receptor. The method of measurement is useful for the quality control in producing the modified antibodies of the invention as a medicine and other purposes.

The modified antibodies can be mono-specific modified antibodies or multi-specific modified antibodies like bi-specific modified antibodies. Preferable are mono-specific modified antibodies.

The present invention also relates to modified antibodies whose H chain V region and/or L chain V region is H chain V region derived from human antibody and/or L chain V region derived from human antibody. The H chain V region and/or L chain V region derived from human antibody can be obtained by screening human monoclonal antibody library as described in WO99/10494. The H chain V region and L chain V region derived from human monoclonal antibodies produced by transgenic mouse and the like are also included.

The present invention further relates to modified antibodies whose H chain V regions and/or L chain V regions are humanized H chain V regions and/or humanized L chain V regions. Specifically, the humanized modified antibodies consist of the humanized L chain V region which comprises framework regions (FR) derived from an L chain V region of human monoclonal antibody and complementarity determining regions (hereinafter "CDR") derived from an L chain V region of non-human mammalian (e.g. mouse, rat, bovine, sheep, ape) monoclonal antibody and/or the humanized H chain V region which comprises FR derived from an H chain V region of human monoclonal antibody and CDR derived from an H chain V region of non-human mammalian (e.g. mouse, rat, bovine, sheep, ape) monoclonal antibody. In this case, the amino acid sequences of CDR and FR may be partially altered, e.g. deleted, replaced or added.

H chain V regions and/or L chain V regions of the modified antibodies of the invention can be H chain V regions and/or L chain V regions derived from monoclonal antibodies of animals other than human (such as mouse, rat, bovine, sheep, ape, chicken and the like). In this case, the amino acid sequences of CDR and FR may be partially altered, e.g. deleted, replaced or added.

The invention also relates to DNAs encoding the various modified antibodies as mentioned above and genetic engineering techniques for producing recombinant vectors comprising the DNAs.

The invention also relates to host cells transformed with the recombinant vectors. Examples of host cells are animal cells such as human cells, mouse cells or the like and microorganisms such as *E. coli, Bacillus subtilis*, yeast or the like.

The invention relates to a process for producing the modified antibodies, which comprises culturing the above-mentioned hosts and extracting the modified antibodies from the culture thereof.

The present invention further relates to a process for producing a dimer of the single chain Fv which comprises culturing host animal cells producing the single chain Fv in a serum-free medium to secrete the single chain Fv into the medium and isolating the diner of the single chain Fv formed in the medium.

The present invention also relates to the use of the modified antibodies as TPO agonist. That is, it relates to a signal-transduction agonist which comprises as an active ingredient the modified antibody obtained as mentioned in the above.

Therefore, the pharmaceutical preparations containing TPO agonist modified antibodies of the invention as an active ingredient are useful as preventives and/or remedies for platelet-reduction-related blood diseases, thrombocytopenia caused by chemotherapy of cancers or leukemia, and the like.

The modified antibodies of the present invention comprise two or more H chain V regions and two or more L chain V regions derived from antibodies. The structure of the modified antibodies may be a dimer of single chain Fv comprising one H chain V region and one L chain V region or a polypeptide comprising two H chain V regions and two L chain V regions. In the modified antibodies of the invention, the V regions of H chain and L chain are preferably linked through a peptide linker which consists of one or more amino acids. The resulting modified antibodies contain variable regions of antibodies and bind to the antigen with the same specificity as that of the original monoclonal antibodies.

H Chain V Region

In the present invention, the H chain V region derived from an antibody recognizes TPO receptor and oligomerizes, for example, dimerizes through crosslinking said molecule, and thereby transduces a signal into the cells. The H chain V region of the invention includes H chain V regions derived from a mammal (e.g. human, mouse, rat, bovine, sheep, ape etc.) and H chain V regions having partially modified amino acid sequences of the H chain V regions. More preferable is a humanized H chain V region containing FR of H chain V region of a human monoclonal antibody and CDR of H chain V region of a mouse monoclonal antibody. Also preferable is an H chain V region having an amino acid sequence derived from a human, which can be produced by recombination technique. The H chain V region of the invention may be a fragment of aforementioned H chain V region, which fragment preserves the antigen binding capacity.

L Chain V Region

In the present invention, the L chain V region recognizes TPO receptor and oligomerizes, for example, dimerizes through crosslinking said molecule, and thereby transduces a signal into the cells. The L chain V region of the invention includes L chain V regions derived from a mammal (e.g. human, mouse, rat, bovine, sheep, ape etc.) and L chain V regions having partially modified amino acid sequences of the L chain V regions. More preferable is a humanized L chain V region containing FR of L chain V region of human monoclonal antibody and CDR of L chain V region of mouse monoclonal antibodies. Also preferable is an L chain V region having an amino acid sequence derived from a human, which can be produced by recombination technique. The L chain V regions of the invention may be fragments of L chain region, which fragments preserve the antigen binding capacity.

Complementarity Determining Region (CDR)

Each V region of L chain and H chain forms an antigen-binding site. The variable region of the L and H chains is composed of comparatively conserved four common framework regions linked to three hypervariable regions or complementarity determining regions (CDR) (Kabat, E. A. et al., "Sequences of Protein of Immunological Interest", US Dept. Health and Human Services, 1983).

Major portions in the four framework regions (FRs) form β-sheet structures and thus three CDRs form a loop. CDRs may form a part of the β-sheet structure in certain cases. The three CDRs are held sterically close position to each other by FR, which contributes to the formation of the antigen-binding site together with three CDRs.

These CDRs can be identified by comparing the amino acid sequence of V region of the obtained antibody with known amino acid sequences of V regions of known antibodies according to the empirical rule in Kabat, E. A. et al., "Sequences of Protein of Immunological Interest".

Single Chain Fv

A single chain Fv is a polypeptide monomer comprising an H chain V region and an L chain V region linked each other which are derived from antibodies. The resulting single chain Fvs contain variable regions of the original antibodies and preserve the complementarity determining region thereof, and therefore the single chain Fvs bind to the antigen by the same specificity as that of the original antibodies (JP-Appl. 11-63557). A part of the variable region and/or CDR of the single chain Fv of the invention or a part of the amino acid sequence thereof may be partially altered, for example, deleted, replaced or added. The H chain V region and L chain V region composing the single chain Fv of the invention are mentioned before and may be linked directly or through a linker, preferably a peptide linker. The constitution of the single chain Fv may be [H chain V region]-[L chain V region] or [L chain V region]-[H chain V region]. In the present invention, it is possible to make the single chain Fv to form a dimer, a trimer or a tetramer, from which the modified antibody of the invention can be formed.

Single Chain Modified Antibody

The single chain modified antibodies of the present invention comprising two or more H chain V regions and two or more L chain V regions, preferably each two to four, especially preferable each two, comprise two or more H chain V regions and L chain V regions as mentioned above. Each region of the peptide should be arranged such that the modified single chain antibody forms a specific steric structure, concretely mimicking a steric structure formed by the diner of single chain Fv. For instance, the V regions are arranged in the order of the following manner:

[H chain V region]-[L chain V region]-[H chain V region]-[L chain V region]; or

[L chain V region]-[H chain V region]-[L chain V region]-[H chain V region], wherein these regions are connected through a peptide linker, respectively.

Linker

In this invention, the linkers for the connection between the H chain V region and the L chain V region may be any peptide linker which can be introduced by the genetic engineering procedure or any linker chemically synthesized. For instance, linkers disclosed in literatures, e.g. Protein Engineering, 9(3), 299-305, 1996 may be used in the invention. These linkers can be the same or different in the same molecule. If peptide linkers are required, the following are cited as example linkers:

Ser

Gly-Ser

Gly-Gly-Ser

Ser-Gly-Gly

| Gly-Gly-Gly-Ser | (SEQ ID NO: 174) |
| Ser-Gly-Gly-Gly | (SEQ ID NO: 175) |
| Gly-Gly-Gly-Gly-Ser | (SEQ ID NO: 176) |
| Ser-Gly-Gly-Gly-Gly | (SEQ ID NO: 177) |
| Gly-Gly-Gly-Gly-Gly-Ser | (SEQ ID NO: 178) |
| Ser-Gly-Gly-Gly-Gly-Gly | (SEQ ID NO: 179) |
| Gly-Gly-Gly-Gly-Gly-Gly-Ser | (SEQ ID NO: 180) |
| Ser-Gly-Gly-Gly-Gly-Gly-Gly | (SEQ ID NO: 181) |
| (Gly-Gly-Gly-Gly-Ser)$_n$ | (SEQ ID NO: 182) | and

| (Ser-Gly-Gly-Gly-Gly)$_n$ | (SEQ ID NO: 183) | wherein n is an integer not less than one. Preferable length of the linker peptide varies dependent upon the receptor to be the antigen, in the case of single chain Fvs, the range of 1 to 20 amino acids is normally preferable. In the case of single chain modified antibodies comprising two or more H chain V regions and two or more L chain V regions, the peptide linkers connecting those forming the same antigen binding site comprising [H chain V region]-[L chain V region] (or [L chain V region]-[H chain V region]) have lengths of 1-30 amino acids, preferably 1-20 amino acids, more preferably 3-18 amino acids. The peptide linkers connecting those not forming the same antigen biding site comprising [H chain V region]-[L chain V region] or ([L chain V region]-[H chain V region]) have lengths of 1-40 amino acids, preferably 3-30 amino acids, more preferably 5-20 amino acids. The method for introducing those linkers will be described in the explanation for DNA construction coding for modified antibodies of the invention.

The chemically synthesized linkers, i.e. the chemical crosslinking agents, according to the invention can be any linkers conventionally employed for the linkage of peptides. Examples of the linkers may include N-hydroxy succinimide (NHS), disuccinimidyl suberate (DSS), bis(sulfosuccinimidyl)suberate ($BS^3$), dithiobis(succinimidyl propionate) (DSP), dithiobis(sulfosuccinimidyl propionate) (DTSSP), ethylene glycolbis(succinimidyl succinate) (EGS), ethylene glycolbis(sulfosuccinimidyl succinate) (sulfo-EGS), disuccinimidyl tartrate (DST), disulfosuccinimidyl tartrate (sulfo-DST), bis[2-(succinimido oxycarbonyloxy)ethyl]sulfone (BSOCOES), bis[2-(sulfosuccinimido oxycarbonyloxy) ethyl]sulfone (sulfo-BSOCOES) or the like. These are commercially available. It is preferable for the chemically synthesized linkers to have the length equivalent to that of peptide linkers.

To form a dimer of the single chain Fv it is preferable to select a linker suitable to dimerize in the solution such as culture medium more than 20%, preferably more than 50%, more preferably more than 80%, most preferably more than 90% of the single chain Fv produced in the host cells. Specifically, preferable is a linker composed of 2 to 12 amino acids, preferably 3 to 10 amino acids or other linkers corresponding thereto.

Preparation of Modified Antibodies

The modified antibodies can be produced by connecting, through the aforementioned linker, an H chain V region and an L chain V region derived from known or novel antibodies specifically binding to TPO receptor. As examples of the single chain Fvs are cited those having H chain V region and L chain V region of antibody 12B5 and antibody 12E10 described in WO99/10494. As examples of the modified antibodies of the invention having two or more H chain V regions and two or more L chain V regions are cited sc12B5 dimer (linker: 15 amino acids), sc12E10 dimer (linker: 15 amino acids), db12B5 dimer (linker: 5 amino acids), db12E10 dimer (linker: 5 amino acids), sc12B5sc$(FV)_2$ and sc12E10sc$(FV)_2$ which contain H chain V regions and L chain V regions derived from the above-mentioned monoclonal antibodies.

For the preparation of the modified antibodies, a signal peptide may be attached to its N-terminal if the polypeptide is desired to be a secretory peptide. A well-known amino acid sequence useful for the purification of polypeptide such as the FLAG sequence may be attached for the efficient purification of the polypeptide. In this case a dimer can be formed by using an ANTI-FLAG antibody.

For the preparation of the modified antibody of the invention, it is necessary to obtain a DNA, i.e. a DNA encoding the single chain Fv or a DNA encoding reconstructed single chain polypeptide. These DNAs, especially for sc12B5, db12B5, sc12E10 and/or db12E10 are obtainable from the DNAs encoding the H chain V regions and the L chain V regions derived from said Fvs. They are also obtainable by polymerase chain reaction (PCR) method using those DNAs as a template and amplifying the part of DNA contained therein encoding desired amino acid sequence with the aid of a pair of primers corresponding to both ends thereof.

In the case where each V region having partially modified amino acid sequence is desired, the V regions in which one or some amino acids are modified, i.e. deleted, replaced or added can be obtained by a procedure known in the art using PCR. A part of the amino acid sequence in the V region is preferably modified by the PCR known in the art in order to prepare the modified antibody which is sufficiently active against the specific antigen.

For the determination of primers for the PCR amplification, the types of H chain and L chain, if a monoclonal antibody is used as a starting material, are determined by a typing method known in the technical field.

For the amplification of the L chain V regions of antibody 12B5 and antibody 12E10 by PCR, 5'-end and 3'-end oligonucleotide primers are decided as aforementioned. In the same manner, 5'-end and 3'-end oligonucleotide primers are decided for the amplification of the H chain V regions of antibody 12B5 and antibody 12E10.

In embodiments of the invention, the 5'-end primers which contain a sequence "GANTC" providing the restriction enzyme Hinf I recognition site at the neighborhood of 5'-terminal thereof are used and the 3'-end primers which contain a nucleotide sequence "CCCGGG" providing the XmaI recognition site at the neighborhood of 5'-terminal thereof are used. Other restriction enzyme recognition site may be used instead of these sites as long as they are used for subcloning a desired DNA fragment into a cloning vector.

Specifically designed PCR primers are employed to provide suitable nucleotide sequences at 5'-end and 3'-end of the cDNAs encoding the V regions of the antibodies 12B5 and 12E10 so that the cDNAs are readily inserted into an expression vector and appropriately function in the expression vector (e.g. this invention devises to increase transcription efficiency by inserting Kozak sequence). The V regions of the antibodies 12B5 and 12E10 obtained by amplifying by PCR using these primers are inserted into HEF expression vector containing the desired human C region (see WO92/19759). The cloned DNAs can be sequenced by using any conventional process, for example, by the automatic DNA sequencer (Applied Biosystems).

A linker such as a peptide linker can be introduced into the modified antibody of the invention in the following manner. Primers which have partially complementary sequence with the primers for the H chain V regions and the L chain V regions as described above and which code for the N-terminal or the C-terminal of the linker are designed. Then, the PCR procedure can be carried out using these primers to prepare a DNA encoding the peptide linker having desired amino acid sequence and length. The DNAs encoding the H chain V region and the L chain V region can be connected through the resulting DNA to produce the DNA encoding the modified antibody of the invention which has the desired peptide linker. Once the DNA encoding one of the modified antibodies is prepared, the DNAs encoding the modified antibodies with or without the desired peptide linker can readily be produced by designing various primers for the linker and then carrying out the PCR using the primers and the aforementioned DNA as a template.

Each V region of the modified antibody of the present invention can be humanized by using conventional techniques (e.g. Sato, K. et al., Cancer Res., 53, 1-6 (1993)). Once a DNA encoding each of humanized Fvs is prepared, a humanized single chain Fv, a fragment of the humanized single chain Fv, a humanized monoclonal antibody and a fragment of the humanized monoclonal antibody can readily be produced according to conventional methods. Preferably, amino acid sequences of the V regions thereof may be partially modified, if necessary.

Furthermore, a DNA derived from other mammalian origin, for example a DNA encoding each of V regions of human antibody, can be produced in the same manner as used to produce DNA encoding the H chain V region and the L chain V region derived from mouse by conventional methods as mentioned in the above. The resulting DNA can be used to prepare an H chain V region and an L chain V region of other mammal, especially derived from human antibody, a single chain Fv derived from human and a fragment thereof, and a monoclonal antibody of human origin and a fragment thereof.

When the modified antibodies of the invention is bi-specific modified antibodies, they can be produced by known methods (for example, the method described in WO9413804).

As mentioned above, when the aimed DNAs encoding the V regions of the modified antibodies and the V regions of the humanized modified antibodies are prepared, the expression vectors containing them and hosts transformed with the vectors can be obtained according to conventional methods. Further, the hosts can be cultured according to a conventional method to produce the reconstructed single chain Fv, the reconstructed humanized single chain Fv, the humanized monoclonal antibodies and fragments thereof. They can be isolated from cells or a medium and can be purified into a homogeneous mass. For this purpose any isolation and purification methods conventionally used for proteins, e.g. chromatography, ultra-filtration, salting-out and dialysis, may be employed in combination, if necessary, without limitation thereto.

When the reconstructed single chain Fv of the present invention is produced by culturing an animal cell such as COS7 cells or CHO cells, preferably CHO cells, in a serum-free medium, the dimer of said single chain Fv formed in the medium can be stably recovered and purified in a high yield. Thus purified dimer can be stably preserved for a long period. The serum-free medium employed in the invention may be any medium conventionally used for the production of a recombinant protein without limit thereto.

For the production of the modified antibodies of the present invention, any expression systems can be employed, for example, eukaryotic cells such as animal cells, e.g., established mammalian cell lines, filamentous fungi and yeast, and prokaryotic cells such as bacterial cells e.g., *E. coli*. Preferably, the modified antibodies of the invention are expressed in mammalian cells, for example COS7 cells or CHO cells.

In these cases, conventional promoters useful for the expression in mammalian cells can be used. Preferably, human cytomegalovirus (HCMV) immediate early promoter is used. Expression vectors containing the HCMV promoter include HCMV-VH-HCγ 1, HCMV-VL-HCK and the like which are derived from pSV2neo (WO92/19759).

Additionally, other promoters for gene expression in mammal cell which may be used in the invention include virus promoters derived form retrovirus, polyoma virus, adenovirus and simian virus 40 (SV40) and promoters derived from mammal such as human polypeptide-chain elongation factor-1α (HEF-1α). SV40 promoter can easily be used according to the method of Mulligan, R. C., et al. (Nature 277, 108-114 (1979)) and HEF-1α promoter can also be used according to the methods of Mizushima, S. et al. (Nucleic Acids Research, 18, 5322 (1990)).

Replication origin (ori) which can be used in the invention includes ori derived from SV40, polyoma virus, adenovirus, bovine papilloma virus (BPV) and the like. An expression vector may contain, as a selection marker, phosphotransferase APH (3') II or I (neo) gene, thymidine kinase (TK) gene, *E. coli* xanthine-guanine phosphoribosyl transferase (Ecogpt) gene or dihydrofolate reductase (DHFR) gene.

The antigen-binding activity of the modified antibody prepared in the above can be evaluated by a conventional method such as radio immunoassay (RIA), enzyme-linked immunosorbent assay (ELISA) or surface plasmon resonance. It can also be evaluated using the binding-inhibitory ability of original antibody as an index, for example in terms of the absence or presence of concentration-dependent inhibition of the binding of said monoclonal antibody to the antigen.

More in detail, animal cells transformed with an expression vector containing a DNA encoding the modified antibody of the invention, e.g., COS7 cells or CHO cells, are cultured. The cultured cells and/or the supernatant of the medium or the modified antibody purified from them are used to determine the binding to antigen. As a control is used a supernatant of the culture medium in which cells transformed only with the expression vector were cultured. In the case of an antigen, for example, the antibody 12B5 and the antibody 12E10, a test sample of the modified antibody of the invention or a supernatant of the control is added to Ba/F3 cells expressing human MPL and then an assay such as the flow cytometry is carried out to evaluate the antigen-binding activity.

In vitro evaluation of the signal transduction effect (for example, proliferation, differentiation-induction or growth stimulation of megakaryocyte, platelet production, or phosphorylation of TPO receptor protein) is performed in the following manner. A test sample of the above-mentioned modified antibody is added to the cells which are expressing the antibody or cells into which the gene for the antibody has been introduced, and is evaluated by the change caused by the signal transduction (for example, human MPL antigen-specific proliferation, measurement of protein phosphorylation, or expression of platelet-specific antigen) using conventional methods.

In vivo evaluation is carried out by administering a monoclonal antibody recognizing MPL, a modified antibody of the invention and PBS as control to mice, and evaluating the strength of the activity by the change of the amount of platelet in mouse serum.

As mentioned above the modified antibodies of the invention can be obtained by preparing modified antibodies which contain two or more H chain V regions and two or more L chain V regions and specifically bind to TPO receptor and screening the modified antibodies by in vivo or in vitro evaluation as mentioned in the above.

The modified antibodies of the invention, which comprises two or more H chain V regions and two or more L chain V regions, preferably each two to four, more preferably each two, may be a dimer of the single chain Fv comprising one H chain V region and one L chain V region, or a single chain polypeptide in which two or more H chain V regions and two or more L chain V regions are connected. It is considered that owing to such construction the peptide mimics three dimensional structure of TPO and therefore retains an excellent antigen-binding property and TPO agonist activity.

The modified antibodies of the invention have a remarkably lowered molecular size compared with parent antibody molecule (e.g. IgG), and, therefore, have a superior permeability into tissues and tumors and a higher activity than parent monoclonal antibody molecule. Therefore, the modified antibodies of the invention can efficiently transduce TPO signal into cells. The pharmaceutical preparations containing them are useful for treating platelet-reduction-related blood diseases and thrombocytopenia caused by chemotherapy for cancers or leukemia. It is further expected that the antibody of the invention can be used as a contrast agent by RI-labeling. The effect can be enhanced by attaching to a RI-compound or a toxin.

BEST MODE FOR WORKING THE INVENTION

The present invention will concretely be illustrated in reference to the following examples, which in no way limit the scope of the invention.

For illustrating the production process of the modified antibodies of the invention, examples of producing single chain Fvs are shown below. Mouse antibodies against human IAP, MABL-1 and MABL-2 were used in the examples of producing the modified antibodies. Hybridomas MABL-1 and MABL-2 producing them respectively were internationally deposited as FERM BP-6100 and FERM BP-6101 with the National Institute of Bioscience and Human Technology, Agency of Industrial Science and Technology, Minister of International Trade and Industry (1-3 Higasi 1-chome, Tsukuba-shi, Ibaraki-ken, Japan), an authorized depository for microorganisms, on Sep. 11, 1997.

EXAMPLES

Example 1

Cloning of DNAs Encoding V Region of Mouse Monoclonal Antibodies to Human IAP

DNAs encoding variable regions of the mouse monoclonal antibodies to human IAP, MABL-1 and MABL-2, were cloned as follows.

1.1 Preparation of Messenger RNA (mRNA)

mRNAs of the hybridomas MABL-1 and MABL-2 were obtained by using mRNA Purification Kit (Pharmacia Biotech).

1.2 Synthesis of Double-Stranded cDNA

Double-stranded cDNA was synthesized from about 1 μg of the mRNA using Marathon cDNA Amplification Kit (CLONTECH) and an adapter was linked thereto.

1.3 PCR Amplification of Genes Encoding Variable Regions of an Antibody by

PCR was carried out using Thermal Cycler (PERKIN ELMER).

(1) Amplification of a Gene Coding for L Chain V Region of MABL-1

Primers used for the PCR method are Adapter Primer-1 (CLONTECH) shown in SEQ ID No. 1, which hybridizes to a partial sequence of the adapter, and MKC (Mouse Kappa Constant) primer (Bio/Technology, 9, 88-89, 1991) shown in SEQ ID No. 2, which hybridizes to the mouse kappa type L chain V region.

50 μl of the PCR solution contains 5 μl of 10×PCR Buffer II, 2 mM MgCl$_2$, 0.16 mM dNTPs (DATP, dGTP, dCTP and dTTP), 2.5 units of a DNA polymerase, AMPLITAQ GOLD AmpliTaq (PERKIN ELMER), 0.2 μM of the adapter primer of SEQ ID No. 1, 0.2 μM of the MKC primer of SEQ ID No. 2 and 0.1 μg of the double-stranded cDNA derived from MABL-1. The solution was preheated at 94° C. of the initial temperature for 9 minutes and then heated at 94° C. for 1 minute, at 60° C. for 1 minute and at 72° C. for 1 minute 20 seconds in order. This temperature cycle was repeated 35 times and then the reaction mixture was further heated at 72° C. for 10 minutes.

(2) Amplification of cDNA Encoding H Chain V Region of MabL-1

The Adapter Primer-1 shown in SEQ ID No. 1 and MHC-γ1 (Mouse Heavy Constant) primer (Bio/Technology, 9, 88-89, 1991) shown in SEQ ID No. 3 were used as primers for PCR.

The amplification of cDNA was performed according to the method of the amplification of the L chain V region gene, which was described in Example 1.3-(1), except for using 0.2 μM of the MHC-γ1 primer instead of 0.2 μM of the MKC primer.

(3) Amplification of cDNA Encoding L Chain V Region of MABL-2

The Adapter Primer-1 of SEQ ID No. 1 and the MKC primer of SEQ ID No. 2 were used as primers for PCR.

The amplification of cDNA was carried out according to the method of the amplification of the L chain V region gene of MABL-1 which was described in Example 1.3-(1), except for using 0.1 μg of the double-stranded cDNA derived from MABL-2 instead of 0.1 μg of the double-stranded cDNA from MABL-1.

(4) Amplification of cDNA Encoding H Chain V Region of MABL-2

The Adapter Primer-1 of SEQ ID No. 1 and MHC-γ2a primer (Bio/Technology, 9, 88-89, 1991) shown in SEQ ID No. 4 were used as primers for PCR.

The amplification of cDNA was performed according to the method of the amplification of the L chain V region gene, which was described in Example 1.3-(3), except for using 0.2 μM of the MHC-γ2a primer instead of 0.2 μM of the MKC primer.

1.4 Purification of PCR Products

The DNA fragment amplified by PCR as described above was purified using the QIAquick PCR Purification Kit (QIAGEN) and dissolved in 10 mM Tris-HCl (pH 8.0) containing 1 mM EDTA.

1.5 Ligation and Transformation

About 140 ng of the DNA fragment comprising the gene encoding the mouse kappa type L chain V region derived from MABL-1 as prepared above was ligated with 50 ng of pGEM-T Easy vector (Promega) in the reaction buffer comprising 30 mM Tris-HCl (pH 7.8), 10 mM MgCl$_2$, 10 mM dithiothreitol, 1 mM ATP and 3 units of T4 DNA Ligase (Promega) at 15° C. for 3 hours.

Then, 1 μl of the reaction mixture was added to 50 μl of *E. coli* DH5α competent cells (Toyobo Inc.) and the cells were stored on ice for 30 minutes, incubated at 42° C. for 1 minute and stored on ice for 2 minutes again. 100 μl of SOC medium (GIBCO BRL) was added. The cells of *E. coli* were plated on LB (Molecular Cloning: A Laboratory Manual, Sambrook et al., Cold Spring Harbor Laboratory Press, 1989) agar medium containing 100 μg/ml of ampicillin (SIGMA) and cultured at 37° C. overnight to obtain the transformant of *E. coli*.

The transformant was cultured in 3 ml of LB medium containing 50 μg/ml of ampicillin at 37° C. overnight and the plasmid DNA was prepared from the culture using the QIAprep Spin Miniprep Kit (QIAGEN).

The resulting plasmid comprising the gene encoding the mouse kappa type L chain V region derived from the hybridoma MABL-1 was designated as pGEM-M1L.

According to the same manner as described above, a plasmid comprising the gene encoding the mouse H chain V region derived from the hybridoma MABL-1 was prepared from the purified DNA fragment and designated as pGEM-M1H.

A plasmid comprising the gene encoding the mouse kappa type L chain V region derived from the hybridoma MABL-2 was prepared from the purified DNA fragment and designated as pGEM-M2L.

A plasmid comprising the gene encoding the mouse H chain V region derived from the hybridoma MABL-2 was prepared from the purified DNA fragment and designated as pGEM-M2H.

Example 2

DNA Sequencing

The nucleotide sequence of the cDNA encoding region in the aforementioned plasmids was determined using Auto DNA Sequencer (Applied Biosystem) and ABI PRISM Dye Terminator Cycle Sequencing Ready Reaction Kit (Applied Biosystem) according to the manufacturer's protocol.

The nucleotide sequence of the gene encoding the L chain V region from the mouse antibody MABL-1, which is included in the plasmid pGEM-M1L, is shown in SEQ ID No. 5.

The nucleotide sequence of the gene encoding the H chain V region from the mouse antibody MABL-1, which is included in the plasmid pGEM-M1H, is shown in SEQ ID No. 6.

The nucleotide sequence of the gene encoding the L chain V region from the mouse antibody MABL-2, which is included in the plasmid pGEM-M2L, is shown in SEQ ID No. 7.

The nucleotide sequence of the gene encoding the H chain V region from the mouse antibody MABL-2, which is included in the plasmid pGEM-M2H, is shown in SEQ ID No. 8

Example 3

Determination of CDR

The V regions of L chain and H chain generally have a similarity in their structures and each four framework regions therein are linked by three hypervariable regions, i.e., complementarity determining regions (CDR). An amino acid sequence of the framework is relatively well conserved, while an amino acid sequence of CDR has extremely high variation (Kabat, E. A., et al., "Sequences of Proteins of Immunological Interest", US Dept. Health and Human Services, 1983).

On the basis of these facts, the amino acid sequences of the variable regions from the mouse monoclonal antibodies to human IAP were applied to the database of amino acid sequences of the antibodies made by Kabat et al. to investigate the homology. The CDR regions were determined based on the homology as shown in Table 1.

TABLE 1

| Plasmid | SEQ ID No. | CDR (1) | CDR (2) | CDR (3) |
|---|---|---|---|---|
| pGEM-M1L | 5 | 43-58 | 74-80 | 113-121 |
| pGEM-M1H | 6 | 50-54 | 69-85 | 118-125 |
| pGEM-M2L | 7 | 43-58 | 74-80 | 113-121 |
| pGEM-M2H | 8 | 50-54 | 69-85 | 118-125 |

Example 4

Identification of Cloned cDNA Expression
Preparation of Chimera MABL-1 antibody and
Chimera MABL-2 Antibody 4.1 Preparation of Vectors Expressing Chimera MABL-1 Antibody cDNA clones, pGEM-M1L and pGEM M1H, encoding the V regions of the L chain and the H chain of the mouse antibody MABL-1, respectively, were modified by the PCR method and introduced into the HEF expression vector (WO92/19759) to prepare vectors expressing chimera MABL-1 antibody.

A forward primer MLS (SEQ ID No. 9) for the L chain V region and a forward primer MHS (SEQ ID No. 10) for the H chain V region were designed to hybridize to a DNA encoding the beginning of the leader sequence of each V region and to contain the Kozak consensus sequence (J. Mol. Biol., 196, 947-950, 1987) and HindIII restriction enzyme site. A reverse primer MLAS (SEQ ID No. 11) for the L chain V region and a reverse primer MHAS (SEQ ID No. 12) for the H chain V region were designed to hybridize to a DNA encoding the end of the J region and to contain the splice donor sequence and BamHI restriction enzyme site.

100 µl of a PCR solution comprising 10 µl of 10×PCR Buffer II, 2 mM $MgCl_2$, 0.16 mM dNTPs (DATP, dGTP, dCTP and dTTP), 5 units of DNA polymerase AMPLITAQ GOLD, 0.4 µM each of primers and 8 ng of the template DNA (pGEM-M1L or pGEM-M1H) was preheated at 94° C. of the initial temperature for 9 minutes and then heated at 94° C. for 1 minute, at 60° C. for 1 minute and at 72° C. for 1 minute 20 seconds in order. This temperature cycle was repeated 35 times and then the reaction mixture was further heated at 72° C. for 10 minutes.

The PCR product was purified using the QIAquick PCR Purification Kit (QIAGEN) and then digested with HindIII and BamHI. The product from the L chain V region was cloned into the HEF expression vector, HEF-κ and the product from the H chain V region was cloned into the HEF expression vector, HEF-γ. After DNA sequencing, plasmids containing a DNA fragment with a correct DNA sequence are designated as HEF-M1L and HEF-M1H, respectively.

4.2 Preparation of Vectors Expressing Chimera MABL-2 Antibodies

Modification and cloning of cDNA were performed in the same manner described in Example 4.1 except for using pGEM-M2L and pGEM-M2H as template DNA instead of pGEM-M1L and pGEM-M1H. After DNA sequencing, plasmids containing DNA fragments with correct DNA sequences are designated as HEF-M2L and HEF-M2H, respectively.

4.3 Transfection to COS7 Cells

The aforementioned expression vectors were tested in COS7 cells to observe the transient expression of the chimera MABL-1 and MABL-2 antibodies.

(1) Transfection with Genes for the Chimera MABL-1 Antibody

COS7 cells were co-transformed with the HEF-M1L and HEF-M1H vectors by electroporation using the Gene Pulser apparatus (BioRad). Each DNA (10 µg) and 0.8 ml of PBS with $1 \times 10^7$ cells/ml were added to a cuvette. The mixture was treated with pulse at 1.5 kV, 25 µF of electric capacity.

After the restoration for 10 minutes at a room temperature, the electroporated cells were transferred into DMEM culture medium (GIBCO BRL) containing 10% γ-globulin-free fetal bovine serum. After culturing for 72 hours, the supernatant was collected, centrifuged to remove cell fragments and recovered.

(2) Transfection with Genes Coding for the Chimera MABL-2 Antibody

The co-transfection to COS7 cells with the genes coding for the chimera MABL-2 antibody was carried out in the same manner as described in Example 4.3-(1) except for using the HEF-M2L and HEF-M2H vectors instead of the HEF-M1L and HEF-M1H vectors. The supernatant was recovered in the same manner.

4.4 Flow Cytometry

Flow cytometry was performed using the aforementioned culture supernatant of COS7 cells to measure binding to the antigen. The culture supernatant of the COS7 cells expressing the chimera MABL-1 antibody or the COS7 cells expressing the chimera MABL-2 antibody, or human IgG antibody (SIGMA) as a control was added to $4\times10^5$ cells of mouse leukemia cell line L1210 expressing human IAP and incubated on ice. After washing, the FITC-labeled anti-human IgG antibody (Cappel) was added thereto. After incubating and washing, the fluorescence intensity thereof was measured using the FACScan apparatus (BECTON DICKINSON).

Figure 2:
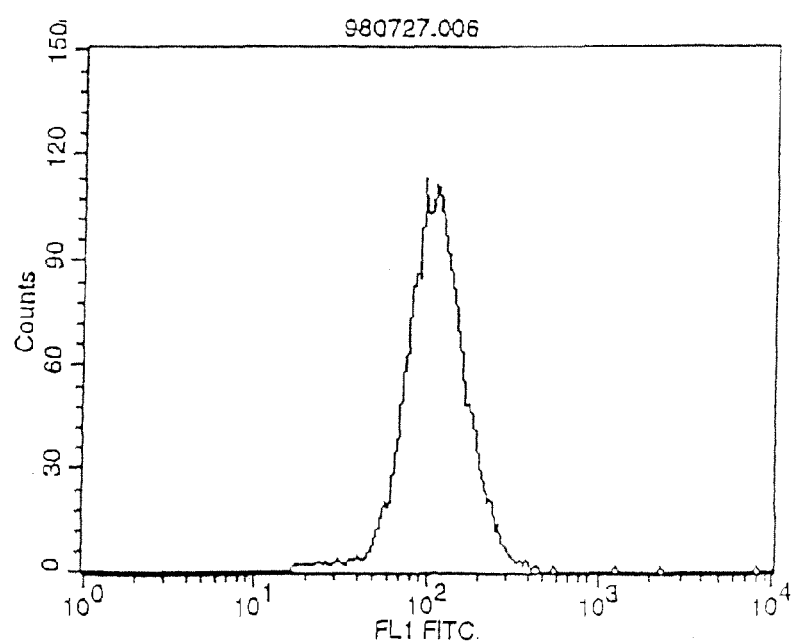
FIG. 2 shows the result of flow cytometry, illustrating that the chimera MABL-1 antibody specifically binds to L1210 cells expressing human IAP (hIAP/L1210).
Figure 3:
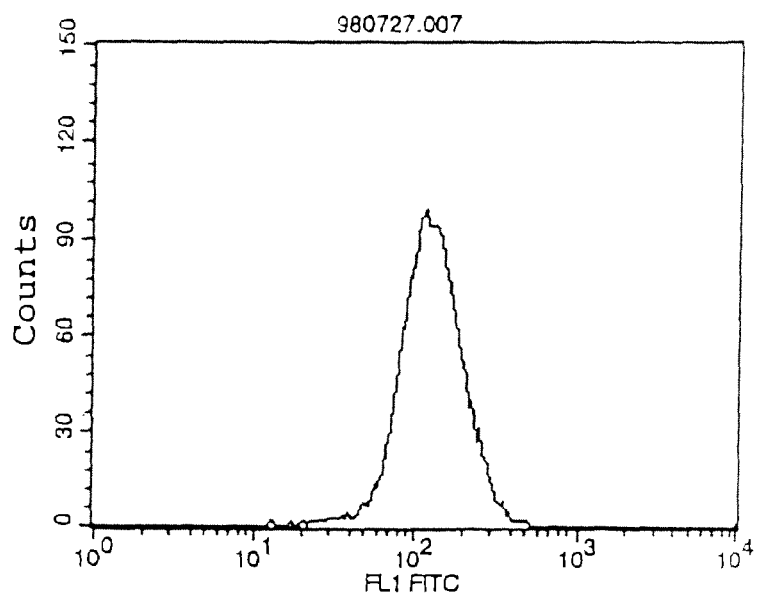
FIG. 3 shows the result of flow cytometry, illustrating that the chimera MABL-2 antibody specifically binds to L1210 cells expressing human IAP (hIAP/L1210).

Since the chimera MABL-1 and MABL-2 antibodies were specifically bound to L1210 cells expressing human IAP, it is confirmed that these chimera antibodies have proper structures of the V regions of the mouse monoclonal antibodies MABL-1 and MABL-2, respectively (FIGS. 1-3).

Example 5

Preparation of Reconstructed Single Chain Fv (scFv) of the Antibody MABL-1 and Antibody MABL-2

5.1 Preparation of Reconstructed Single Chain Fv of Antibody MABL-1

Figure 4:
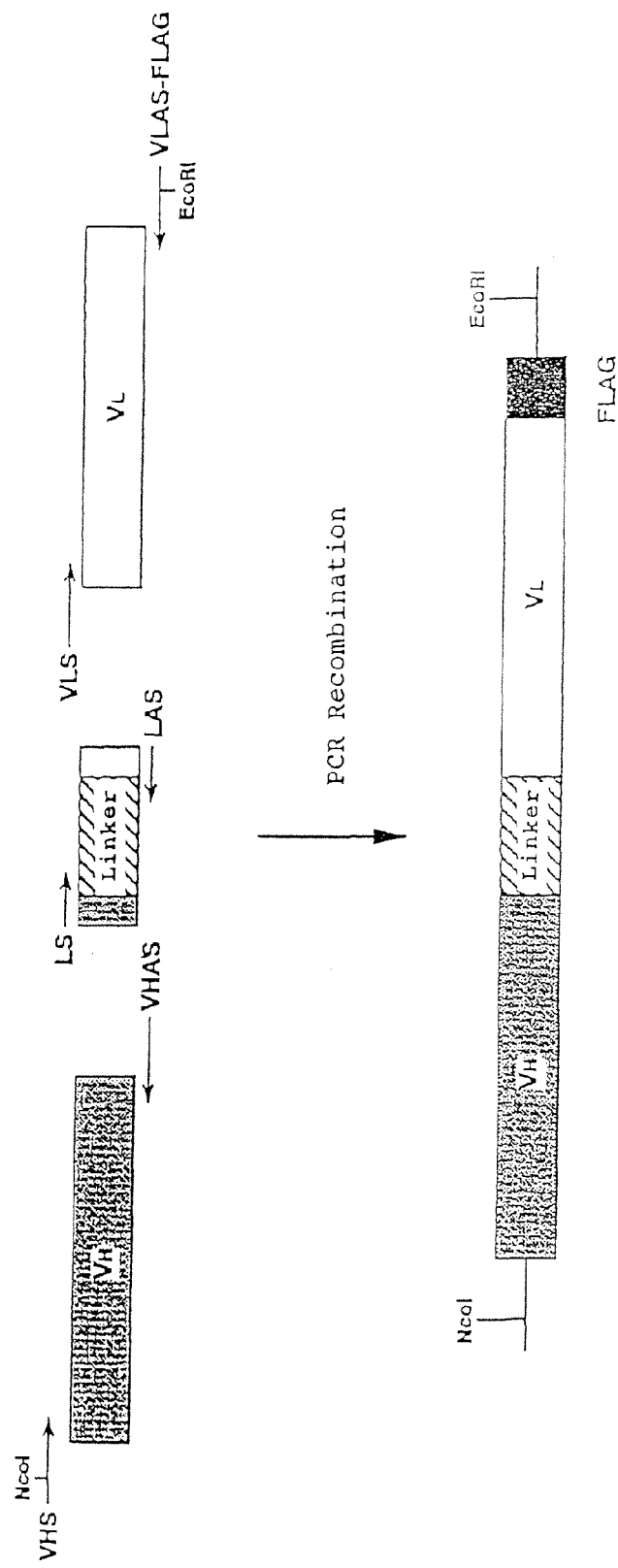
FIG. 4 schematically illustrates the process for producing the single chain Fv according to the present invention.

The reconstructed single chain Fv of antibody MABL-1 was prepared as follows. The H chain V region and the L chain V of antibody MABL-1, and a linker were respectively amplified by the PCR method and were connected to produce the reconstructed single chain Fv of antibody MABL-1. The production method is illustrated in FIG. 4. Six primers (A-F) were employed for the production of the single chain Fv of antibody MABL-1. Primers A, C and E have a sense sequence and primers B, D and F have an antisense sequence.

The forward primer VHS for the H chain V region (Primer A, SEQ ID No. 13) was designed to hybridize to a DNA encoding the N-terminal of the H chain V region and to contain NcoI restriction enzyme recognition site. The reverse primer VHAS for H chain V region (Primer B, SEQ ID No. 14) was designed to hybridize to a DNA coding the C-terminal of the H chain V region and to overlap with the linker.

The forward primer LS for the linker (Primer C, SEQ ID No. 15) was designed to hybridize to a DNA encoding the N-terminal of the linker and to overlap with a DNA encoding the C-terminal of the H chain V region. The reverse primer LAS for the linker (Primer D, SEQ ID No. 16) was designed to hybridize to a DNA encoding the C-terminal of the linker and to overlap with a DNA encoding the N-terminal of the L chain V region.

The forward primer VLS for the L chain V region (Primer E, SEQ ID No. 17) was designed to hybridize to a DNA encoding the C-terminal of the linker and to overlap with a DNA encoding the N-terminal of the L chain V region. The reverse primer VLAS-FLAG for L chain V region (Primer F, SEQ ID No. 18) was designed to hybridize to a DNA encoding the C-terminal of the L chain V region and to have a sequence encoding the FLAG peptide (Hopp. T. P. et al., Bio/Technology, 6, 1204-1210, 1988), two stop codons and EcoRI restriction enzyme recognition site.

In the first PCR step, three reactions, A-B, C-D and E-F, were carried out and PCR products thereof were purified. Three PCR products obtained from the first PCR step were assembled by their complementary. Then, the primers A and F were added and the full length DNA encoding the reconstructed single chain Fv of antibody MABL-1 was amplified (Second PCR). In the first PCR, the plasmid pGEM-M1H encoding the H chain V region of antibody MABL-1 (see Example 2), a plasmid pSC-DP1 which comprises a DNA sequence (SEQ ID NO: 19) encoding a linker region comprising: Gly Gly Gly Gly Ser Gly Gly Gly Gly Ser Gly Gly Gly Gly Ser (SEQ ID NO. 118) (Huston, J. S., et al., Proc. Natl. Acad. Sci. USA, 85, 5879-5883, 1988) and the plasmid pGEN-M1L encoding the L chain V region of antibody MABL-1 (see Example 2) were employed as template, respectively.

50 µl of the solution for the first PCR step comprises 5 µl of 10×PCR Buffer II, 2 mM MgCl$_2$, 0.16 mM dNTPs, 2.5 units of DNA polymerase, AMPLITAQ GOLD (PERKIN ELMER), 0.4 µM each of primers and 5 ng each of template DNA. The PCR solution was preheated at 94° C. of the initial temperature for 9 minutes and then heated at 94° C. for 1 minute, at 65° C. for 1 minute and at 72° C. for 1 minute and 20 seconds in order. This temperature cycle was repeated 35 times and then the reaction mixture was further heated at 72° C. for 7 minutes.

The PCR products A-B (371 bp), C-D (63 bp) and E-F (384 bp) were purified using the QIAquick PCR Purification Kit (QIAGEN) and were assembled in the second PCR. In the second PCR, 98 µl of a PCR solution comprising 120 ng of the first PCR product A-B, 20 ng of the PCR product C-D and 120 ng of the PCR product E-F, 10 µl of 10×PCR Buffer II, 2 mM MgCl$_2$, 0.16 mM dNTPs, 5 units of DNA polymerase AMPLITAQ GOLD (PERKIN ELMER) was preheated at 94° C. of the initial temperature for 8 minutes and then heated at 94° C. for 2 minutes, at 65° C. for 2 minutes and at 72° C. for 2 minutes in order. This temperature cycle was repeated twice and then 0.4 µM each of primers A and F were added into the reaction, respectively. The mixture was preheated at 94° C. of the initial temperature for 1 minutes and then heated at 94° C. for 1 minute, at 65° C. for 1 minute and at 72° C. for 1 minute and 20 seconds in order. This temperature cycle was repeated 35 times and then the reaction mixture was further heated at 72° C. for 7 minutes.

Figure 5:
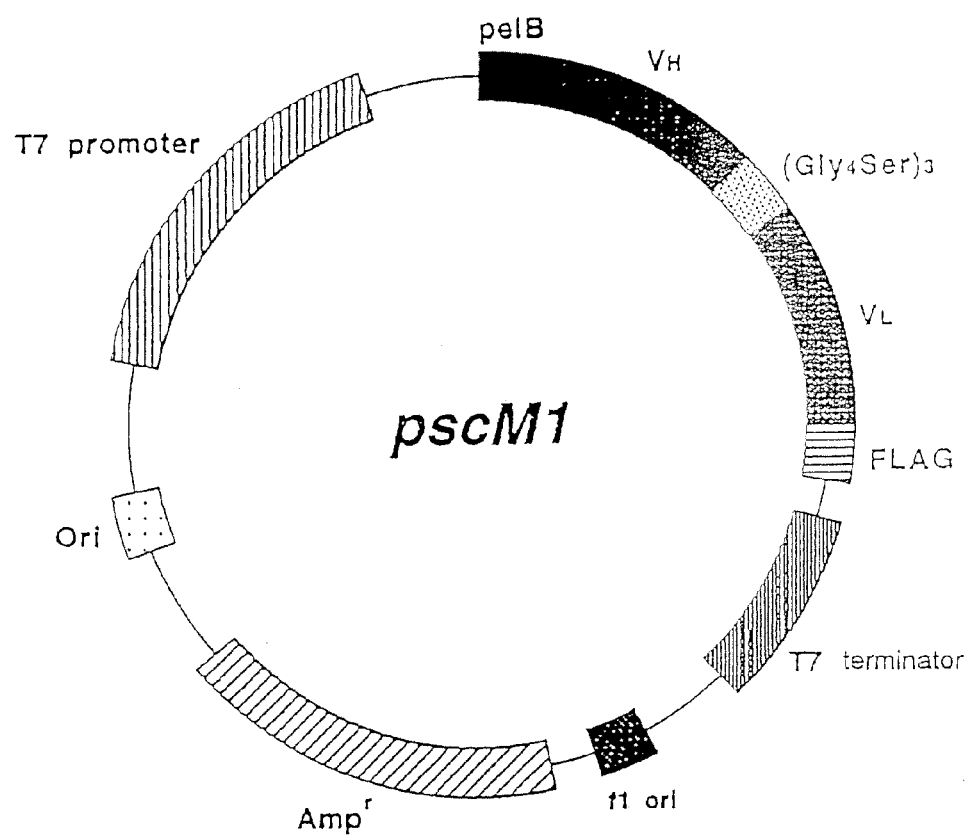
FIG. 5 illustrates a structure of an expression plasmid which can be used to express a DNA encoding the single chain Fv of the invention in E. coli. The $(Gly_4Ser)_3$ linker is shown in SEQ ID NO:118.

A DNA fragment of 843 by produced by the second PCR was purified and digested by NcoI and EcoRI. The resultant DNA fragment was cloned into pSCFVT7 vector. The expression vector pSCFVT7 contains a pelB signal sequence suitable for *E. coli* periplasmic expression system (Lei, S. P., et al., J. Bacteriology, 169, 4379-4383, 1987). After the DNA sequencing, the plasmaid containing the DNA fragment encoding correct amino acid sequence of the reconstructed single chain Fv of antibody MABL-1 is designated as "pscMl" (see FIG. 5). The nucleotide sequence (SEQ ID NO: 20) and the amino acid sequence (SEQ ID NO: 119) of the reconstructed single chain Fv of antibody MABL-1 contained in the plasmid pscMl are shown in SEQ ID No. 20.

The pscM1 vector was modified by the PCR method to prepare a vector expressing the reconstructed single chain Fv of antibody MABL-1 in mammalian cells. The resultant DNA fragment was introduced into pCHO1 expression vector. This expression vector, pCHO1, was constructed by digesting DHFR-ΔE-rvH-PM1-f (WO92/19759) with EcoRI and Sinai to eliminate the antibody gene and connecting the EcoRI-NotI-BamHI Adapter (Takara Shuzo) thereto.

As a forward primer for PCR, Sal-VHS primer shown in SEQ ID No. 21 was designed to hybridize to a DNA encoding the N-terminal of the H chain V region and to contain SalI restriction enzyme recognition site. As a reverse primer for PCR, FRH1anti primer shown in SEQ ID No. 22 was designed to hybridize to a DNA encoding the end of the first framework sequence.

100 µl of PCR solution comprising 10 µl of 10×PCR Buffer II, 2 mM MgCl$_2$, 0.16 mM dNTPs, 5 units of the DNA polymerase, AMPLITAQ GOLD, 0.4 µM each of primer and 8 ng of the template DNA (pscM1) was preheated at 95° C. of the initial temperature for 9 minutes and then heated at 95° C. for 1 minute, at 60° C. for 1 minute and at 72° C. for 1 minute and 20 seconds in order. This temperature cycle was repeated 35 times and then the reaction mixture was further heated at 72° C. for 7 minutes.

Figure 6:
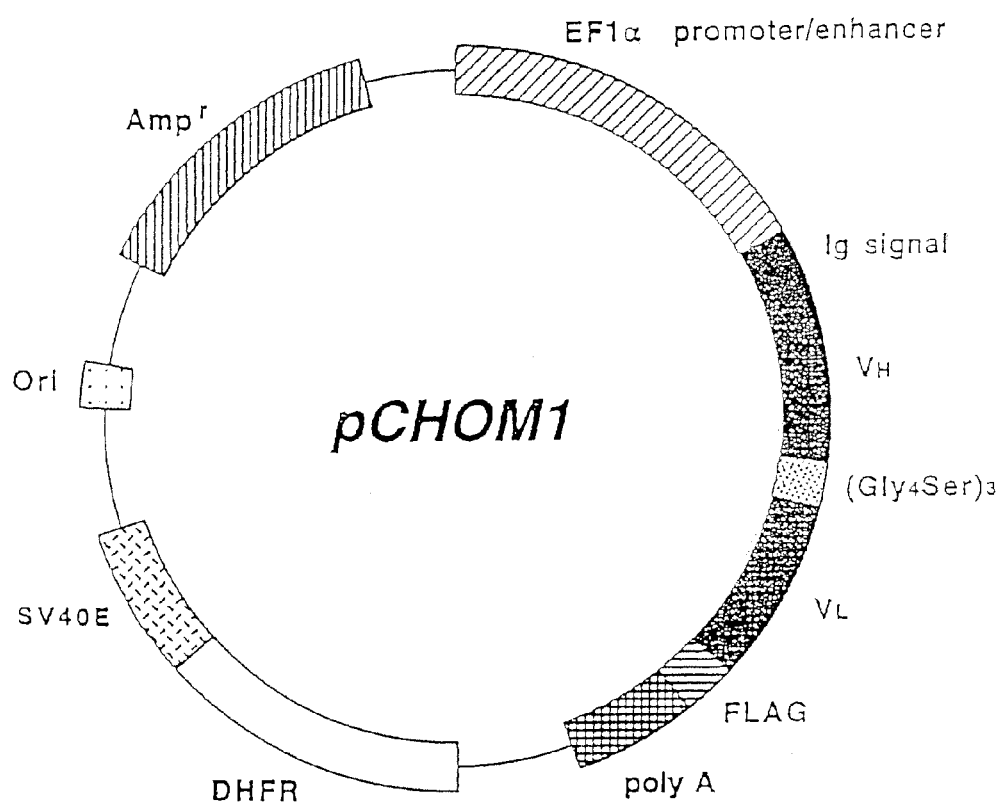
FIG. 6 illustrates a structure of an expression plasmid which is used to express a DNA encoding the single chain Fv of the invention in mammalian cells. The (Gly$_4$Ser)$_3$ linker is shown in SEQ ID NO:118.

The PCR product was purified using the QIAquick PCR Purification Kit (QIAGEN) and digested by SalI and MboII to obtain a DNA fragment encoding the N-terminal of the reconstructed single chain Fv of antibody MABL-1 The pscMl vector was digested by MboII and EcoRI to obtain a DNA fragment encoding the C-terminal of the reconstructed single chain Fv of antibody MABL-1. The SalI-MboII DNA fragment and the MboII-EcoRI DNA fragment were cloned into pCHO1-Igs vector. After DNA sequencing, the plasmid comprising the desired DNA sequence was designated as "pCHOM1" (see FIG. 6). The expression vector, pCHO1-Igs, contains a mouse IgGi signal sequence suitable for the secretion-expression system in mammalian cells (Nature, 322, 323-327, 1988). The nucleotide sequence (SEQ ID NO: 23) and the amino acid sequence (SEQ ID NO: 120) of the reconstructed single chain Fv of antibody MABL-1 contained in the plasmid pCHOM1 are shown in SEQ ID NO. 23.

5.2 Preparation of Reconstructed Single Chain Fv of Antibody MABL-2

The reconstructed single chain Fv of antibody MABL-2 was prepared in accordance with the aforementioned Example 5.1. Employed in the first PCR step were plasmid pGEN-N2H encoding the H chain V region of MABL-2 (see Example 2) instead of pGEN-M1H and plasmid pGEM-M2L encoding the L chain V region of MA.BL-2 (see Example 2) instead of pGEM-M1L, to obtain a plasmid pscM2 which comprises a DNA fragment encoding the desired amino acid sequence of the single chain Fv of antibody MABL-2. The nucleotide sequence (SEQ ID NO: 24) and the amino acid sequence (SEQ ID NO: 121) of the reconstructed single chain Fv of antibody MAEL-2 contained in the plasmid pscM2 are shown in SEQ ID NO. 24.

The pscM2 vector was modified by the PCR method to prepare a vector, pCHOM2, for the expression in mammalian cells which contains the DNA fragment encoding the correct amino acid sequence of reconstructed the single chain Fv, of antibody MABL-2. The nucleotide sequence (SEQ ID NO: 25) and the amino acid sequence (SEQ ID NO: 122) of the reconstructed single chain Fv of antibody MABL-2 contained in the plasmid pCHOM2 are shown in SEQ ID No. 25.

5.3 Transfection to COS7 Cells

The pCHOM2 vector was tested in COS7 cells to observe the transient expression of the reconstructed single chain Fv of antibody MABL-2.

The COS7 cells were transformed with the pCHOM2 vector by electroporation using the Gene Pulser apparatus (Bio-Rad). The DNA (10 µg) and 0.8 ml of PBS with 1×10$^7$ cells/ml were added to a cuvette. The mixture was treated with pulse at 1.5 kV, 25 µF of electric capacity.

After the restoration for 10 minutes at a room temperature, the electroporated cells were transferred into IMDM culture medium (GIBCO BRL) containing 10% fetal bovine serum. After culturing for 72 hours, the supernatant was collected, centrifuged to remove cell fragments and recovered.

5.4 Detection of the Reconstructed Single Chain Fv of Antibody MABL-2 in Culture Supernatant of COS7 Cells The existence of the single chain Fv of antibody MABL-2 in the culture supernatant of COS7 cells which had been transfected with the pCHOM2 vector was confirmed by the Western Blotting method.

Figure 7:
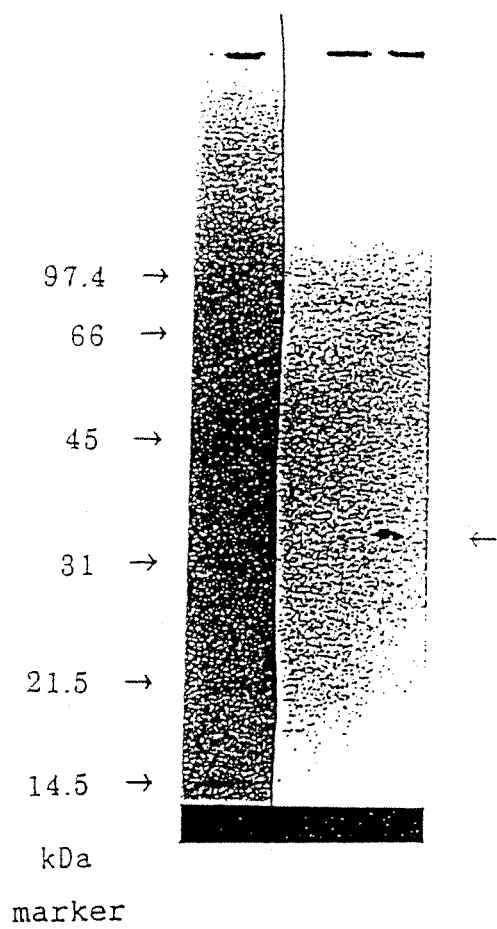
FIG. 7 shows the result of western blotting in Example 5.4.
Figure 8:
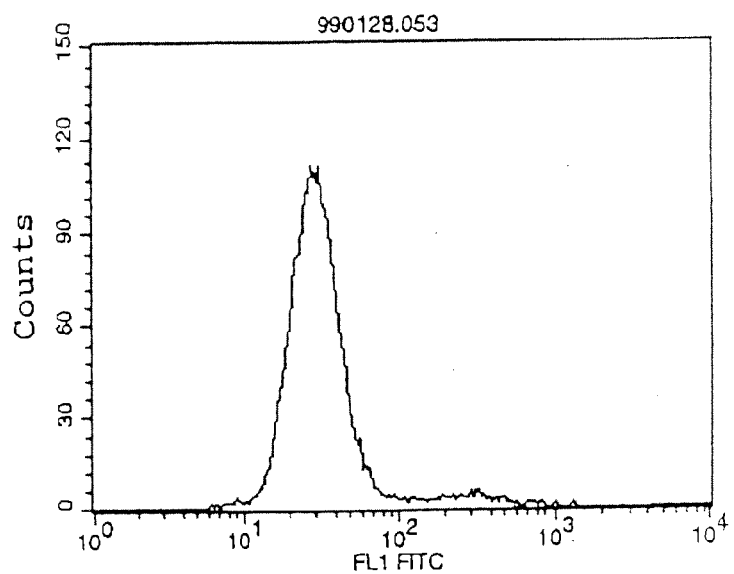
FIG. 8 shows the result of flow cytometry, illustrating that an antibody in the culture supernatant of pCHO1/COS7 cell as a control does not bind to pCOS1/L1210 cell as a control.
Figure 9:
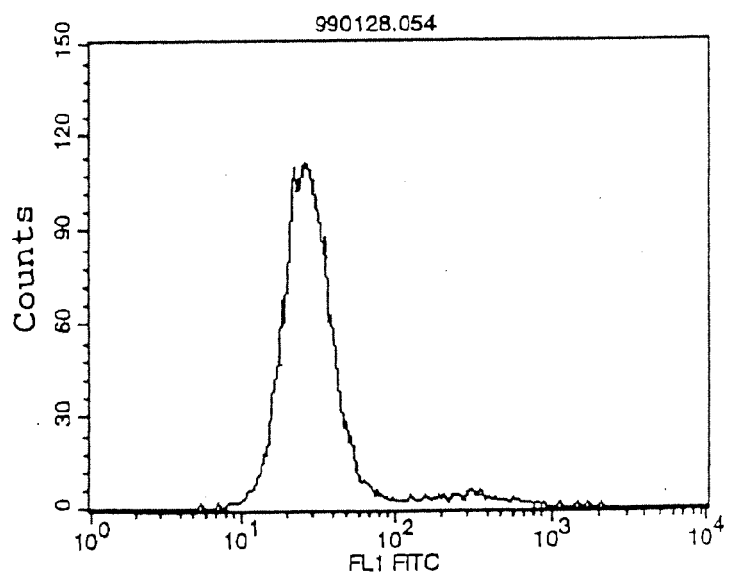
FIG. 9 shows the result of flow cytometry, illustrating that an antibody in the culture supernatant of MABL2-scFv/COS7 cells does not bind to pCOS1/L1210 cells as a control.
Figure 10:
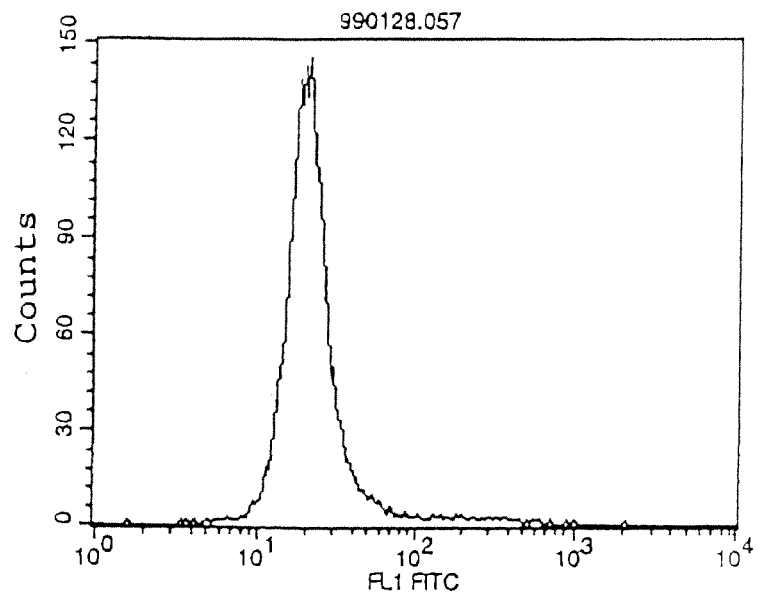
FIG. 10 shows the result of flow cytometry, illustrating that an antibody in the culture supernatant of pCOS1/COS7 cells as a control does not bind to hIAP/L1210 cells.
Figure 11:
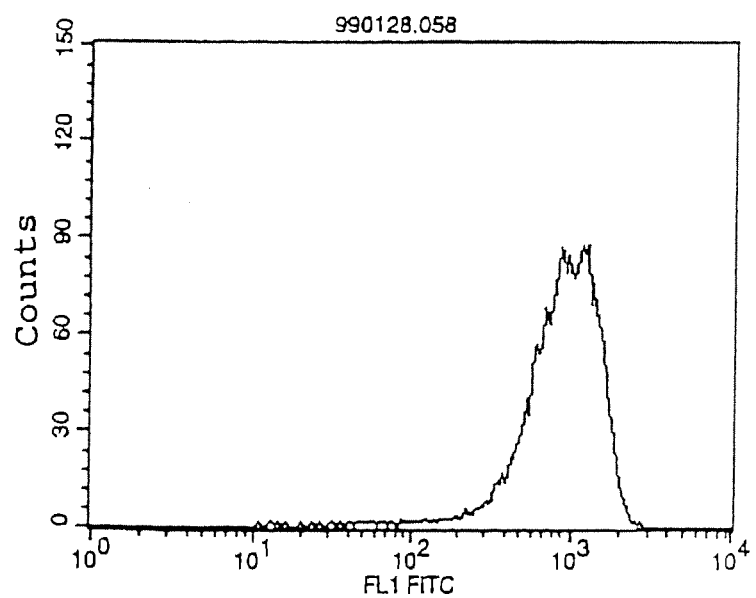
FIG. 11 shows the result of flow cytometry, illustrating that an antibody in the culture supernatant of MABL2-scFv/COS7 cells specifically binds to hIAP/L1210 cells.

The culture supernatant of COS7 cells transfected with the pCHOM2 vector and the culture supernatant of COS7 cells transfected with the pCHO1 as a control were subjected to SDS electrophoresis and transferred to REINFORCED NC membrane (Schleicher & Schuell). The membrane was blocked with 5% skim milk (Morinaga Nyu-gyo), washed with 0.05% Tween 20-PBS and mixed with an ANTI-FLAG antibody (SIGMA). The membrane was incubated at room temperature, washed and mixed with alkaline phosphatase-conjugated mouse IgG antibody (Zymed). After incubating and washing at room temperature, the substrate solution (Kirkegaard Perry Laboratories) was added to develop color (FIG. 7).

A FLAG-peptide-specific protein was detected only in the culture supernatant of the pCHOM2 vector-introduced COS7 cells and thus it is confirmed that the reconstructed single chain Fv of antibody MABL-2 was secreted in this culture supernatant.

5.5 Flow Cytometry

Flow cytometry was performed using the aforementioned COS7 cells culture supernatant to measure the binding to the antigen. The culture supernatant of the COS7 cells expressing the reconstructed single chain Fv of antibody MABL-2 or the culture supernatant of COS7 cells transformed with pCHO1 vector as a control was added to 2×10$^5$ cells of the mouse leukemia cell line L1210 expressing human Integrin Associated Protein (IAP) or the cell line L1210 transformed with pCOS1 as a control. After incubating on ice and washing, the mouse ANTI-FLAG antibody (SIGMA) was added. Then the cells were incubated and washed. Then, the FITC labeled anti-mouse IgG antibody (BECTON DICKINSON) was added thereto and the cells were incubated and washed again. Subsequently, the fluorescence intensity was measured using the FACScan apparatus (BECTON DICKINSON).

Since the single chain Fv of antibody MABL-2 was specifically bound to L1210 cells expressing human IAP, it is confirmed that the reconstructed single chain Fv of antibody MABL-2 has an affinity to human Integrin Associated Protein (LAP) (see FIGS. 8-11).

5.6 Competitive ELISA

The binding activity of the reconstructed single chain Fv of antibody MABL-2 was measured based on the inhibiting activity against the binding of mouse monoclonal antibodies to the antigen.

The ANTI-FLAG antibody adjusted to 1 µg/ml was added to each well on 96-well plate and incubated at 37° C. for 2 hours. After washing, blocking was performed with 1% BSA-PBS. After incubating and washing at a room temperature, the culture supernatant of COS7 cells into which the secretion-type human 1AP antigen gene (SEQ ID NO 26; encoded protein shown in SEQ ID NO: 123) had been introduced was diluted with PBS into twofold volume and added to each well. After incubating and washing at a room temperature, a mixture of 50 µl of the biotinized MABL-2 antibody adjusted to 100 ng/ml and 50 µl of sequentially diluted supernatant of the COS7 cells expressing the reconstructed single chain Fv of antibody MABL-2 were added into each well. After incubating and washing at a room temperature, the alkaline phosphatase-conjugated streptoavidin (Zymed) was added into each well. After incubating and washing at a room temperature, the substrate solution (SIGMA) was added and absorbance of the reaction mixture in each well was measured at 405 nm.

Figure 12:
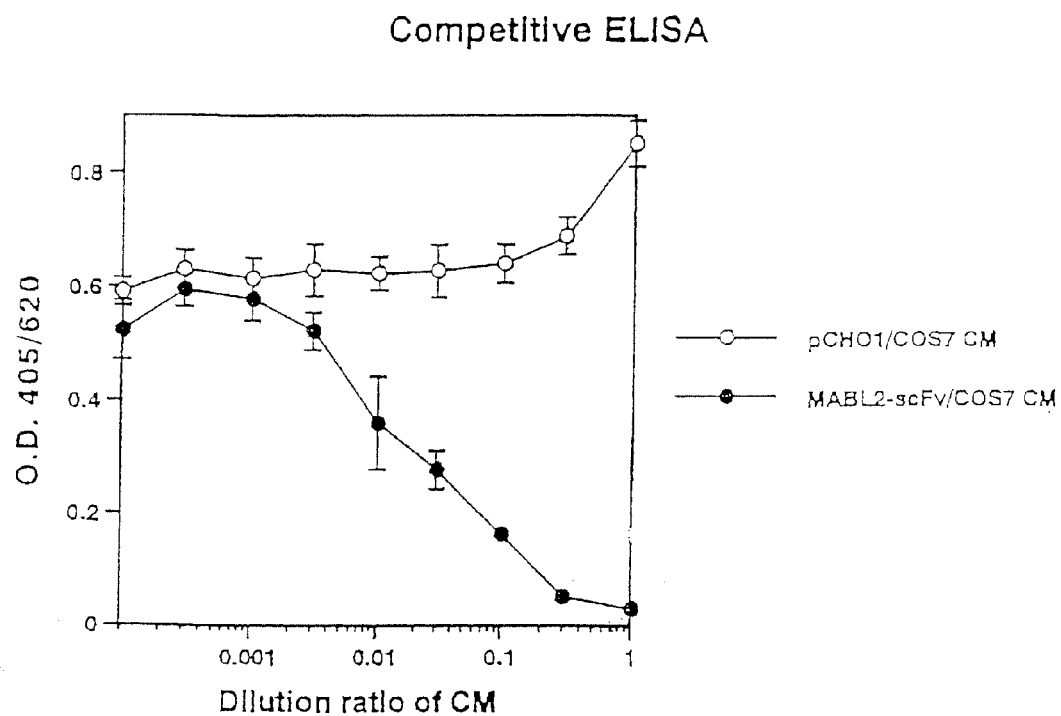
FIG. 12 shows the result of the competitive ELISA in Example 5.6.
Figure 13:
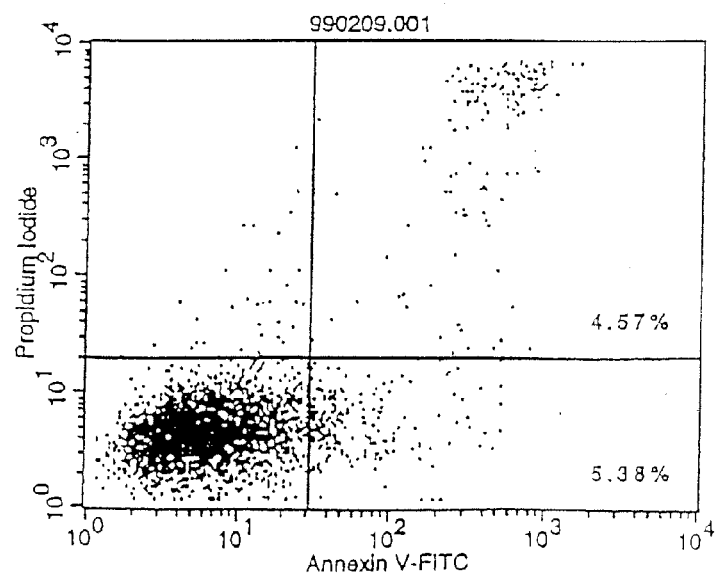
FIG. 13 shows the results of the apoptosis-inducing effect in Example 5.7, illustrating that the antibody in the culture supernatant of pCHO1/COS7 cells as a control does not induce the apoptosis of pCOS1/L1210 cells as a control.
Figure 14:
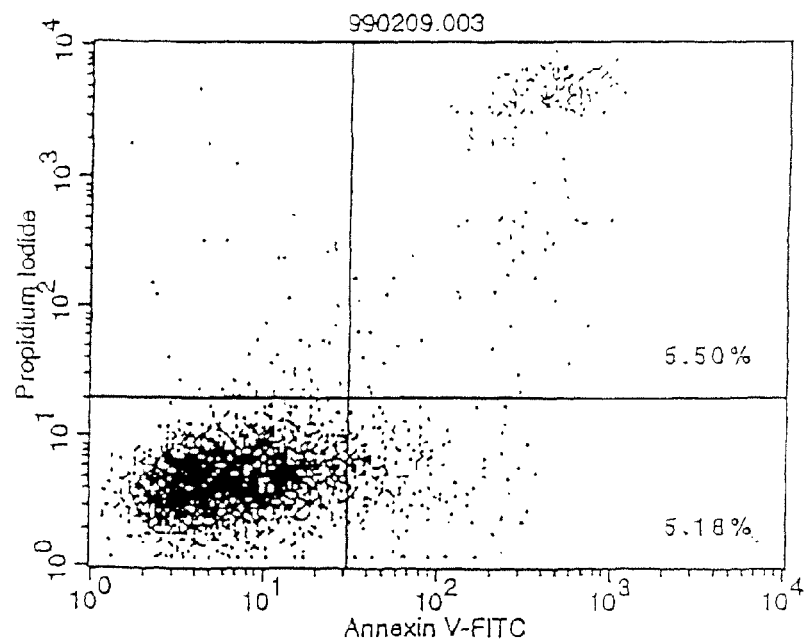
FIG. 14 shows the results of the apoptosis-inducing effect in Example 5.7, illustrating that the antibody in the culture supernatant of MABL2-scFv/COS7 cells does not induce apoptosis of pCOS1/L1210 cells as a control.
Figure 15:
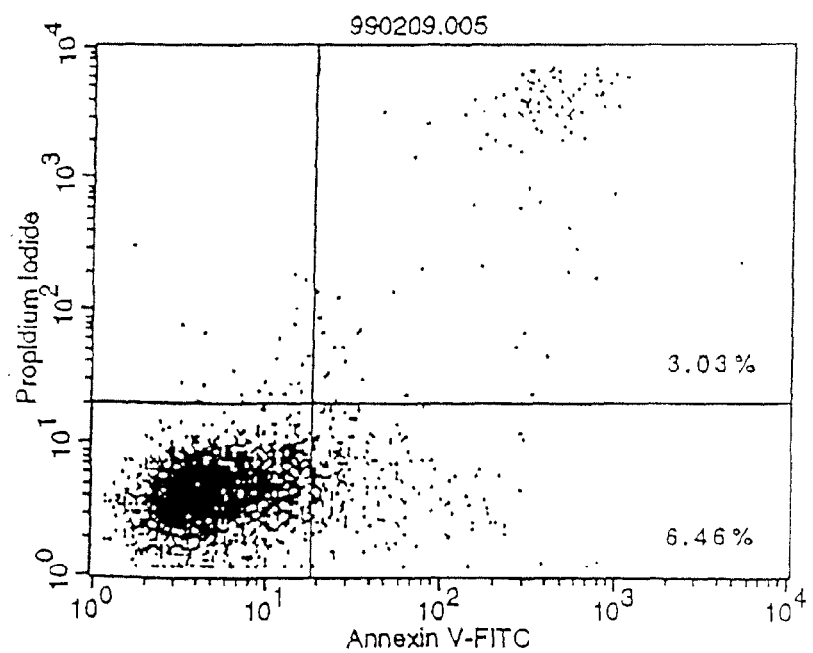
FIG. 15 shows the results of the apoptosis-inducing effect in Example 5.7, illustrating that the antibody in the culture supernatant of pCHO1/COS7 cells as a control does not induce apoptosis of hIAP/L1210 cells.
Figure 16:
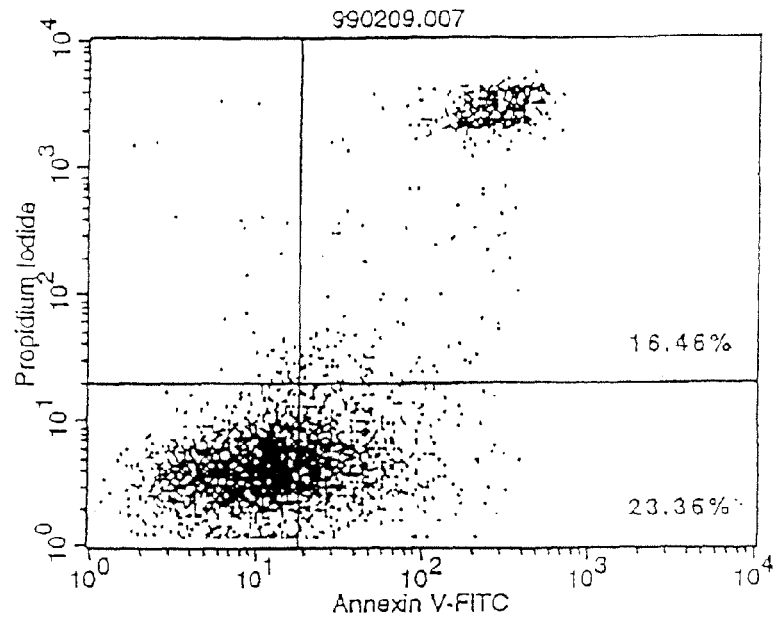
FIG. 16 shows the results of the apoptosis-inducing effect in Example 5.7, illustrating that the antibody in the culture supernatant of MABL2-scFv/COS7 cells specifically induces apoptosis of hIAP/L1210 cells.

The results revealed that the reconstructed single chain Fv of antibody MABL-2 (MABL2-scFv) evidently inhibited concentration-dependently the binding of the mouse antibody MABL-2 to human LAP antigen in comparison with the culture supernatant of the PCHO1-introduced COS7 cells as a control (FIG. 12). Accordingly, it is suggested that the reconstructed single chain Fv of antibody MABL-2 has the correct structure of each of the V regions from the mouse monoclonal antibody MABL-2.

5.7 Apoptosis-Inducing Effect in Vitro

An apoptosis-inducing action of the reconstructed single chain Fv of antibody MABL-2 was examined by Annexin-V staining (Boehringer Mannheim) using the L1210 cells transfected with human LAP gene, the L1210 cells transfected with the pCOS1 vector as a control and CCRF-CEM cells.

To each $1 \times 10^5$ cells of the above cells was added the culture supernatant of the COS7 cells expressing the reconstructed single chain Fv of antibody MABL-2 or the culture supernatant of COS7 cells transfected with the pCHO1 vector as a control at 50% final concentration and the mixtures were cultured for 24 hours. Then, the Annexin-V staining was performed and the fluorescence intensity was measured using the FACScan apparatus (BECTON DICKINSON).

Figure 17:
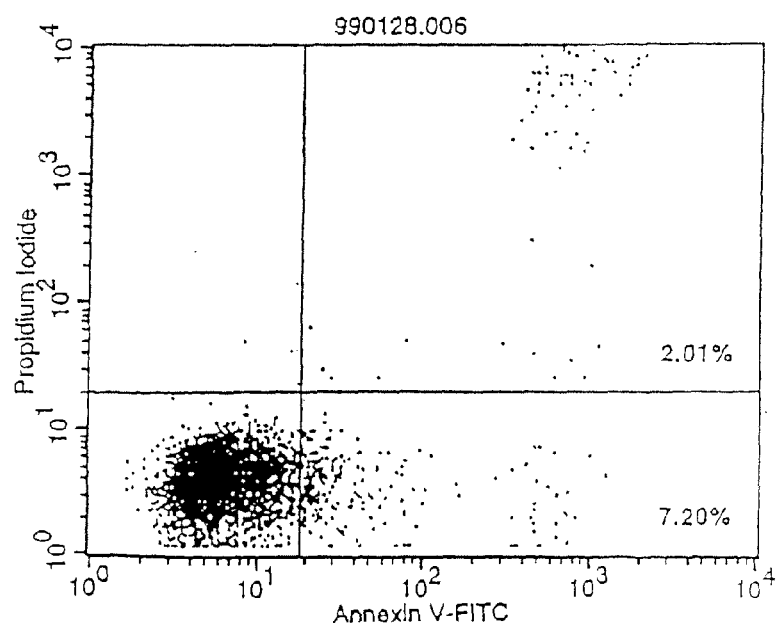
FIG. 17 shows the results of the apoptosis-inducing effect in Example 5.7, illustrating that the antibody in the culture supernatant of pCHO1/COS7 cells as a control does not induce apoptosis of CCRF-CEM cells.
Figure 18:
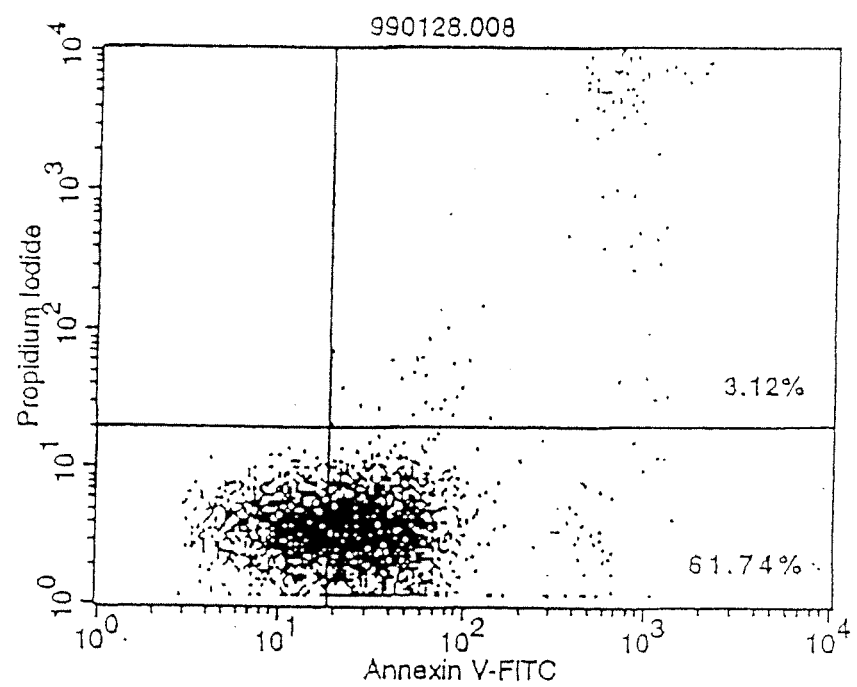
FIG. 18 shows the results of the apoptosis-inducing effect in Example 5.7, illustrating that the antibody in the culture supernatant of MABL2-scFv/COS7 cells specifically induces apoptosis of CCRF-CEM cells.

Results of the Annexin-V staining are shown in FIGS. 13-18, respectively. Dots in the left-lower region represent living cells and dots in the right-lower region represent cells at the early stage of apoptosis and dots in the right-upper region represent cells at the late stage of apoptosis. The results show that the reconstructed single chain Fv of antibody MABL-2 (MABL2-scFv) remarkably induced cell death of L1210 cells specific to human IAP antigen (FIGS. 13-16) and that the reconstructed single chain Fv also induced remarkable cell death of CCRF-CEM cells in comparison with the control (FIGS. 17-18).

5.8 Expression of MABL-2 Derived Single Chain Fv in CHO Cells

CHO cells were transfected with the pCHOM2 vector to establish a CHO cell line which constantly expresses the single chain Fv (polypeptide) derived from the antibody MABL-2.

CHO cells were transformed with the pCHOM2 vector by the electroporation using the Gene Pulser apparatus (Bio-Rad). A mixture of DNA (10 µg) and 0.7 ml of PBS with CHO cells ($1 \times 10^7$ cells/ml) was added to a cuvette. The mixture was treated with pulse at 1.5 kV, 25 µF of electric capacity. After the restoration for 10 minutes at a room temperature, the electroporated cells were transferred into nucleic acid free α-MEM medium (GIBCO BRL) containing 10% fetal bovine serum and cultured. The expression of desired protein in the resultant clones was confirmed by SDS-PAGE and a clone with a high expression level was selected as a cell line producing the single chain Fv derived from the antibody MABL-2. The cell line was cultured in serum-free medium CHO-S-SFM II (GIBCO BRL) containing 10 nM methotrexate (SIGMA). Then, the culture supernatant was collected, centrifuged to remove cell fragments and recovered.

5.9 Purification of MABL-2 Derived Single Chain Fv Produced in CHO Cells

The culture supernatant of the CHO cell line expressing the single chain Fv obtained in Example 5.8 was concentrated up to twenty times using a cartridge for the artificial dialysis (PAN130SF, ASAHI MEDICALS). The concentrated solution was stored at −20° C. and thawed on purification.

Purification of the single chain Fv from the culture supernatant of the CHO cells was performed using three kinds of chromatography, i.e., Blue-sepharose, a hydroxyapatite and a gel filtration.

(1) Blue-Sepharose Column Chromatography

The concentrated supernatant was diluted to ten times with 20 mM acetate buffer (pH 6.0) and centrifuged to remove insoluble materials (10000×rpm, 30 minutes). The supernatant was applied onto a Blue-sepharose column (20 ml) equilibrated with the same buffer. After washing the column with the same buffer, proteins adsorbed in the column were eluted by a stepwise gradient of NaCl in the same buffer, 0.1, 0.2, 0.3, 0.5 and up to 1.0 M. The pass-through fraction and each eluted fraction were analyzed by SDS-PAGE. The fractions in which the single chain Fv were confirmed (the fractions eluted at 0.1 to 0.3M NaCl) were pooled and concentrated up to approximately 20 times using CentriPrep-10 (AMICON).

(2) Hydroxyapatite

Figure 19:
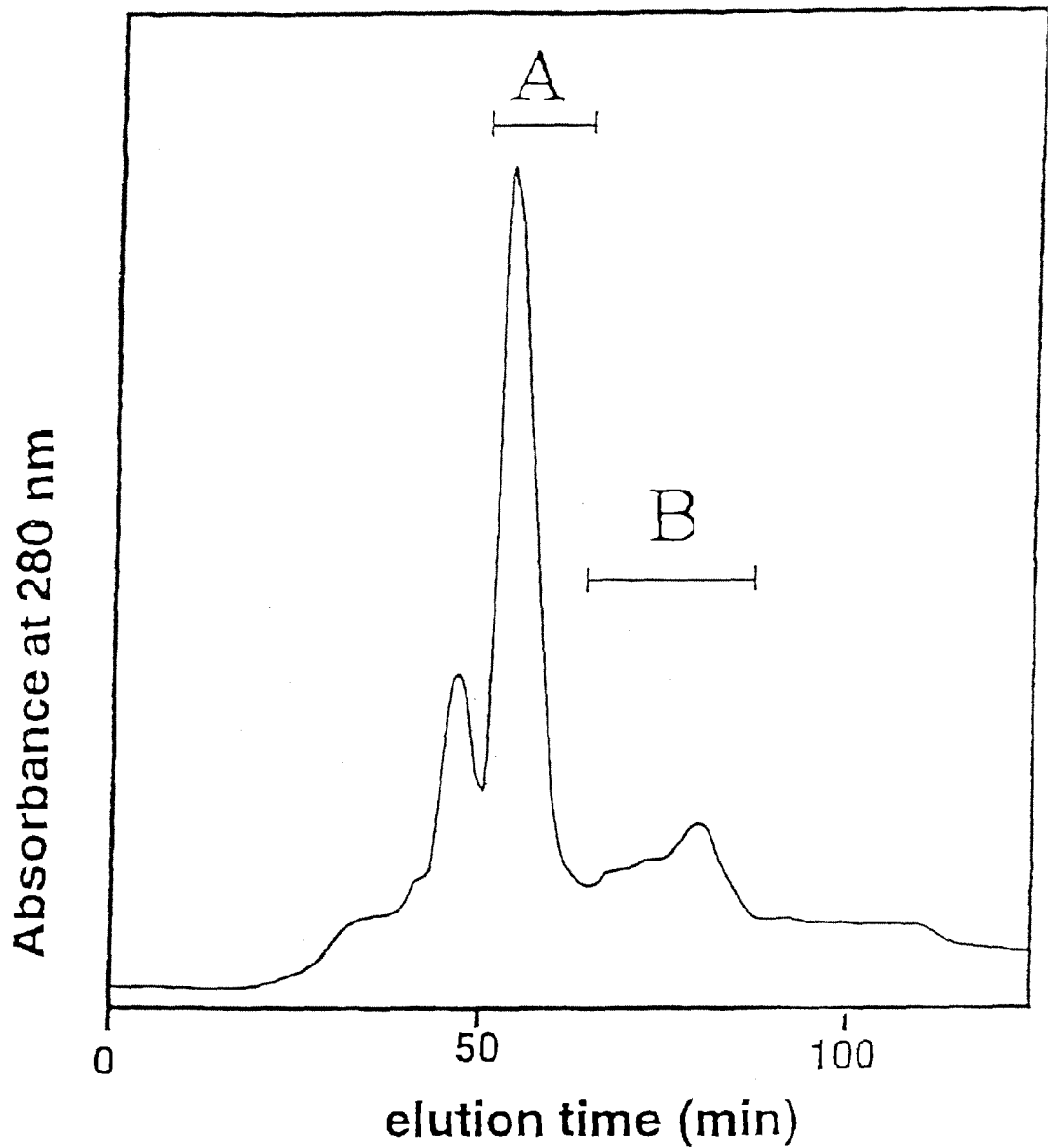
FIG. 19 shows the chromatogram obtained in the purification of the single chain Fv derived form the antibody MABL-2 produced by the CHO cells in Example 5.9, illustrating that fraction A and fraction B were obtained as the major peaks when the fraction from Blue-sepharose column was purified with hydroxyapatite column.

The concentrated solution obtained in (1) was diluted to 10 times with 10 mM phosphate buffer (pH 7.0) and applied onto the hydroxyapatite column (20 ml, BIORAD). The column was washed with 60 ml of 10 mM phosphate buffer (pH 7.0). Then, proteins adsorbed in the column were eluted by a linear gradient of sodium phosphate buffer up to 200 mM (see FIG. 19). The analysis of each fraction by SDS-PAGE confirmed the single chain Fv in fraction A and fraction B.

(3) Gel Filtration

Figure 20:
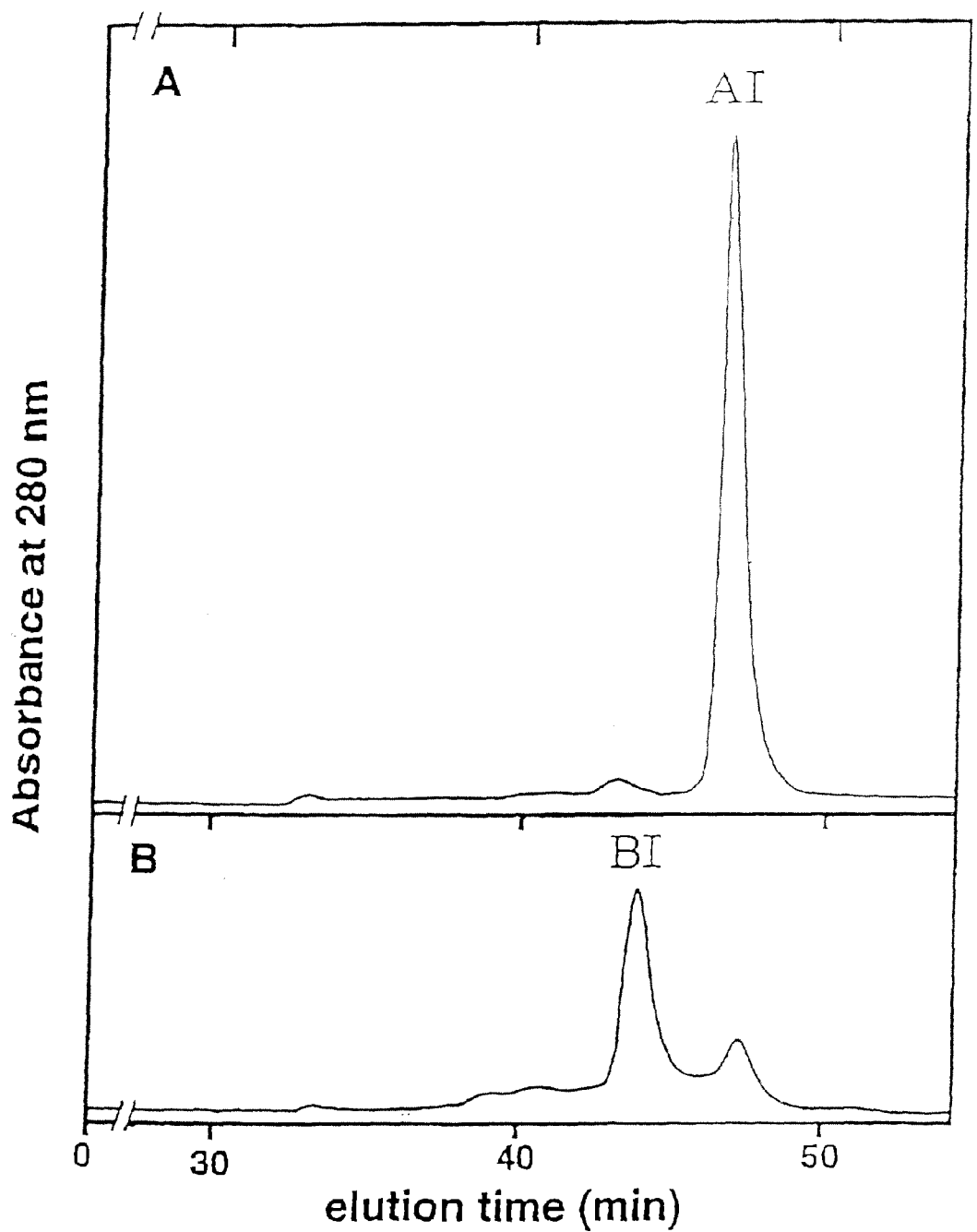
FIG. 20 shows the results of purification by gel filtration of fraction A and fraction B obtained in Example 5.9-(2), illustrating that the major peaks (AI and BI, respectively) were eluted from fraction A at approximately 36 kD of the apparent molecular weight and from fraction B at approximately 76 kD.
Figure 22:
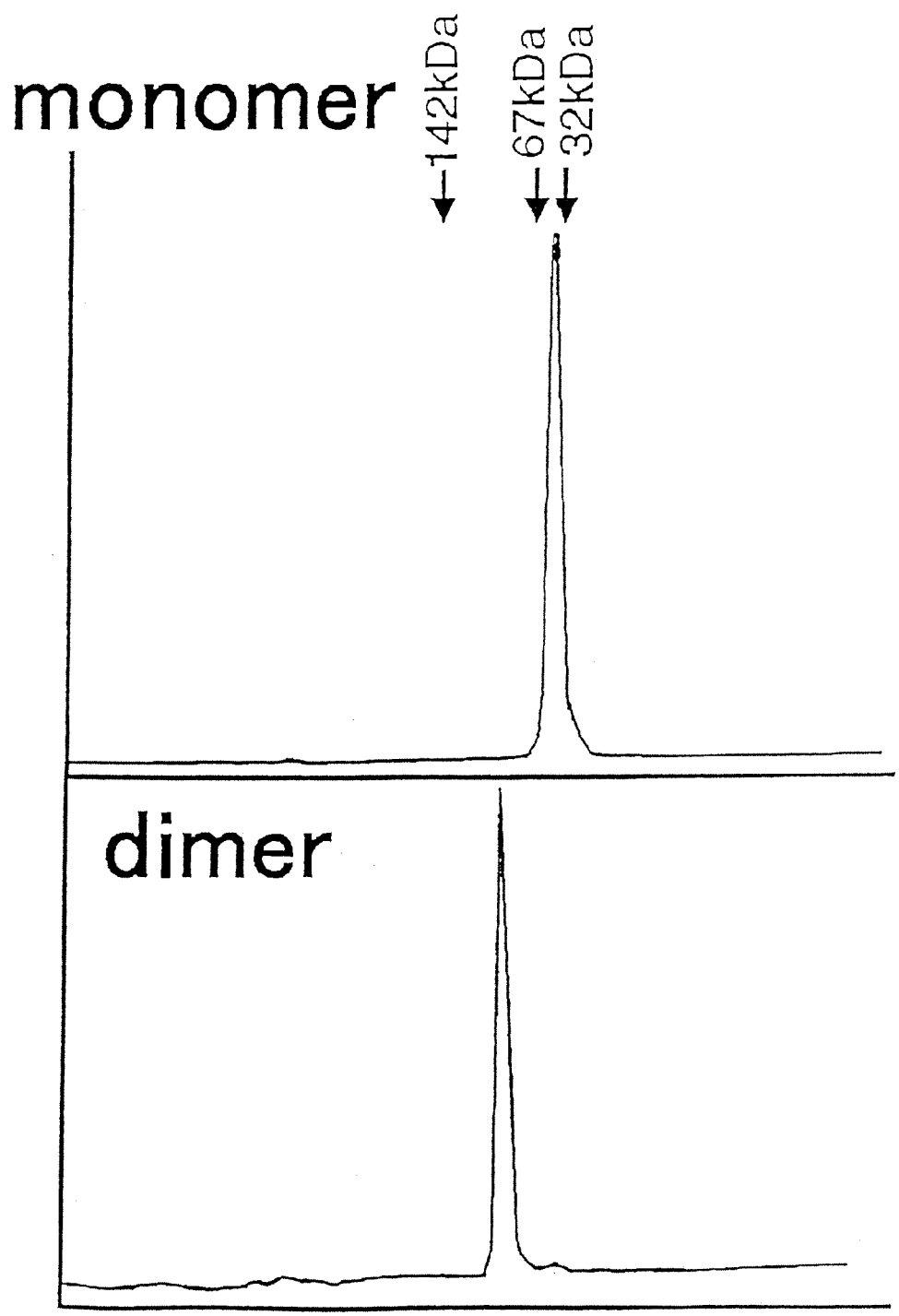
FIG. 22 shows the results of analysis of fractions AI and BI obtained by gel filtration in the purification of the single chain Fv derived from the antibody MABL-2 produced by the CHO cells.

Each of fractions A and B in (2) was separately concentrated with CentriPrep-10 and applied onto TSKgel G3000SWG column (21.5×600 mm) equilibrated with 20 mM acetate buffer (pH 6.0) containing 0.15 M NaCl. Chromatograms are shown in FIG. 20. The analysis of the fractions by SDS-PAGE confirmed that both major peaks (AI and BI) are of desired single chain Fv. In the gel filtration analysis, the fraction A was eluted at 36 kDa of apparent molecular weight and the fraction B was eluted at 76 kDa. The purified single chain Fvs (AI, BI) were analyzed with 15% SDS polyacrylamide gel. Samples were treated in the absence or presence of a reductant and the electrophoresis was carried out in accordance with the Laemmli's method. Then the protein was stained with Coomassie Brilliant Blue. As shown in FIG. 21, both AI and BI gave a single band at 35 kDa of apparent molecular weight, regardless of the absence or presence of the reductant. From the above, it is concluded that AI is a monomer of the single chain Fv and BI is a non-covalently bound dimer of the single chain Fv. The gel filtration analysis of the fractions AI and BI with TSKgel G3000SW column (7.5×60 mm) revealed that a peak of the monomer is detected only in the fraction AI and a peak of the dimer is detected only in the fraction BI (FIG. 22). The dimer fraction (fraction BI) accounted for 4 period of total single chain Fvs. More than 90% of the dimer in the dimer fraction was stably preserved for more than a month at 4° C.

5.10 Construction of Vector Expressing Single Chain Fv Derived from Antibody MABL-2 in *E. Coli* Cell The pscM2 vector was modified by the PCR method to prepare a vector effectively expressing the single chain Fv from the antibody MABL-2 in *E. coli* cells. The resultant DNA fragment was introduced into pSCFVT7 expression vector.

As a forward primer for PCR, Nde-VHSm02 primer shown in SEQ ID No. 27 was designed to hybridize to a DNA encoding the N-terminal of the H chain V region and to contain a start codon and NdeI restriction enzyme recognition site. As a reverse primer for PCR, VLAS primer shown in SEQ ID No. 28 was designed to hybridize to a DNA encoding the C-terminal of the L chain V region and to contain two stop codons and EcoRI restriction enzyme recognition site. The forward primer, Nde-VHSm02, comprises five point mutations in the part hybridizing to the DNA encoding the N-terminal of the H chain V region for the effective expression in *E. coli*.

100 μl of a PCR solution comprising 10 μl of 10×PCR Buffer #1, 1 mM MgCl$_2$, 0.2 mM dNTPs, 5 units of KOD DNA polymerase (all from TOYOBO), 1 μM of each primer and 100 ng of a template DNA (pscM2) was heated at 98° C. for 15 seconds, at 65° C. for 2 seconds and at 74° C. for 30 seconds in order. This temperature cycle was repeated 25 times.

Figure 23:
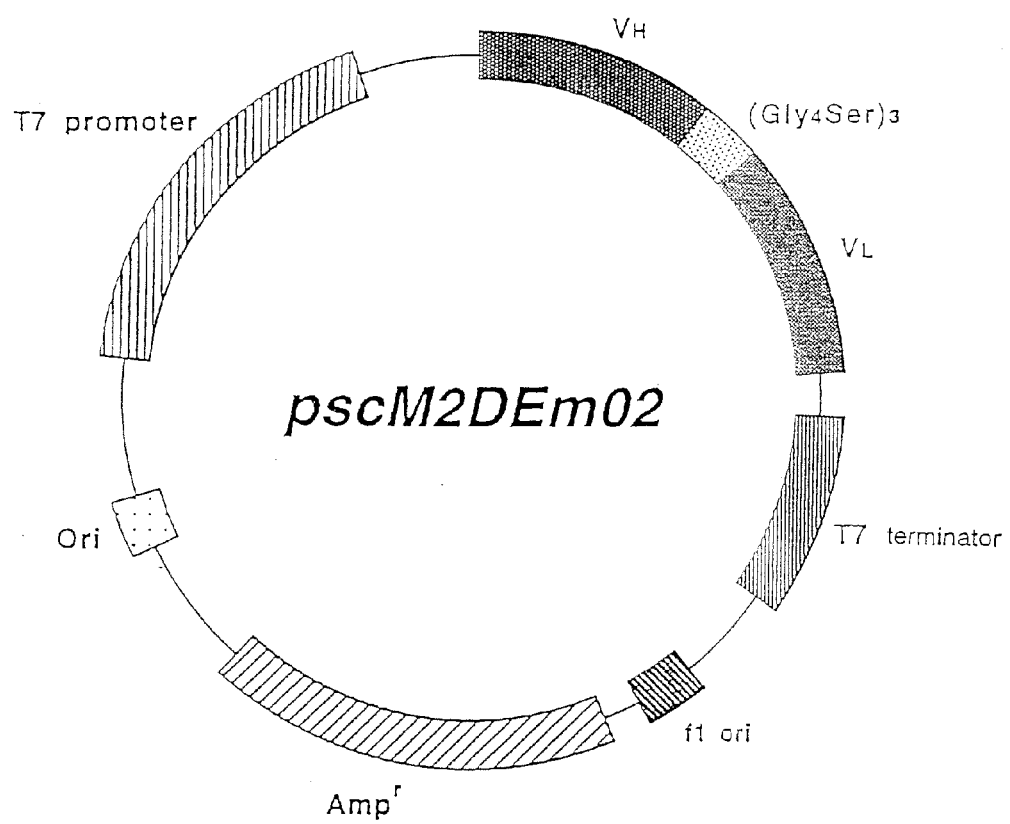
FIG. 23 illustrates a structure of an expression plasmid which can be used to express a DNA encoding the single chain Fv of the invention in *E. coli*. The (Gly$_4$Ser)$_3$ linker is shown in SEQ ID NO:118.

The PCR product was purified using the QIAquick PCR Purification Kit (QIAGEN) and digested by NdeI and EcoRI, and then the resulting DNA fragment was cloned into pSCFVT7 vector, from which pelB signal sequence had been eliminated by the digestion with NdeI and EcoRI. After DNA sequencing, the resulting plasmid comprising a DNA fragment with the desired DNA sequence is designated as "pscM2Dem02" (see FIG. 23). The nucleotide sequence (SEQ ID NO: 29) and the amino acid sequence (SEQ ID NO: 124) of the single chain Fv derived from the antibody MABL-2 contained in the plasmid pscM2Dem02 are shown in SEQ ID No 29.

5.11 Expression of Single Chain Fv Derived from Antibody MABL-2 in *E. coli* Cells

*E. coli* BL21 (DE3)pLysS (STRATAGENE) was transformed with pscM2DEm02 vector to obtain a strain of *E. coli* expressing the single chain Fv derived from antibody MABL-2. The resulting clones were examined for the expression of the desired protein using SDS-PAGE, and a clone with a high expression level was selected as a strain producing the single chain Fv derived from antibody MABL-2.

5.12 Purification of Single Chain Fv Derived from Antibody MABL-2 Produced in *E. coli*

A single colony of *E. coli* obtained by the transformation was cultured in 3 ml of LB medium at 28° C. for 7 hours and then in 70 ml of LB medium at 28° C. overnight. This pre-culture was transplanted to 7 L of LB medium and cultured at 28° C. with stirring at 300 rpm using the Jar-fermenter. When an absorbance of the medium reached O.D.=1.5, the bacteria were induced with 1 mM IPTG and then cultured for 3 hours.

The culture medium was centrifuged (10000×g, 10 minutes) and the precipitated bacteria were recovered. To the bacteria was added 50 mM Tris-HCl buffer (pH 8.0) containing 5 mM EDTA, 0.1 M NaCl and 1% Triton X-100 and the bacteria were disrupted by ultrasonication (out put: 4, duty cycle: 70%, 1 minute×10 times). The suspension of disrupted bacteria was centrifuged (12000×g, 10 minutes) to precipitate inclusion body. Isolated inclusion body was mixed with 50 mM Tris-HCl buffer (pH 8.0) containing 5 mM EDTA, 0.1 M NaCl and 4% Triton X-100, treated by ultrasonication (out put: 4, duty cycle: 50%, 30 seconds×2 times) again and centrifuged (12000×g, 10 minutes) to isolate the desired protein as precipitate and to remove containment proteins included in the supernatant.

The inclusion body comprising the desired protein was lysed in 50 mM Tris-HCl buffer (pH 8.0) containing 6 M Urea, 5 mM EDTA and 0.1 M NaCl and applied onto Sephacryl S-300 gel filtration column (5×90 cm, Amersharm Pharmacia) equilibrated with 50 mM Tris-HCl buffer (pH 8.0) containing 4M Urea, 5 mM EDTA, 0.1 M NaCl and 10 mM mercaptoethanol at a flow rate of 5 ml/minutes to remove associated single chain Fvs with high-molecular weight. The obtained fractions were analyzed with SDS-PAGE and the fractions with high purity of the protein were diluted with the buffer used in the gel filtration up to O.D.$_{280}$=0.25. Then, the fractions were dialyzed three times against 50 mM Tris-HCl buffer (pH 8.0) containing 5 mM EDTA, 0.1 M NaCl, 0.5 M Arg, 2 mM glutathione in the reduced form and 0.2 mM glutathione in the oxidized form in order for the protein to be refolded. Further, the fraction was dialyzed three times against 20 mM acetate buffer (pH 6.0) containing 0.15 M NaCl to exchange the buffer.

Figure 24:
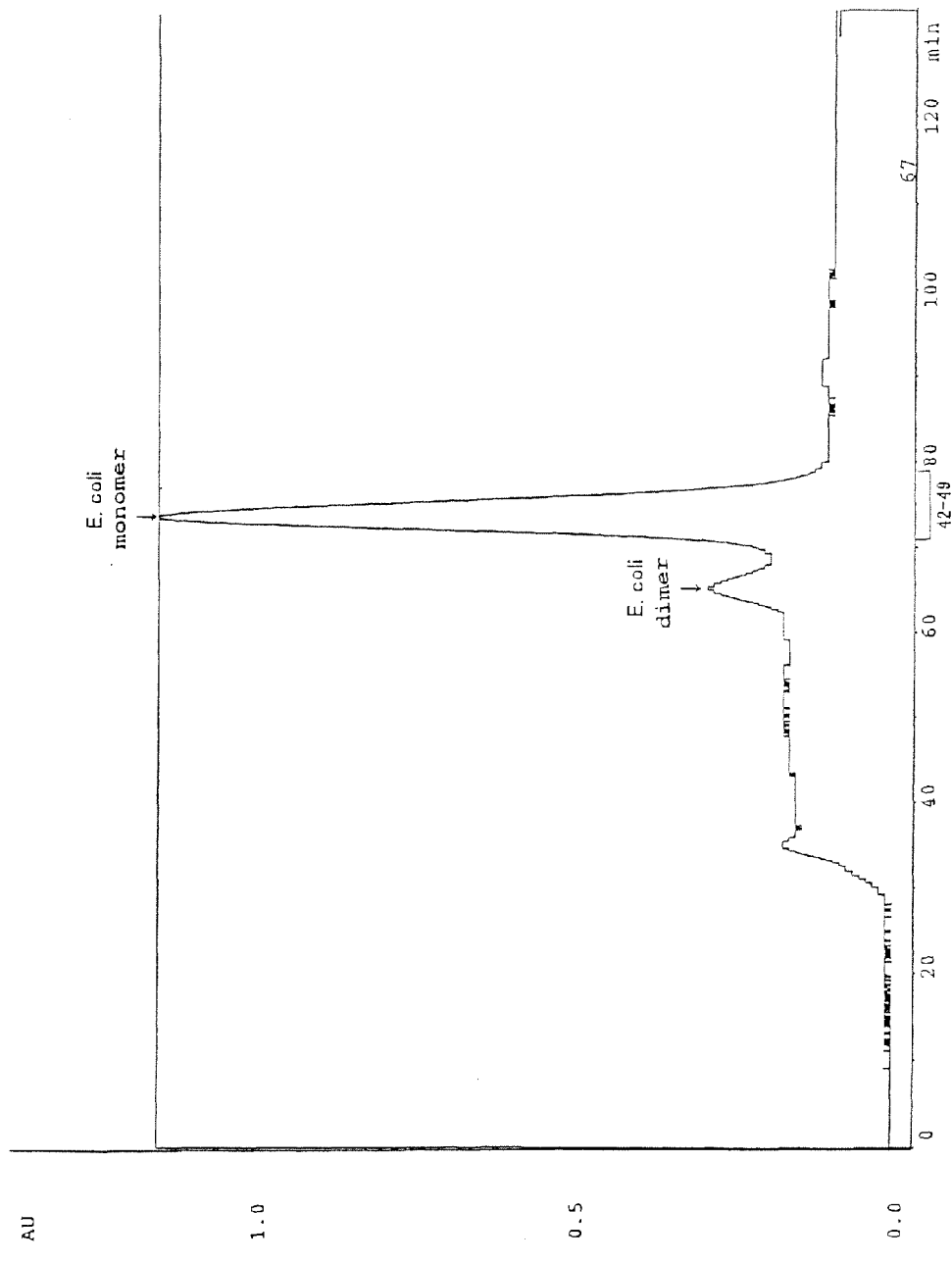
FIG. 24 shows the results of purification on the gel filtration column of crude products of the single chain Fv polypeptide derived from the antibody MABL-2 produced by *E. coli* obtained in Example 5.12.
Figure 25:
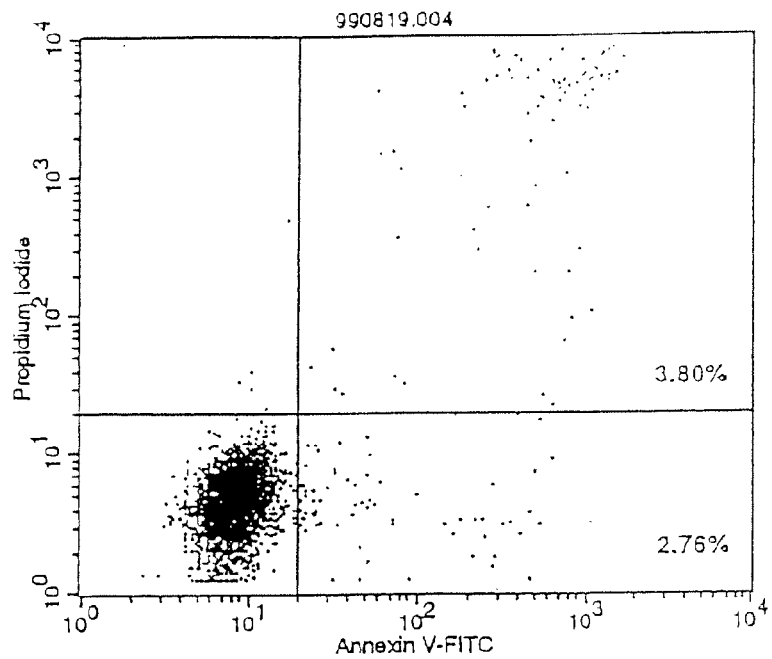
FIG. 25 shows the results of the apoptosis-inducing effect in Example 5.13, illustrating that mouse IgG antibody as a control does not induce apoptosis of hIAP/L1210 cells.
Figure 26:
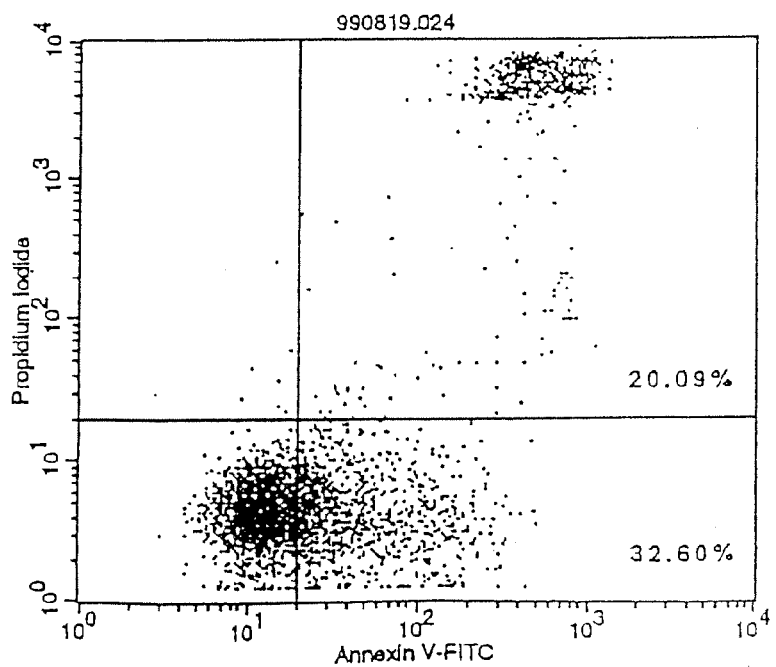
FIG. 26 shows the results of the apoptosis-inducing effect in Example 5.13, illustrating that the dimer of MABL2-scFv produced by the CHO cells remarkably induces apoptosis of hIAP/L1210 cells.
Figure 27:
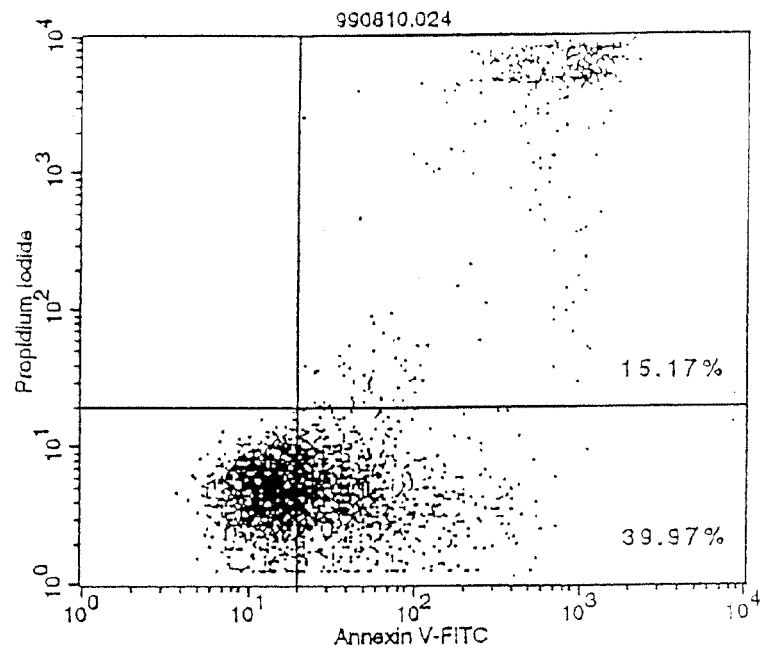
FIG. 27 shows the results of the apoptosis-inducing effect in Example 5.13, illustrating that the dimer of MABL2-scFv produced by *E. coli* remarkably induces apoptosis of hIAP/L1210 cells.

The dialysate product was applied onto Superdex 200 pg gel filtration column (2.6×60 cm, Amersharm Pharmacia) equilibrated with 20 mM acetate buffer (pH 6.0) containing 0.15 M NaCl to remove a small amount of high molecular weight protein which was intermolecularly crosslinked by S—S bonds. As shown in FIG. 24, two peaks, major and sub peaks, were eluted after broad peaks which are expectedly attributed to an aggregate with a high molecular weight. The analysis by SDS-PAGE (see FIG. 21) and the elution positions of the two peaks in the gel filtration analysis suggest that the major peak is of the monomer of the single chain Fv and the sub peak is of the non-covalently bound dimer of the single chain Fv. The non-covalently bound dimer accounted for 4 percent of total single chain Fvs.

5.13 Apoptosis-Inducing Activity In Vitro of Single Chain Fv Derived from Antibody MABL-2

An apoptosis-inducing action of the single chain Fv from antibody MABL-2 (MABL2-scFv) produced by the CHO cells and *E. coli* was examined according to two protocols by Annexin-V staining (Boehringer Mannheim) using the L1210 cells (hIAP/L1210) into which human IAP gene had been introduced.

In the first protocol sample antibodies at the final concentration of 3 μg/ml were added to 5×10$^4$ cells of hIAP/L1210 cell line and cultured for 24 hours. Sample antibodies, i.e., the monomer and the dimer of the single chain Fv of MABL-2 from the CHO cells obtained in Example 5.9, the monomer and the dimer of the single chain Fv of MABL-2 from *E. coli* obtained in Example 5.12, and the mouse IgG antibody as a control were analyzed. After culturing, the Annexin-V staining was carried out and the fluorescence intensity thereof was measured using the FACScan apparatus (BECTON DICKINSON).

In the second protocol sample antibodies at the final concentration of 3 μg/ml were added to 5×10$^4$ cells of hIAP/L1210 cell line, cultured for 2 hours and mixed with ANTI-FLAG antibody (SIGMA) at the final concentration of 15 μg/ml and further cultured for 22 hours. Sample antibodies of the monomer of the single chain Fv of MABL-2 from the CHO cells obtained in Example 5.9 and the mouse IgG antibody as a control were analyzed. After culturing, the Annexin-V staining was carried out- and the fluorescence intensity thereof was measured using the FACScan apparatus.

Figure 28:
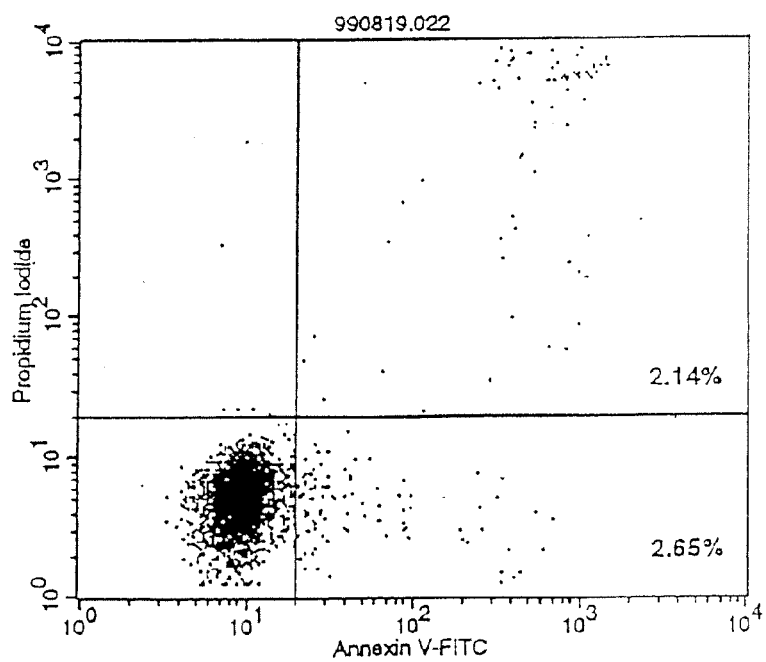
FIG. 28 shows the results of the apoptosis-inducing effect in Example 5.13, illustrating that apoptosis induction to hIAP/L1210 cells by the MABL2-scFv monomer produced by the CHO cells is the same level as that of the control.
Figure 29:
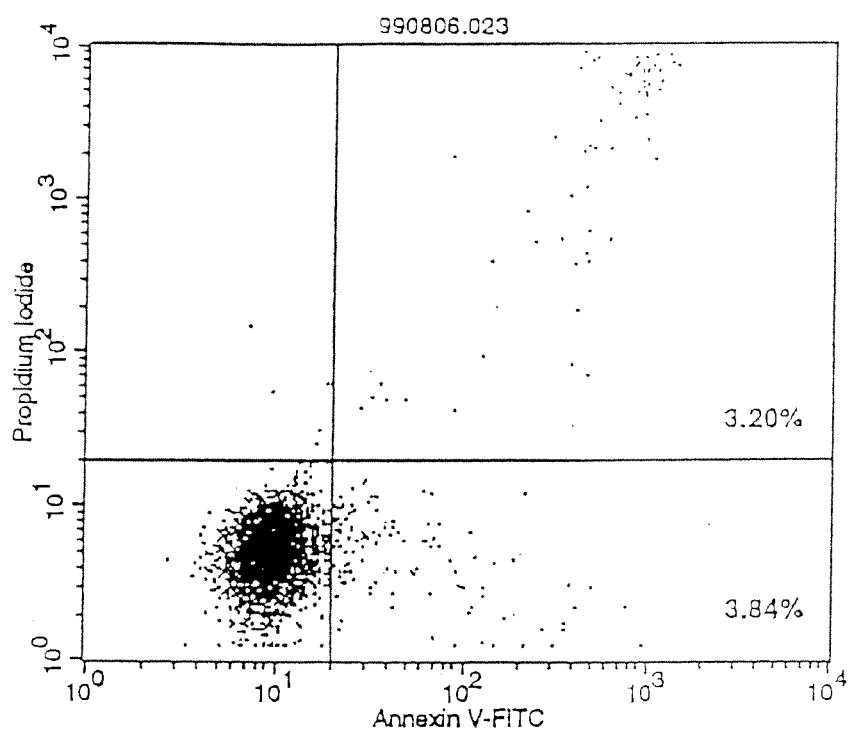
FIG. 29 shows the results of the apoptosis-inducing effect in Example 5.13, illustrating that apoptosis induction to hIAP/L1210 cells of the MABL2-scFv monomer produced by *E. coli* is the same level as that of control.
Figure 30:
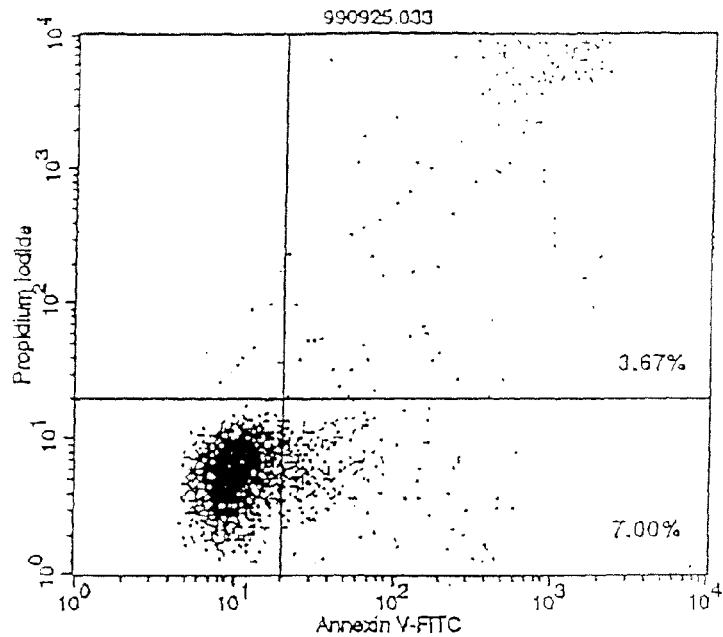
FIG. 30 shows the results of the apoptosis-inducing effect in Example 5.13, illustrating that mouse IgG antibody used as a control does not induce apoptosis of hIAP/L1210 cells even when anti-FLAG antibody is added.
Figure 31:
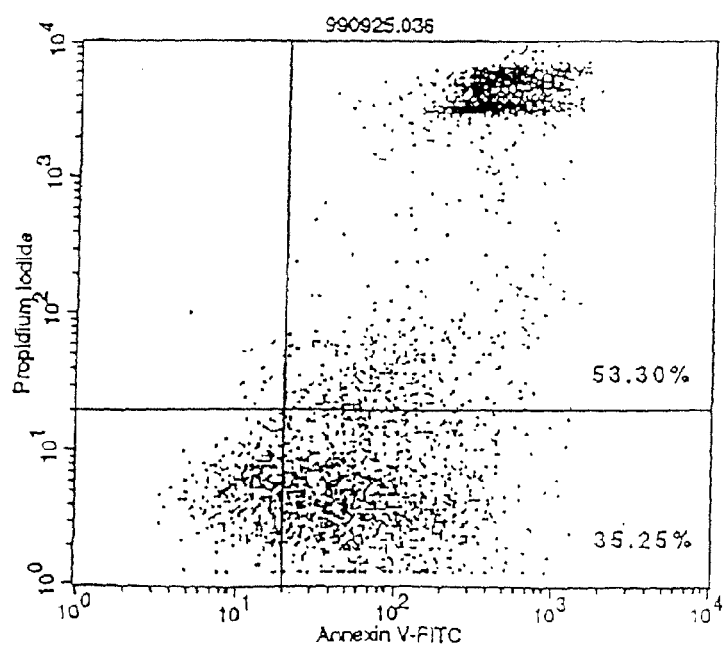
FIG. 31 shows the results of the apoptosis-inducing effect in Example 5.13, illustrating that MABL2scFv monomer produced by the CHO cells remarkably induces apoptosis of hIAP/L1210 cells when anti-FLAG antibody is added.

Results of the analysis by the Annexin-V staining are shown in FIGS. 25-31. The results show that the dimers of the single chain Fv polypeptide of MABL-2 produced in the CHO cells and *E. coli* remarkably induced cell death (FIGS. 26, 27) in comparison with the control (FIG. 25), while no apoptosis-inducing action was observed in the monomers of the single chain Fv polypeptide of MABL-2 produced in the CHO cells and *E. coli* (FIGS. 28, 29). When ANTI-FLAG anti FLAG antibody was used together, the monomer of the single chain Fv polypeptide derived from antibody MABL-2 produced in the CHO cells induced remarkably cell death (FIG. 31) in comparison with the control (FIG. 30).

5.14 Antitumor Effect of the Monomer and the Dimer of scFv/CHO Polypeptide with a Model Mouse of Human Myeloma (1) Quantitative Measurement of Human IgG in Mouse Serum Measurement of human IgG (M protein) produced by human myeloma cell and contained in mouse serum was carried out by the following ELISA. 100 µL of goat anti-human IgG antibody (BIOSOURCE, Lot#7902) diluted to 1 µg/mL with 0.1% bicarbonate buffer (pH 9.6) was added to each well on 96 wells plate (Nunc) and incubated at 4° C. overnight so that the antibody was immobilized. After blocking, 100 µL of the stepwisely diluted mouse serum or human IgG (CAPPEL, Lot#00915) as a standard was added to each well and incubated for 2 hours at a room temperature. After washing, 100 µL of alkaline phosphatase-labeled anti-human IgG antibody (BIOSOURCE, Lot#6202) which had been diluted to 5000 times was added, and incubation was carried out for 1 hour at a room temperature. After washing, a substrate solution was added. After incubation, absorbance at 405 nm was measured using the MICROPLATE READER Model 3550 (BioRad). The concentration of human IgG in the mouse serum was calculated based on the calibration curve obtained from the absorbance values of human IgG as the standard.

(2) Preparation of Antibodies for Administration

The monomer and the dimer of the scFv/CHO polypeptide were respectively diluted to 0.4 mg/mL or 0.25 mg/mL with sterile filtered PBS(−) on the day of administration to prepare samples for the administration.

(3) Preparation of a Mouse Model of Human Myeloma

A mouse model of human myeloma was prepared as follows. KPMM2 cells passaged in vivo (JP-Appl. 7-236475) by SCID mouse (Japan Clare) were suspended in RPMI1640 medium (GIBCO-BRL) containing 10% fetal bovine serum (GIBCO-BRL) and adjusted to $3 \times 10^7$ cells/mL. 200 µL of the KPMM2 cell suspension ($6 \times 10^6$ cells/mouse) was transplanted to the SCID mouse (male, 6 week-old) via caudal vein thereof, which had been subcutaneously injected with the asialo GM1 antibody (WAKO JUNYAKU, 1 vial dissolved in 5 mL) a day before the transplantation.

(4) Administration of Antibodies

The samples of the antibodies prepared in (2), the monomer (250 µL) and the dimer (400 µL), were administered to the model mice of human myeloma prepared in (3) via caudal vein thereof. The administration was started from three days after the transplantation of KPMM2 cells and was carried out twice a day for three days. As a control, 200 µL of sterile filtered PBS(−) was likewise administered twice a day for three days via caudal vein. Each group consisted of seven mice.

Figure 32:
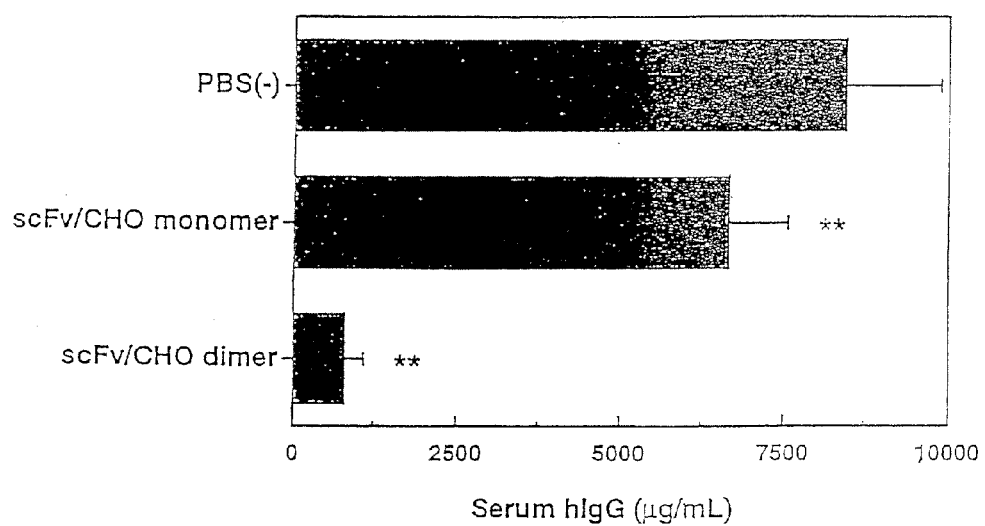
FIG. 32 shows the results of quantitative measurement of human IgG in the serum of a human myeloma cell line KPMM2-transplanted mouse.
Figure 33:
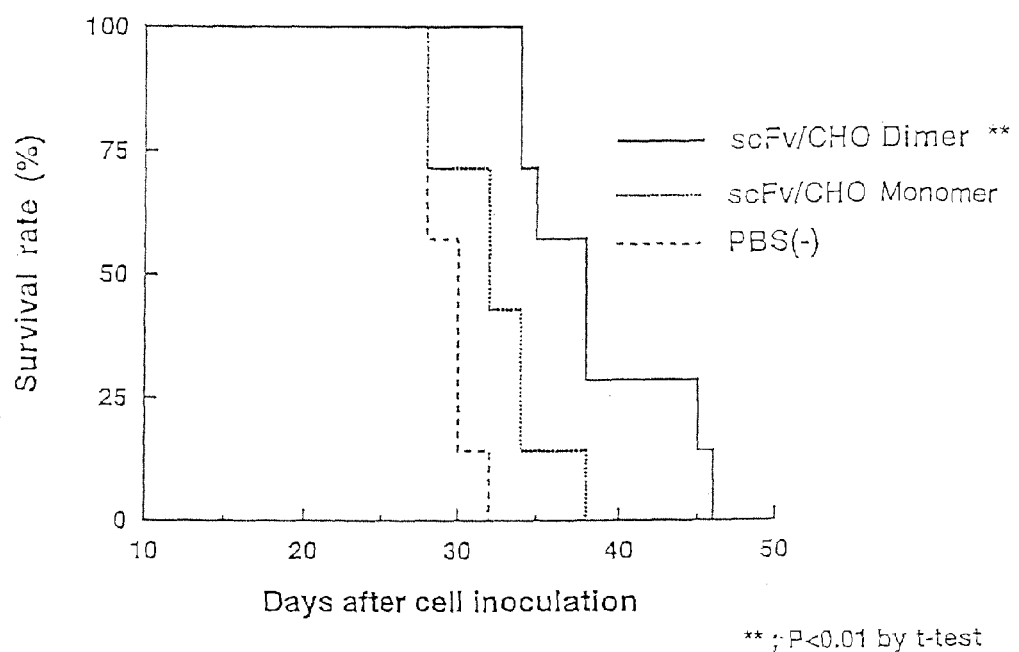
FIG. 33 shows the survival time of the mouse after the transplantation of tumor

(5) Evaluation of Antitumor Effect of the Monomer and the Dimer of scFv/CHO Polypeptide with the Model Mouse of Human Myeloma The antitumor effect of the monomer and the dimer of scFv/CHO polypeptide with the model mice of human myeloma was evaluated in terms of the change of human IgG (M protein) concentration in the mouse serum and survival time of the mice. The change of human IgG concentration was determined by measuring it in the mouse serum collected at 24 days after the transplantation of KPMM2 cells by ELISA described in the above (1). The amount of serum human IgG (M protein) in the serum of the PBS(−)-administered group (control) increased to about 8500 µg/mL, whereas the amount of human IgG of the scFv/CHO dimer-administered group was remarkably low, that is, as low as one-tenth or less than that of the control group. Thus, the results show that the dimer of scFv/CHO strongly inhibits the growth of the KPMM2 cells (FIG. 32). As shown in FIG. 33, a remarkable elongation of the survival time was observed in the scFv/CHO dimer-administered group in comparison with the PBS(−)-administered group.

From the above, it is confirmed that the dimer of scFv/CHO has an antitumor effect for the human myeloma model mice.

It is considered that the antitumor effect of the dimer of scFv/CHO, the modified antibody of the invention, results from the apoptosis-inducing action of the modified antibody.

5.15 Hemagglutination Test

Hemagglutination test and determination of hemagglutination were carried out in accordance with "Immuno-Biochemical Investigation", Zoku-Seikagaku Jikken Koza, edited by the Biochemical Society of Japan, published by Tokyo Kagaku Dojin.

Blood was taken from a healthy donor using heparin-treated syringes and washed with PBS(−) three times, and then erythrocyte suspension with a final concentration of 2% in PBS(−) was prepared. Test samples were the antibody MABL-2, the monomer and the dimer of the single chain Fv polypeptide produced by the CHO cells, and the monomer and the dimer of the single chain Fv polypeptide produced by E. coli, and the control was mouse IgG (ZYMED). For the investigation of the hemagglutination effect, round bottom 96-well plates available from Falcon were used. 50 µL per well of the aforementioned antibody samples and 50 µL of the 2% erythrocyte suspension were added and mixed in the well. After incubation for 2 hours at 37° C., the reaction mixtures were stored at 4° C. overnight and the hemagglutination thereof was determined. As a control, 50 µL per well of PBS(−) was used and the hemagglutination test was carried out in the same manner. The mouse IgG and antibody MABL-2 were employed at 0.01, 0.1, 1.0, 10.0 or 100.0 µg/mL of the final concentration of the antibodies. The single chain Fvs were employed at 0.004, 0.04, 0.4, 4.0, 40.0 or 80.0 µg/mL of the final concentration and further at 160.0 µg/mL only in the case of the dimer of the polypeptide produced by E. coli. Results are shown in the Table 2. In the case of antibody MABL-2, the hemagglutination was observed at a concentration of more than 0.1 µg/mL, whereas no hemagglutination was observed for both the monomer and the dimer of the single chain Fv.

TABLE 2

| Hemagglutination Test | | | | | | |
|---|---|---|---|---|---|---|
| | Control | 0.01 | 0.1 | 1 | 10 | 100 µg/mL |
| mIgG | − | − | − | − | − | − |
| MABL-2 (intact) | − | − | + | +++ | +++ | ++ |
| | Control | 0.004 | 0.04 | 0.4 | 4 | 40 | 80 µg/mL |
| scFv/CHO monomer | − | − | − | − | − | − | − |
| scFv/CHO dimer | − | − | − | − | − | − | − |
| | Control | 0.004 | 0.04 | 0.4 | 4 | 40 | 80 | 160 µg/mL |
| scFv/E. coli monomer | − | − | − | − | − | − | − | − |
| scFv/E. coli dimer | − | − | − | − | − | − | − | − |

Example 6

Modified Antibody sc(Fv)$_2$ Comprising Two H Chain V Regions and Two L Chain V Regions and Antibody MABL-2 scFvs Having Linkers with Different Length 6.1 Construction of Plasmid Expressing Antibody MABL-2 sc(Fv)$_2$ For the preparation of a plasmid expressing the modified antibody [sc(Fv)$_2$] which comprises two H chain V regions and two L chain V regions derived from the antibody MABL-2, the aforementioned pCHOM2, which comprises the DNA encoding scFv derived from the MABL-2 described above, was modified by the PCR method as mentioned below and the resulting DNA fragment was introduced into pCHOM2.

Primers employed for the PCR are EF1 primer (SEQ ID NO: 30) as a sense primer, which is designed to hybridize to a DNA encoding EF1α, and an antisense primer (SEQ ID NO: 19), which is designed to hybridize to the DNA encoding C-terminal of the L chain V region and to contain a DNA sequence coding for a linker region, and VLLAS primer containing SalI restriction enzyme recognition site (SEQ ID NO 31).

100 µl of the PCR solution comprises 10 µl of 10×PCR Buffer #1, 1 mM MgCl$_2$, 0.2 mM dNTPs (dATP, dGTP, dCTP and dTTP), 5 units of KOD DNA polymerase (Toyobo, Inc.), 1 µM of each primer and 100 ng of the template DNA (pCHOM2). The PCR solution was heated at 94° C. for 30 seconds, at 50° C. for 30 seconds and at 74° C. for 1 minute in order. This temperature cycle was repeated 30 times.

Figure 34:
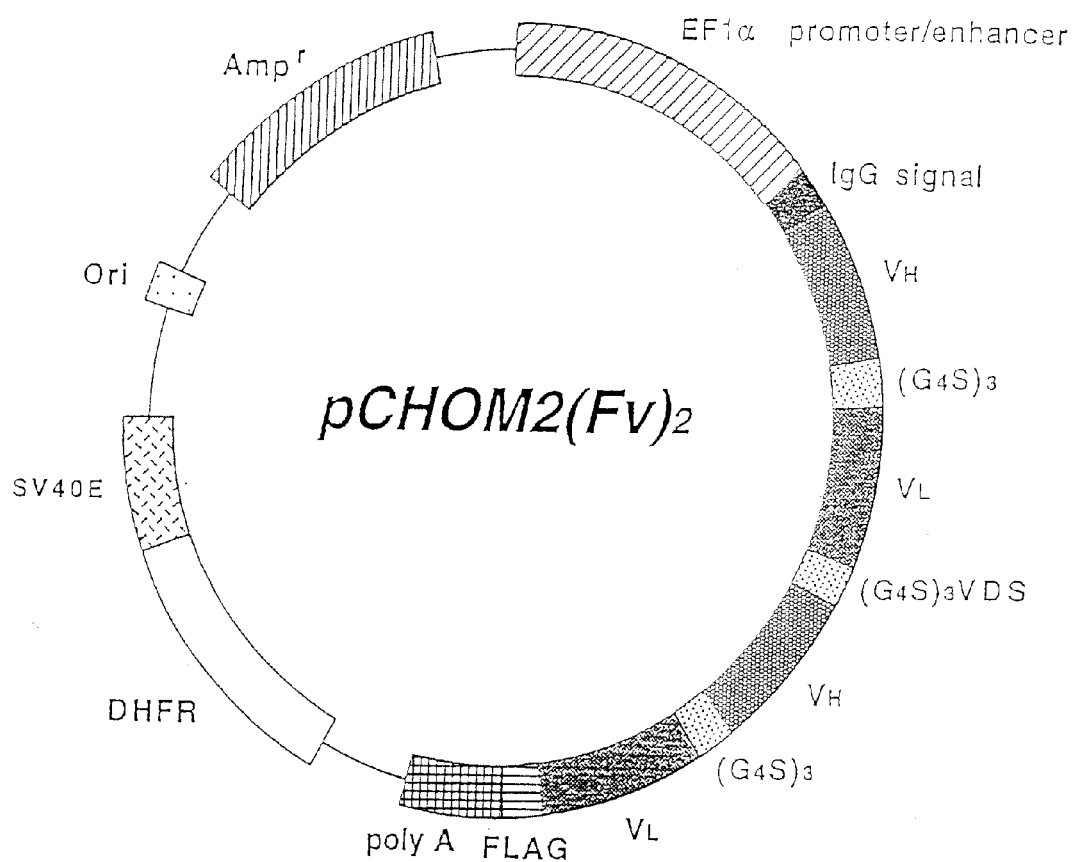
FIG. 34 illustrates a structure of an expression plasmid which expresses a modified antibody [sc(Fv)$_2$]. The (G$_4$S)$_3$ linker is shown in SEQ ID NO:118 while the (G$_4$S)$_3$VDS linker is shown in SEQ ID NO:145.

The PCR product was purified using the QIAquick PCR Purification Kit (QIAGEN) and digested by SalI. The resultant DNA fragment was cloned into pBluescript K5$^+$ vector (Toyobo, Inc.). After DNA sequencing, a plasmid comprising the desired DNA sequence was digested by SalI and the obtained DNA fragment was connected using Rapid DNA Ligation Kit (BOEHRINGER MANMHEIM) to pCHOM2 digested by SalI. After DNA sequencing, a plasmid comprising the desired DNA sequence is designated as "pCHOM2 (Fv)$_2$," (see FIG. 34). The nucleotide sequence (SEQ ID NO: 32) and the amino acid sequence (SEQ ID NO: 125) of the antibody MABL-2 sc(Fv)$_2$ region contained in the plasmid pCHOM2(Fv)$_2$ are shown in SEQ ID NO 32.

6.2 Preparation of Plasmid Expressing Antibody MABL-2 scFvs Having Linkers with Various Length The scFvs containing linkers with different length and the V regions which are designed in the order of [H chain]-[L chain] (hereinafter "HL") or [L chain]-[H chain] (hereinafter "LH") were prepared using, as a template, cDNAs encoding the H chain and the L chain derived from the MABL-2 as mentioned below.

To construct HL type scFv the PCR procedure was carried out using pCHOM2(Fv)$_2$ as a template. In the PCR step, a pair of CFHL-F1 primer (SEW ID NO: 33) and CFHL-R2 primer (SEQ ID NO: 34) or a pair of CFHL-F2 primer (SEQ ID NO: 35) and CFHL-R1 primer (SEQ ID NO: 36) and KOD polymerase were employed. The PCR procedure was carried out by repeating 30 times the temperature cycle consisting of 94° C. for 30 seconds, 60° C. for 30 seconds and 72° C. for 1 minute in order to produce a cDNA for the H chain containing a leader sequence at 5'-end or a cDNA for the L chain containing FLAG sequence at 3'-end thereof. The resultant cDNAs for the H chain and the L chain were mixed and PCR was carried out by repeating 5 times the temperature cycle consisting of 94° C. for 30 seconds, 60° C. for 30 seconds and 72° C. for 1 minute in order using the mixture as templates and the KOD polymerase. To the reaction mixture were added CFHL-F1 and CFHL-R1 primers and then the PCR reaction was performed by repeating 30 times of the aforementioned temperature cycle to produce a cDNA for HL-0 type without a linker.

To construct LH type scFv, the PCR reaction was carried out using, as a template, pGEM-M2L and pGEM-M2H which contain cDNAs encoding the L chain V region and the H chain V region from the antibody MABL-2, respectively (see JP-Appl. 11-63557). A pair of T7 primer (SEQ ID NO: 37) and CFLH-R2 primer(SEQ ID NO: 38) or a pair of CFLH-F2 primer (SEQ ID NO: 39) and CFLH-R1 (SEQ ID NO: 40) and the KOD polymerase (Toyobo Inc.) were employed. The PCR reaction was performed by repeating 30 times the temperature cycle consisting of 94° C. for 30 seconds, 60° C. for 30 seconds and 72° C. for 1 minute in sequential order to produce a cDNA of an L chain containing a leader sequence at 5'-end or a cDNA of an H chain containing FLAG sequence at 3'-end thereof. The resultant cDNAs of the L chain and the H chain were mixed and PCR was carried out using this mixture as templates and the KOD polymerase by repeating 5 times the temperature cycle consisting of 94° C. for 30 seconds, 60° C. for 30 seconds and 72° C. for 1 minute in order. To the reaction mixture were added T7 and CFLH-R1 primers and the reaction was performed by repeating 30 times of the aforementioned temperature cycle. The reaction product was used as a template and PCR was carried out using a pair of CFLH-F4 primer (SEQ ID NO: 41) and CFLH-R1 primer by repeating 30 times the temperature cycle consisting of 94° C. for 30 seconds, 60° C. for 30 seconds and 72° C. for 1 minute in order to produce a cDNA of LH-0 type without a linker.

The resultant cDNAs of LH-0 and HL-0 types were digested by EcoRI and BamHI restriction enzymes (Takara Shuzo) and the digested cDNAs were introduced into an expression plasmid INPEP4 for mammalian cells using Ligation High (Toyobo Inc.), respectively. Competent *E. coli* JM109 (Nippon Gene) was transformed with each plasmid and the desired plasmids were isolated from the transformed *E. coli* using QIAGEN Plasmid Maxi Kit (QUIAGEN). Thus plasmids pCF2LH-0 and pCF2HL-0 were prepared.

To construct the expression plasmids of HL type containing linkers with different size, pCF2HL-0, as a template, and CFHL-X3 (SEQ ID NO: 42), CFHL-X4 (SEQ ID NO: 43), CFHL-X5 (SEQ ID NO: 44), CFHL-X6 (SEQ ID NO: 45) or CFHL-X7 (SEQ ID NO: 46), as a sense primer, and BGH-1 (SEQ ID NO: 47) primer, as an antisense primer, which is complementary with the vector sequence were employed. PCR reaction was carried out using the KOD polymerase by repeating 30 times the temperature cycle consisting of 94° C. for 30 seconds, 60° C. for 30 seconds and 72° C. for 1 minute in order and the reaction products were digested by restriction enzymes XhoI and BamHI (Takara Shuzo). The digested fragments were introduced between XhoI and BamHI sites in the pCF2HL-0 using Ligation High (Toyobo Inc.), respectively. Competent *E. coli* JM109 was transformed with each plasmid and the desired plasmids were isolated from the transformed *E. coli* by using Qiagen Plasmid Maxi kit. Thus expression plasmids pCF2HL-3, pCF2HL-4, pCF2HL-5, pCF2HL-6 and pCF2HL-7 were prepared.

To construct expression plasmid for the transient expression in COST cells the plasmids pCF2HL-0, pCF2HL-3, pCF2HL-4, pCF2HL-5, pCF2HL-6 and pCF2HL-7 were digested by restriction enzymes EcoRI and BamHI (Takara Shuzo) and the resultant fragments of approximately 800 by were purified with agarose gel electrophoresis. The obtained fragments were introduced between EcoRI and BamHI sites in an expression plasmid pCOS1 for the expression in mammalian cells by using Ligation High (Toyobo Inc.), respectively. Competent *E. coli* DH5α (Toyobo Inc.) was transformed with each plasmid and the desired plasmids were isolated from the transformed *E. coli* using Qiagen Plasmid Maxi kit. Thus the expression plasmids CF2HL-0/pCOS1, CF2HL-3/pCOS1, CF2HL-4/pCOS1, CF2HL-5/pCOS1, CF2HL-6/pCOS1 and CF2HL-7/pCOS1 were prepared.

Figure 35:
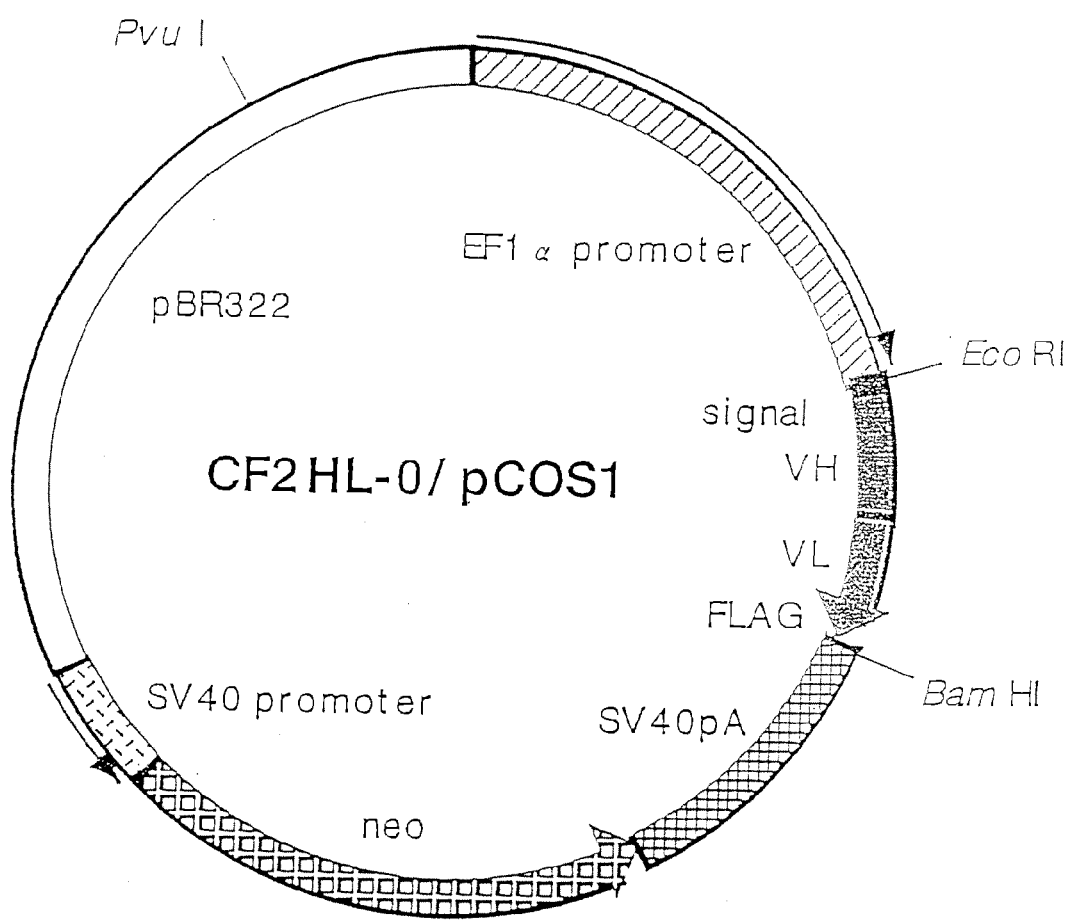
FIG. 35 illustrates a structure of a plasmid which expresses a scFv (HL type).

As a typical example of these plasmids, the construction of the plasmid CF2HL-0/pCOS1 is illustrated in FIG. 35 and the nucleotide sequence (SEQ ID NO: 48) and the amino acid sequence (SEQ ID NO: 126) of MABL2-scFv <HL-0> contained in the plasmid are shown in SEQ ID NO 48. Nucleotide sequences and amino acid sequences (SEQ ID NOS 146-159, respectively, in order of appearance) of the linker regions in these plasmids are also shown in FIG. 36.

To construct the expression plasmids of LH type containing linkers with different size, pCF2LH-0, as a template, and CFLH-X3 (SEQ ID NO: 49), CFLH-X4 (SEQ ID NO: 50), CFLH-X5 (SEQ ID NO: 51), CFLH-X6 (SEQ ID NO: 52) or CFLH-X7 (SEQ ID NO: 53), as a sense primer, and BGH-1 primer, as an antisense primer, which is complementary with the vector sequence were employed. PCR reaction was carried out using the KOD polymerase by repeating 30 times the temperature cycle consisting of 94° C. for 30 seconds, 60° C. for 30 seconds and 72° C. for 1 minute in order and the reaction products were digested by restriction enzymes XhoI and BamHI. The digested fragments were introduced into the pCF2LH-0 between XhoI and BamHI sites using Ligation High, respectively. Competent $E.\ coli$ DH5α (Toyobo Inc.) was transformed with each plasmid and the desired plasmids were isolated from the transformed $E.\ coli$ using Qiagen Plasmid Maxi kit. Thus expression plasmids pCF2LH-3, pCF2LH-4, pCF2LH-5, pCF2LH-6 and pCF2LH-7 were prepared.

To construct expression plasmid for the transient expression in COST cells the plasmids pCF2LH-0, pCF2LH-3, pCF2LH-4, pCF2LH-5, pCF2LH-6 and pCF2LH-7 were digested by restriction enzymes EcoRI and BamHI (Takara Shuzo) and the resultant fragments of approximately 800 bp were purified with agarose gel electrophoresis. The obtained fragments were introduced between XhoI and BamHI sites in an expression plasmid pCOS1 for the expression in mammalian cells by using the Ligation High, respectively. Competent $E.\ coli$ DH5α (Toyobo Inc.) was transformed with each plasmid and the desired plasmids were isolated from the transformed $E.\ coli$ using the Qiagen Plasmid Maxi kit. Consequently, the expression plasmids CF2LH-0/pCOS1, CF2LH-3/pCOS1, CF2LH-4/pCOS1, CF2LH-5/pCOS1, CF2LH-6/pCOS1 and CF2LH-7/pCOS1 were prepared.

Figure 37:
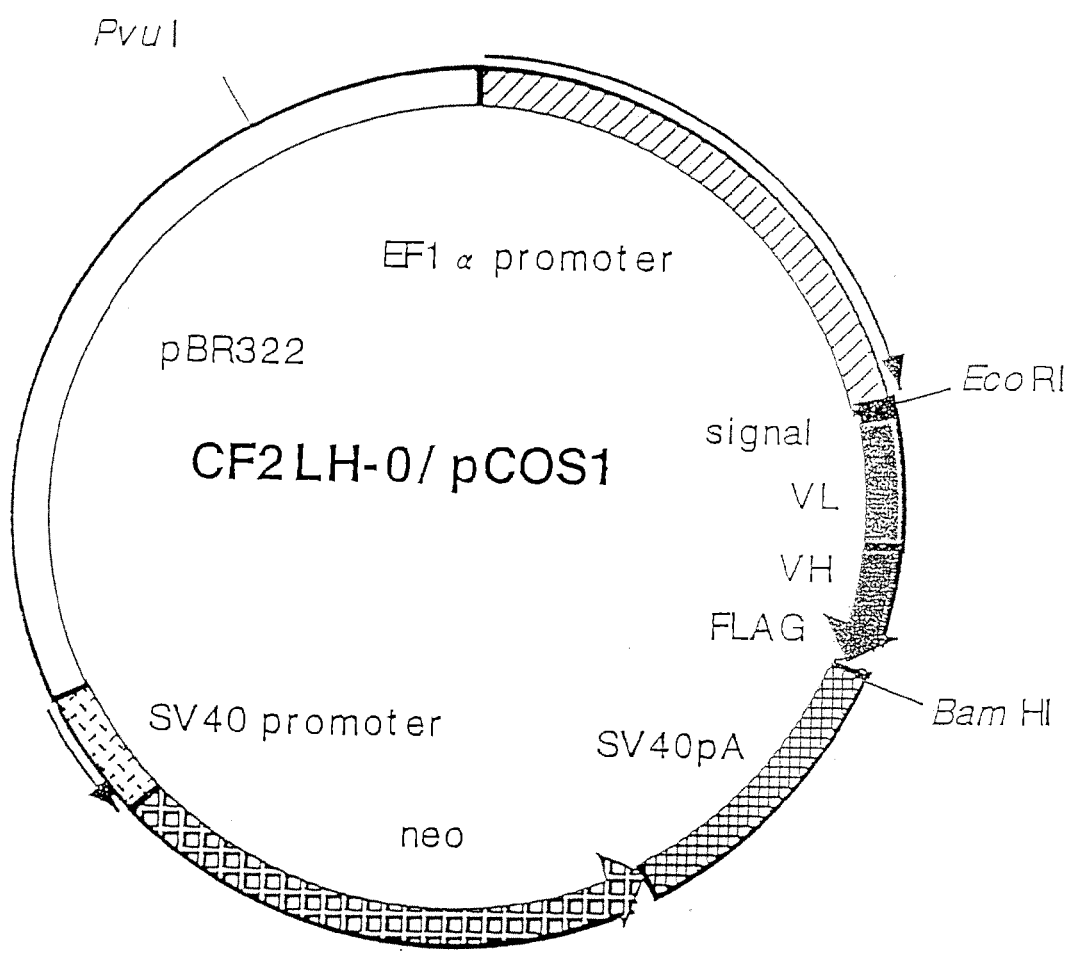
FIG. 37 illustrates a structure of a plasmid which expresses a scFv (LH type) wherein the V regions are linked in the manner of [L chain]-[H chain] without a peptide linker.

As a typical example of these plasmids, the construction of the plasmid CF2LH-0/pCOS1 is illustrated in FIG. 37 and the nucleotide sequence (SEQ ID NO: 54) and the amino acid (SEQ ID NO: 127) sequence of MABL2-scFv <LH-0> contained in the plasmid are shown in SEQ ID No 54. Nucleotide sequences and amino acid sequences (SEQ ID NOS 160-173, respectively, in order of appearance) of the linker regions in these plasmids are also shown in FIG. 38.

6.3 Expression of scFvs and sc(Fv)$_2$ in COS7 Cells (1) Preparation of Culture Supernatant Using Serum-Containing Culture Medium The HL type and LH type of scFvs and sc(Fv)$_2$ were transiently expressed in COS7 cells (JCRB9127, Japan Health Sciences Foundation). COS7 cells were subcultured in DMEM media (GIBCO BRL) containing 10% fetal bovine serum (HyClone) at 37° C. in carbon dioxide atmosphere incubator. The COS7 cells were transfected with CF2HL-0, 3~7/pCOS1, or CF2LH-0, 3~7/pCOS1 prepared in Example 6.2 or pCHOM2(Fv)$_2$ vectors by electroporation using the Gene Pulser apparatus (BioRad). The DNA (10 μg) and 0.25 ml of $2 \times 10^7$ cells/ml in DMEM culture medium containing 10% FBS and 5 mM BES (SIGMA) were added to a cuvette. After standing for 10 minutes the mixtures were treated with pulse at 0.17 kV, 950 μF of electric capacity. After the restoration for 10 minutes at room temperature, the electroporated cells were transferred into the DMEM culture medium (10% FBS) in 75 cm$^3$ flask. After culturing for 72 hours, the culture supernatant was collected and centrifuged to remove cell fragments. The culture supernatant was subjected to the filtration using 0.22 μm bottle top filter (FALCON) to obtain the culture supernatant (hereinafter "CM").

(2) Preparation of Culture Supernatant Using Serum-Free Culture Medium

Cells transfected in the same manner as (1) were transferred to the DMEM medium (10% FBS) in 75 cm$^3$ flask and cultured overnight. After the culture, the supernatant was discarded and the cells were washed with PBS and then added to CHO-S-SFM II medium (GIBCO BRL). After culturing for 72 hours, the culture supernatant was collected, centrifuged to remove cell fragments and filtered using 0.22 μm bottle top filter (FALCON) to obtain CM.

6.4 Detection of scFvs and sc(Fv)$_2$ in CM of COS7

The various MABL2-scFVs and sc(Fv)$_2$ in CM of COS7 prepared in the aforementioned Example 6.3 (2) were detected by Western Blotting method.

Each CM of COST was subjected to SDS-PAGE electrophoresis and transferred to REINFORCED NC membrane (Schleicher & Schuell). The membrane was blocked with 5% skim milk (Morinaga Nyu-gyo) and washed with TBS. Then an ANTI-FLAG anti FLAG antibody (SIGMA) was added thereto. The membrane was incubated at room temperature and washed. A peroxidase labeled mouse IgG antibody (Jackson Immuno Research) was added.

Figure 39:
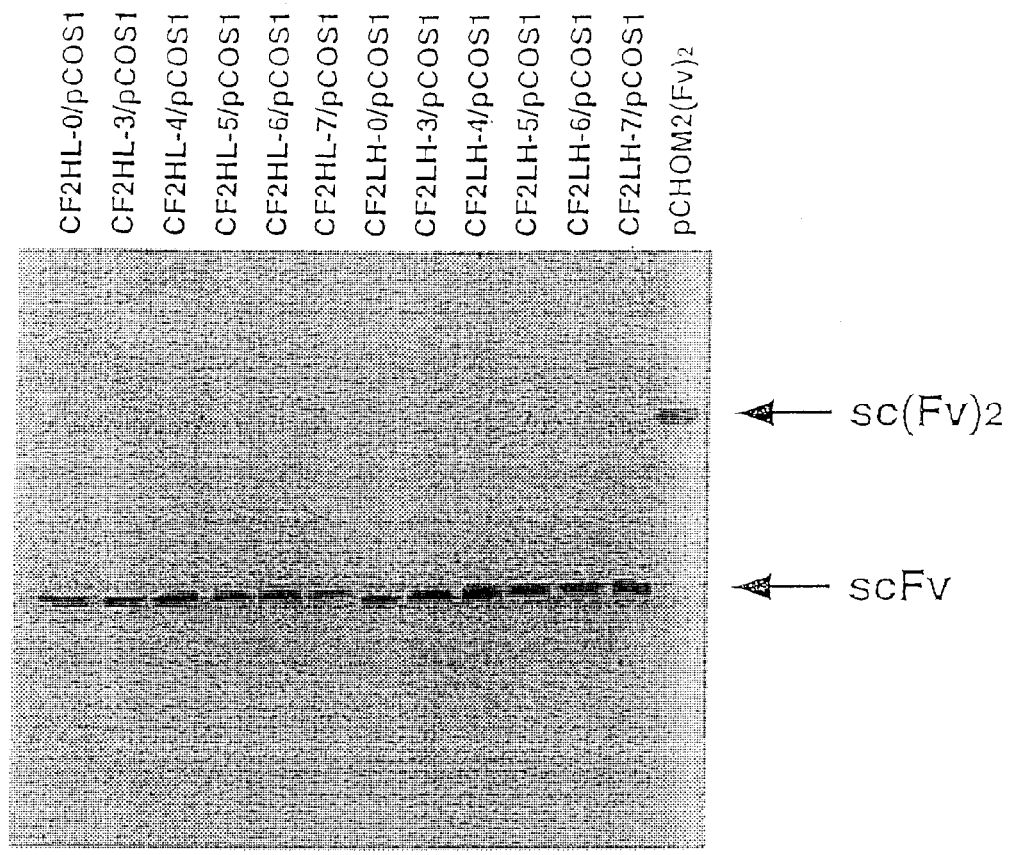
FIG. 39 shows the results of the western blotting in Example 6.4.

After incubating and washing at room temperature, the substrate solution (Kirkegaard Perry Laboratories) was added to develop color (FIG. 39).

6.5 Flow Cytometry

Figure 40A:
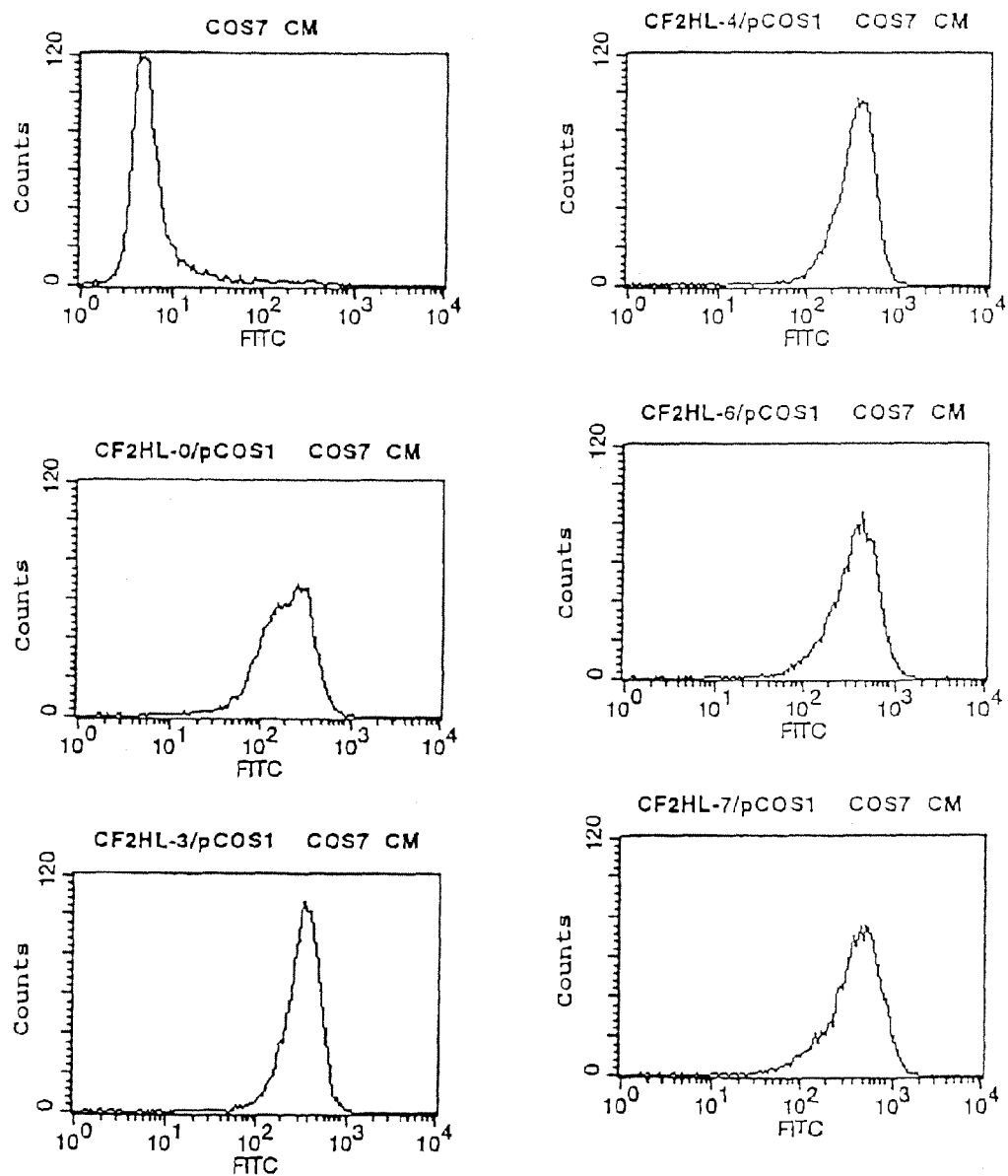
FIGS. 40a and 40b show the results of flow cytometry using the culture supernatant of COS7 cells prepared in Example 6.3 (1).
Figure 40B:
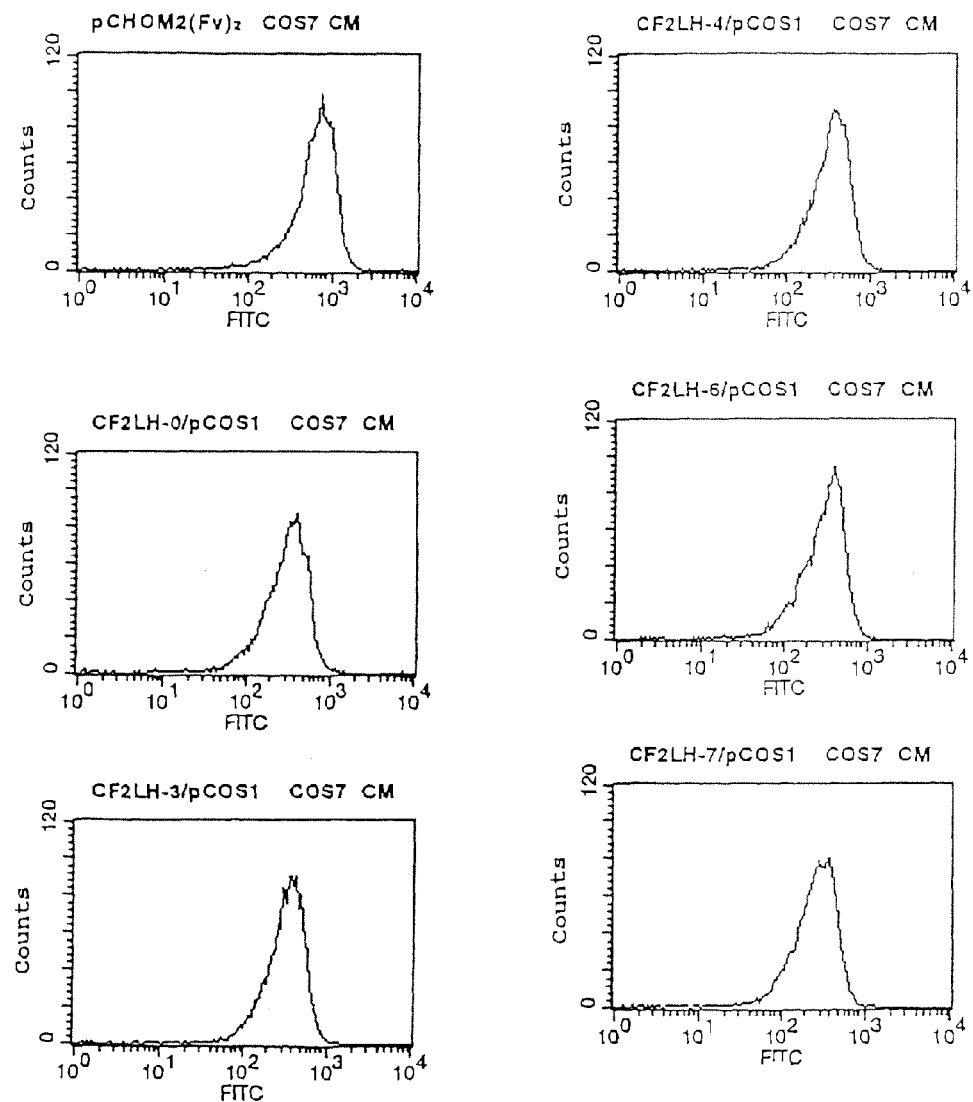

Flow cytometry was performed using the culture supernatants of COS7 cells prepared in Example 6.3 (1) to measure the binding of the MABL2-scFVs and sc(Fv)$_2$ to human Integrin Associated Protein (IAP) antigen. The culture supernatants to be tested or a culture supernatant of COS7 cells as a control was added to $2 \times 10^5$ cells of the mouse leukemia cell line L1210 expressing human IAP. After incubating on ice and washing, 10 μg/mL of the mouse ANTI-FLAG antibody (SIGMA) was added and then the cells were incubated and washed. Then, the FITC labeled anti-mouse IgG antibody (BECTON DICKINSON) was added thereto and the cells were incubated and washed again. The fluorescence intensity was measured using the FACScan apparatus (BECTON DICKINSON). The results of the flow cytometry show that the MABL2-scFvs having linkers with different length and the sc(Fv)$_2$ in the culture supernatants of COS7 have high affinity to human IAP (see FIGS. 40a and 40b).

6.6 Apoptosis-Inducing Effect in vitro

An apoptosis-inducing action of the culture supernatants of COS7 prepared in Example 6.3 (1) was examined by Annexin-V staining (Boehringer Mannheim) using the L1210 cells transfected with human LAP gene (hIAP/L1210).

Figure 41A:
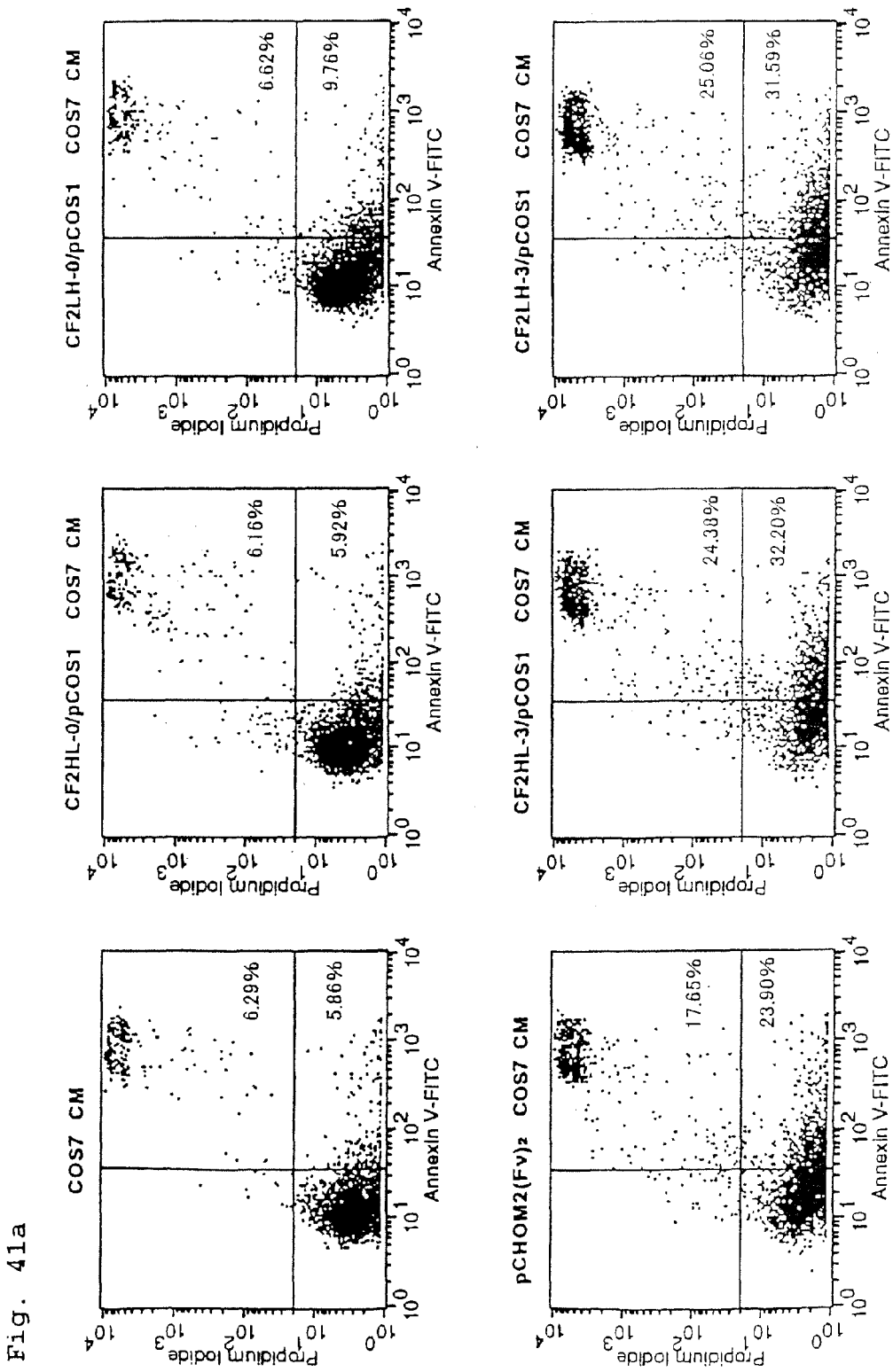
FIGS. 41a and 41b show the results of the apoptosis-inducing effect in Example 6.6.
Figure 41B:
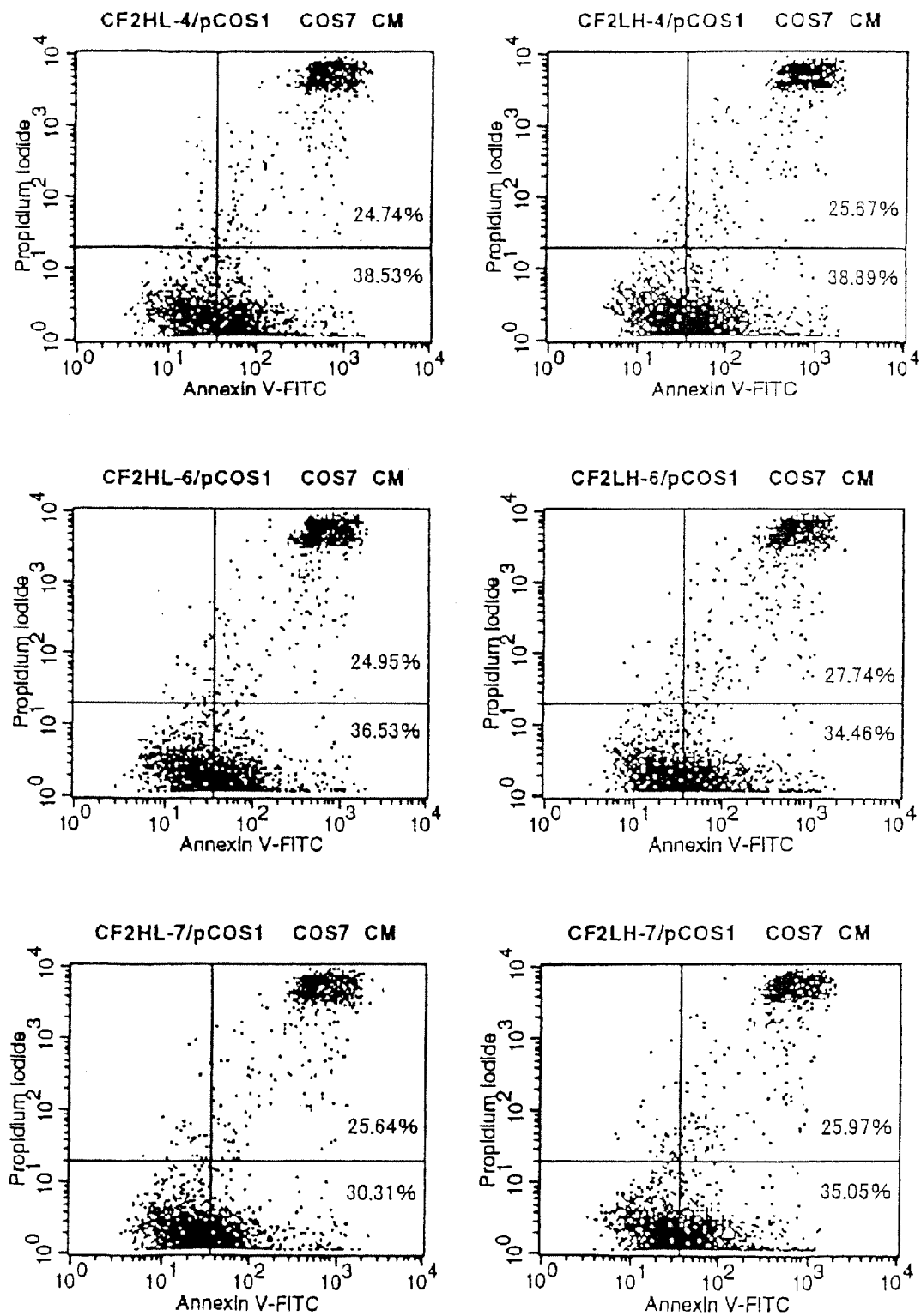

To $5 \times 10^4$ cells of the hIAP/L1210 cells were added the culture supernatants of COS7 cells transfected with each vectors or a culture supernatant of COS7 cells as a control at 10% of the final concentration and the mixtures were cultured for 24 hours. Then, the Annexin-V/PI staining was performed and the fluorescence intensity was measured using the FACScan apparatus (BECTON DICKINSON). The results revealed that scFvs <HL3, 4, 6, 7, LH3, 4, 6, 7> and sc(Fv)$_2$ in CM of COST induced remarkable cell death of hIAP/L1210 cells. These results are shown in FIG. 41.

6.7 Construction of Vectors for the Expression of scFvs and sc(Fv)₂ in CHO Cells To isolate and purify MABL2-scFvs and sc(Fv)₂ from culture supernatant, the expression vectors for expressing in CHO cells were constructed as below.

The EcoRI-BamHI fragments of pCF2HL-0, 3~7, and pCF2LH-0, 3~7 prepared in Example 6.2 were introduced between EcoRI and BamHI sites in an expression vector pCHO1 for CHO cells using the Ligation High. Competent *E. coli* DH5α was transformed with them. The plasmids were isolated from the transformed *E. coli* using QIAGEN Plasmid Midi kit (QIAGEN) to prepare expression plasmids pCHOM2HL-0, 3~7, and pCHOM2LH-0, 3~7.

6.8 Production of CHO Cells Expressing MABL2-scFvs <HL-0, 3~7>, MABL2-scFvs <LH-0, 3~7> and sc(Fv)₂ and Preparation of the Culture Supernatants Thereof CHO cells were transformed with each of the expression plasmids pCHOM2HL-0, 3~7, and pCHOM2LH-0, 3~7, constructed in Example 6.7 and pCHOM2(Fv)₂ vector to prepare the CHO cells constantly expressing each modified antibody. As a typical example thereof, the production of the CHO cells constantly expressing MABL2-scFv <HL-5> or sc(Fv)₂ is illustrated as follows.

The expression plasmids pCHOM2HL-5 and pCHOM2 (Fv)₂ were linearized by digesting with a restriction enzyme PvuI and subjected to transfection to CHO cells by electroporation using Gene Pulser apparatus (BioRad). The DNA (10 μg) and 0.75 ml of PBS with 1×10⁷ cells/ml were added to a cuvette and treated with pulse at 1.5 kV, 25 μF of electric capacity. After the restoration for 10 minutes at room temperature, the electroporated cells were transferred into nucleic acid-containing α-MEM culture medium (GIBCO BRL) containing 10% fetal bovine serum and cultured. After culturing overnight, the supernatant was discarded. The cells were washed with PBS and added to nucleic acid-free α-MEM culture medium (GIBCO BRL) containing 10% fetal bovine serum. After culturing for two weeks, the cells were cultured in a medium containing 10 nM (final concentration) methotrexate (SIGMA), then 50 nM and 100 nM methotrexate. The resultant cells were cultured in serum-free CHO-S-SFM II medium (GIBCO BRL) in a roller bottle. The culture supernatant was collected, centrifuged to remove cell fragments and filtered using a filter with 0.22 μm of pore size to obtain CM, respectively.

According to the above, CHO cells which constantly express MABL2-scFvs <HL-0, -3, -4, -6, -7> and <LH-0, -3, -4, -5, -6, -7> and CMs thereof were obtained.

6.9 Purification of Dimer of MABL2-scFv <HL-5> and sc(Fv)₂

The MABL2-scFv <HL-5> and the sc(Fv)₂ were purified from CMs prepared in Example 6.8 by two types of purification method as below.

<Purification Method 1>

HL-5 and sc(Fv)₂ were purified by the ANTI-FLAG antibody affinity column chromatography utilizing the FLAG sequence located at C-terminal of the polypeptides and by gel filtration. One liter of CM as obtained in 6.8 was applied onto a column (7.9 ml) prepared with ANTI-FLAG M2 AFFINITY GEL (SIGMA) equilibrated with 50 mM Tris-HCl buffer (TBS, pH 7.5) containing 150 mM NaCl. After washing the column with TBS, the scFv was eluted by 0.1 M glycine-HCl buffer, pH 3.5. The resultant fractions were analyzed by SDS-PAGE and the elution of the scFv was confirmed. The scFv fraction was mixed with Tween 20 up to 0.01% of the final concentration and concentrated using Centricon-10 (MILIPORE). The concentrate was applied onto TSKgel G3000SWG column (7.5×600 mm) equilibrated with 20 mM acetate buffer (pH 6.0) containing 150 mM NaCl and 0.01% Tween 20. At 0.4 mL/minute of the flow rate, the scFv was detected by the absorption at 280 nm. The HL-5 was eluted as the major fraction in the position of the dimer and the sc(Fv)₂ was eluted in the position of the monomer.

<Purification Method 2>

HL-5 and sc(Fv)₂ were purified using three steps comprising ion exchange chromatography, hydroxyapatite and gel filtration. In the ion exchange chromatography, Q sepharose fast flow column (Pharmacia) was employed for HL-5 and SP-sepharose fast flow column was employed for sc(Fv)₂. In and after the second step, HL-5 and sc(Fv)₂ were processed by the same procedure.

First Step for HL-5

CM of HL-5 was diluted to two times with 20 mM Tris-HCl buffer (pH 9.0) containing 0.02% Tween 20 and then the pH was adjusted to 9.0 with 1 M Tris. The solution was applied onto Q Sepharose fast flow column equilibrated with 20 mM Tris-HCl buffer (pH 8.5) containing 0.02% Tween 20. A polypeptide adsorbed to the column was eluted by a linear gradient of NaCl in the same buffer, from 0.1 to 0.55 M. Monitoring the eluted fractions by SDS-PAGE, the fractions containing HL-5 were collected and subjected to hydroxyapatite of the second step.

First Step for sc(Fv)₂

CM of the sc(Fv)₂ was diluted to two times with 20 mM acetate buffer (pH 5.5) containing 0.02% Tween 20 and its pH was adjusted to 5.5 with 1 M acetic acid. The solution was applied onto a SP-Sepharose fast flow column equilibrated with 20 mM acetate buffer (pH 5.5) containing 0.02% Tween 20. A polypeptide adsorbed to the column was eluted by a linear gradient of NaCl in the buffer, from 0 to 0.5 M. Monitoring the eluted fractions by SDS-PAGE, the fractions containing the sc(Fv)₂ were collected and subjected to hydroxyapatite of the second step.

Second Step: Hydroxyapatite Chromatography of HL-5 and sc(Fv)₂

The fractions of HL-5 and sc(Fv)₂ obtained in the first step were separately applied onto the hydroxyapatite column (Type I, BIORAD) equilibrated with 10 mM phosphate buffer containing 0.02% Tween 20, pH 7.0. After washing the column with the same buffer, polypeptides adsorbed to the column were eluted by a linear gradient of the phosphate buffer up to 0.5 M. Monitoring the eluted fractions by SDS-PAGE, the fractions containing the desired polypeptides were collected.

Third Step: Gel Filtration of HL-5 and sc(Fv)₂

Each fraction obtained at the second step was separately concentrated with CentriPrep-10 (MILIPORE) and applied onto a Superdex 200 column (2.6×60 cm, Pharmacia) equilibrated with 20 mM acetate buffer (pH 6.0) containing 0.02% Tween 20 and 0.15 M NaCl. HL-5 was eluted in the position of the dimer, and sc(Fv)HL-5 and sc(Fv)₂ were eluted in the position of the monomer as a major peek respectively.

Since the monomer of HL-5 was hardly detected by both purification methods, it is proved that the dimers of single chain Fvs are formed in high yields when the linker for the single chain Fv contains around 5 amino acids. Furthermore, the dimer of HL-5 and the sc(Fv)₂ were stably preserved for a month at 4° C. after the purification.

6.10 Evaluation of the Binding Activity of Purified Dimer of scFv <HL-5> and sc(Fv)₂ Against Antigen Flow cytometry was performed using the purified dimer of MABL2-scFv <HL-5> and the purified sc(Fv)₂ in order to evaluate the binding to human Integrin Associated Protein (IAP) antigen. 10 μg/ml of the purified dimer of MABL2-scFv <HL-5>, the purified sc(Fv)₂, the antibody MABL-2 as a positive control or a mouse IgG (Zymed) as a negative control was added to 2×10⁵ cells of the mouse leukemia cell line L1210 expressing human IAP (hIAP/L1210) or the cell line L1210 transformed with pCOS1 (pCOS1/L1210) as a control. After incubating on ice and washing, 10 μg/mL of the mouse ANTI-FLAG antibody (SIGMA) was added and then the cells were incubated and washed. FITC labeled anti-mouse IgG antibody (BECTON DICKINSON) was added thereto and the cells were incubated and washed again. Then the fluorescence intensity was measured using the FACScan apparatus (BECTON DICKINSON).

Figure 42:
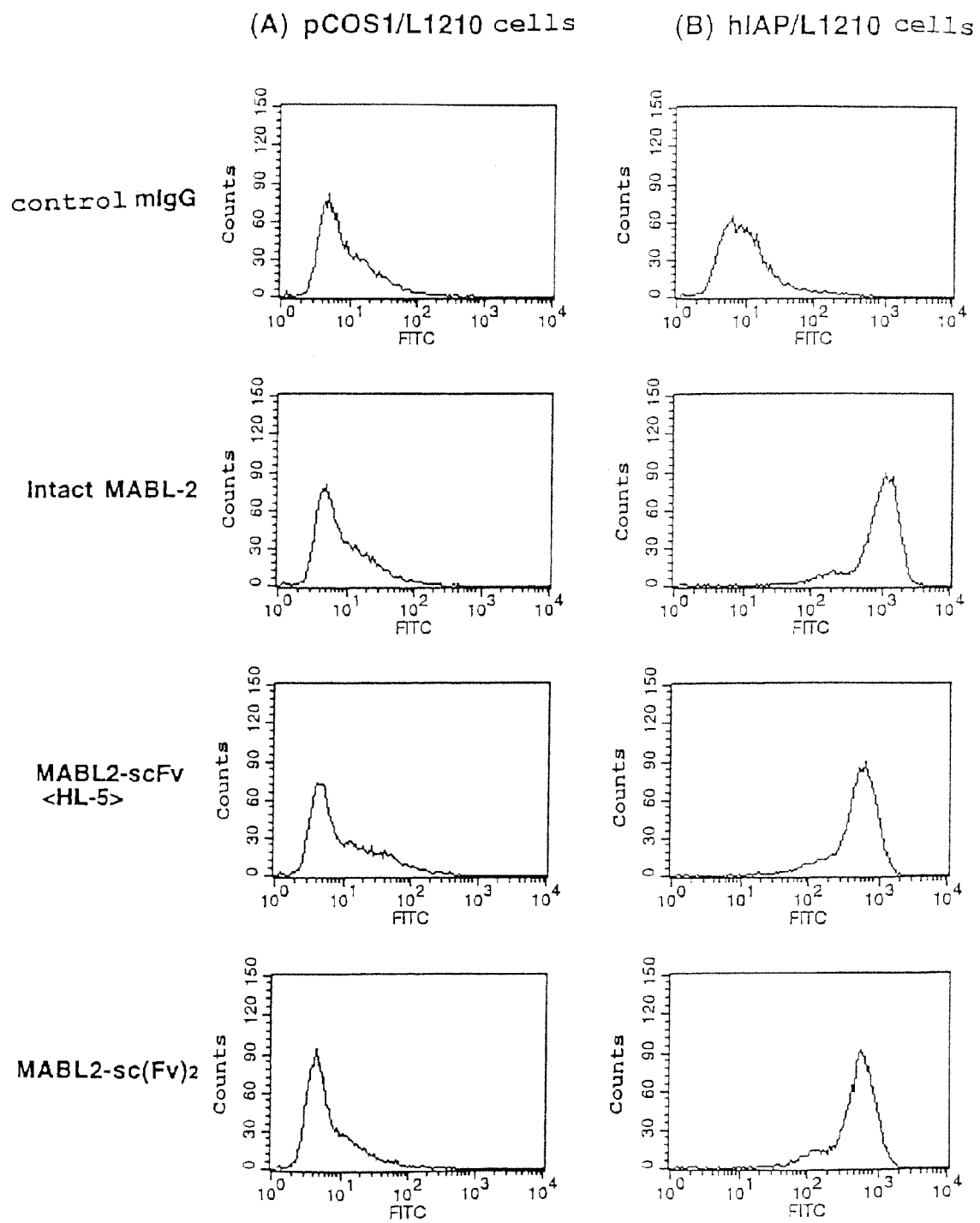
FIG. 42 shows the results of the evaluation of antigen binding capacity in Example 6.10.

Since the purified dimer of MABL2-scFv <HL-5> and the purified sc(Fv)$_2$ were specifically bound to hIAP/L1210 cells, it is confirmed that the dimer of scFv <HL-5> and the sc(Fv)$_2$ have high affinity to human LAP (see FIG. 42).

6.11 Apoptosis-Inducing Activity In Vitro of Purified Dimer of scFv <HL-5> and sc(Fv)$_2$ An apoptosis-inducing action of the purified dimer of MABL2-scFv <HL-5> and the purified sc(Fv)$_2$ were examined by Annexin-V staining (Boehringer Mannheim) using the L1210 cells (hIAP/L1210) in which human IAP gene had been introduced and cells of human leukemic cell line CCRF-CEM.

Figure 43:
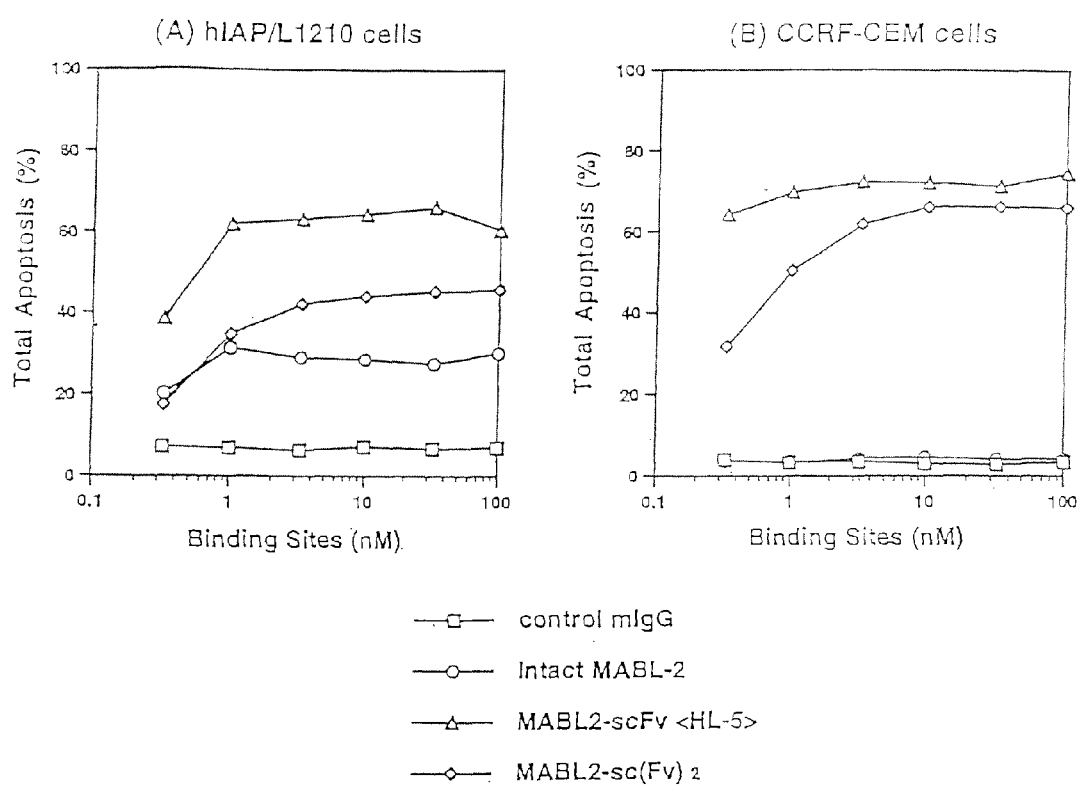
FIG. 43 shows the results of the in vitro apoptosis-inducing effect in Example 6.11.

Different concentrations of the purified dimer of MABL2-scFv <HL-5>, the purified MABL2-sc(Fv)$_2$, the antibody MABL-2 as a positive control or a mouse IgG as a negative control were added to 5×10⁴ cells of hIAP/L1210 cell line or 1×10⁵ cells of CCRF-CEM cell line. After culturing for 24 hours, the Annexin-V staining was carried out and the fluorescence intensity thereof was measured using the FACScan apparatus (BECTON DICKINSON). As a result the dimer of MABL2-scFv <HL-5> and the MABL2-sc(Fv)$_2$ remarkably induced cell death of hHIAP/L1210 and CCRF-CEM in concentration-dependent manner (see FIG. 43). As a result it was shown that the dimer of MABL2-scFv <HL-5> and MABL2-sc(Fv)$_2$, had improved efficacy of inducing apoptosis compared with original antibody MABL-2.

6.12 Hemagglutination Test of the Purified Dimer of scFv <HL-5> and the sc(Fv)$_2$ Hemagglutination test was carried out using different concentrations of the purified dimer of scFv <HL-5> and the purified sc(Fv)$_2$ in accordance with Example 5.15.

The hemagglutination was observed with the antibody MABL-2 as a positive control, whereas no hemagglutination was observed with both the single chain antibody MABL2-sc(Fv)$_2$ and the MABL2-scFv <HL-5>. Further, there was no substantial difference in the hemagglutination between two buffers employed with the antibody MABL-2. These results are shown in Table 3.

TABLE 3

Hemagglutination Test

Diluent: PBS (μg/ml)

| | cont | 28.9 | 14.45 | 7.225 | 3.6125 | 1.8063 | 0.9031 | 0.4516 | 0.2258 |
|---|---|---|---|---|---|---|---|---|---|
| MABL2-sc(Fv)$_2$ | − | − | − | − | − | − | − | − | − |
| | | 0.1129 | 0.0564 | 0.0282 | 0.0141 | 0.0071 | 0.0035 | 0.0018 | |
| MABL2-sc(Fv)$_2$ | | − | − | − | − | − | − | − | |
| | cont | 28.0 | 14.0 | 7.0 | 3.5 | 1.75 | 0.875 | 0.4375 | 0.2188 |
| MABL2-sc(Fv) <HL5> | − | − | − | − | − | − | − | − | − |
| | | 0.1094 | 0.0547 | 0.0273 | 0.0137 | 0.0068 | 0.0034 | 0.0017 | |
| MABL2-sc(Fv) <HL5> | | − | − | − | − | − | − | − | |
| | cont | 80 | 40 | 20 | 10 | 5 | 2.5 | 1.25 | 0.625 |
| MABL2 (intact) | − | + | + | + | + | + | + | + | + |
| mIgG | − | − | − | − | − | − | − | − | − |
| | | 0.3125 | 0.1563 | 0.0781 | 0.0391 | 0.0195 | 0.0098 | 0.0049 | |
| MABL2 (intact) | | + | ± | − | − | − | − | − | |
| mIgG | | − | − | − | − | − | − | − | |

Diluent: Acetate Buffer (μg/ml)

| | cont | 80 | 40 | 20 | 10 | 5 | 2.5 | 1.25 | 0.625 |
|---|---|---|---|---|---|---|---|---|---|
| MABL2 (intact) | − | + | + | + | + | + | + | + | + |

TABLE 3-continued

| Hemagglutination Test | | | | | | |
|---|---|---|---|---|---|---|
| 0.3125 | 0.1563 | 0.0781 | 0.0391 | 0.0195 | 0.0098 | 0.0049 |
| MABL2 (intact) + | + | + | − | − | − | − |

6.13 Antitumor Effect of the Purified Dimer of scFv <Hl-5> and the sc(Fv)$_2$ for a Model Mouse of Human Myeloma The antitumor effects were tested for the dimer of scFv <HL-5> and the sc(Fv)$_2$ prepared and purified in Examples 6.8 and 6.9. The test was performed by using the mouse model for human myeloma produced in Example 5.1 and determining the amount of M protein produced by human myeloma cells in the mouse serum using ELISA and examining survival time of the mice. Then, the antitumor effects of the dimer of scFv <HL-5> and the sc(Fv)$_2$ were evaluated in terms of the change of the amount of M protein in the mouse serum and the survival time of the mice.

In the test, the HL-5 and the sc(Fv)$_2$ were employed as a solution at 0.01, 0.1 or 1 mg/mL in vehicle consisting of 150 mM NaCl, 0.02% Tween and 20 mM acetate buffer, pH 6.0 and administered to the mice at 0.1, 1 or 10 mg/kg of dosage. Control group of mice were administered only with the vehicle.

Figure 44:
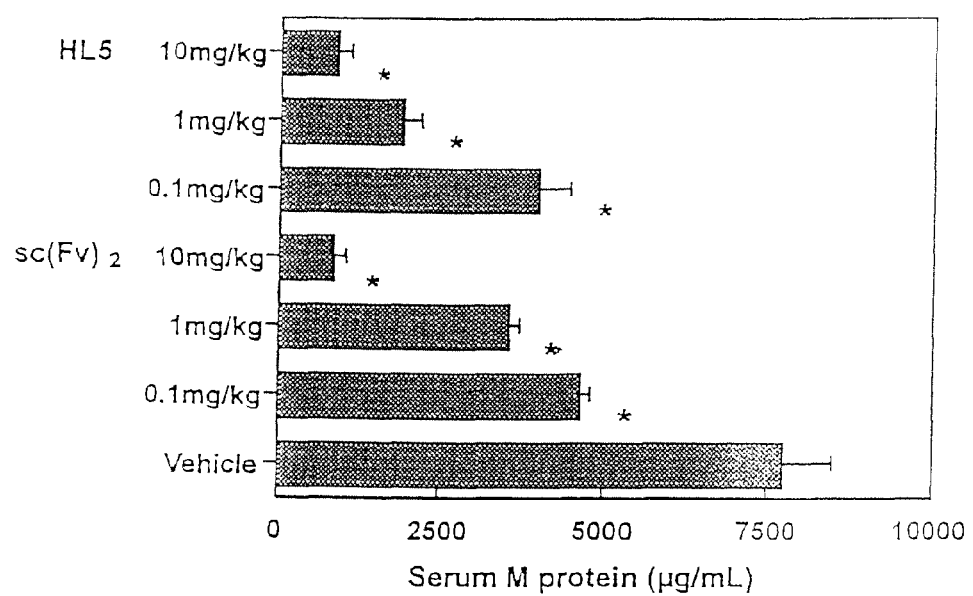
FIG. 44 shows the results of the quantitative measurement of M protein produced by a human myeloma cell line KPMM2 in the serum of the human myeloma celltransplanted mouse.
Figure 45:
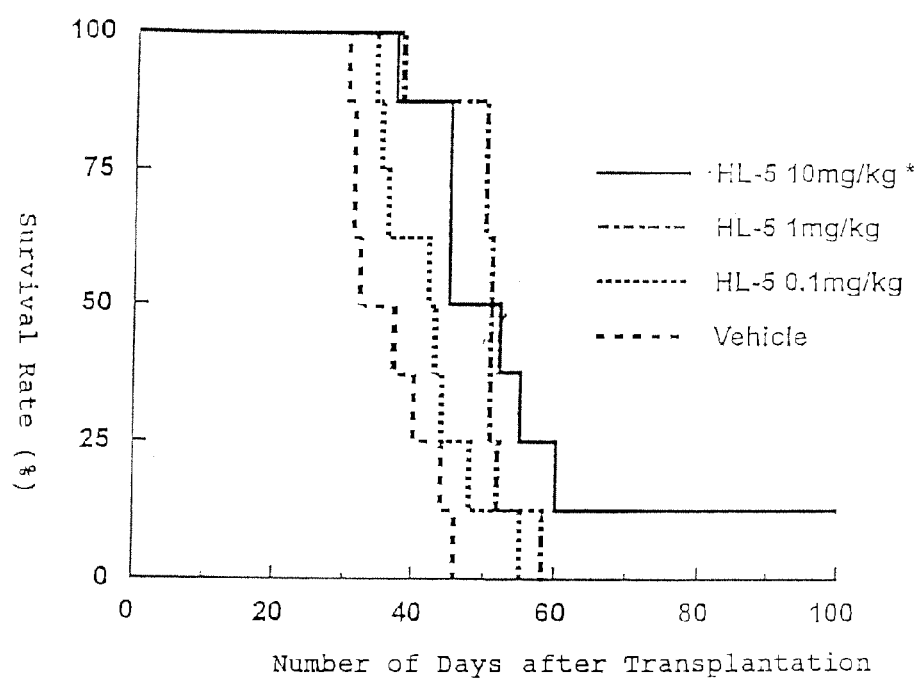
FIG. 45 shows the survival time (days) of mice after the transplantation of tumor.
Figure 46:
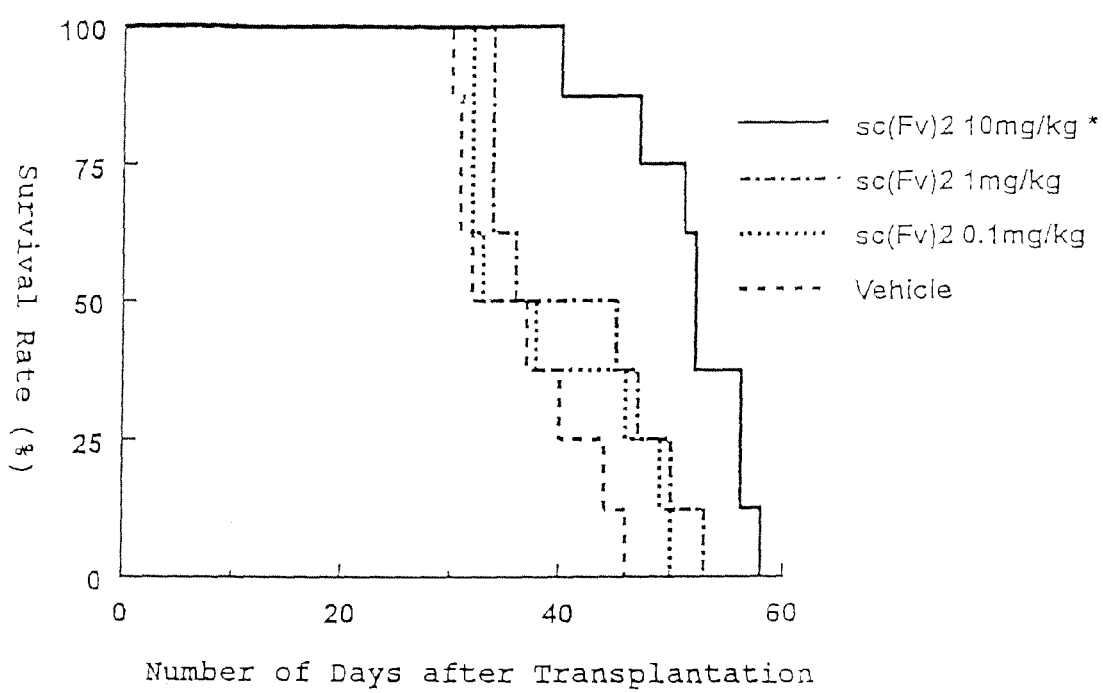
FIG. 46 shows the survival time (days) of mice after the transplantation of tumor.

The mouse serum was gathered 26 days after the transplantation of the human myeloma cells and the amount of M protein in the serum was measured using ELISA according to Example 5.14. As a result, the amount of M protein in the serum of both mice groups administered with HL-5, the dimer and the sc(Fv)$_2$ decreased in dose-dependent manner (see FIG. 44). Furthermore, a significant elongation of the survival time was observed in both groups administered with the HL-5 (FIG. 45) and with the sc(Fv)$_2$ (FIG. 46) in comparison with the control group administered with the vehicle. These results show that the HL-5 and the sc(Fv)$_2$ of the invention have excellent antitumor effect in vivo.

Example 7

Single Chain Fv Comprising H Chain V Region and L Chain V Region of Human Antibody 12B5 Against Human MPL A DNA encoding V regions of human monoclonal antibody 12B5 against human MPL was constructed as follows:
7.1 Construction of a Gene Encoding H Chain V Region of 12B5

The gene encoding H chain V region of human antibody 12B5 binding to human MPL was designed by connecting the nucleotide sequence of the gene thereof (SEQ ID NO: 55; encoded protein shown in SEQ ID NO: 128) at the 5'-end to the leader sequence (SEQ ID NO: 56; encoded protein shown in SEQ ID NO: 129) originated from human antibody gene (Eur. J. Immunol. 1996; 26: 63-69). The designed nucleotide sequence was divided into four oligonucleotides having overlapping sequences of 15 by each (12B5VH-1, 12B5VH-2, 12B5VH-3, 12B5VH-4). 12B5VH-1 (SEQ ID NO: 57) and 12B5VH-3 (SEQ ID NO: 59) were synthesized in the sense direction, and 12B5VH-2 (SEQ ID NO: 58) and 12B5VH-4 (SEQ ID NO: 60) in the antisense direction, respectively. After assembling each synthesized oligonucleotide by respective complementarity, the outside primers (12B5VH-S and 12B5VH-A) were added to amplify the full length of the gene. 12B5VH-S (SEQ ID NO: 61) was designed to hybridize to 5'-end of the leader sequence by the forward primer and to have Hind III restriction enzyme recognition site and Kozak sequence, and 12B5VH-A (SEQ ID NO: 62) was designed to hybridize to the nucleotide sequence encoding C-terminal of H chain V region by the reverse primer and to have a splice donor sequence and BamHI restriction enzyme recognition site, respectively.

100 μl of the PCR solution containing 10 μl of 10×PCR GOLD BUFFER II, 1.5 mM MgCl$_2$, 0.08 mM dNTPs (DATP, dGTP, dCTP, dTTP), 5 units of DNA-polymerase AMPLI-TAQ GOLD (all by PERKIN ELMER) and each 2.5 p mole of each synthesized oligonucleotide (12B5VH-1 to −4) was heated at 94° C. of the initial temperature for 9 minutes, at 94° C. for 2 minutes, at 55° C. for 2 minutes and 72° C. for 2 minutes. After repeating the cycle two times each 100 pmole of external primer 12B5VH-S and 12B5VH-A was added. The mixture was subjected to the cycle consisting of at 94° C. for 30 seconds, at 55° C. for 30 seconds and 72° C. for 1 minute 35 times and heated at 72° C. for further 5 minutes.

The PCR product was purified by 1.5% low-melting-temperature agarose gel (Sigma), digested by restriction enzymes BamHI and Hind III, and cloned into expression vector HEF-gγ1 for human H chain. After determining the DNA sequence the plasmid containing the correct DNA sequence was named HEF-12B5H-gγ1.

The HEF-12B5H-gγ1 was digested by restriction enzymes EcoRI and BamHI to produce the gene encoding 12B5VH which was then cloned into an expression vector pCOS-Fd for human Fab H chain to produce pFd-12B5H. The expression vector for human Fab H chain was constructed by amplifying the DNA (SEQ ID NO: 63) containing the intron region existing between the genes encoding human antibody H chain V region and the constant region, and the gene encoding a part of the constant region of human H chain by PCR, and inserting the PCR product into animal cell expression vector pCOS1. The human H chain constant region was amplified for the gene under the same conditions mentioned above using as the template HEF-gγ1, as the forward primer G1CH1-S (SEQ ID NO: 64) which was designed to hybridize to 5'-end sequence of intron 1 and to have restriction enzyme recognition sites EcoRI and BamHI and as the reverse primer G1CH1-A (SEQ ID NO: 65) which was designed to hybridize to 3'-end DNA of human H chain constant region CH1 domain and to have a sequence encoding a part of hinge region, two stop codons and restriction enzyme recognition site Bg1 II.

The nucleotide sequence (SEQ ID NO: 66) and amino acid sequence (SEQ ID NO: 131) of the reconstructed 12B5H chain variable region which were included in plasmids HEF-12B5H-gγ1 and pFd-12B5H are shown in SEQ ID NO: 66.
7.2 Construction of the Gene Encoding 12B5 L Chain V Region The gene encoding L chain V region of human antibody 12B5 binding to human MPL was designed by connecting the nucleotide sequence of gene (SEQ ID NO: 67; encoded protein shown in SEQ ID NO: 132) at the 5'-end to the leader sequence (SEQ ID NO: 68; encoded protein shown in SEQ ID NO: 133) originated from human antibody gene 3D6 (Nuc.

Acid Res. 1990: 18; 4927). In the same way as mentioned above the designed nucleotide sequence was divided into four oligonucleotides having overlapping sequences of 15 by each (12B5VL-1, 12B5VL-2, 12B5VL-3, 12B5VL-4) and synthesized respectively. 12B5VL-1 (SEQ ID NO: 69) and 12B5VL-3 (SEQ ID NO: 71) had sense sequences, and 12B5VL-2 (SEQ ID NO: 70) and 12B5VL-4 (SEQ ID NO: 72) had antisense sequences, respectively. Each of the synthesized oligonucleotides was assembled by respective complementarity and mixed with the external primer (12B5VL-S and 12B5VL-A) to amplify the full length of the gene. 12B5VL-S (SEQ ID NO: 73) was designed to hybridize to 5'-end of the leader sequence by the forward primer and to have Hind III restriction enzyme recognition site and Kozak sequence. 12B5VL-A (SEQ ID NO: 74) was designed to hybridize to the nucleotide sequence encoding C-terminal of L chain V region by the reverse primer and to have a splice donor sequence and BamHI restriction enzyme recognition site.

Performing the PCR as mentioned above, the PCR product was purified by 1.50 low-melting-temperature agarose gel (Sigma), digested by restriction enzymes BamHI and Hind III, and cloned into an expression vector HEF-gκ for human L chain. After determining the DNA sequence the plasmid containing the correct DNA sequence was named HEF-12B5L-gκ. The nucleotide sequence (SEQ ID NO: 75) and amino acid sequence (SEQ ID NO: 134) of the reconstructed 12B5 L chain V region which were included in plasmid HEF-12B5L-gκ are shown in SEQ ID NO: 75.

7.3 Production of Reconstructed 12B5 Single Chain Fv (scFv)

The reconstructed 12B5 antibody single chain Fv was designed to be in the order of 12B5VH-linker-12B5VL and to have FLAG sequence (SEQ ID NO: 76; encoded protein shown in SEQ ID NO: 135) at C-terminal to facilitate the detection and purification. The reconstructed 12B5 single chain Fv (sc12B5) was constructed using a linker sequence consisting of 15 amino acids represented by $(Gly_4Ser)_3$ (SEQ ID NO: 118).

Figure 47:
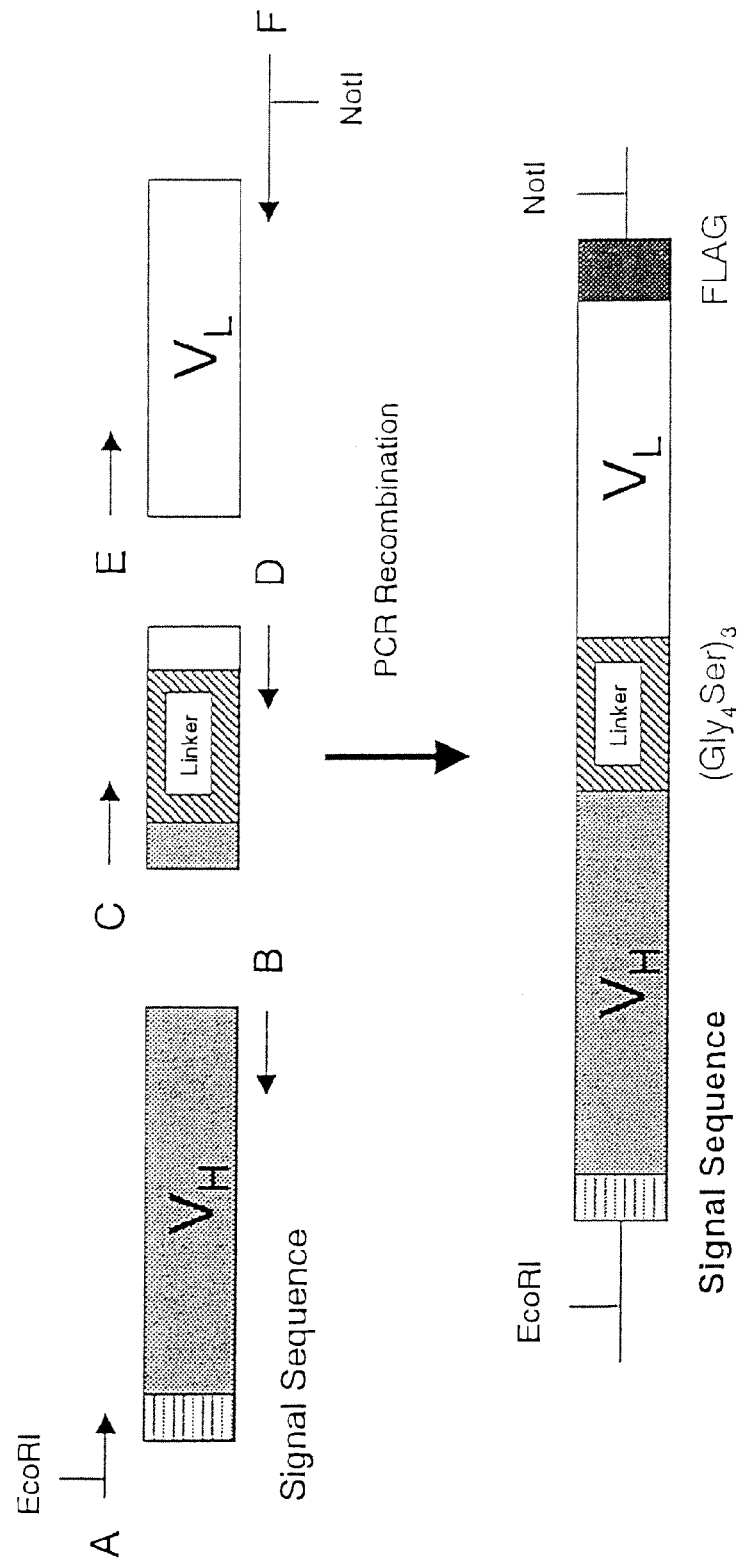
FIG. 47 is a scheme showing the method for constructing DNA fragment encoding the reconstructed 12B5 single chain Fv containing the linker sequence. The (Gly$_4$Ser)$_3$ linker is shown in SEQ ID NO:118.

(1) Production of the Reconstructed 12B5 Single Chain Fv Using the Linker Sequence Consisting of 15 Amino Acids The gene encoding the reconstructed 12B5 antibody single chain Fv, which contained the linker sequence consisting of 15 amino acids, was constructed by connecting 12B5 H chain V region, linker region and 12B5 L chain V region which was amplified by PCR respectively. This method is schematically shown in FIG. 47. Six PCR primers (A-F) were used for production of the reconstructed 12B5 single chain Fv. Primers A, C, and E had sense sequences, and primers B, D, and F had antisense sequences.

The forward primer 12B5-S (Primer A, SEQ ID NO: 77) for H chain V region was designed to hybridize to 5'-end of H chain leader sequence and to have EcoRI restriction enzyme recognition site. The reverse primer HuVHJ3 (Primer B, SEQ ID NO: 78) for H chain V region was designed to hybridize to DNA encoding C-terminal of H chain V region.

The forward primer RHuJH3 (Primer C, SEQ ID NO: 79) for the linker was designed to hybridize to DNA encoding the N-terminal of the linker and to overlap DNA encoding the C-terminal of H chain V region. The reverse primer RHuVK1 (Primer D, SEQ ID NO: 80) for the linker was designed to hybridize to DNA encoding the C-terminal of the linker and overlap DNA encoding the N-terminal of L chain V region.

The forward primer HuVK1.2 (Primer E, SEQ ID NO: 81) for L chain V region was designed to hybridize to DNA encoding the N-terminal of L chain V region. The reverse primer 12B5F-A for L chain V region (Primer F, SEQ ID NO: 82) was designed to hybridize to DNA encoding C-terminal of L chain V region and to have the sequence encoding FLAG peptide (Hopp, T. P. et al., Bio/Technology, 6, 1204-1210, 1988), two transcription stop codons and NotI restriction enzyme recognition site.

In the first PCR step, three reactions A-B, C-D, and E-F were performed, and the three PCR products obtained from the first step PCR were assembled by respective complementarity. After adding primers A and F the full length DNA encoding the reconstructed 12B5 single chain Fv having the linker consisting of 15 amino acids was amplified (the second PCR). In the first step PCR, the plasmid HEF12B5H-gγ1 (see Example 7. 1) encoding the reconstructed 12B5 H chain V region, pSCFVT7-hM21 (humanized ONS-M21 antibody) (Ohtomo et al., Anticancer Res. 18 (1998), 4311-4316) containing DNA (SEQ ID NO: 83) encoding the linker region consisting of Gly Gly Gly Gly Ser Gly Gly Gly Gly Ser Gly Gly Gly Gly Ser (SEQ ID NO: 136) (Huston et al., Proc. Natl. Acad. Sci. USA, 85, 5879-5883, 1988) and the plasmid HEF-12B5L-gκ (see Example 7. 2) encoding the reconstructed 12B5 L chain V region were used as templates, respectively.

50 μl of PCR solution for the first step contained 5 μl of 10×PCR GOLD BUFFER II, 1.5 mM $MgCl_2$, 0.08 mM dNTPs, 5 units of DNA polymerase AMPLITAQ GOLD (all by PERKIN ELMER), each 100 pmole of each primer and 10 ng of each template DNA. The PCR solution was heated at 94° C. of the initial temperature for 9 minutes, at 94 for 30 seconds, 55° C. for 30 seconds and 72° C. for 1 minute. After repeating the cycle 35 times the reaction mixture was further heated 72° C. for 5 minutes.

The PCR products A-B, C-D, and E-F were assembled by the second PCR. PCR mixture solution for the second step of 98 μl containing as the template 1>1 of the first PCR product A-B, 0.5 μl of PCR product C-D and 1 μl of PCR product E-F, 10 μl of 10×PCR GOLD BUFFER II, 1.5 mM $MgCl_2$, 0.08 mM dNTPs, 5 units of DNA polymerase AMPLITAQ GOLD (all by PERKIN ELMER) was heated at 94° C. of the initial temperature for 9 minutes, at 94° C. for 2 minutes, at 65° C. for 2 minutes and 72° C. for 2 minutes. After repeating the cycle two times, each 100 pmole of each of primers A and F were added. After repeating the cycle consisting of at 94° C. for 30 seconds, 55° C. for 30 seconds and 72° C. for 1 minute 35 times, the reaction mixture was heated at 72° C. for 5 minutes.

The DNA fragments produced by the second PCR were purified using 1.5% low-melting-temperature agarose gel, digested by EcoRI and NotI, and cloned into pCH01 vector and pCOS1 vector (Japanese Patent Application No. 8-255196). The expression vector pCH01 was a vector constructed by deleting the antibody gene from DHFR-ΔE-rvH-PM1-f (see WO92/19759) by EcoRI and SmaI digestion, and connecting to EcoRI-NotI-BamHI Adaptor (TAKARA SHUZO). After determining the DNA sequence the plasmids containing the DNA fragment encoding the correct amino acid sequence of reconstructed 12B5 single chain Fv were named pCHO-sc12B5 and pCOS-sc12B5. The nucleotide sequence (SEQ ID NO: 84) and amino acid sequence (SEQ ID NO: 137) of the Fv included in the plasmids shown in SEQ ID NO: 84.

7.4 Expression of Antibody 12B5 (IgG, Fab) and Single Chain Fv Polypeptide by Animal Cell Antibody 12B5 (IgG, Fab) and single chain Fv derived from antibody 12B5 were expressed by using COS-7 cells or CHO cells.

The transient expression using COS-7 cells was performed as follows. The transfection was performed by electroporation method using Gene Pulser equipment (BioRad). For the expression of antibody 12B5 (IgG) each 10 μg of the above-mentioned expression vector HEF-12B5H-gγ1 and HEF-12B5L-gκ were added, for the expression of 12B5Fab fragment each 10 μg of pFd-12B5H and HEF-12B5L-gκ were added and for the expression of single chain Fv 14 μg of pCOS-sc12B5 was added to COS-7 cells (1×10⁷ cells/ml) suspended in 0.8 ml of PBS. The mixture kept in a cuvette was treated by pulse at the capacity of 1.5 kV, 24 μFD. After recovering for 10 minutes in a room temperature the electroporated cells were added to DMEM culture medium (GIBCO BRL) containing 10% bovine fetal serum cultivated. After cultivating overnight the cells were washed once by PBS, added to serum-free medium CHO-S-SFM II and cultivated for 2 days. The culture medium was centrifuged to remove cell debris and filtered with 0.22 μm filter to prepare the culture supernatant.

To establish a stable expression CHO cell line for the single chain Fv (polypeptide) derived from antibody 12B5, the expression vector pCHO-sc12B5 was introduced into CHO cells as follows.

The expression vector was introduced into CHO cells by electroporation method using Gene Pulser equipment (Bio-Rad). Linearized DNA (100 μg) obtained by digestion with restriction enzyme PvuI and CHO cells (1×10⁷ cells/ml) suspended in 0.8 ml of PBS were mixed in a cuvette, left stationary on ice for 10 minutes and treated with pulse at the capacity of 1.5 kV, 25 μFD. After recovering for 10 minutes at a room temperature the electroporated cells were added to CHO-S-SFM II (GIBCO BRL) containing 10% bovine fetal serum and cultivated. After cultivating for 2 days the cultivation was continued in CHO-S-SFM II (GIBCO BRL) containing 5 nM methotrexate (SIGMA) and 10% bovine fetal serum. From thus obtained clones a clone with high expression rate was selected as the production cell line for 12B5 single chain Fv. After cultivating in serum-free medium CHO-S-SFM II (GIBCO BRL) containing 5 nM methotrexate (SIGMA), the culture supernatant was obtained by centrifugal separation of cell debris.

7.5 Purification of Single Chain Fv Derived from 12B5 Produced by CHO Cells

The culture supernatant of CHO cell line expressing 12B5 single chain Fv obtained in 7.4 was purified by ANTI-FLAG antibody column and gel filtration column.

(1) ANTI-FLAG Antibody Column

The culture supernatant was added to ANTI-FLAG M2 AFFINITY GEL (SIGMA) equilibrated by PBS. After washing the column by the same buffer the proteins adsorbed to the column were eluted by 0.1 M glycine-HCl buffer (pH 3.5). The eluted fractions were immediately neutralized by adding 1M Tris-HCl buffer (pH 8.0). The eluted fractions were analyzed by SDS-PAGE and the fraction which was confirmed to contain the single chain Fv was concentrated using Centricon-10 (MILLIPORE).

(2) Gel Filtration

The concentrated solution obtained in (1) was added to Superdex200 column (10×300 mm, AMERSHAM PHARMACIA) equilibrated by PBS containing 0.01% Tween20.

Figure 48:
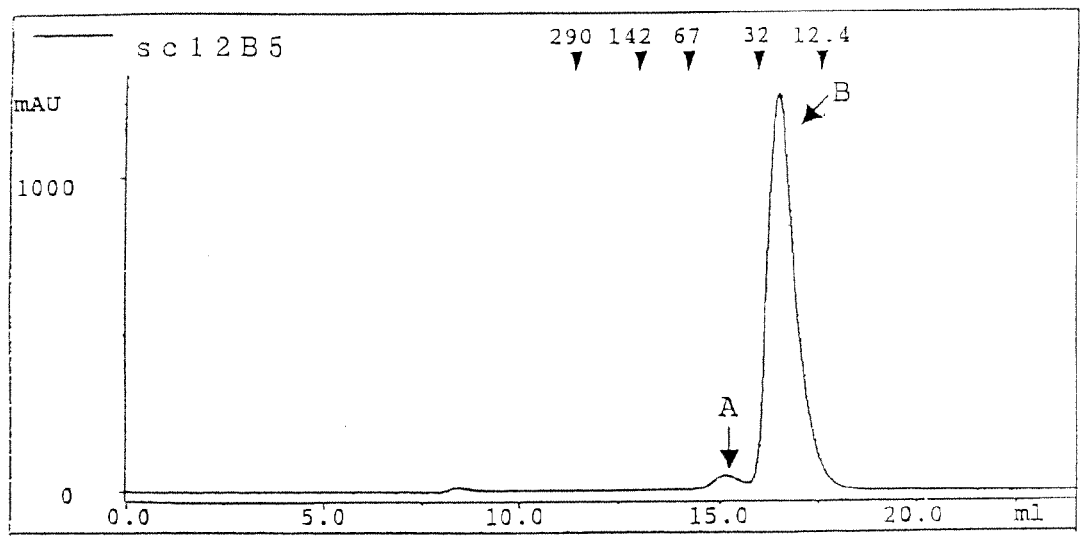
FIG. 48 shows the purification result of each 12B5 single chain Fv by gel filtration obtained in Example 7.5 (1).
Figure 49:
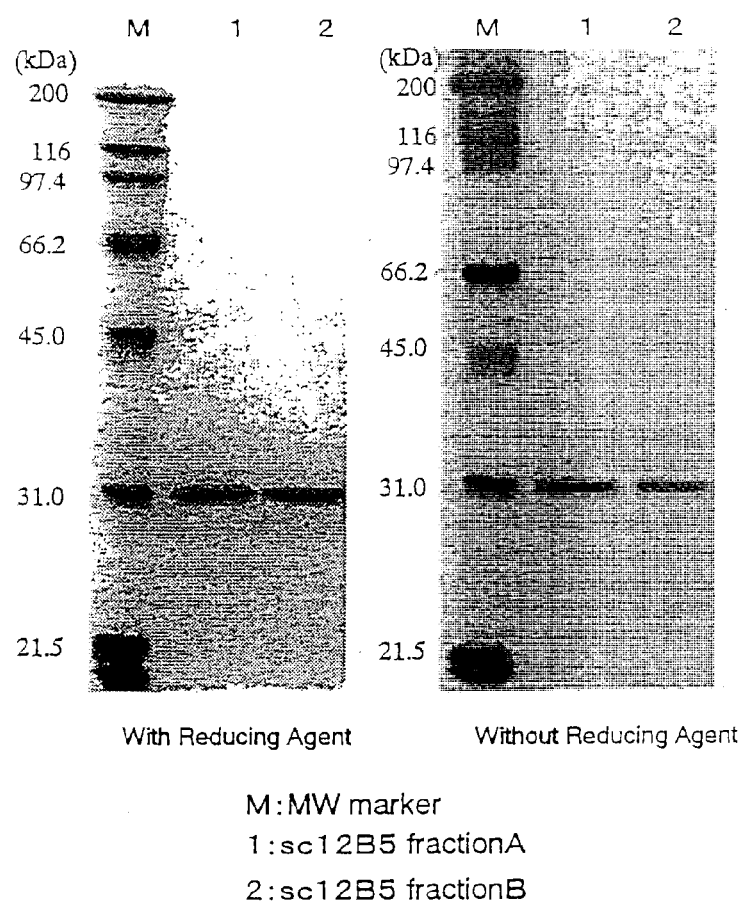
FIG. 49 shows the analytical result of each fraction A and B b SDS-PAGE performed in Example 7.5 (2).
Figure 50:
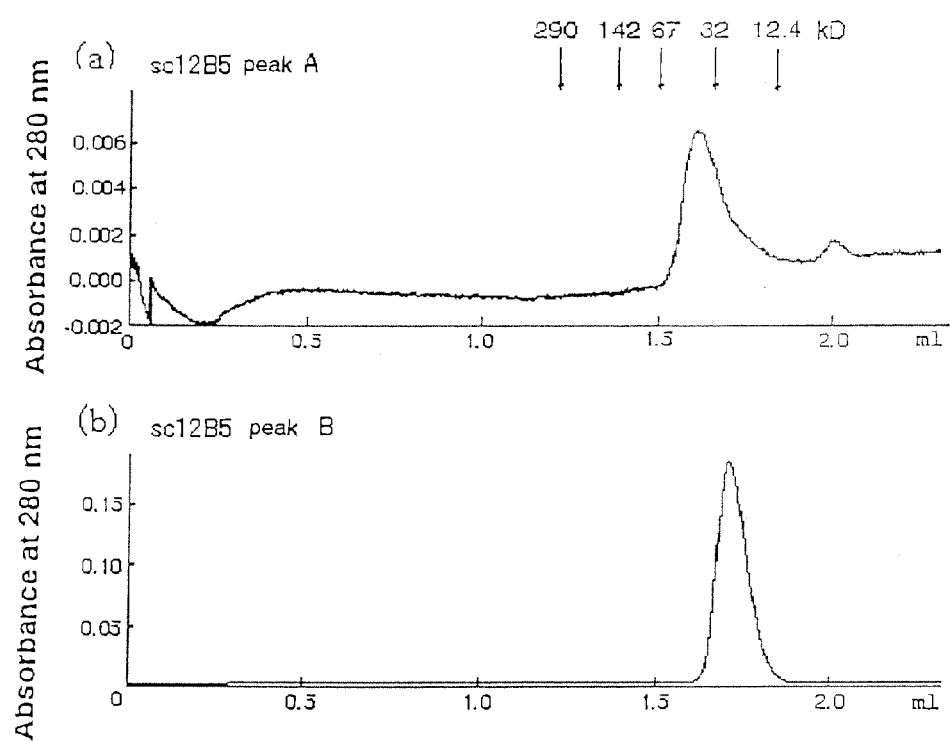
FIG. 50 shows the analytical result of each fraction A and B by Superdex200 column performed in Example 7.5 (2).

The product sc12B5 was eluted in two peaks (A, B) (see FIG. 48). The fractions A and B were analyzed using the 14%-SDS-polyacrylamide gel. The sample was processed by electrophoresis in the presence and absence of a reducing agent according to Laemmli method, and stained by Coomassie Brilliant Blue after the electrophoresis. As shown in FIG. 49 the fractions A and B, regardless of the presence of the reducing agent or its absence, produced a single band having an apparent molecular weight of about 31 kD. When the fractions A and B were analyzed by gel filtration using Superdex200 PC 3.2/30 (3.2×300 mm, AMERSHAM PHARMACIA), the fraction A produced an eluted product at an apparent molecular weight of about 44 kD and the fraction B produced at 22 kD (see FIGS. 50a and b). The results show that the fraction A is the non-covalent bond dimer of sc12B5 single chain Fv, and B is the monomer.

7.6 Measurement of TPO-Like Agonist Activity of Various Single Chain Fvs

The TPO-like activity of anti-MPL single chain antibody was evaluated by measuring the proliferation activity to Ba/F3 cells (BaF/mpl) expressing human TPO receptor (MPL). After washing BaF/Mpl cells two times by RPMI1640 culture medium (GIBCO) containing 10% bovine fetal serum (GIBCO), the cells were suspended in the culture medium at cell density of 5×10⁵ cells/ml. The anti-MPL single chain antibody and human TPO(R&D Systems) was diluted with the culture medium, respectively. 50 μl of the cell suspension and 50 μl of the diluted antibody or human TPO were added in 96-well microplate (flat bottom) (Falcon), and cultivated in $CO_2$ incubator ($CO_2$ concentration: 5%) for 24 hours. After the incubation 10 μl of WST-8 reagent (reagent for measuring the number of raw cells SF: Nacalai Tesque) was added and the absorbance was immediately measured at measurement wavelength of 450 nm and at refference wavelength of 620 nm using fluorescence absorbency photometer SPECTRA Fluor (TECAN). After incubating in $CO_2$ incubator ($CO_2$ concentration: 5%) for 2 hours, the absorbance at 450 nm of measurement wavelength and 620 nm of refference wavelength was again measured using SPECTRA Fluor. Since WST-8 reagent developed the color reaction depending upon the number of live cells at wavelength of 450 nm, the proliferation activity of BaF/Mpl based on the change of absorbance in 2 hours was evaluated by ED 50 calculated as follows. In the proliferation reaction curve wherein the absorbance was plotted on the ordinate against the antibody concentration on the abscissa, the absorbance at the plateau was set 100% reaction rate. Obtaining an approximation formula by straight line approximation method based on the plotted values close to 50% reaction rate, the antibody concentration of 50% reaction rate was calculated and adopted as ED 50.

Figure 51:
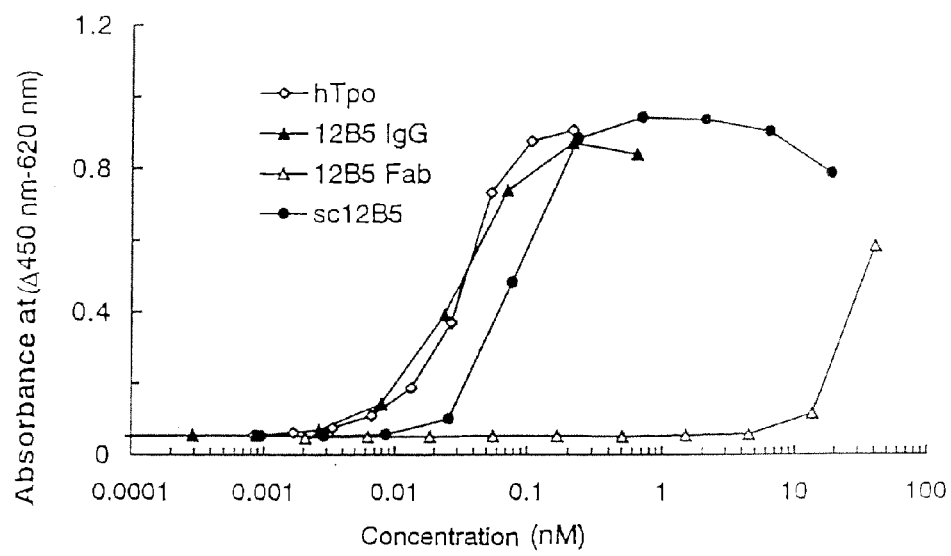
FIG. 51 shows the measurement result of the TPO-like agonist activity of sc12B5 and antibody 12B5.
Figure 52:
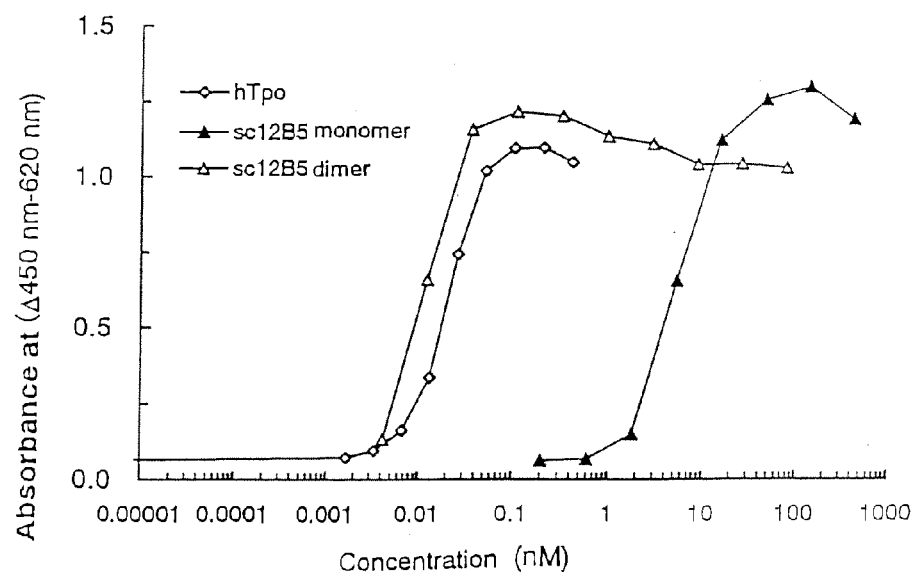
FIG. 52 shows the measurement result of TOP-like agonist activity of sc12B5 monomer and dimer.

The results of the agonist activity to MPL measured by using culture supernatants of COS-7 cells expressing various 12B5 antibody molecules showed as illustrated in FIG. 51 that 12B5IgG having bivalent antigen-binding site increased the absorbance in concentration-dependent manner and had TPO-like agonist activity (ED50; 29 nM), while the agonist activity of 12B5Fab having monovalent antigen-biding site was very weak (ED50; 34,724 nM). On the contrary the single chain Fv (sc12B5) having monovalent antigen-binding site like Fab showed strong agonist activity at a level that ED50 was 75 nM. However it has been known that variable regions of H chain and L chain of the single chain Fv are associated through non-covalent bond and, therefore, each variable region is dissociated in a solution and can be associated with variable region of other molecule to form multimers like dimers. When the molecular weight of sc12B5 purified by gel filtration was measured, it was confirmed that that there were molecules recognized to be monomer and dimer (see FIG. 48). Then monomer sc12B5 and dimer sc12B5 were isolated (see FIG. 50) and measured for the agonist activity to MPL. As shown in FIGS. 51 and 52, ED50 of sc12B5 monomer was 4438.7 nM, which confirmed that the agonist activity was reduced compared with the result using culture supernatant of COS-7 cells. On the contrary single chain Fv (sc12B5 dimer) having bivalent antigen-binding site showed about 400-fold stronger agonist activity (ED50; 10.1 nM) compared with monovalent sc12B5. Furthermore, the bivalent single chain Fv showed the agonist activity equivalent to or higher than the agonist activity of human TPO and 12B5IgG.

Example 8

Construction of a Gene Encoding the Variable Region of Human Antibody 12E10 Against Human MPL A DNA encoding variable region of human monoclonal antibody 12E10 against human MPL was constructed as follows:

8.1 Construction of a Gene Encoding 12E10 H Chain V Region

The nucleotide sequence SEQ ID NO:86 was designed as a gene encoding H chain V region of human antibody 12E10 binding to human MPL on the basis of the amino acid sequence described in WO99/10494 (SEQ ID NO:85). The full length of nucleotide sequence was designed by connecting to its 5'-end the leader sequence (SEQ ID NO:87; encoded protein shown in SEQ ID NO:138) derived from human antibody gene (GenBank accession No. AF062252). The designed nucleotide sequence was divided into four oligonucleotides having overlapping sequences of 15 by each (12E10VH1, 12E10VH2, 12E10VH3, 12E10VH4), 12E10VH1 (SEQ ID NO: 88) and 12E10VH3 (SEQ ID NO: 90) were synthesized in the sense direction, and 12E10VH2 (SEQ ID NO: 89) and 12E10VH4 (SEQ ID NO: 91) in the antisense direction, respectively. After assembling each synthesized oligonucleotide by respective complementarity, the external primers (12E10VHS and 12E10VHA) were added to amplify the full length of the gene. 12E10VHS (SEQ ID NO: 92) was designed to hybridize to 5'-end of the leader sequence by the forward primer and to have Hind III restriction enzyme recognition site and Kozak sequence, and 12E10VHA (SEQ ID NO: 93) was designed to hybridize to the nucleotide sequence encoding C-terminal of H chain V region by the reverse primer and to have a splice donor sequence and BamHI restriction enzyme recognition site, respectively.

100 μl of the PCR solution containing 10 μl of 10×PCR GOLD BUFFER II, 1.5 mM MgCl$_2$, 0.08 mM dNTPs (dATP, dGTP, dCTP, dTTP), 5 units of DNA-polymerase AMPLITAQ GOLD (all by PERKIN ELMER) and each 2.5 pmole of each synthesized oligonucleotide (12E10VH-1 to -4) was heated at 94° C. of the initial temperature for 9 minutes, at 94° C. for 2 minutes, at 55° C. for 2 minutes and 72° C. for 2 minutes. After repeating the cycle two times each 100 pmole of external primer 12E10VHS and 12E10VHA were added. The mixture was subjected to the cycle consisting of at 94° C. for 30 seconds, at 55° C. for 30 seconds and 72° C. for 1 minute 35 times and heated at 72° C. for further 5 minutes.

The PCR product was purified by 1.5% low-melting-temperature agarose gel (Sigma), digested by restriction enzymes BamHI and Hind III, and cloned into a human H chain expression vector HEF-gγ1. After determining the DNA sequence the plasmid containing the correct DNA sequence was named HEF-12E10H-gγ1.

The HEF-12E10H-gγ1 was digested by restriction enzymes EcoRI and BamHI to produce the gene encoding 12E10VH and then cloned into a human Fab H chain expression vector pCOS-Fd to produce pFd-12E10H. The human Fab H chain expression vector was constructed by amplifying the DNA (SEQ ID NO: 63; encoded protein shown in SEQ ID NO: 130) containing the intron region existing between the genes encoding human antibody H chain V region and the constant region, and the gene encoding a part of the human H chain constant region by PCR, and inserting the PCR product into animal cell expression vector pCOSb. The human H chain constant region was amplified for the gene under the same conditions mentioned above using as the template HEF-gγ1, as the forward primer G1CH1-S (SEQ ID NO: 64) which was designed to hybridize to 5'-end sequence of intron 1 and to have restriction enzyme recognition sites EcoRI and BamHI and as the reverse primer G1CH1-A (SEQ ID NO: 65) which was designed to hybridize to 3'-end DNA of human H chain constant region CR1 domain and to have a sequence encoding a part of hinge region, two stop codons and restriction enzyme recognition site Bg1 H.

The nucleotide sequence (SEQ ID NO: 94) and amino acid sequence (SEQ ID NO: 139) of the reconstructed 12E10 H chain variable region which were included in plasmids HEF-12E10H-gγ1 and pFd-12E10H are shown in SEQ ID NO: 94.

8.2 Construction of a Gene Encoding 12E10 L Chain V Region

The nucleotide sequence SEQ ID NO:96 was designed as a gene encoding L chain V region of human antibody12E10 binding to human MPL on the basis of the amino acid sequence described in WO99/10494 (SEQ ID NO:95). It was further designed by connecting to its 5'-end the leader sequence (SEQ ID NO: 97; encoded protein shown in SEQ ID NO: 140) derived from human antibody gene (Mol. Immunol. 1992; 29: 1515-1518). In the same way as mentioned above the designed nucleotide sequence was divided into four oligonucleotides having overlapping sequences of 15 by each (12E10VL1, 12E10VL2, 12E10VL3, 12E10VL4) and synthesized respectively. 12E10VL1 (SEQ ID NO: 98) and 12E10VL3 (SEQ ID NO: 100) had sense sequences, and 12E10VL2 (SEQ ID NO: 99) and 12E10VL4 (SEQ ID NO: 101) had antisense sequences, respectively. Each of the synthesized oligonucleotides was assembled by respective complementarity and mixed with the external primers (12E10VLS and 12E10VLA) to amplify the full length of the gene. 12E10VLS (SEQ ID NO: 102) was designed to hybridize to 5'-end of the leader sequence by the forward primer and to have EcoRI restriction enzyme recognition site and Kozak sequence. 12E10VLA (SEQ ID NO: 103) was designed to hybridize to the nucleotide sequence encoding C-terminal of L chain V region by the reverse primer and to have a B1 nI restriction enzyme recognition site.

Performing the PCR as mentioned above, the PCR product was purified by 1.5% low-melting-temperature agarose gel (Sigma), digested by restriction enzymes EcoRI and BinI, and cloned into pUCl9 containing a gene for human lambda chain constant region. After determining the DNA sequence the plasmid containing the correct DNA sequence was digested by EcoRI to produce a gene encoding 12E10 L chain V region and human lambda chain constant region and then inserted in expression vector pCOS1. The plasmid having 12E10 L chain gene (SEQ ID NO: 104; encoded protein shown in SEQ ID NO: 141) was named pCOS-12E10L.

8.3 Production of reconstructed 12E10 single chain Fv

The reconstructed 12E10 antibody single chain Fv was designed to be in the order of 12E10VH-linker-12E10VL and to have FLAG sequence (SEQ ID NO: 105; encoded protein shown in SEQ ID NO: 142) at C-terminal to facilitate the detection and purification. The reconstructed b2E10 chain Fvs (sc12E10 and db12E10) were constructed using a linker sequence consisting of 15 amino acids represented by (Gly$_4$Ser)$_3$ (SEQ ID NO: 118) or 5 amino acids represented by (Gly$_4$Ser)$_1$ (SEQ ID NO: 176).

The gene encoding the reconstructed 12E10 single chain Fv, which contained the linker sequence consisting of 5 amino acids, was constructed by introducing the nucleotide sequence for the linker (Gly$_4$Ser)$_1$ (SEQ ID NO:176) to 3'-end of the gene encoding 12E10 H chain V region and to 5'-end of the gene encoding 12E10 L chain V region, amplifying thus obtained respective gene by PCR and connecting the amplified genes. Four PCR primers (A-D) were used to produce the reconstructed 12E10 single chain Fv. Primers A and C had sense sequences, and primers B and D had antisense sequences.

The forward primer for H chain V region was 12E10S (Primer A, SEQ ID NO: 106). The reverse primer DB2 (Primer B, SEQ ID NO: 107) for H chain V region was designed to hybridize to DNA encoding C-terminal of H chain V region and to have the nucleotide sequence encoding the linker (Gly$_4$Ser)$_1$ (SEQ ID NO: 176) and the nucleotide sequence encoding N-terminal of L chain V region.

The forward primer DB1 (Primer C, SEQ ID NO: 108) for L chain V region was designed to hybridize to DNA encoding the N-terminal of L chain V region and to have the nucleotide sequence encoding the linker (Gly$_4$Ser)$_1$ (SEQ ID NO: 176) and the nucleotide sequence encoding C-terminal of H chain V region. The reverse primer 12E10FA (Primer D, SEQ ID NO: 109) for L chain V region was designed to hybridize to DNA encoding the C-terminal of L chain V region and to have the nucleotide sequence encoding FLAG and NotI restriction enzyme recognition site.

In the first PCR step, two reactions A-B and C-D were performed, and the two PCR products obtained from the first step PCR were assembled by respective complementarity. After adding primers A and D the full length DNA encoding the reconstructed 12E10 single chain Fv having the linker consisting of 5 amino acids was amplified (the second PCR). In the first step PCR, the plasmid HEF-12E10H-gγ1 (see Example 8.2) encoding the reconstructed 12E10 H chain V region and pCOS-12E10L (see Example 8.1) encoding the reconstructed 12E10 L chain V region were used as templates, respectively.

50 μl of the first step PCR solution contained 5 μl of 10×PCR GOLD BUFFER II, 1.5 mM MgCl$_2$, 0.8 mM dNTPs, 5 units of DNA polymerase AMPLITAQ GOLD (by PERKIN ELMER), each 100 pmole of each primer and 100 ng of each template DNA. The PCR solution was heated at 94° C. of the initial temperature for 9 minutes, at 94 for 30 seconds, 55° C. for 30 seconds and 72° C. for 1 minute. After repeating the cycle 35 times the reaction mixture was further heated at 72° C. for 5 minutes.

The PCR products A-B (429 bp) and C-D (395 bp) were assembled by the second PCR. The second step PCR mixture solution (9811) containing 1 μl each of the first PCR product A-B and C-D as templates, 100 pmole each of each primer, 10 μl of 10×PCR GOLD BUFFER II, 1.5 mM MgCl$_2$, 0.08 mM dNTPs and 5 units of DNA polymerase AMPLITAQ GOLD (by PERKIN ELMER) was reacted under the same conditions as mentioned above.

The DNA fragment of 795 bp produced by the second PCR was purified using 1.5% low-melting-temperature agarose gel, digested by EcoRI and NotI, and cloned into pCH01 vector or constructed by deleting the antibody gene from DHFR-ΔE-RVH-PM1-f (see WO92/19759) by EcoRI and SmaI digestion, and connecting to EcoRI-NotI-Bam-HI Adaptor (TAKARA SHUZO). After determining the DNA sequence the plasmids containing the DNA fragment encoding the correct amino acid sequence of reconstructed 12E10 single chain Fv were named pCHO-db12E10 and pCOS-db12E10. The nucleotide sequence (SEQ ID NO: 110) and amino acid sequence (SEQ ID NO: 143) of the reconstructed 12E10 single chain Fv included in the plasmids pCHO-db12E10 and pCOS-db12E10 are shown in SEQ ID NO: 110.

(2) Production of the Reconstructed 12E10 Single Chain Fv Using the Linker Sequence Consisting of 15 Amino Acids The gene encoding the reconstructed 12E10 antibody single chain Fv, which contained the linker sequence consisting of 15 amino acids, was constructed by introducing the nucleotide sequence for the linker (Gly$_4$Ser)$_3$ (SEQ ID NO: 118) to 3'-end of the gene encoding b2E10 H chain V region and to 5'-end of the gene encoding 12E10 L chain V region, amplifying thus obtained respective gene by PCR and connecting the amplified genes. Four PCR primers (A-D) were used for production of the reconstructed 12E10 single chain Fv. Primers A and C had sense sequences, and primers B and D had antisense sequences.

The forward primer for H chain V region was 12E10S (Primer A, SEQ ID NO: 106). The reverse primer sc4.3 (Primer 3, SEQ ID NO: 111) for H chain V region was designed to hybridize to DNA encoding C-terminal of H chain V region and to have the nucleotide sequence encoding the linker (Gly$_4$Ser)$_3$ (SEQ ID NO: 118) and the nucleotide sequence encoding N-terminal of L chain V region.

The forward primer sc1.3 (Primer C, SEQ ID NO: 112) for L chain V region was designed to hybridize to DNA encoding the N-terminal of L chain V region and to have the nucleotide sequence encoding the linker (Gly$_4$Ser)$_3$ (SEQ ID NO: 118) and the nucleotide sequence encoding C-terminal of H chain V region. The reverse primer 12E10FA (Primer D, SEQ ID NO: 109) for L chain V region was designed to hybridize to DNA encoding the C-terminal of L chain V region and to have the nucleotide sequence encoding FLAG and NotI restriction enzyme recognition site.

In the first PCR step, two reactions A-B and C-D were performed, and the two PCR products obtained from the first step PCR were assembled by respective complementarity. After adding primers A and D the full length DNA encoding the reconstructed 12E10 single chain Fv having the linker consisting of 15 amino acids was amplified (the second PCR). In the first step PCR, the plasmid pCOS-db12E10 (see Example 8.3(1)) encoding the reconstructed 12E10 single chain Fv was used as template.

50 μl of the first step PCR solution contained 5 μl of 10× ExTaq Buffer, 0.4 mM dNTPs, 2.5 units of DNA polymerase TaKaRa ExTaq (by TAKARA), each 100 pmole of each primer and 10 ng of each template DNA. The PCR solution was heated at 94° C. of the initial temperature for 30 seconds, at 94 for 15 seconds and 72° C. for 2 minute, and the cycle was repeated 5 times. After repeating 28 times the cycle of at 94° C. for 15 seconds and at 70° C. for 2 minutes, the reaction mixture was further heated at 72° C. for 5 minutes.

The PCR products A-B (477 bp) and C-D (447 bp) were assembled by the second PCR. The second step PCR mixture solution (98 μl) containing 1 μl each of the first PCR products A-B and C-D as templates, 100 pmole each of each primer A and D, 5 μl of 10× ExTaq Buffer, 0.4 mM dNTPs, 2.5 units of DNA polymerase TaKaRa ExTaq (by TAKARA) was reacted under the same conditions as mentioned above.

The DNA fragment of 825 bp produced by the second PCR was purified using 1.0% low-melting-temperature agarose gel, digested by EcoRI and NotI. Thus obtained DNA fragment was cloned into pCHO1 vector or pCOS1 vector. After determining the DNA sequence the plasmids containing the DNA fragment encoding the correct amino acid sequence of reconstructed 12E10 single chain Fv were named pCHO-sc12E10 and pCOSsc12E10. The nucleotide sequence (SEQ ID NO: 113) and amino acid sequence (SEQ ID NO: 144) of the reconstructed 12E10 single chain Fv included in the plasmids pCHO-sc12E10 and pCOS-sc12E10 are shown in SEQ ID NO: 113.

8.4 Expression of Antibody 12E10 (IgG, Fab) and Single Chain Fv Polypeptide by Animal Cell Antibody 12E10 (IgG, Fab) and single chain Fv derived from antibody 12E10 (linker sequence 5 amino acids, 15 amino acids) were expressed by using COS-7 cells or CHO cells.

The transient expression using COS-7 cells was performed as follows. The transfection was performed by electroporation method using Gene Pulser II equipment (BioRad). For the expression of antibody 12E10 (IgG) each 10 µg of the above-mentioned expression vector HEF-12E10H-gγ1 and pCOs-12E10L were added, for the expression of 12E10Fab fragment each 10 µg of pFd-12E10H and pCOs-12E10L were added and for the expression of single chain Fv of pCOS-sc12E10 (10 µg) or pCOS-db12E10 (10 µg) was added to COS-7 cells ($1 \times 10^7$ cells/ml) suspended in 0.8 ml of PBS. The mixture kept in a cuvette was treated by pulse at the capacity of 1.5 kV, 25 µFD. After recovering for 10 minutes in a room temperature the electroporated cells were added to DMEM medium (GIBCO BRL) containing 10% bovine fetal serum and cultivated. After cultivating overnight the cells were washed once by PBS, added to serum-free medium CHO-S-SFM II (GIBCO BRL) and cultivated for 3 days. The culture supernatant was centrifuged to remove cell debris and filtered with 0.22 µm filter.

To establish a stable expression CHO cell line for the single chain Fv (polypeptide) derived from antibody 12E10, the expression vector pCHO-sc12E10 or pCHO-ds12E10 was introduced into CHO cells respectively.

Each expression vector was introduced into CHO cells by electroporation method using Gene Pulser II equipment (Bio-Rad). Linearized DNA (100 µg) obtained by digestion with restriction enzyme PvuI and CHO cells ($1 \times 10^7$ cells/ml) suspended in 0.8 ml of PBS were mixed in a cuvette, left stationary on ice for 10 minutes and treated with pulse at the capacity of 1.5 kV, 25 µFD. After recovering for 10 minutes at a room temperature the electroporated cells were added to CHO-S-SFM II medium (GIBCO BRL) containing 10% dialyzed bovine fetal serum and nucleic acid and cultivated. After cultivating for 2 days the cultivation was continued in nucleic acid-free CHO-S-SFM II medium (GIBCO BRL) containing 10% dialyzed bovine fetal serum. From thus obtained clones a clone with high expression rate was selected as the production cell line for 12E10 single chain Fv. After cultivating in serum-free CHO-S-SFM II medium (GIBCO BRL), the culture supernatant was centrifuged to remove cell debris and filtered with 0.22 µm filter.

8.5 Purification of Single Chain Fv Derived from 12E10 Produced by CHO Cells The culture supernatants produced by CHO cell lines expressing 12E10 single chain Fvs (sc12E10, db12E10) obtained in Example 8.4 were purified by ANTI-FLAG antibody column and gel filtration column respectively to produce purified single chain Fvs.

(1) Purification with ANTI-FLAG Antibody Column

Each culture supernatant (sc12E10, db12E10) was added to ANTI-FLAG M2 AFFINITY GEL column (SIGMA) equilibrated by 50 mM Tris-HCl buffer (pH7.4) containing 150 mM NaCl. After washing the column by the same buffer the proteins adsorbed to the column were eluted by 100 mM glycine buffer (pH 3.5). The eluted fractions were immediately neutralized by adding 1M Tris-HCl buffer (pH 8.0) and analyzed by SDS-PAGE. The fraction which was confirmed to contain the single chain Fv was pooled and concentrated about 20-fold using Centricon-10 (AMICON).

(2) Gel Filtration

Figure 53:
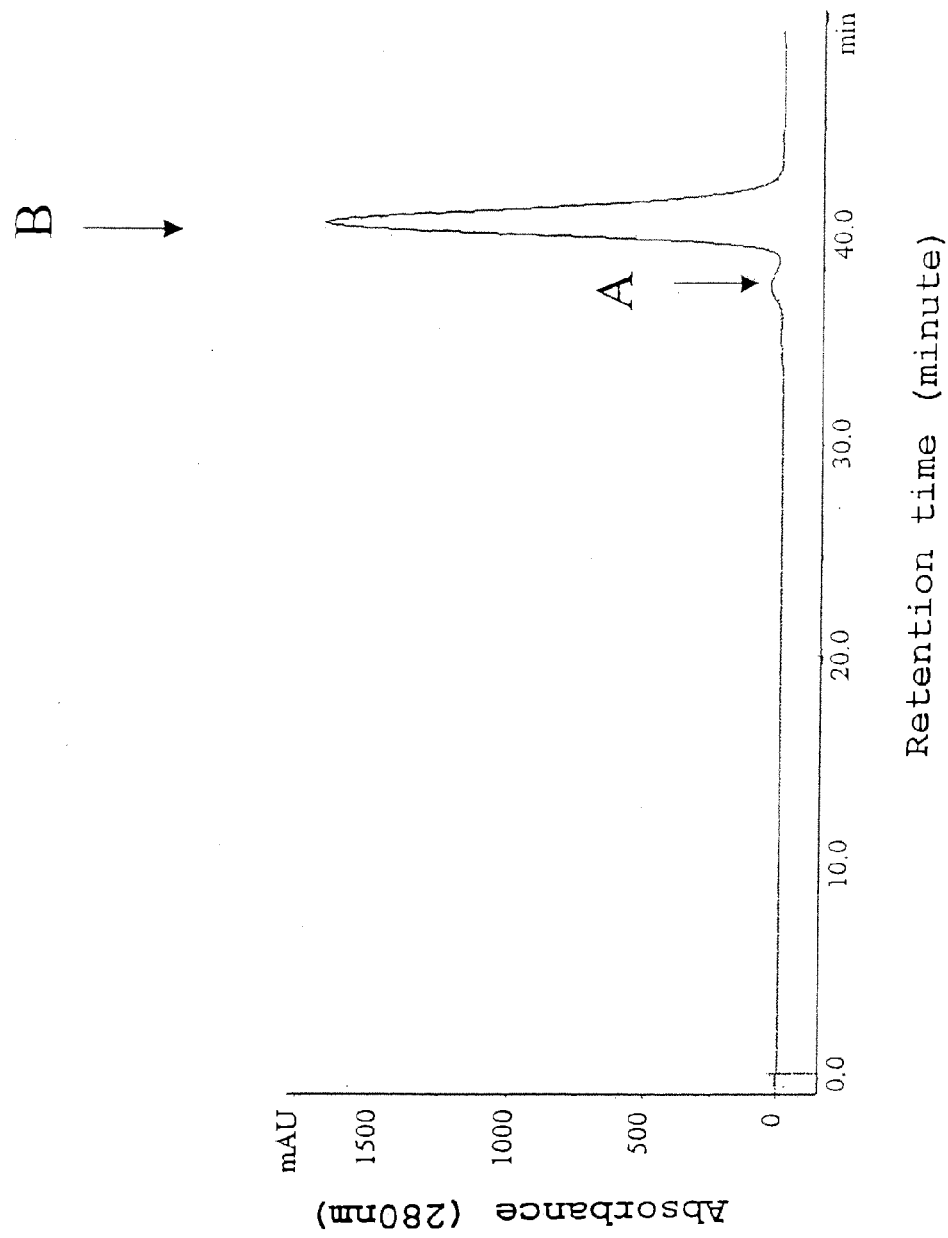
FIG. 53 shows the purification result of obtained sc12E10 single chain antibody by gel filtration chromatography using SUPERDEX200HR column.
Figure 54:
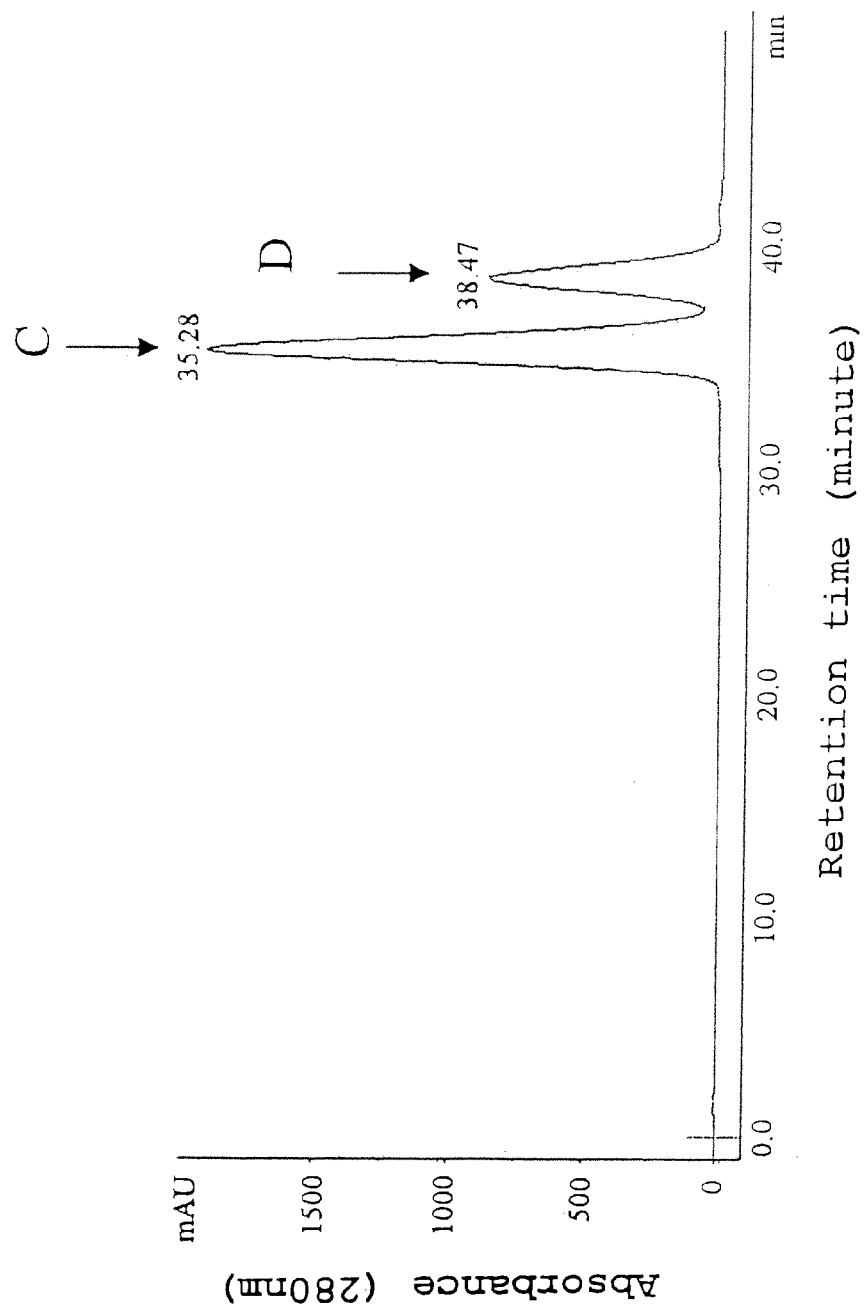
FIG. 54 shows the purification result of obtained db12E10 single chain antibody by gel filtration chromatography using SUPERDEX200HR column.
Figure 55:
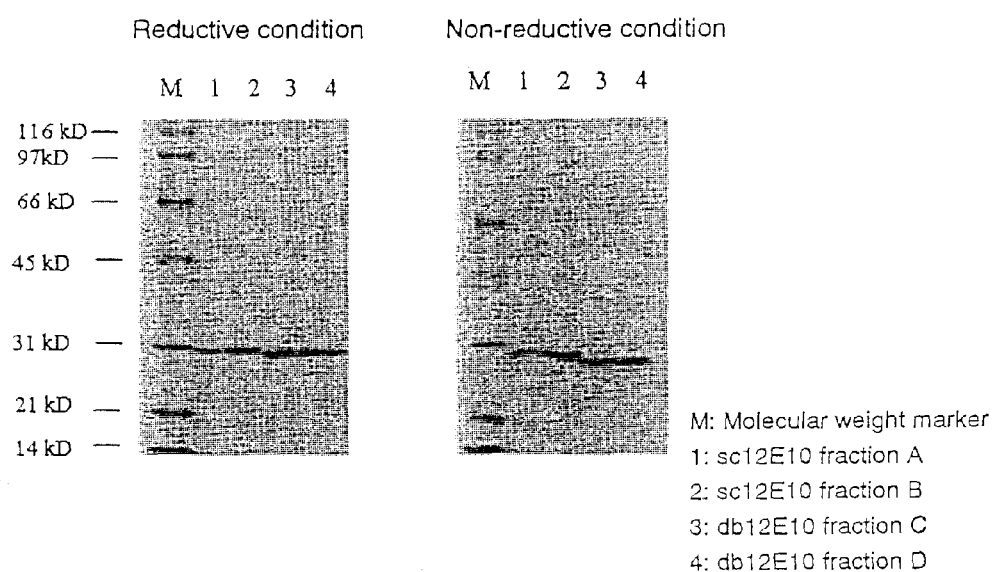
FIG. 55 shows SDS-PAGE analysis of fractions A and B (sc12E10) and fractions C and D (db12E10) under the reductive or non-reductive condition.
Figure 56:
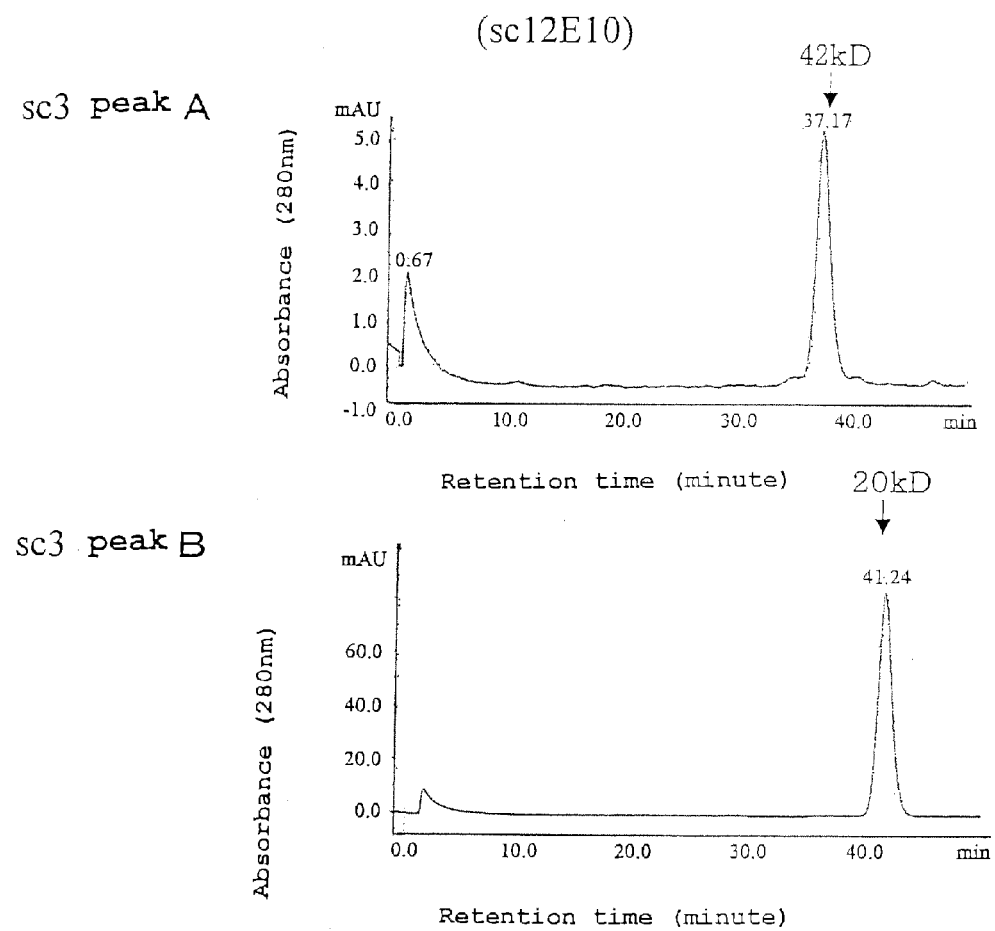
FIG. 56 shows the analytical result of fractions A and B by gel filtration chromatography using SUPERDEX200HR column.
Figure 57:
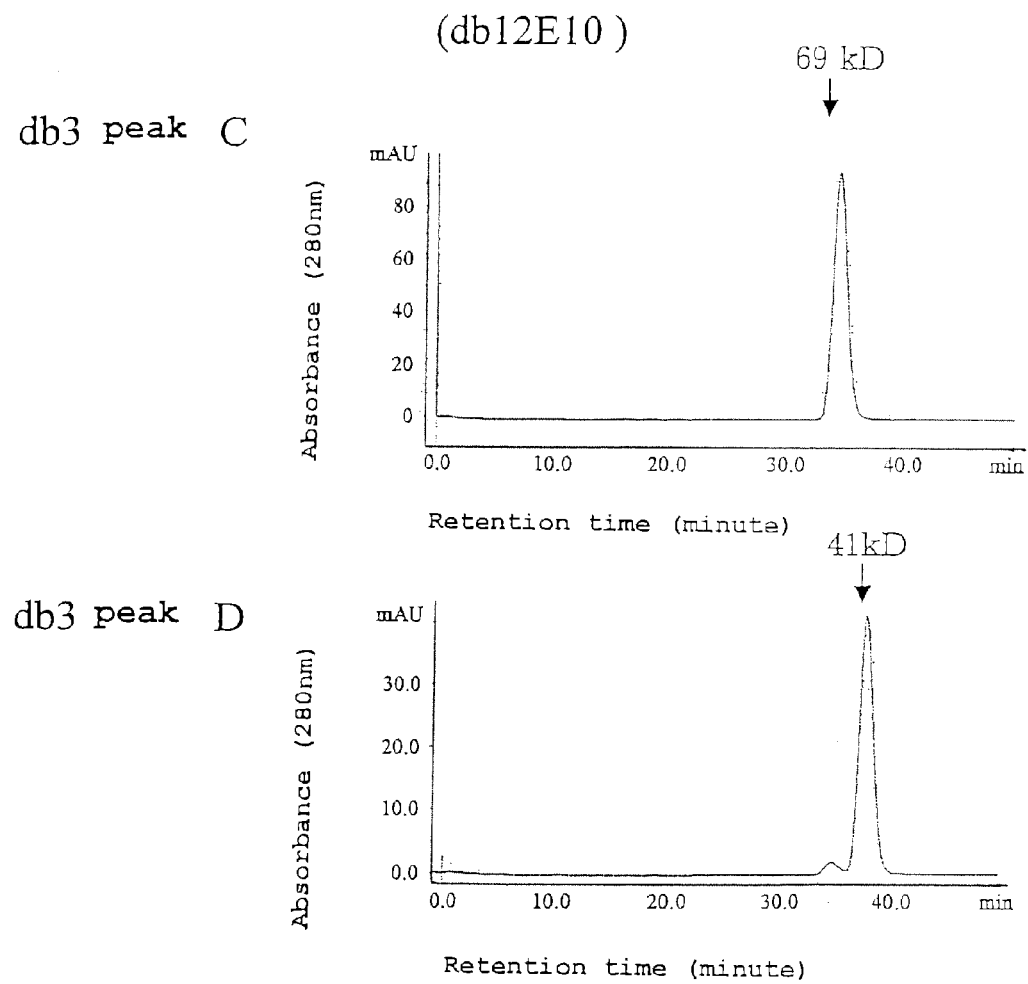
FIG. 57 shows the analytical result of fractions C and D by gel filtration chromatography using SUPERDEX200HR column.

The concentrated solution obtained in (1) was added to Superdex200 column HR (10×300 mm, AMERSHAM PHARMACIA) equilibrated by PBS containing 0.01% Tween20. Chlomatograms were shown in FIGS. 53 and 54. The product sc12E10 was eluted in two peaks (A, B) (see FIG. 53). The product db12E10 was eluted in two peaks (C, D) (see FIG. 54). Each peak fraction was collected, treated in the presence and absence of a reducing agent, processed by electrophoresis according to Laemmli method and stained by Coomassie Brilliant Blue after the electrophoresis. As shown in FIG. 55 the all of fractions A, B, C and D, regardless of the presence or absence of the reducing agent, produced a single band having an apparent molecular weight of about 31 kD. When these fractions were analyzed by gel filtration using Superdex200 HR. the fraction A produced a product eluted at an apparent molecular weight of about 42 kD, the fraction B at 20 kD (see FIG. 56), fraction C at 69 kD and fraction D at 41 kD (see FIG. 57). The results suggest that sc12E10-derived fraction A is the non-covalent bond dimer of single chain Fv and the fraction B is the monomer of single chain Fv, and the db12E10-derived fraction C is the non-covalent bond trimer of single chain Fv and D is non-covalent bond dimer of single chain Fv.

8.6 Measurement of TPO-Like Agonist Activity of Various Single Chain Fvs

The TPO-like activity of anti-mpl single chain antibody was evaluated by measuring the proliferation activity to Ba/F3 cells (BaF/mpl) expressing human TPO receptor (MPL).

After washing BaF/mpl cells two times by RPMI1640 medium (GIBCO) containing 1% bovine fetal serum (GIBCO), the cells were suspended in the medium at cell density of $5 \times 10^5$ cells/mL. The anti-MPL single chain antibody or human TPO (R&D Systems) was diluted with the medium, respectively. 50 µl of the cell suspension and 50 µl of the diluted antibody or human TPO were added in 96-well microplate (flat bottom) (Corning), and cultivated in $CO_2$ incubator ($CO_2$ concentration: 5%) for 24 hours. After the incubation 10 µl of WST-8 reagent (reagent for measuring the number of raw cells SF: Nacalai Tesque) was added and the absorbance was immediately measured at measurement wavelength of 450 nm and at reference wavelength of 655 nm using absorbency photometer Benchmark Plus (BioRad). After incubating in $CO_2$ incubator ($CO_2$ concentration: 5%) for 2 hours, the absorbance at 450 nm of measurement wavelength and 655 nm of reference wavelength was again measured using Benchmark Plus. Since WST-8 reagent developed the color reaction depending upon the number of live cells at wavelength of 450 nm, the proliferation activity of BaF/mpl was evaluated based on the change of absorbance in 2 hours.

Figure 58:
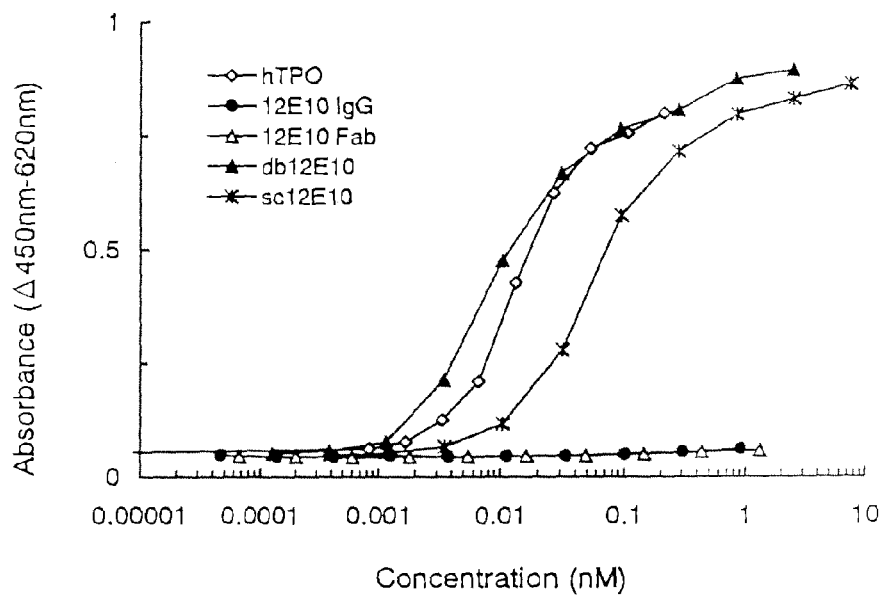
FIG. 58 is a graph showing the agonist activity of various 12E10 antibody molecules on MPL, illustrating that single chain Fvs (sc12E10, db12E10).

The agonist activity to MPL measured by using culture supernatants of COS-7 cells expressing various 12E10 antibody molecules are shown in FIG. 58. Single chain Fvs having the 5-amino-acid-linker (ds12E10) and the 15-amino-acid-linker (sc12E10) increased the absorbance in concentration-dependent manner, showing TPO-like agonist activity (ED50; 9 pM and 51 pM respectively), while 12E10IgG and 12E10Fab had no activity.

Figure 59:
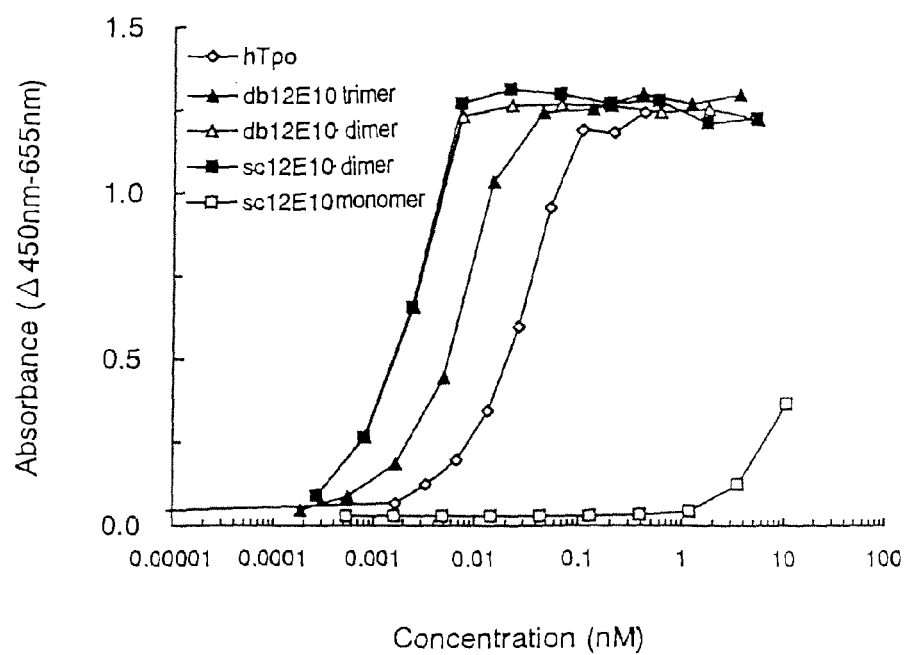
FIG. 59 is a graph showing the agonist activity of monomer and dimer of sc12E10 and dimer and trimer of db12E10 on MPL.

It has been known that H chain and L chain of the single chain Fv are associated not only within a molecule but also between molecules to form multimers such as dimer. When the culture supernatants of CHO cells expressing single chain Fvs of 12E10 were gel filtrated and tested for agonist activity on MPL. The results were shown in FIG. 59. The dimer, which was contained in sc12E10 in a small amount, showed about 5000-fold stronger TPO-like agonist activity (sc12E10 dimer, ED50; 1.9 pM) compared with the monomer (sc12E10 monomer, ED50; >10 nM). The activity was higher than that of TPO (ED50; 27 pM). The dimer of db12E10 (db12E10 dimer, ED50; 2.0 pM) showed strong activity comparable to that of sc12E10 dimer. db12E10 trimer (ED50; 7.4 pM), which was presumed to be a trimer from molecular weight obtained by gel filtration, showed a high activity which is lower than that of db12E10 dimer. Those results suggest that it is important for the activity of agonist antibody 12E10 that the antigen-binding site is bivalent (dimer). Considering the fact that 12E10 IgG had no activity, other factors than being bivalent are presumed to be important such as the location of antigen-binding site, the distance or the angle.

INDUSTRIAL APPLICABILITY

The modified antibodies of the invention have an agonist action capable of transducing a signal into cells by crosslinking a cell surface molecule(s) and are advantageous in that the permeability to tissues and tumors is high due to the lowered molecular size compared with antibody molecule (whole IgG). This invention provides the modified antibodies with an agonist activity remarkably higher than TPO or parent antibodies (whole IgG). Especially even parent antibodies without agonist activity can be altered into the modified antibodies with an agonist activity higher than TPO. Therefore the modified antibodies can be used as signal-transducing agonists. The modification of antibody molecule results in the reduction of side effects caused by intercellular crosslinking and provides novel medicines inducing only required action by crosslinking a cell surface molecule(s). Medical preparations containing as active ingredient the modified antibodies of the invention are useful as preventives and/or remedies for platelet-related-blood diseases, thrombocytopenia caused by chemotherapy for cancers or leukemia and the like.

The invention claimed is:

1. An isolated DNA that encodes a modified antibody comprising two H chain V regions and two L chain V regions of an antibody, showing TPO agonist action by crosslinking TPO receptors of the same cell, wherein:
   said modified antibody is a dimer of single chain Fv comprising one H chain V region and one L chain V region, wherein the H chain V region and L chain V region are connected through a peptide linker having 15 amino acids, and
   at least one of the H chain V regions comprises a polypeptide having a sequence encoded by SEQ ID NO. 66 or SEQ ID NO. 94, and/or at least one of the L chain V regions comprises a polypeptide having a sequence encoded by SEQ ID NO. 75 or SEQ ID NO. 104.

2. The isolated DNA of claim 1, wherein the modified antibody further comprises an amino acid sequence(s) for peptide purification.

3. The isolated DNA of claim 1, wherein the modified antibody is a mono-specific modified antibody.

4. The isolated DNA of claim 1, wherein the modified antibody is a multi-specific modified antibody.

5. The isolated DNA of claim 1, wherein the modified antibody is a bi-specific modified antibody.

6. The isolated DNA of claim 1, wherein the two L chain V regions and the two H chain V regions are from the same monoclonal antibody.

7. The isolated DNA of claim 1, wherein the modified antibody substantially has no intercellular adhesion action.

8. The isolated DNA of claim 1, wherein the modified antibody has a TPO agonist action equivalent to or greater than that of thrombopoietin.

9. An isolated DNA that encodes a modified antibody comprising two H chain V regions and two L chain V regions of an antibody, showing TPO agonist action by crosslinking TPO receptors of the same cell, wherein:
   said modified antibody is a dimer of a single chain Fv comprising one H chain V region and one L chain V region,
   at least one of the H chain V regions comprises a polypeptide having a sequence encoded by SEQ ID NO. 66 or SEQ ID NO. 94, and/or at least one of the L chain V regions comprises a polypeptide having a sequence encoded by SEQ ID NO. 75 or SEQ ID NO. 104, and
   the peptide linker that connects the H chain V region and L chain V region is selected from the group consisting of:

```
Gly-Gly-Ser

Ser-Gly-Gly

Gly-Gly-Gly-Ser                  (SEQ ID NO: 174)

Ser-Gly-Gly-Gly                  (SEQ ID NO: 175)

Gly-Gly-Gly-Gly-Ser              (SEQ ID NO: 176)

Ser-Gly-Gly-Gly-Gly              (SEQ ID NO: 177)

Gly-Gly-Gly-Gly-Gly-Ser          (SEQ ID NO: 178)

Ser-Gly-Gly-Gly-Gly-Gly          (SEQ ID NO: 179)

Gly-Gly-Gly--Gly-Gly-Gly-Ser     (SEQ ID NO: 180)

Ser-Gly-Gly-Gly-Gly-Gly-Gly.     (SEQ ID NO: 181)
```

10. An animal cell that produces a modified antibody comprising two H chain V regions and two L chain V regions of an antibody, showing TPO agonist action by crosslinking TPO receptors of the same cell, wherein:
    said modified antibody is a dimer of single chain Fv comprising one H chain V region and one L chain V region, wherein the H chain V region and L chain V region are connected through a peptide linker having 15 amino acids, and
    at least one of the H chain V regions comprises a polypeptide having a sequence encoded by SEQ ID NO. 66 or SEQ ID NO. 94, and/or at least one of the L chain V regions comprises a polypeptide having a sequence encoded by SEQ ID NO. 75 or SEQ ID NO. 104.

11. The animal cell of claim 10, wherein the modified antibody further comprises an amino acid sequence(s) for peptide purification.

12. The animal cell of claim 10, wherein the modified antibody is a mono-specific modified antibody.

13. The animal cell of claim 10, wherein the modified antibody is a multi-specific modified antibody.

14. The animal cell of claim 10, wherein the modified antibody is a bi-specific modified antibody.

15. The animal cell of claim 10, wherein the two L chain V regions and the two H chain V regions are from the same monoclonal antibody.

16. The animal cell of claim 10, wherein the modified antibody substantially has no intercellular adhesion action.

17. The animal cell of claim 10, wherein the modified antibody has a TPO agonist action equivalent to or greater than that of thrombopoietin.

18. An animal cell which produces a modified antibody comprising two H chain V regions and two L chain V regions of an antibody, showing TPO agonist action by crosslinking TPO receptors of the same cell, wherein:
said modified antibody is a dimer of a single chain Fv comprising one H chain V region and one L chain V region,
at least one of the H chain V regions comprises a polypeptide having a sequence encoded by SEQ ID NO. 66 or SEQ ID NO. 94, and/or at least one of the L chain V regions comprises a polypeptide having a sequence encoded by SEQ ID NO. 75 or SEQ ID NO. 104,
the peptide linker that connects the H chain V region and L chain V region is selected from the group consisting of:

```
Gly-Gly-Ser

Ser-Gly-Gly

Gly-Gly-Gly-Ser              (SEQ ID NO: 174)

Ser-Gly-Gly-Gly              (SEQ ID NO: 175)

Gly-Gly-Gly-Gly-Ser          (SEQ ID NO: 176)

Ser-Gly-Gly-Gly-Gly          (SEQ ID NO: 177)

Gly-Gly-Gly-Gly-Gly-Ser      (SEQ ID NO: 178)

Ser-Gly-Gly-Gly-Gly-Gly      (SEQ ID NO: 179)

Gly-Gly-Gly--Gly-Gly-Gly-Ser (SEQ ID NO: 180)

Ser-Gly-Gly-Gly-Gly-Gly-Gly. (SEQ ID NO: 181)
```

19. A microorganism that produces a modified antibody comprising two H chain V regions and two L chain V regions of an antibody, showing TPO agonist action by crosslinking TPO receptors of the same cell, wherein:
said modified antibody is a dimer of single chain Fv comprising one H chain V region and one L chain V region, wherein the H chain V region and L chain V region are connected through a peptide linker having 15 amino acids, and
at least one of the H chain V regions comprises a polypeptide having a sequence encoded by SEQ ID NO. 66 or SEQ ID NO. 94, and/or at least one of the L chain V regions comprises a polypeptide having a sequence encoded by SEQ ID NO. 75 or SEQ ID NO. 104.

20. The microorganism of claim 19, wherein the modified antibody further comprises an amino acid sequence(s) for peptide purification.

21. The microorganism of claim 19, wherein the modified antibody is a mono-specific modified antibody.

22. The microorganism of claim 19, wherein the modified antibody is a multi-specific modified antibody.

23. The microorganism of claim 19, wherein the modified antibody is a bi-specific modified antibody.

24. The microorganism of claim 19, wherein the two L chain V regions and the two H chain V regions are from the same monoclonal antibody.

25. The microorganism of claim 19, wherein the modified antibody substantially has no intercellular adhesion action.

26. The microorganism of claim 19, wherein the modified antibody has a TPO agonist action equivalent to or greater than that of thrombopoietin.

27. A microorganism which produces a modified antibody comprising two H chain V regions and two L chain V regions of an antibody, showing TPO agonist action by crosslinking TPO receptors of the same cell, wherein:
said modified antibody is a dimer of a single chain Fv comprising one H chain V region and one L chain V region,
at least one of the H chain V regions comprises a polypeptide having a sequence encoded by SEQ ID NO. 66 or SEQ ID NO. 94, and/or at least one of the L chain V regions comprises a polypeptide having a sequence encoded by SEQ ID NO. 75 or SEQ ID NO. 104,
the peptide linker that connects the H chain V region and L chain V region is selected from the group consisting of:

```
Gly-Gly-Ser

Ser-Gly-Gly

Gly-Gly-Gly-Ser              (SEQ ID NO: 174)

Ser-Gly-Gly-Gly              (SEQ ID NO: 175)

Gly-Gly-Gly-Gly-Ser          (SEQ ID NO: 176)

Ser-Gly-Gly-Gly-Gly          (SEQ ID NO: 177)

Gly-Gly-Gly-Gly-Gly-Ser      (SEQ ID NO: 178)

Ser-Gly-Gly-Gly-Gly-Gly      (SEQ ID NO: 179)

Gly-Gly-Gly--Gly-Gly-Gly-Ser (SEQ ID NO: 180)

Ser-Gly-Gly-Gly-Gly-Gly-Gly. (SEQ ID NO: 181)
```

* * * * *

SEQUENCE LISTING

```
<160> NUMBER OF SEQ ID NOS: 183

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: PCR primer

<400> SEQUENCE: 1
ccatcctaat acgactcact atagggc                                         27

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: PCR primer

<400> SEQUENCE: 2
ggatcccggg tggatggtgg gaagatg                                         27

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: PCR primer

<400> SEQUENCE: 3
ggatcccggg ccagtggata gacagatg                                        28

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: PCR primer

<400> SEQUENCE: 4
ggatcccggg agtggataga ccgatg                                          26

<210> SEQ ID NO 5
<211> LENGTH: 394
<212> TYPE: DNA
<213> ORGANISM: Mus sp.
```

-continued

```
<220> FEATURE:
<221> NAME/KEY: CDS
<222> LOCATION: (1)..(393)
<223> OTHER INFORMATION: pGEM-M1L.
<220> FEATURE:
<221> NAME/KEY: sig_peptide
<222> LOCATION: (1)..(57)
<220> FEATURE:
<221> NAME/KEY: mat_peptide
<222> LOCATION: (58)..(393)

<400> SEQUENCE: 5 atg aag ttg cct gtt agg ctg ttg gtg ctg atg ttc tgg att cct gcg    48
Met Lys Leu Pro Val Arg Leu Leu Val Leu Met Phe Trp Ile Pro Ala
            -15                 -10                 -5 tcc agc agt gat gtt gtg atg acc caa act cca ctc tcc ctg cct gtc    96
Ser Ser Ser Asp Val Val Met Thr Gln Thr Pro Leu Ser Leu Pro Val
     -1   1               5                  10 agt ctt gga gat caa gcc tcc atc tct tgc aga tct agt cag agc ctt   144
Ser Leu Gly Asp Gln Ala Ser Ile Ser Cys Arg Ser Ser Gln Ser Leu
        15                  20                  25 cta cac agt aaa gga aac acc tat tta caa tgg tac cta cag aag cca   192
Leu His Ser Lys Gly Asn Thr Tyr Leu Gln Trp Tyr Leu Gln Lys Pro
 30                  35                  40                  45 ggc cag tct cca aag ctc ctg atc tac aaa gtt tcc aac cga ttt tct   240
Gly Gln Ser Pro Lys Leu Leu Ile Tyr Lys Val Ser Asn Arg Phe Ser
             50                  55                  60 ggg gtc cca gac agg ttc agt ggc agt gga tca ggg aca gat ttc aca   288
Gly Val Pro Asp Arg Phe Ser Gly Ser Gly Ser Gly Thr Asp Phe Thr
         65                  70                  75 ctc aag atc agc aga gtg gag gct gag gat ctg gga gtt tat ttc tgc   336
Leu Lys Ile Ser Arg Val Glu Ala Glu Asp Leu Gly Val Tyr Phe Cys
     80                  85                  90 tct caa agt aca cat gtt ccg tac acg tcc gga ggg ggg acc aag ctg   384
Ser Gln Ser Thr His Val Pro Tyr Thr Ser Gly Gly Gly Thr Lys Leu
 95                 100                 105 gaa ata aaa c                                                     394
Glu Ile Lys
110

<210> SEQ ID NO 6
<211> LENGTH: 409
<212> TYPE: DNA
<213> ORGANISM: Mus sp.
<220> FEATURE:
<221> NAME/KEY: CDS
<222> LOCATION: (1)..(408)
<223> OTHER INFORMATION: pGEM-M1H
<220> FEATURE:
<221> NAME/KEY: sig_peptide
<222> LOCATION: (1)..(57)
<220> FEATURE:
<221> NAME/KEY: mat_peptide
<222> LOCATION: (58)..(408)

<400> SEQUENCE: 6 atg gaa tgg agc tgg ata ttt ctc ttc ctc ctg tca gga act gca ggt    48
Met Glu Trp Ser Trp Ile Phe Leu Phe Leu Leu Ser Gly Thr Ala Gly
            -15                 -10                 -5 gtc cac tcc cag gtc cag ctg cag cag tct gga cct gac ctg gta aag    96
Val His Ser Gln Val Gln Leu Gln Gln Ser Gly Pro Asp Leu Val Lys
     -1   1               5                  10 cct ggg gct tca gtg aag atg tcc tgc aag gct tct gga tac acc ttc   144
Pro Gly Ala Ser Val Lys Met Ser Cys Lys Ala Ser Gly Tyr Thr Phe
        15                  20                  25 gtt aac cat gtt atg cac tgg gtg aag cag aag cca ggg cag ggc ctt   192
```

```
Val Asn His Val Met His Trp Val Lys Gln Lys Pro Gly Gln Gly Leu
 30              35                  40                  45 gag tgg att gga tat att tat cct tac aat gat ggt act aag tac aat     240
Glu Trp Ile Gly Tyr Ile Tyr Pro Tyr Asn Asp Gly Thr Lys Tyr Asn
             50                  55                  60 gag aag ttc aag ggc aag gcc aca ctg act tca gag aaa tcc tcc agc     288
Glu Lys Phe Lys Gly Lys Ala Thr Leu Thr Ser Glu Lys Ser Ser Ser
         65                  70                  75 gca gcc tac atg gag ctc agc agc ctg gcc tct gag gac tct gcg gtc     336
Ala Ala Tyr Met Glu Leu Ser Ser Leu Ala Ser Glu Asp Ser Ala Val
     80                  85                  90 tac tac tgt gca aga ggg ggt tac tat agt tac gac gac tgg ggc caa     384
Tyr Tyr Cys Ala Arg Gly Gly Tyr Tyr Ser Tyr Asp Asp Trp Gly Gln
 95                 100                 105 ggc acc act ctc aca gtc tcc tca g                                   409
Gly Thr Thr Leu Thr Val Ser Ser
110                 115

<210> SEQ ID NO 7
<211> LENGTH: 394
<212> TYPE: DNA
<213> ORGANISM: Mus sp.
<220> FEATURE:
<221> NAME/KEY: CDS
<222> LOCATION: (1)..(393)
<223> OTHER INFORMATION: pGEM-M2L.
<220> FEATURE:
<221> NAME/KEY: sig_peptide
<222> LOCATION: (1)..(57)
<220> FEATURE:
<221> NAME/KEY: mat_peptide
<222> LOCATION: (58)..(393)

<400> SEQUENCE: 7 atg aag ttg cct gtt agg ctg ttg gtg ctg atg ttc tgg att cct ggt      48
Met Lys Leu Pro Val Arg Leu Leu Val Leu Met Phe Trp Ile Pro Gly
            -15                 -10                  -5 tcc agc agt gat gtt gtg atg acc caa agt cca ctc tcc ctg cct gtc      96
Ser Ser Ser Asp Val Val Met Thr Gln Ser Pro Leu Ser Leu Pro Val
         -1   1               5                  10 agt ctt gga gat caa gcc tcc atc tct tgc aga tca agt cag agc ctt     144
Ser Leu Gly Asp Gln Ala Ser Ile Ser Cys Arg Ser Ser Gln Ser Leu
     15                  20                  25 gta cac agt aat gga aag acc tat tta cat tgg tac ctg cag aag cca     192
Val His Ser Asn Gly Lys Thr Tyr Leu His Trp Tyr Leu Gln Lys Pro
 30                  35                  40                  45 ggc cag tct cca aaa ctc ctg atc tac aaa gtt tcc aac cga ttt tct     240
Gly Gln Ser Pro Lys Leu Leu Ile Tyr Lys Val Ser Asn Arg Phe Ser
             50                  55                  60 ggg gtc cca gac agg ttc agt ggc agt gga tca gtg aca gat ttc aca     288
Gly Val Pro Asp Arg Phe Ser Gly Ser Gly Ser Val Thr Asp Phe Thr
         65                  70                  75 ctc atg atc agc aga gtg gag gct gag gat ctg gga gtt tat ttc tgc     336
Leu Met Ile Ser Arg Val Glu Ala Glu Asp Leu Gly Val Tyr Phe Cys
     80                  85                  90 tct caa agt aca cat gtt ccg tac acg ttc gga ggg ggg acc aag ctg     384
Ser Gln Ser Thr His Val Pro Tyr Thr Phe Gly Gly Gly Thr Lys Leu
 95                 100                 105 gaa ata aaa c                                                       394
Glu Ile Lys
110

<210> SEQ ID NO 8
<211> LENGTH: 409
```

```
<212> TYPE: DNA
<213> ORGANISM: Mus sp.
<220> FEATURE:
<221> NAME/KEY: CDS
<222> LOCATION: (1)..(408)
<223> OTHER INFORMATION: pGEM-M2H.
<220> FEATURE:
<221> NAME/KEY: sig_peptide
<222> LOCATION: (1)..(57)
<220> FEATURE:
<221> NAME/KEY: mat_peptide
<222> LOCATION: (58)..(408)

<400> SEQUENCE: 8
```

| | | | | | | | | | | | | | | | | |
|---|---|---|---|---|---|---|---|---|---|---|---|---|---|---|---|---|
| atg | gaa | tgg | agc | tgg | ata | ttt | ctc | ttc | ctc | ctg | tca | gga | act | gca | ggt | 48 |
| Met | Glu | Trp | Ser | Trp | Ile | Phe | Leu | Phe | Leu | Leu | Ser | Gly | Thr | Ala | Gly | |
| | | | -15 | | | | -10 | | | | | -5 | | | | |
| gtc | cac | tcc | cag | gtc | cag | ctg | cag | cag | tct | gga | cct | gaa | ctg | gta | aag | 96 |
| Val | His | Ser | Gln | Val | Gln | Leu | Gln | Gln | Ser | Gly | Pro | Glu | Leu | Val | Lys | |
| | -1 | 1 | | | 5 | | | | | 10 | | | | | | |
| cct | ggg | gct | tca | gtg | aag | atg | tcc | tgc | aag | gct | tct | gga | tac | acc | ttc | 144 |
| Pro | Gly | Ala | Ser | Val | Lys | Met | Ser | Cys | Lys | Ala | Ser | Gly | Tyr | Thr | Phe | |
| | 15 | | | | 20 | | | | | 25 | | | | | | |
| gct | aac | cat | gtt | att | cac | tgg | gtg | aag | cag | aag | cca | ggg | cag | ggc | ctt | 192 |
| Ala | Asn | His | Val | Ile | His | Trp | Val | Lys | Gln | Lys | Pro | Gly | Gln | Gly | Leu | |
| 30 | | | | | 35 | | | | | 40 | | | | | 45 | |
| gag | tgg | att | gga | tat | att | tat | cct | tac | aat | gat | ggt | act | aag | tat | aat | 240 |
| Glu | Trp | Ile | Gly | Tyr | Ile | Tyr | Pro | Tyr | Asn | Asp | Gly | Thr | Lys | Tyr | Asn | |
| | | | 50 | | | | | 55 | | | | | 60 | | | |
| gag | aag | ttc | aag | gac | aag | gcc | act | ctg | act | tca | gac | aaa | tcc | tcc | acc | 288 |
| Glu | Lys | Phe | Lys | Asp | Lys | Ala | Thr | Leu | Thr | Ser | Asp | Lys | Ser | Ser | Thr | |
| | | 65 | | | | | 70 | | | | | 75 | | | | |
| aca | gcc | tac | atg | gac | ctc | agc | agc | ctg | gcc | tct | gag | gac | tct | gcg | gtc | 336 |
| Thr | Ala | Tyr | Met | Asp | Leu | Ser | Ser | Leu | Ala | Ser | Glu | Asp | Ser | Ala | Val | |
| | | | 80 | | | | | 85 | | | | | 90 | | | |
| tat | tac | tgt | gca | aga | ggg | ggt | tac | tat | act | tac | gac | gac | tgg | ggc | caa | 384 |
| Tyr | Tyr | Cys | Ala | Arg | Gly | Gly | Tyr | Tyr | Thr | Tyr | Asp | Asp | Trp | Gly | Gln | |
| | | 95 | | | | | 100 | | | | | 105 | | | | |
| ggc | acc | act | ctc | aca | gtc | tcc | tca | g | | | | | | | | 409 |
| Gly | Thr | Thr | Leu | Thr | Val | Ser | Ser | | | | | | | | | |
| 110 | | | | | 115 | | | | | | | | | | | |

```
<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: PCR primer

<400> SEQUENCE: 9
cccaagcttc caccatgaag ttgcctgtta gg                                      32

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: PCR primer

<400> SEQUENCE: 10
cccaagcttc caccatggaa tggagctgga ta                                      32

<210> SEQ ID NO 11
<211> LENGTH: 34
<212> TYPE: DNA
<213> ORGANISM: Artificial Sequence
```

```
<220> FEATURE:
<223> OTHER INFORMATION: Description of Artificial Sequence: PCR primer

<400> SEQUENCE: 11
cgcggatcca ctcacgtttt atttccagct tggt                                    34

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: PCR primer

<400> SEQUENCE: 12
cgcggatcca ctcacctgag gagactgtga gagt                                    34

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 13
catgccatgg cgcaggtcca gctgcagcag                                         30

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: PCR primer

<400> SEQUENCE: 14
accaccacct gaggagactg tgagagt                                            27

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: PCR primer

<400> SEQUENCE: 15
gtctcctcag gtggtggtgg ttcgggt                                            27

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: PCR primer

<400> SEQUENCE: 16
cacaacatcc gatccgccac cacccga                                            27

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: PCR primer

<400> SEQUENCE: 17
ggcggatcgg atgttgtgat gacccaa                                            27
```

<210> SEQ ID NO 18
<211> LENGTH: 57
<212> TYPE: DNA
<213> ORGANISM: Artificial Sequence
<220> FEATURE:
<223> OTHER INFORMATION: Description of Artificial Sequence: PCR primer

<400> SEQUENCE: 18
ccggaattct cattatttat cgtcatcgtc tttgtagtct tttatttcca gcttggt    57

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Linker
      nucleotide sequence
<220> FEATURE:
<221> NAME/KEY: CDS
<222> LOCATION: (1)..(45)

<400> SEQUENCE: 19

| ggt | ggt | ggt | ggt | tcg | ggt | ggt | ggt | ggt | tcg | ggt | ggt | ggc | gga | tcg | 45 |
| Gly | Gly | Gly | Gly | Ser | Gly | Gly | Gly | Gly | Ser | Gly | Gly | Gly | Gly | Ser | |
| 1 | | | | 5 | | | | | 10 | | | | | 15 | |

<210> SEQ ID NO 20
<211> LENGTH: 828
<212> TYPE: DNA
<213> ORGANISM: Mus sp.
<220> FEATURE:
<221> NAME/KEY: CDS
<222> LOCATION: (1)..(822)
<223> OTHER INFORMATION: pscM1. MABL1-scFv

<400> SEQUENCE: 20

| atg | aaa | tac | cta | ttg | cct | acg | gca | gcc | gct | gga | ttg | tta | tta | ctc | gct | 48 |
| Met | Lys | Tyr | Leu | Leu | Pro | Thr | Ala | Ala | Ala | Gly | Leu | Leu | Leu | Leu | Ala | |
| 1 | | | | 5 | | | | | 10 | | | | | 15 | | |

| gcc | caa | cca | gcc | atg | gcg | cag | gtc | cag | ctg | cag | cag | tct | gga | cct | gac | 96 |
| Ala | Gln | Pro | Ala | Met | Ala | Gln | Val | Gln | Leu | Gln | Gln | Ser | Gly | Pro | Asp | |
| | | | 20 | | | | | 25 | | | | | 30 | | | |

| ctg | gta | aag | cct | ggg | gct | tca | gtg | aag | atg | tcc | tgc | aag | gct | tct | gga | 144 |
| Leu | Val | Lys | Pro | Gly | Ala | Ser | Val | Lys | Met | Ser | Cys | Lys | Ala | Ser | Gly | |
| | 35 | | | | | 40 | | | | | 45 | | | | | |

| tac | acc | ttc | gtt | aac | cat | gtt | atg | cac | tgg | gtg | aag | cag | aag | cca | ggg | 192 |
| Tyr | Thr | Phe | Val | Asn | His | Val | Met | His | Trp | Val | Lys | Gln | Lys | Pro | Gly | |
| 50 | | | | | 55 | | | | | 60 | | | | | | |

| cag | ggc | ctt | gag | tgg | att | gga | tat | att | tat | cct | tac | aat | gat | ggt | act | 240 |
| Gln | Gly | Leu | Glu | Trp | Ile | Gly | Tyr | Ile | Tyr | Pro | Tyr | Asn | Asp | Gly | Thr | |
| 65 | | | | 70 | | | | | 75 | | | | | 80 | | |

| aag | tac | aat | gag | aag | ttc | aag | ggc | aag | gcc | aca | ctg | act | tca | gag | aaa | 288 |
| Lys | Tyr | Asn | Glu | Lys | Phe | Lys | Gly | Lys | Ala | Thr | Leu | Thr | Ser | Glu | Lys | |
| | | | | 85 | | | | | 90 | | | | | 95 | | |

| tcc | tcc | agc | gca | gcc | tac | atg | gag | ctc | agc | agc | ctg | gcc | tct | gag | gac | 336 |
| Ser | Ser | Ser | Ala | Ala | Tyr | Met | Glu | Leu | Ser | Ser | Leu | Ala | Ser | Glu | Asp | |
| | | | 100 | | | | | 105 | | | | | 110 | | | |

| tct | gcg | gtc | tac | tac | tgt | gca | aga | ggg | ggt | tac | tat | agt | tac | gac | gac | 384 |
| Ser | Ala | Val | Tyr | Tyr | Cys | Ala | Arg | Gly | Gly | Tyr | Tyr | Ser | Tyr | Asp | Asp | |
| | 115 | | | | | 120 | | | | | 125 | | | | | |

| tgg | ggc | caa | ggc | acc | act | ctc | aca | gtc | tcc | tca | ggt | ggt | ggt | ggt | tcg | 432 |
| Trp | Gly | Gln | Gly | Thr | Thr | Leu | Thr | Val | Ser | Ser | Gly | Gly | Gly | Gly | Ser | |
| 130 | | | | | 135 | | | | | 140 | | | | | | |

| ggt | ggt | ggt | ggt | tcg | ggt | ggt | ggc | gga | tcg | gat | gtt | gtg | atg | acc | caa | 480 |
| Gly | Gly | Gly | Gly | Ser | Gly | Gly | Gly | Gly | Ser | Asp | Val | Val | Met | Thr | Gln | |
| 145 | | | | | 150 | | | | | 155 | | | | | 160 | |

```
act cca ctc tcc ctg cct gtc agt ctt gga gat caa gcc tcc atc tct      528
Thr Pro Leu Ser Leu Pro Val Ser Leu Gly Asp Gln Ala Ser Ile Ser
            165                 170                 175 tgc aga tct agt cag agc ctt cta cac agt aaa gga aac acc tat tta      576
Cys Arg Ser Ser Gln Ser Leu Leu His Ser Lys Gly Asn Thr Tyr Leu
        180                 185                 190 caa tgg tac cta cag aag cca ggc cag tct cca aag ctc ctg atc tac      624
Gln Trp Tyr Leu Gln Lys Pro Gly Gln Ser Pro Lys Leu Leu Ile Tyr
            195                 200                 205 aaa gtt tcc aac cga ttt tct ggg gtc cca gac agg ttc agt ggc agt      672
Lys Val Ser Asn Arg Phe Ser Gly Val Pro Asp Arg Phe Ser Gly Ser
        210                 215                 220 gga tca ggg aca gat ttc aca ctc aag atc agc aga gtg gag gct gag      720
Gly Ser Gly Thr Asp Phe Thr Leu Lys Ile Ser Arg Val Glu Ala Glu
225                 230                 235                 240 gat ctg gga gtt tat ttc tgc tct caa agt aca cat gtt ccg tac acg      768
Asp Leu Gly Val Tyr Phe Cys Ser Gln Ser Thr His Val Pro Tyr Thr
                245                 250                 255 tcc gga ggg ggg acc aag ctg gaa ata aaa gac tac aaa gac gat gac      816
Ser Gly Gly Gly Thr Lys Leu Glu Ile Lys Asp Tyr Lys Asp Asp Asp
            260                 265                 270 gat aaa taatga                                                        828
Asp Lys <210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: PCR primer

<400> SEQUENCE: 21
acgcgtcgac tcccaggtcc agctgcagca g                                   31

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: PCR primer

<400> SEQUENCE: 22
gaaggtgtat ccagaagc                                                  18

<210> SEQ ID NO 23
<211> LENGTH: 819
<212> TYPE: DNA
<213> ORGANISM: Mus sp.
<220> FEATURE:
<221> NAME/KEY: CDS
<222> LOCATION: (1)..(813)
<223> OTHER INFORMATION: pCHOM1. MABL1-scFv

<400> SEQUENCE: 23 atg gga tgg agc tgt atc atc ctc ttc ttg gta gca aca gct aca ggt      48
Met Gly Trp Ser Cys Ile Ile Leu Phe Leu Val Ala Thr Ala Thr Gly
1               5                   10                  15 gtc gac tcc cag gtc cag ctg cag cag tct gga cct gac ctg gta aag      96
Val Asp Ser Gln Val Gln Leu Gln Gln Ser Gly Pro Asp Leu Val Lys
            20                  25                  30 cct ggg gct tca gtg aag atg tcc tgc aag gct tct gga tac acc ttc     144
Pro Gly Ala Ser Val Lys Met Ser Cys Lys Ala Ser Gly Tyr Thr Phe
        35                  40                  45
```

-continued

| | | |
|---|---|---|
| gtt aac cat gtt atg cac tgg gtg aag cag aag cca ggg cag ggc ctt<br>Val Asn His Val Met His Trp Val Lys Gln Lys Pro Gly Gln Gly Leu<br>50              55                  60 | | 192 |
| gag tgg att gga tat att tat cct tac aat gat ggt act aag tac aat<br>Glu Trp Ile Gly Tyr Ile Tyr Pro Tyr Asn Asp Gly Thr Lys Tyr Asn<br>65              70                  75                  80 | | 240 |
| gag aag ttc aag ggc aag gcc aca ctg act tca gag aaa tcc tcc agc<br>Glu Lys Phe Lys Gly Lys Ala Thr Leu Thr Ser Glu Lys Ser Ser Ser<br>            85                  90                  95 | | 288 |
| gca gcc tac atg gag ctc agc agc ctg gcc tct gag gac tct gcg gtc<br>Ala Ala Tyr Met Glu Leu Ser Ser Leu Ala Ser Glu Asp Ser Ala Val<br>        100                 105                 110 | | 336 |
| tac tac tgt gca aga ggg ggt tac tat agt tac gac gac tgg ggc caa<br>Tyr Tyr Cys Ala Arg Gly Gly Tyr Tyr Ser Tyr Asp Asp Trp Gly Gln<br>            115                 120                 125 | | 384 |
| ggc acc act ctc aca gtc tcc tca ggt ggt ggt ggt tcg ggt ggt ggt<br>Gly Thr Thr Leu Thr Val Ser Ser Gly Gly Gly Gly Ser Gly Gly Gly<br>        130                 135                 140 | | 432 |
| ggt tcg ggt ggt ggc gga tcg gat gtt gtg atg acc caa act cca ctc<br>Gly Ser Gly Gly Gly Gly Ser Asp Val Val Met Thr Gln Thr Pro Leu<br>145                 150                 155                 160 | | 480 |
| tcc ctg cct gtc agt ctt gga gat caa gcc tcc atc tct tgc aga tct<br>Ser Leu Pro Val Ser Leu Gly Asp Gln Ala Ser Ile Ser Cys Arg Ser<br>            165                 170                 175 | | 528 |
| agt cag agc ctt cta cac agt aaa gga aac acc tat tta caa tgg tac<br>Ser Gln Ser Leu Leu His Ser Lys Gly Asn Thr Tyr Leu Gln Trp Tyr<br>        180                 185                 190 | | 576 |
| cta cag aag cca ggc cag tct cca aag ctc ctg atc tac aaa gtt tcc<br>Leu Gln Lys Pro Gly Gln Ser Pro Lys Leu Leu Ile Tyr Lys Val Ser<br>            195                 200                 205 | | 624 |
| aac cga ttt tct ggg gtc cca gac agg ttc agt ggc agt gga tca ggg<br>Asn Arg Phe Ser Gly Val Pro Asp Arg Phe Ser Gly Ser Gly Ser Gly<br>210                 215                 220 | | 672 |
| aca gat ttc aca ctc aag atc agc aga gtg gag gct gag gat ctg gga<br>Thr Asp Phe Thr Leu Lys Ile Ser Arg Val Glu Ala Glu Asp Leu Gly<br>225                 230                 235                 240 | | 720 |
| gtt tat ttc tgc tct caa agt aca cat gtt ccg tac acg tcc gga ggg<br>Val Tyr Phe Cys Ser Gln Ser Thr His Val Pro Tyr Thr Ser Gly Gly<br>            245                 250                 255 | | 768 |
| ggg acc aag ctg gaa ata aaa gac tac aaa gac gat gac gat aaa<br>Gly Thr Lys Leu Glu Ile Lys Asp Tyr Lys Asp Asp Asp Asp Lys<br>        260                 265                 270 | | 813 |
| taatga | | 819 |

<210> SEQ ID NO 24
<211> LENGTH: 828
<212> TYPE: DNA
<213> ORGANISM: Mus sp.
<220> FEATURE:
<221> NAME/KEY: CDS
<222> LOCATION: (1)..(822)
<223> OTHER INFORMATION: pscM2.MABL2-scFv

<400> SEQUENCE: 24

| | | |
|---|---|---|
| atg aaa tac cta ttg cct acg gca gcc gct gga ttg tta tta ctc gct<br>Met Lys Tyr Leu Leu Pro Thr Ala Ala Ala Gly Leu Leu Leu Leu Ala<br>1               5                   10                  15 | | 48 |
| gcc caa cca gcc atg gcg cag gtc cag ctg cag cag tct gga cct gaa<br>Ala Gln Pro Ala Met Ala Gln Val Gln Leu Gln Gln Ser Gly Pro Glu<br>            20                  25                  30 | | 96 |
| ctg gta aag cct ggg gct tca gtg aag atg tcc tgc aag gct tct gga<br>Leu Val Lys Pro Gly Ala Ser Val Lys Met Ser Cys Lys Ala Ser Gly | | 144 |

```
                         35                   40                    45
tac acc ttc gct aac cat gtt att cac tgg gtg aag cag aag cca ggg     192
Tyr Thr Phe Ala Asn His Val Ile His Trp Val Lys Gln Lys Pro Gly
         50                   55                    60 cag ggc ctt gag tgg att gga tat att tat cct tac aat gat ggt act     240
Gln Gly Leu Glu Trp Ile Gly Tyr Ile Tyr Pro Tyr Asn Asp Gly Thr
 65                   70                    75                   80 aag tat aat gag aag ttc aag gac aag gcc act ctg act tca gac aaa     288
Lys Tyr Asn Glu Lys Phe Lys Asp Lys Ala Thr Leu Thr Ser Asp Lys
                 85                    90                    95 tcc tcc acc aca gcc tac atg gac ctc agc agc ctg gcc tct gag gac     336
Ser Ser Thr Thr Ala Tyr Met Asp Leu Ser Ser Leu Ala Ser Glu Asp
            100                   105                   110 tct gcg gtc tat tac tgt gca aga ggg ggt tac tat act tac gac gac     384
Ser Ala Val Tyr Tyr Cys Ala Arg Gly Gly Tyr Tyr Thr Tyr Asp Asp
        115                   120                   125 tgg ggc caa ggc acc act ctc aca gtc tcc tca ggt ggt ggt ggt tcg     432
Trp Gly Gln Gly Thr Thr Leu Thr Val Ser Ser Gly Gly Gly Gly Ser
130                   135                   140 ggt ggt ggt ggt tcg ggt ggt ggc gga tcg gat gtt gtg atg acc caa     480
Gly Gly Gly Gly Ser Gly Gly Gly Gly Ser Asp Val Val Met Thr Gln
145                   150                   155                   160 agt cca ctc tcc ctg cct gtc agt ctt gga gat caa gcc tcc atc tct     528
Ser Pro Leu Ser Leu Pro Val Ser Leu Gly Asp Gln Ala Ser Ile Ser
                165                   170                   175 tgc aga tca agt cag agc ctt gta cac agt aat gga aag acc tat tta     576
Cys Arg Ser Ser Gln Ser Leu Val His Ser Asn Gly Lys Thr Tyr Leu
            180                   185                   190 cat tgg tac ctg cag aag cca ggc cag tct cca aaa ctc ctg atc tac     624
His Trp Tyr Leu Gln Lys Pro Gly Gln Ser Pro Lys Leu Leu Ile Tyr
        195                   200                   205 aaa gtt tcc aac cga ttt tct ggg gtc cca gac agg ttc agt ggc agt     672
Lys Val Ser Asn Arg Phe Ser Gly Val Pro Asp Arg Phe Ser Gly Ser
    210                   215                   220 gga tca gtg aca gat ttc aca ctc atg atc agc aga gtg gag gct gag     720
Gly Ser Val Thr Asp Phe Thr Leu Met Ile Ser Arg Val Glu Ala Glu
225                   230                   235                   240 gat ctg gga gtt tat ttc tgc tct caa agt aca cat gtt ccg tac acg     768
Asp Leu Gly Val Tyr Phe Cys Ser Gln Ser Thr His Val Pro Tyr Thr
                245                   250                   255 ttc gga ggg ggg acc aag ctg gaa ata aaa gac tac aaa gac gat gac     816
Phe Gly Gly Gly Thr Lys Leu Glu Ile Lys Asp Tyr Lys Asp Asp Asp
            260                   265                   270 gat aaa taatga                                                      828
Asp Lys

<210> SEQ ID NO 25
<211> LENGTH: 819
<212> TYPE: DNA
<213> ORGANISM: Mus sp.
<220> FEATURE:
<221> NAME/KEY: CDS
<222> LOCATION: (1)..(813)
<223> OTHER INFORMATION: pCHOM2. MABL2-scFv

<400> SEQUENCE: 25 atg gga tgg agc tgt atc atc ctc ttc ttg gta gca aca gct aca ggt      48
Met Gly Trp Ser Cys Ile Ile Leu Phe Leu Val Ala Thr Ala Thr Gly
 1               5                   10                  15 gtc gac tcc cag gtc cag ctg cag cag tct gga cct gaa ctg gta aag      96
Val Asp Ser Gln Val Gln Leu Gln Gln Ser Gly Pro Glu Leu Val Lys
            20                  25                  30
```

| | | |
|---|---|---|
| cct ggg gct tca gtg aag atg tcc tgc aag gct tct gga tac acc ttc<br>Pro Gly Ala Ser Val Lys Met Ser Cys Lys Ala Ser Gly Tyr Thr Phe<br>                  35                      40                  45 | | 144 |
| gct aac cat gtt att cac tgg gtg aag cag aag cca ggg cag ggc ctt<br>Ala Asn His Val Ile His Trp Val Lys Gln Lys Pro Gly Gln Gly Leu<br> 50                      55                      60 | | 192 |
| gag tgg att gga tat att tat cct tac aat gat ggt act aag tat aat<br>Glu Trp Ile Gly Tyr Ile Tyr Pro Tyr Asn Asp Gly Thr Lys Tyr Asn<br>65                    70                      75                      80 | | 240 |
| gag aag ttc aag gac aag gcc act ctg act tca gac aaa tcc tcc acc<br>Glu Lys Phe Lys Asp Lys Ala Thr Leu Thr Ser Asp Lys Ser Ser Thr<br>                  85                      90                      95 | | 288 |
| aca gcc tac atg gac ctc agc agc ctg gcc tct gag gac tct gcg gtc<br>Thr Ala Tyr Met Asp Leu Ser Ser Leu Ala Ser Glu Asp Ser Ala Val<br>                  100                      105                      110 | | 336 |
| tat tac tgt gca aga ggg ggt tac tat act tac gac gac tgg ggc caa<br>Tyr Tyr Cys Ala Arg Gly Gly Tyr Tyr Thr Tyr Asp Asp Trp Gly Gln<br>                115                      120                      125 | | 384 |
| ggc acc act ctc aca gtc tcc tca ggt ggt ggt ggt tcg ggt ggt ggt<br>Gly Thr Thr Leu Thr Val Ser Ser Gly Gly Gly Gly Ser Gly Gly Gly<br>130                      135                      140 | | 432 |
| ggt tcg ggt ggt ggc gga tcg gat gtt gtg atg acc caa agt cca ctc<br>Gly Ser Gly Gly Gly Gly Ser Asp Val Val Met Thr Gln Ser Pro Leu<br>145                      150                      155                      160 | | 480 |
| tcc ctg cct gtc agt ctt gga gat caa gcc tcc atc tct tgc aga tca<br>Ser Leu Pro Val Ser Leu Gly Asp Gln Ala Ser Ile Ser Cys Arg Ser<br>                  165                      170                      175 | | 528 |
| agt cag agc ctt gtg cac agt aat gga aag acc tat tta cat tgg tac<br>Ser Gln Ser Leu Val His Ser Asn Gly Lys Thr Tyr Leu His Trp Tyr<br>                180                      185                      190 | | 576 |
| ctg cag aag cca ggc cag tct cca aaa ctc ctg atc tac aaa gtt tcc<br>Leu Gln Lys Pro Gly Gln Ser Pro Lys Leu Leu Ile Tyr Lys Val Ser<br>                  195                      200                      205 | | 624 |
| aac cga ttt tct ggg gtc cca gac agg ttc agt ggc agt gga tca gtg<br>Asn Arg Phe Ser Gly Val Pro Asp Arg Phe Ser Gly Ser Gly Ser Val<br>                210                      215                      220 | | 672 |
| aca gat ttc aca ctc atg atc agc aga gtg gag gct gag gat ctg gga<br>Thr Asp Phe Thr Leu Met Ile Ser Arg Val Glu Ala Glu Asp Leu Gly<br>225                      230                      235                      240 | | 720 |
| gtt tat ttc tgc tct caa agt aca cat gtt ccg tac acg ttc gga ggg<br>Val Tyr Phe Cys Ser Gln Ser Thr His Val Pro Tyr Thr Phe Gly Gly<br>                  245                      250                      255 | | 768 |
| ggg acc aag ctg gaa ata aaa gac tac aaa gac gat gac gat aaa<br>Gly Thr Lys Leu Glu Ile Lys Asp Tyr Lys Asp Asp Asp Asp Lys<br>                260                      265                      270 | | 813 |
| taatga | | 819 |

```
<210> SEQ ID NO 26
<211> LENGTH: 456
<212> TYPE: DNA
<213> ORGANISM: Mus sp.
<220> FEATURE:
<221> NAME/KEY: CDS
<222> LOCATION: (1)..(450)
<223> OTHER INFORMATION: pCHO-shIAP. Soluble Homo sapiens IAP

<400> SEQUENCE: 26
```

| | | |
|---|---|---|
| atg tgg ccc ctg gta gcg gcg ctg ttg ctg ggc tcg gcg tgc tgc gga<br>Met Trp Pro Leu Val Ala Ala Leu Leu Leu Gly Ser Ala Cys Cys Gly<br>1                    5                      10                      15 | | 48 |
| tca gct cag cta cta ttt aat aaa aca aaa tct gta gaa ttc acg ttt | | 96 |

```
                Ser Ala Gln Leu Leu Phe Asn Lys Thr Lys Ser Val Glu Phe Thr Phe
                                20                  25                  30 tgt aat gac act gtc gtc att cca tgc ttt gtt act aat atg gag gca          144
Cys Asn Asp Thr Val Val Ile Pro Cys Phe Val Thr Asn Met Glu Ala
             35                  40                  45 caa aac act act gaa gta tac gta aag tgg aaa ttt aaa gga aga gat          192
Gln Asn Thr Thr Glu Val Tyr Val Lys Trp Lys Phe Lys Gly Arg Asp
 50                  55                  60 att tac acc ttt gat gga gct cta aac aag tcc act gtc ccc act gac          240
Ile Tyr Thr Phe Asp Gly Ala Leu Asn Lys Ser Thr Val Pro Thr Asp
 65                  70                  75                  80 ttt agt agt gca aaa att gaa gtc tca caa tta cta aaa gga gat gcc          288
Phe Ser Ser Ala Lys Ile Glu Val Ser Gln Leu Leu Lys Gly Asp Ala
                 85                  90                  95 tct ttg aag atg gat aag agt gat gct gtc tca cac aca gga aac tac          336
Ser Leu Lys Met Asp Lys Ser Asp Ala Val Ser His Thr Gly Asn Tyr
            100                 105                 110 act tgt gaa gta aca gaa tta acc aga gaa ggt gaa acg atc atc gag          384
Thr Cys Glu Val Thr Glu Leu Thr Arg Glu Gly Glu Thr Ile Ile Glu
        115                 120                 125 cta aaa tat cgt gtt gtt tca tgg ttt tct cca aat gaa aat gac tac          432
Leu Lys Tyr Arg Val Val Ser Trp Phe Ser Pro Asn Glu Asn Asp Tyr
    130                 135                 140 aag gac gac gat gac aag tgatag                                           456
Lys Asp Asp Asp Asp Lys
145                 150

<210> SEQ ID NO 27
<211> LENGTH: 46
<212> TYPE: DNA
<213> ORGANISM: Artificial Sequence
<220> FEATURE:
<223> OTHER INFORMATION: Description of Artificial Sequence: PCR primer

<400> SEQUENCE: 27
ggaattccat atgcaagtgc aacttcaaca gtctggacct gaactg                       46

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: PCR primer

<400> SEQUENCE: 28
ggaattctca ttattttatt tccagcttgg t                                       31

<210> SEQ ID NO 29
<211> LENGTH: 741
<212> TYPE: DNA
<213> ORGANISM: Mus sp.
<220> FEATURE:
<221> NAME/KEY: CDS
<222> LOCATION: (1)..(735)
<223> OTHER INFORMATION: pscM2DEm02. MABL2-scFv

<400> SEQUENCE: 29 atg caa gtg caa ctt caa cag tct gga cct gaa ctg gta aag cct ggg           48
Met Gln Val Gln Leu Gln Gln Ser Gly Pro Glu Leu Val Lys Pro Gly
  1               5                  10                  15 gct tca gtg aag atg tcc tgc aag gct tct gga tac acc ttc gct aac           96
Ala Ser Val Lys Met Ser Cys Lys Ala Ser Gly Tyr Thr Phe Ala Asn
             20                  25                  30 cat gtt att cac tgg gtg aag cag aag cca ggg cag ggc ctt gag tgg          144
His Val Ile His Trp Val Lys Gln Lys Pro Gly Gln Gly Leu Glu Trp
```

```
                His Val Ile His Trp Val Lys Gln Lys Pro Gly Gln Gly Leu Glu Trp
                             35                  40                  45 att gga tat att tat cct tac aat gat ggt act aag tat aat gag aag        192
Ile Gly Tyr Ile Tyr Pro Tyr Asn Asp Gly Thr Lys Tyr Asn Glu Lys
 50                  55                  60 ttc aag gac aag gcc act ctg act tca gac aaa tcc tcc acc aca gcc        240
Phe Lys Asp Lys Ala Thr Leu Thr Ser Asp Lys Ser Ser Thr Thr Ala
 65                  70                  75                  80 tac atg gac ctc agc agc ctg gcc tct gag gac tct gcg gtc tat tac        288
Tyr Met Asp Leu Ser Ser Leu Ala Ser Glu Asp Ser Ala Val Tyr Tyr
                 85                  90                  95 tgt gca aga ggg ggt tac tat act tac gac gac tgg ggc caa ggc acc        336
Cys Ala Arg Gly Gly Tyr Tyr Thr Tyr Asp Asp Trp Gly Gln Gly Thr
            100                 105                 110 act ctc aca gtc tcc tca ggt ggt ggt ggt tcg ggt ggt ggt ggt tcg        384
Thr Leu Thr Val Ser Ser Gly Gly Gly Gly Ser Gly Gly Gly Gly Ser
            115                 120                 125 ggt ggt ggc gga tcg gat gtt gtg atg acc caa agt cca ctc tcc ctg        432
Gly Gly Gly Gly Ser Asp Val Val Met Thr Gln Ser Pro Leu Ser Leu
130                 135                 140 cct gtc agt ctt gga gat caa gcc tcc atc tct tgc aga tca agt cag        480
Pro Val Ser Leu Gly Asp Gln Ala Ser Ile Ser Cys Arg Ser Ser Gln
145                 150                 155                 160 agc ctt gtg cac agt aat gga aag acc tat tta cat tgg tac ctg cag        528
Ser Leu Val His Ser Asn Gly Lys Thr Tyr Leu His Trp Tyr Leu Gln
                165                 170                 175 aag cca ggc cag tct cca aaa ctc ctg atc tac aaa gtt tcc aac cga        576
Lys Pro Gly Gln Ser Pro Lys Leu Leu Ile Tyr Lys Val Ser Asn Arg
            180                 185                 190 ttt tct ggg gtc cca gac agg ttc agt ggc agt gga tca gtg aca gat        624
Phe Ser Gly Val Pro Asp Arg Phe Ser Gly Ser Gly Ser Val Thr Asp
            195                 200                 205 ttc aca ctc atg atc agc aga gtg gag gct gag gat ctg gga gtt tat        672
Phe Thr Leu Met Ile Ser Arg Val Glu Ala Glu Asp Leu Gly Val Tyr
        210                 215                 220 ttc tgc tct caa agt aca cat gtt ccg tac acg ttc gga ggg ggg acc        720
Phe Cys Ser Gln Ser Thr His Val Pro Tyr Thr Phe Gly Gly Gly Thr
225                 230                 235                 240 aag ctg gaa ata aaa taatga                                             741
Lys Leu Glu Ile Lys
            245

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: PCR primer

<400> SEQUENCE: 30
cagacagtgg ttcaaagt                                                    18

<210> SEQ ID NO 31
<211> LENGTH: 72
<212> TYPE: DNA
<213> ORGANISM: Artificial Sequence
<220> FEATURE:
<223> OTHER INFORMATION: Description of Artificial Sequence: PCR primer

<400> SEQUENCE: 31
cgcgtcgacc gatccgccac cacccgaacc accaccaccc gaaccaccac cacctttat     60 ttccagcttg gt                                                          72
```

<210> SEQ ID NO 32
<211> LENGTH: 1605
<212> TYPE: DNA
<213> ORGANISM: Mus sp.
<220> FEATURE:
<221> NAME/KEY: CDS
<222> LOCATION: (1)..(1599)
<223> OTHER INFORMATION: pCHOM2(Fv)2. MABL2-sc(Fv)2

<400> SEQUENCE: 32

```
atg gga tgg agc tgt atc atc ctc ttc ttg gta gca aca gct aca ggt      48
Met Gly Trp Ser Cys Ile Ile Leu Phe Leu Val Ala Thr Ala Thr Gly
 1               5                  10                  15 gtc gac tcc cag gtc cag ctg cag cag tct gga cct gaa ctg gta aag      96
Val Asp Ser Gln Val Gln Leu Gln Gln Ser Gly Pro Glu Leu Val Lys
             20                  25                  30 cct ggg gct tca gtg aag atg tcc tgc aag gct tct gga tac acc ttc     144
Pro Gly Ala Ser Val Lys Met Ser Cys Lys Ala Ser Gly Tyr Thr Phe
         35                  40                  45 gct aac cat gtt att cac tgg gtg aag cag aag cca ggg cag ggc ctt     192
Ala Asn His Val Ile His Trp Val Lys Gln Lys Pro Gly Gln Gly Leu
     50                  55                  60 gag tgg att gga tat att tat cct tac aat gat ggt act aag tat aat     240
Glu Trp Ile Gly Tyr Ile Tyr Pro Tyr Asn Asp Gly Thr Lys Tyr Asn
 65                  70                  75                  80 gag aag ttc aag gac aag gcc act ctg act tca gac aaa tcc tcc acc     288
Glu Lys Phe Lys Asp Lys Ala Thr Leu Thr Ser Asp Lys Ser Ser Thr
                 85                  90                  95 aca gcc tac atg gac ctc agc agc ctg gcc tct gag gac tct gcg gtc     336
Thr Ala Tyr Met Asp Leu Ser Ser Leu Ala Ser Glu Asp Ser Ala Val
            100                 105                 110 tat tac tgt gca aga ggg ggt tac tat act tac gac gac tgg ggc caa     384
Tyr Tyr Cys Ala Arg Gly Gly Tyr Tyr Thr Tyr Asp Asp Trp Gly Gln
        115                 120                 125 ggc acc act ctc aca gtc tcc tca ggt ggt ggt ggt tcg ggt ggt ggt     432
Gly Thr Thr Leu Thr Val Ser Ser Gly Gly Gly Gly Ser Gly Gly Gly
    130                 135                 140 ggt tcg ggt ggt ggc gga tcg gat gtt gtg atg acc caa agt cca ctc     480
Gly Ser Gly Gly Gly Gly Ser Asp Val Val Met Thr Gln Ser Pro Leu
145                 150                 155                 160 tcc ctg cct gtc agt ctt gga gat caa gcc tcc atc tct tgc aga tca     528
Ser Leu Pro Val Ser Leu Gly Asp Gln Ala Ser Ile Ser Cys Arg Ser
                165                 170                 175 agt cag agc ctt gta cac agt aat gga aag acc tat tta cat tgg tac     576
Ser Gln Ser Leu Val His Ser Asn Gly Lys Thr Tyr Leu His Trp Tyr
            180                 185                 190 ctg cag aag cca ggc cag tct cca aaa ctc ctg atc tac aaa gtt tcc     624
Leu Gln Lys Pro Gly Gln Ser Pro Lys Leu Leu Ile Tyr Lys Val Ser
        195                 200                 205 aac cga ttt tct ggg gtc cca gac agg ttc agt ggc agt gga tca gtg     672
Asn Arg Phe Ser Gly Val Pro Asp Arg Phe Ser Gly Ser Gly Ser Val
    210                 215                 220 aca gat ttc aca ctc atg atc agc aga gtg gag gct gag gat ctg gga     720
Thr Asp Phe Thr Leu Met Ile Ser Arg Val Glu Ala Glu Asp Leu Gly
225                 230                 235                 240 gtt tat ttc tgc tct caa agt aca cat gtt ccg tac acg ttc gga ggg     768
Val Tyr Phe Cys Ser Gln Ser Thr His Val Pro Tyr Thr Phe Gly Gly
                245                 250                 255 ggg acc aag ctg gaa ata aaa ggt ggt ggt ggt tcg ggt ggt ggt ggt     816
Gly Thr Lys Leu Glu Ile Lys Gly Gly Gly Gly Ser Gly Gly Gly Gly
            260                 265                 270
```

```
tcg ggt ggt ggc gga tcg gtc gac tcc cag gtc cag ctg cag cag tct      864
Ser Gly Gly Gly Gly Ser Val Asp Ser Gln Val Gln Leu Gln Gln Ser
            275                 280                 285 gga cct gaa ctg gta aag cct ggg gct tca gtg aag atg tcc tgc aag      912
Gly Pro Glu Leu Val Lys Pro Gly Ala Ser Val Lys Met Ser Cys Lys
290                 295                 300 gct tct gga tac acc ttc gct aac cat gtt att cac tgg gtg aag cag      960
Ala Ser Gly Tyr Thr Phe Ala Asn His Val Ile His Trp Val Lys Gln
305                 310                 315                 320 aag cca ggg cag ggc ctt gag tgg att gga tat att tat cct tac aat     1008
Lys Pro Gly Gln Gly Leu Glu Trp Ile Gly Tyr Ile Tyr Pro Tyr Asn
                325                 330                 335 gat ggt act aag tat aat gag aag ttc aag gac aag gcc act ctg act     1056
Asp Gly Thr Lys Tyr Asn Glu Lys Phe Lys Asp Lys Ala Thr Leu Thr
            340                 345                 350 tca gac aaa tcc tcc acc aca gcc tac atg gac ctc agc agc ctg gcc     1104
Ser Asp Lys Ser Ser Thr Thr Ala Tyr Met Asp Leu Ser Ser Leu Ala
            355                 360                 365 tct gag gac tct gcg gtc tat tac tgt gca aga ggg ggt tac tat act     1152
Ser Glu Asp Ser Ala Val Tyr Tyr Cys Ala Arg Gly Gly Tyr Tyr Thr
370                 375                 380 tac gac gac tgg ggc caa ggc acc act ctc aca gtc tcc tca ggt ggt     1200
Tyr Asp Asp Trp Gly Gln Gly Thr Thr Leu Thr Val Ser Ser Gly Gly
385                 390                 395                 400 ggt ggt tcg ggt ggt ggt ggt tcg ggt ggt ggc gga tcg gat gtt gtg     1248
Gly Gly Ser Gly Gly Gly Gly Ser Gly Gly Gly Gly Ser Asp Val Val
                405                 410                 415 atg acc caa agt cca ctc tcc ctg cct gtc agt ctt gga gat caa gcc     1296
Met Thr Gln Ser Pro Leu Ser Leu Pro Val Ser Leu Gly Asp Gln Ala
            420                 425                 430 tcc atc tct tgc aga tca agt cag agc ctt gtg cac agt aat gga aag     1344
Ser Ile Ser Cys Arg Ser Ser Gln Ser Leu Val His Ser Asn Gly Lys
            435                 440                 445 acc tat tta cat tgg tac ctg cag aag cca ggc cag tct cca aaa ctc     1392
Thr Tyr Leu His Trp Tyr Leu Gln Lys Pro Gly Gln Ser Pro Lys Leu
450                 455                 460 ctg atc tac aaa gtt tcc aac cga ttt tct ggg gtc cca gac agg ttc     1440
Leu Ile Tyr Lys Val Ser Asn Arg Phe Ser Gly Val Pro Asp Arg Phe
465                 470                 475                 480 agt ggc agt gga tca gtg aca gat ttc aca ctc atg atc agc aga gtg     1488
Ser Gly Ser Gly Ser Val Thr Asp Phe Thr Leu Met Ile Ser Arg Val
                485                 490                 495 gag gct gag gat ctg gga gtt tat ttc tgc tct caa agt aca cat gtt     1536
Glu Ala Glu Asp Leu Gly Val Tyr Phe Cys Ser Gln Ser Thr His Val
            500                 505                 510 ccg tac acg ttc gga ggg ggg acc aag ctg gaa ata aaa gac tac aaa     1584
Pro Tyr Thr Phe Gly Gly Gly Thr Lys Leu Glu Ile Lys Asp Tyr Lys
            515                 520                 525 gac gat gac gat aaa taatga                                          1605
Asp Asp Asp Asp Lys
        530
```

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 33
tgaggaattc ccaccatggg atg                                            23

<210> SEQ ID NO 34
<211> LENGTH: 40
<212> TYPE: DNA
<213> ORGANISM: Artificial Sequence
<220> FEATURE:
<223> OTHER INFORMATION: Description of Artificial Sequence: PCR primer

<400> SEQUENCE: 34
cacgacgtca ctcgagactg tgagagtggt gccttggccc        40

<210> SEQ ID NO 35
<211> LENGTH: 40
<212> TYPE: DNA
<213> ORGANISM: Artificial Sequence
<220> FEATURE:
<223> OTHER INFORMATION: Description of Artificial Sequence: PCR primer

<400> SEQUENCE: 35
agtctcgagt gacgtcgtga tgacccaaag tccactctcc        40

<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence: PCR primer

<400> SEQUENCE: 36
gactggatcc tcattattta tcgtcatcgt c        31

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 37
cgcgtaatac gactcactat ag        22

<210> SEQ ID NO 38
<211> LENGTH: 46
<212> TYPE: DNA
<213> ORGANISM: Artificial Sequence
<220> FEATURE:
<223> OTHER INFORMATION: Description of Artificial Sequence: PCR primer

<400> SEQUENCE: 38
gcaattggac ctgttttatc tcgagcttgg tcccccctcc gaacgt        46

<210> SEQ ID NO 39
<211> LENGTH: 45
<212> TYPE: DNA
<213> ORGANISM: Artificial Sequence
<220> FEATURE:
<223> OTHER INFORMATION: Description of Artificial Sequence: PCR primer

<400> SEQUENCE: 39
gctcgagata aaacaggtcc aattgcagca gtctggacct gaact        45

<210> SEQ ID NO 40
<211> LENGTH: 60
<212> TYPE: DNA
<213> ORGANISM: Artificial Sequence
<220> FEATURE:
<223> OTHER INFORMATION: Description of Artificial Sequence: PCR primer

<400> SEQUENCE: 40
gactggatcc tcattattta tcgtcatcgt ctttgtagtc tgaggagact gtgagagtgg    60

<210> SEQ ID NO 41
<211> LENGTH: 32
<212> TYPE: DNA
<213> ORGANISM: Artificial Sequence
<220> FEATURE:
<223> OTHER INFORMATION: Description of Artificial Sequence: PCR primer

<400> SEQUENCE: 41
gactgaattc ccaccatgaa gttgcctgtt ag    32

<210> SEQ ID NO 42
<211> LENGTH: 40
<212> TYPE: DNA
<213> ORGANISM: Artificial Sequence
<220> FEATURE:
<223> OTHER INFORMATION: Description of Artificial Sequence: PCR primer

<400> SEQUENCE: 42
cagtctcgag tggtggttcc gacgtcgtga tgacccaaag    40

<210> SEQ ID NO 43
<211> LENGTH: 43
<212> TYPE: DNA
<213> ORGANISM: Artificial Sequence
<220> FEATURE:
<223> OTHER INFORMATION: Description of Artificial Sequence: PCR primer

<400> SEQUENCE: 43
cagtctcgag tggtggtggt tccgacgtcg tgatgaccca aag    43

<210> SEQ ID NO 44
<211> LENGTH: 46
<212> TYPE: DNA
<213> ORGANISM: Artificial Sequence
<220> FEATURE:
<223> OTHER INFORMATION: Description of Artificial Sequence: PCR primer

<400> SEQUENCE: 44
cagtctcgag tggtggtggt ggttccgacg tcgtgatgac ccaaag    46

<210> SEQ ID NO 45
<211> LENGTH: 49
<212> TYPE: DNA
<213> ORGANISM: Artificial Sequence
<220> FEATURE:
<223> OTHER INFORMATION: Description of Artificial Sequence: PCR primer

<400> SEQUENCE: 45
cagtctcgag tggtggtggt ggtggttccg acgtcgtgat gacccaaag    49

<210> SEQ ID NO 46
<211> LENGTH: 52
<212> TYPE: DNA
<213> ORGANISM: Artificial Sequence
<220> FEATURE:
<223> OTHER INFORMATION: Description of Artificial Sequence: PCR primer

<400> SEQUENCE: 46
cagtctcgag tggtggtggt ggtggtggtt ccgacgtcgt gatgacccaa ag    52

<210> SEQ ID NO 47
<211> LENGTH: 20

<212> TYPE: DNA
<213> ORGANISM: Artificial Sequence
<220> FEATURE:
<223> OTHER INFORMATION: Description of Artificial Sequence: PCR primer

<400> SEQUENCE: 47
ggccgcatgt tgtcacgaat                                                    20

<210> SEQ ID NO 48
<211> LENGTH: 780
<212> TYPE: DNA
<213> ORGANISM: Mus sp.
<220> FEATURE:
<221> NAME/KEY: CDS
<222> LOCATION: (1)..(768)
<223> OTHER INFORMATION: CF2HL-0/pCOS1. MABL2-scFv<HL-0>

<400> SEQUENCE: 48

```
atg gga tgg agc tgt atc atc ctc ttc ttg gta gca aca gct aca ggt      48
Met Gly Trp Ser Cys Ile Ile Leu Phe Leu Val Ala Thr Ala Thr Gly
 1               5                  10                  15 gtc gac tcc cag gtc cag ctg cag cag tct gga cct gaa ctg gta aag      96
Val Asp Ser Gln Val Gln Leu Gln Gln Ser Gly Pro Glu Leu Val Lys
             20                  25                  30 cct ggg gct tca gtg aag atg tcc tgc aag gct tct gga tac acc ttc     144
Pro Gly Ala Ser Val Lys Met Ser Cys Lys Ala Ser Gly Tyr Thr Phe
         35                  40                  45 gct aac cat gtt att cac tgg gtg aag cag aag cca ggg cag ggc ctt     192
Ala Asn His Val Ile His Trp Val Lys Gln Lys Pro Gly Gln Gly Leu
     50                  55                  60 gag tgg att gga tat att tat cct tac aat gat ggt act aag tat aat     240
Glu Trp Ile Gly Tyr Ile Tyr Pro Tyr Asn Asp Gly Thr Lys Tyr Asn
 65                  70                  75                  80 gag aag ttc aag gac aag gcc act ctg act tca gac aaa tcc tcc acc     288
Glu Lys Phe Lys Asp Lys Ala Thr Leu Thr Ser Asp Lys Ser Ser Thr
                 85                  90                  95 aca gcc tac atg gac ctc agc agc ctg gcc tct gag gac tct gcg gtc     336
Thr Ala Tyr Met Asp Leu Ser Ser Leu Ala Ser Glu Asp Ser Ala Val
            100                 105                 110 tat tac tgt gca aga ggg ggt tac tat act tac gac gac tgg ggc caa     384
Tyr Tyr Cys Ala Arg Gly Gly Tyr Tyr Thr Tyr Asp Asp Trp Gly Gln
        115                 120                 125 ggc acc act ctc aca gtc tcg agt gac gtc gtg atg acc caa agt cca     432
Gly Thr Thr Leu Thr Val Ser Ser Asp Val Val Met Thr Gln Ser Pro
    130                 135                 140 ctc tcc ctg cct gtc agt ctt gga gat caa gcc tcc atc tct tgc aga     480
Leu Ser Leu Pro Val Ser Leu Gly Asp Gln Ala Ser Ile Ser Cys Arg
145                 150                 155                 160 tca agt cag agc ctt gtg cac agt aat gga aag acc tat tta cat tgg     528
Ser Ser Gln Ser Leu Val His Ser Asn Gly Lys Thr Tyr Leu His Trp
                165                 170                 175 tac ctg cag aag cca ggc cag tct cca aaa ctc ctg atc tac aaa gtt     576
Tyr Leu Gln Lys Pro Gly Gln Ser Pro Lys Leu Leu Ile Tyr Lys Val
            180                 185                 190 tcc aac cga ttt tct ggg gtc cca gac agg ttc agt ggc agt gga tca     624
Ser Asn Arg Phe Ser Gly Val Pro Asp Arg Phe Ser Gly Ser Gly Ser
        195                 200                 205 gtg aca gat ttc aca ctc atg atc agc aga gtg gag gct gag gat ctg     672
Val Thr Asp Phe Thr Leu Met Ile Ser Arg Val Glu Ala Glu Asp Leu
    210                 215                 220 gga gtt tat ttc tgc tct caa agt aca cat gtt ccg tac acg ttc gga     720
Gly Val Tyr Phe Cys Ser Gln Ser Thr His Val Pro Tyr Thr Phe Gly
225                 230                 235                 240
```

```
ggg ggg acc aag ctg gaa ata aaa gac tac aaa gac gat gac gat aaa      768
Gly Gly Thr Lys Leu Glu Ile Lys Asp Tyr Lys Asp Asp Asp Asp Lys
                245                 250                 255 taatgaggat cc                                                        780

<210> SEQ ID NO 49
<211> LENGTH: 45
<212> TYPE: DNA
<213> ORGANISM: Artificial Sequence
<220> FEATURE:
<223> OTHER INFORMATION: Description of Artificial Sequence: PCR primer

<400> SEQUENCE: 49
caagctcgag ataaaatccg gaggccaggt ccaattgcag cagtc                     45

<210> SEQ ID NO 50
<211> LENGTH: 48
<212> TYPE: DNA
<213> ORGANISM: Artificial Sequence
<220> FEATURE:
<223> OTHER INFORMATION: Description of Artificial Sequence: PCR primer

<400> SEQUENCE: 50
caagctcgag ataaaatccg gaggtggcca ggtccaattg cagcagtc                  48

<210> SEQ ID NO 51
<211> LENGTH: 51
<212> TYPE: DNA
<213> ORGANISM: Artificial Sequence
<220> FEATURE:
<223> OTHER INFORMATION: Description of Artificial Sequence: PCR primer

<400> SEQUENCE: 51
caagctcgag ataaaatccg gaggtggtgg ccaggtccaa ttgcagcagt c               51

<210> SEQ ID NO 52
<211> LENGTH: 54
<212> TYPE: DNA
<213> ORGANISM: Artificial Sequence
<220> FEATURE:
<223> OTHER INFORMATION: Description of Artificial Sequence: PCR primer

<400> SEQUENCE: 52
caagctcgag ataaaatccg gaggtggtgg tggccaggtc caattgcagc agtc            54

<210> SEQ ID NO 53
<211> LENGTH: 57
<212> TYPE: DNA
<213> ORGANISM: Artificial Sequence
<220> FEATURE:
<223> OTHER INFORMATION: Description of Artificial Sequence: PCR primer

<400> SEQUENCE: 53
caagctcgag ataaaatccg gaggtggtgg tggtggccag gtccaattgc agcagtc         57

<210> SEQ ID NO 54
<211> LENGTH: 780
<212> TYPE: DNA
<213> ORGANISM: Mus sp.
<220> FEATURE:
<221> NAME/KEY: CDS
<222> LOCATION: (1)..(768)
<223> OTHER INFORMATION: CF2LH-0/pCOS1. MABL2-scFv<LH-0

<400> SEQUENCE: 54 atg aag ttg cct gtt agg ctg ttg gtg ctg atg ttc tgg att cct ggt       48
```

```
      Met Lys Leu Pro Val Arg Leu Leu Val Leu Met Phe Trp Ile Pro Gly
       1               5                  10                  15 tcc agc agt gat gtt gtg atg acc caa agt cca ctc tcc ctg cct gtc        96
Ser Ser Ser Asp Val Val Met Thr Gln Ser Pro Leu Ser Leu Pro Val
             20                  25                  30 agt ctt gga gat caa gcc tcc atc tct tgc aga tca agt cag agc ctt       144
Ser Leu Gly Asp Gln Ala Ser Ile Ser Cys Arg Ser Ser Gln Ser Leu
         35                  40                  45 gtg cac agt aat gga aag acc tat tta cat tgg tac ctg cag aag cca       192
Val His Ser Asn Gly Lys Thr Tyr Leu His Trp Tyr Leu Gln Lys Pro
     50                  55                  60 ggc cag tct cca aaa ctc ctg atc tac aaa gtt tcc aac cga ttt tct       240
Gly Gln Ser Pro Lys Leu Leu Ile Tyr Lys Val Ser Asn Arg Phe Ser
 65                  70                  75                  80 ggg gtc cca gac agg ttc agt ggc agt gga tca gtg aca gat ttc aca       288
Gly Val Pro Asp Arg Phe Ser Gly Ser Gly Ser Val Thr Asp Phe Thr
                 85                  90                  95 ctc atg atc agc aga gtg gag gct gag gat ctg gga gtt tat ttc tgc       336
Leu Met Ile Ser Arg Val Glu Ala Glu Asp Leu Gly Val Tyr Phe Cys
             100                 105                 110 tct caa agt aca cat gtt ccg tac acg ttc gga ggg ggg acc aag ctc       384
Ser Gln Ser Thr His Val Pro Tyr Thr Phe Gly Gly Gly Thr Lys Leu
         115                 120                 125 gag ata aaa cag gtc caa ttg cag cag tct gga cct gaa ctg gta aag       432
Glu Ile Lys Gln Val Gln Leu Gln Gln Ser Gly Pro Glu Leu Val Lys
     130                 135                 140 cct ggg gct tca gtg aag atg tcc tgc aag gct tct gga tac acc ttc       480
Pro Gly Ala Ser Val Lys Met Ser Cys Lys Ala Ser Gly Tyr Thr Phe
145                 150                 155                 160 gct aac cat gtt att cac tgg gtg aag cag aag cca ggg cag ggc ctt       528
Ala Asn His Val Ile His Trp Val Lys Gln Lys Pro Gly Gln Gly Leu
                 165                 170                 175 gag tgg att gga tat att tat cct tac aat gat ggt act aag tat aat       576
Glu Trp Ile Gly Tyr Ile Tyr Pro Tyr Asn Asp Gly Thr Lys Tyr Asn
             180                 185                 190 gag aag ttc aag gac aag gcc act ctg act tca gac aaa tcc tcc acc       624
Glu Lys Phe Lys Asp Lys Ala Thr Leu Thr Ser Asp Lys Ser Ser Thr
         195                 200                 205 aca gcc tac atg gac ctc agc agc ctg gcc tct gag gac tct gcg gtc       672
Thr Ala Tyr Met Asp Leu Ser Ser Leu Ala Ser Glu Asp Ser Ala Val
     210                 215                 220 tat tac tgt gca aga ggg ggt tac tat act tac gac gac tgg ggc caa       720
Tyr Tyr Cys Ala Arg Gly Gly Tyr Tyr Thr Tyr Asp Asp Trp Gly Gln
225                 230                 235                 240 ggc acc act ctc aca gtc tcc tca gac tac aaa gac gat gac gat aaa       768
Gly Thr Thr Leu Thr Val Ser Ser Asp Tyr Lys Asp Asp Asp Asp Lys
                 245                 250                 255 taatgaggat cc                                                         780

<210> SEQ ID NO 55
<211> LENGTH: 351
<212> TYPE: DNA
<213> ORGANISM: Homo sapiens
<220> FEATURE:
<221> NAME/KEY: CDS
<222> LOCATION: (1)..(351)
<223> OTHER INFORMATION: 12B5HV. 1-351 peptide

<400> SEQUENCE: 55 cag gtg cag ctg gtg cag tct ggg gga ggc ttg gtc cgg ccc ggg ggg        48
Gln Val Gln Leu Val Gln Ser Gly Gly Gly Leu Val Arg Pro Gly Gly
 1               5                  10                  15
```

```
tcc ctg agt ctc tcc tgt gca gtc tct gga atc acc ctc agg acc tac      96
Ser Leu Ser Leu Ser Cys Ala Val Ser Gly Ile Thr Leu Arg Thr Tyr
            20                  25                  30 ggc atg cac tgg gtc cgc cag gct cca ggc aag ggg ctg gag tgg gtg     144
Gly Met His Trp Val Arg Gln Ala Pro Gly Lys Gly Leu Glu Trp Val
        35                  40                  45 gca ggt ata tcc ttt gac gga aga agt gaa tac tat gca gac tcc gtg     192
Ala Gly Ile Ser Phe Asp Gly Arg Ser Glu Tyr Tyr Ala Asp Ser Val
    50                  55                  60 cag ggc cga ttc acc atc tcc aga gac agt tcc aag aac acc ctg tat     240
Gln Gly Arg Phe Thr Ile Ser Arg Asp Ser Ser Lys Asn Thr Leu Tyr
65                  70                  75                  80 ctg caa atg aac agc ctg aga gcc gag gac acg gct gtg tat tac tgt     288
Leu Gln Met Asn Ser Leu Arg Ala Glu Asp Thr Ala Val Tyr Tyr Cys
                85                  90                  95 gcg aga gga gca cat tat ggt ttc gat atc tgg ggc caa ggg aca atg     336
Ala Arg Gly Ala His Tyr Gly Phe Asp Ile Trp Gly Gln Gly Thr Met
            100                 105                 110 gtc acc gtc tcg agt                                                 351
Val Thr Val Ser Ser
        115

<210> SEQ ID NO 56
<211> LENGTH: 57
<212> TYPE: DNA
<213> ORGANISM: Homo sapiens
<220> FEATURE:
<221> NAME/KEY: CDS
<222> LOCATION: (1)..(57)
<223> OTHER INFORMATION: reader sequence

<400> SEQUENCE: 56 atg gag ttt ggg ctg agc tgg gtt ttc ctc gtt gct ctt tta aga ggt      48
Met Glu Phe Gly Leu Ser Trp Val Phe Leu Val Ala Leu Leu Arg Gly
1               5                   10                  15 gtc cag tgt                                                          57
Val Gln Cys <210> SEQ ID NO 57
<211> LENGTH: 115
<212> TYPE: DNA
<213> ORGANISM: Artificial Sequence
<220> FEATURE:
<223> OTHER INFORMATION: Description of Artificial Sequence: 12B5VH-1
      nucleotide sequence

<400> SEQUENCE: 57
atggagtttg gctgagctg ggttttcctc gttgctcttt taagaggtgt ccagtgtcag      60
gtgcagctgt gcagtctgg ggaggcttg gtccggcccg ggggtccct gagtc            115

<210> SEQ ID NO 58
<211> LENGTH: 115
<212> TYPE: DNA
<213> ORGANISM: Artificial Sequence
<220> FEATURE:
<223> OTHER INFORMATION: Description of Artificial Sequence: 12B5VH-2
      nucleotide sequence

<400> SEQUENCE: 58
aaggatatac ctgccaccca ctccagcccc ttgcctggag cctggcggac ccagtgcatg      60
ccgtaggtcc tgagggtgat tccagagact gcacaggaga gactcaggga ccccc          115

<210> SEQ ID NO 59
```

-continued

```
<211> LENGTH: 115
<212> TYPE: DNA
<213> ORGANISM: Artificial Sequence
<220> FEATURE:
<223> OTHER INFORMATION: Description of Artificial Sequence: 12B5VH-3V
      nucleotide sequence

<400> SEQUENCE: 59
ggcaggtata tcctttgacg gaagaagtga atactatgca gactccgtgc agggccgatt    60
caccatctcc agagacagtt ccaagaacac cctgtatctg caaatgaaca gcctg        115

<210> SEQ ID NO 60
<211> LENGTH: 108
<212> TYPE: DNA
<213> ORGANISM: Artificial Sequence
<220> FEATURE:
<223> OTHER INFORMATION: Description of Artificial Sequence: 12B5VH-4
      nucleotide sequence

<400> SEQUENCE: 60
actcgagacg gtgaccattg tcccttggcc ccagatatcg aaaccataat gtgctcctct    60
cgcacagtaa tacacagccg tgtcctcggc tctcaggctg ttcatttg                 108

<210> SEQ ID NO 61
<211> LENGTH: 32
<212> TYPE: DNA
<213> ORGANISM: Artificial Sequence
<220> FEATURE:
<223> OTHER INFORMATION: Description of Artificial Sequence: 12B5VH-S,
      PCR primer

<400> SEQUENCE: 61
ttcaagcttc caccatggag tttgggctga gc                                  32

<210> SEQ ID NO 62
<211> LENGTH: 34
<212> TYPE: DNA
<213> ORGANISM: Artificial Sequence
<220> FEATURE:
<223> OTHER INFORMATION: Description of Artificial Sequence: 12B5VH-A,
      PCR primer

<400> SEQUENCE: 62
ttgggatcca ctcaccactc gagacggtga ccat                                34

<210> SEQ ID NO 63
<211> LENGTH: 558
<212> TYPE: DNA
<213> ORGANISM: Homo sapiens
<220> FEATURE:
<221> NAME/KEY: CDS
<222> LOCATION: (235)..(558)
<223> OTHER INFORMATION: 1-235;intron, 236-558;Homo sapiensIgG constant
      region (partial)

<400> SEQUENCE: 63
gaattcgtga gtggatccca agctagcttt ctggggcagg ccaggcctga ccttggcttt    60
ggggcaggga gggggctaag gtgaggcagg tggcgccagc caggtgcaca cccaatgccc   120
atgagcccag acactggacg ctgaacctcg cggacagtta agaacccagg ggcctctgcg   180
ccctgggccc agctctgtcc cacaccgcgg tcacatggca caacctctct tgca gcc     237
                                                              Ala
                                                               1 tcc acc aag ggc cca tcg gtc ttc ccc ctg gca ccc tcc tcc aag agc     285
Ser Thr Lys Gly Pro Ser Val Phe Pro Leu Ala Pro Ser Ser Lys Ser
      5                  10                  15
```

```
acc tct ggg ggc aca gcg gcc ctg ggc tgc ctg gtc aag gac tac ttc      333
Thr Ser Gly Gly Thr Ala Ala Leu Gly Cys Leu Val Lys Asp Tyr Phe
         20                  25                  30 ccc gaa ccg gtg acg gtg tcg tgg aac tca ggc gcc ctg acc agc ggc      381
Pro Glu Pro Val Thr Val Ser Trp Asn Ser Gly Ala Leu Thr Ser Gly
 35                  40                  45 gtg cac acc ttc ccg gct gtc cta cag tcc tca gga ctc tac tcc ctc      429
Val His Thr Phe Pro Ala Val Leu Gln Ser Ser Gly Leu Tyr Ser Leu
 50                  55                  60                  65 agc agc gtg gtg acc gtg ccc tcc agc agc ttg ggc acc cag acc tac      477
Ser Ser Val Val Thr Val Pro Ser Ser Ser Leu Gly Thr Gln Thr Tyr
                 70                  75                  80 atc tgc aac gtg aat cac aag ccc agc aac acc aag gtg gac aag aaa      525
Ile Cys Asn Val Asn His Lys Pro Ser Asn Thr Lys Val Asp Lys Lys
             85                  90                  95 gtt gag ccc aaa tct tgt gac aaa act cac aca                          558
Val Glu Pro Lys Ser Cys Asp Lys Thr His Thr
             100                 105

<210> SEQ ID NO 64
<211> LENGTH: 27
<212> TYPE: DNA
<213> ORGANISM: Artificial Sequence
<220> FEATURE:
<223> OTHER INFORMATION: Description of Artificial Sequence: G1CH1-S,
      PCR primer

<400> SEQUENCE: 64
tgagaattcg tgagtggatc ccaagct                                         27

<210> SEQ ID NO 65
<211> LENGTH: 60
<212> TYPE: DNA
<213> ORGANISM: Artificial Sequence
<220> FEATURE:
<223> OTHER INFORMATION: Description of Artificial Sequence: G1CH1-A,
      PCR primer

<400> SEQUENCE: 65
aaaagatctt tatcatgtgt gagttttgtc acaagatttg ggctcaactt tcttgtccac     60

<210> SEQ ID NO 66
<211> LENGTH: 432
<212> TYPE: DNA
<213> ORGANISM: Homo sapiens
<220> FEATURE:
<221> NAME/KEY: CDS
<222> LOCATION: (12)..(419)
<223> OTHER INFORMATION: HEF-12B5H-g gamma. 12-419 peptide

<400> SEQUENCE: 66
aagcttccac c atg gag ttt ggg ctg agc tgg gtt ttc ctc gtt gct ctt      50
            Met Glu Phe Gly Leu Ser Trp Val Phe Leu Val Ala Leu
             1               5                  10 tta aga ggt gtc cag tgt cag gtg cag ctg gtg cag tct ggg gga ggc       98
Leu Arg Gly Val Gln Cys Gln Val Gln Leu Val Gln Ser Gly Gly Gly
 15                  20                  25 ttg gtc cgg ccc ggg ggg tcc ctg agt ctc tcc tgt gca gtc tct gga      146
Leu Val Arg Pro Gly Gly Ser Leu Ser Leu Ser Cys Ala Val Ser Gly
         30                  35                  40                  45 atc acc ctc agg acc tac ggc atg cac tgg gtc cgc cag gct cca ggc      194
Ile Thr Leu Arg Thr Tyr Gly Met His Trp Val Arg Gln Ala Pro Gly
                 50                  55                  60 aag ggg ctg gag tgg gtg gca ggt ata tcc ttt gac gga aga agt gaa      242
```

```
Lys Gly Leu Glu Trp Val Ala Gly Ile Ser Phe Asp Gly Arg Ser Glu
            65                  70                  75 tac tat gca gac tcc gtg cag ggc cga ttc acc atc tcc aga gac agt      290
Tyr Tyr Ala Asp Ser Val Gln Gly Arg Phe Thr Ile Ser Arg Asp Ser
        80                  85                  90 tcc aag aac acc ctg tat ctg caa atg aac agc ctg aga gcc gag gac      338
Ser Lys Asn Thr Leu Tyr Leu Gln Met Asn Ser Leu Arg Ala Glu Asp
        95                 100                 105 acg gct gtg tat tac tgt gcg aga gga gca cat tat ggt ttc gat atc      386
Thr Ala Val Tyr Tyr Cys Ala Arg Gly Ala His Tyr Gly Phe Asp Ile
110                 115                 120                 125 tgg ggc caa ggg aca atg gtc acc gtc tcg agt ggtgagtgga tcc           432
Trp Gly Gln Gly Thr Met Val Thr Val Ser Ser
                130                 135
```

<210> SEQ ID NO 67
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: 12B5LV. 1-321 peptide

<400> SEQUENCE: 67

```
gac atc cag atg acc cag tct cct tcc acc ctg tct gca tct att gga      48
Asp Ile Gln Met Thr Gln Ser Pro Ser Thr Leu Ser Ala Ser Ile Gly
 1               5                  10                  15 gac aga gtc acc atc acc tgc cgg gcc agc gag ggt att tat cac tgg      96
Asp Arg Val Thr Ile Thr Cys Arg Ala Ser Glu Gly Ile Tyr His Trp
            20                  25                  30 ttg gcc tgg tat cag cag aag cca ggg aaa gcc cct aaa ctc ctg atc      144
Leu Ala Trp Tyr Gln Gln Lys Pro Gly Lys Ala Pro Lys Leu Leu Ile
        35                  40                  45 tat aag gcc tct agt tta gcc agt ggg gcc cca tca agg ttc agc ggc      192
Tyr Lys Ala Ser Ser Leu Ala Ser Gly Ala Pro Ser Arg Phe Ser Gly
    50                  55                  60 agt gga tct ggg aca gat ttc act ctc acc atc agc agc ctg cag cct      240
Ser Gly Ser Gly Thr Asp Phe Thr Leu Thr Ile Ser Ser Leu Gln Pro
65                  70                  75                  80 gat gat ttt gca act tat tac tgc caa caa tat agt aat tat ccg ctc      288
Asp Asp Phe Ala Thr Tyr Tyr Cys Gln Gln Tyr Ser Asn Tyr Pro Leu
                85                  90                  95 act ttc ggc gga ggg acc aag ctg gag atc aaa                          321
Thr Phe Gly Gly Gly Thr Lys Leu Glu Ile Lys
            100                 105
```

<210> SEQ ID NO 68
<211> LENGTH: 66
<212> TYPE: DNA
<213> ORGANISM: Homo sapiens
<220> FEATURE:
<221> NAME/KEY: CDS
<222> LOCATION: (1)..(66)
<223> OTHER INFORMATION: reader sequence

<400> SEQUENCE: 68

```
atg gac atg agg gtc ccc gct cag ctc ctg ggg ctc ctg ctg ctc tgg      48
Met Asp Met Arg Val Pro Ala Gln Leu Leu Gly Leu Leu Leu Leu Trp
 1               5                  10                  15 ctc cca ggt gcc aaa tgt                                              66
Leu Pro Gly Ala Lys Cys
            20
```

```
<210> SEQ ID NO 69
<211> LENGTH: 110
<212> TYPE: DNA
<213> ORGANISM: Artificial Sequence
<220> FEATURE:
<223> OTHER INFORMATION: Description of Artificial Sequence: 12B5VL-1
      nucleotide sequence

<400> SEQUENCE: 69
atggacatga gggtccccgc tcagctcctg gggctcctgc tgctctggct cccaggtgcc      60
aaatgtgaca tccagatgac ccagtctcct tccaccctgt ctgcatctat                110

<210> SEQ ID NO 70
<211> LENGTH: 110
<212> TYPE: DNA
<213> ORGANISM: Artificial Sequence
<220> FEATURE:
<223> OTHER INFORMATION: Description of Artificial Sequence: 12B5VL-2
      nucleotide sequence

<400> SEQUENCE: 70
ggagtttagg ggcttttccct ggcttctgct gataccaggc caaccagtga taaatacccct   60 cgctggcccg gcaggtgatg gtgactctgt ctccaataga tgcagacagg               110

<210> SEQ ID NO 71
<211> LENGTH: 110
<212> TYPE: DNA
<213> ORGANISM: Artificial Sequence
<220> FEATURE:
<223> OTHER INFORMATION: Description of Artificial Sequence: 12B5VL-3
      nucleotide sequence

<400> SEQUENCE: 71
aagcccctaa actcctgatc tataaggcct ctagtttagc cagtggggcc ccatcaaggt     60
tcagcggcag tggatctggg acagatttca ctctcaccat cagcagcctg               110

<210> SEQ ID NO 72
<211> LENGTH: 103
<212> TYPE: DNA
<213> ORGANISM: Artificial Sequence
<220> FEATURE:
<223> OTHER INFORMATION: Description of Artificial Sequence: 12B5VL-4
      nucleotide sequence

<400> SEQUENCE: 72
tttgatctcc agcttggtcc ctccgccgaa agtgagcgga taattactat attgttggca     60
gtaataagtt gcaaaatcat caggctgcag gctgctgatg gtg                      103

<210> SEQ ID NO 73
<211> LENGTH: 32
<212> TYPE: DNA
<213> ORGANISM: Artificial Sequence
<220> FEATURE:
<223> OTHER INFORMATION: Description of Artificial Sequence: 12B5VL-S,
      PCR primer

<400> SEQUENCE: 73
ttcaagcttc caccatggac atgagggtcc cc                                   32

<210> SEQ ID NO 74
<211> LENGTH: 35
<212> TYPE: DNA
<213> ORGANISM: Artificial Sequence
<220> FEATURE:
<223> OTHER INFORMATION: Description of Artificial Sequence: 12B5VL-A,
      PCR primer
```

<400> SEQUENCE: 74
tctaggatcc actcacgttt gatctccagc ttggt                          35

<210> SEQ ID NO 75
<211> LENGTH: 415
<212> TYPE: DNA
<213> ORGANISM: Homo sapiens
<220> FEATURE:
<221> NAME/KEY: CDS
<222> LOCATION: (12)..(398)
<223> OTHER INFORMATION: HEF-12B5H-g kappa. 12-398 peptide

<400> SEQUENCE: 75

```
aagcttccac c atg gac atg agg gtc ccc gct cag ctc ctg ggg ctc ctg     50
            Met Asp Met Arg Val Pro Ala Gln Leu Leu Gly Leu Leu
              1               5                  10 ctg ctc tgg ctc cca ggt gcc aaa tgt gac atc cag atg acc cag tct     98
Leu Leu Trp Leu Pro Gly Ala Lys Cys Asp Ile Gln Met Thr Gln Ser
    15                  20                  25 cct tcc acc ctg tct gca tct att gga gac aga gtc acc atc acc tgc    146
Pro Ser Thr Leu Ser Ala Ser Ile Gly Asp Arg Val Thr Ile Thr Cys
 30                  35                  40                  45 cgg gcc agc gag ggt att tat cac tgg ttg gcc tgg tat cag cag aag    194
Arg Ala Ser Glu Gly Ile Tyr His Trp Leu Ala Trp Tyr Gln Gln Lys
                 50                  55                  60 cca ggg aaa gcc cct aaa ctc ctg atc tat aag gcc tct agt tta gcc    242
Pro Gly Lys Ala Pro Lys Leu Leu Ile Tyr Lys Ala Ser Ser Leu Ala
             65                  70                  75 agt ggg gcc cca tca agg ttc agc ggc agt gga tct ggg aca gat ttc    290
Ser Gly Ala Pro Ser Arg Phe Ser Gly Ser Gly Ser Gly Thr Asp Phe
         80                  85                  90 act ctc acc atc agc agc ctg cag cct gat gat ttt gca act tat tac    338
Thr Leu Thr Ile Ser Ser Leu Gln Pro Asp Asp Phe Ala Thr Tyr Tyr
     95                 100                 105 tgc caa caa tat agt aat tat ccg ctc act ttc ggc gga ggg acc aag    386
Cys Gln Gln Tyr Ser Asn Tyr Pro Leu Thr Phe Gly Gly Gly Thr Lys
110                 115                 120                 125 ctg gag atc aaa cgtgagtgga tcctaga                                 415
Leu Glu Ile Lys
```

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: FLAG tag
      sequence
<220> FEATURE:
<221> NAME/KEY: CDS
<222> LOCATION: (1)..(24)

<400> SEQUENCE: 76

```
gac tac aag gat gac gac gat aag                                    24
Asp Tyr Lys Asp Asp Asp Asp Lys
 1               5
```

<210> SEQ ID NO 77
<211> LENGTH: 31
<212> TYPE: DNA
<213> ORGANISM: Artificial Sequence
<220> FEATURE:
<223> OTHER INFORMATION: Description of Artificial Sequence: 12B5-S, PCR
      primer

<400> SEQUENCE: 77

```
atagaattcc accatggagt ttgggctgag c                              31
```

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: HuVHJ3, PCR
      primer

<400> SEQUENCE: 78

```
tgaagagacg gtgaccattg tccc                                      24
```

<210> SEQ ID NO 79
<211> LENGTH: 28
<212> TYPE: DNA
<213> ORGANISM: Artificial Sequence
<220> FEATURE:
<223> OTHER INFORMATION: Description of Artificial Sequence: RhuJH3, PCR
      primer

<400> SEQUENCE: 79

```
ggacaatggt caccgtctct tcaggtgg                                  28
```

<210> SEQ ID NO 80
<211> LENGTH: 32
<212> TYPE: DNA
<213> ORGANISM: Artificial Sequence
<220> FEATURE:
<223> OTHER INFORMATION: Description of Artificial Sequence: RhuVK1, PCR
      primer

<400> SEQUENCE: 80

```
ggagactggg tcatctggat gtccgatccg cc                             32
```

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: HuVK1.2,
      PCR primer

<400> SEQUENCE: 81

```
gacatccaga tgacccagtc tcc                                       23
```

<210> SEQ ID NO 82
<211> LENGTH: 59
<212> TYPE: DNA
<213> ORGANISM: Artificial Sequence
<220> FEATURE:
<223> OTHER INFORMATION: Description of Artificial Sequence: 12B5F-A,
      PCR primer

<400> SEQUENCE: 82

```
attgcggccg cttatcactt atcgtcgtca tccttgtagt ctttgatctc cagcttggt    59
```

<210> SEQ ID NO 83
<211> LENGTH: 45
<212> TYPE: DNA
<213> ORGANISM: Artificial Sequence
<220> FEATURE:
<223> OTHER INFORMATION: Description of Artificial Sequence: Linker
      nucleotide sequence
<220> FEATURE:
<221> NAME/KEY: CDS
<222> LOCATION: (1)..(45)

```
<400> SEQUENCE: 83 ggt ggt ggt ggt tcg ggt ggt ggt ggt tcg ggt ggt ggc gga tcg        45
Gly Gly Gly Gly Ser Gly Gly Gly Gly Ser Gly Gly Gly Gly Ser
 1               5                  10                  15

<210> SEQ ID NO 84
<211> LENGTH: 823
<212> TYPE: DNA
<213> ORGANISM: Homo sapiens
<220> FEATURE:
<221> NAME/KEY: CDS
<222> LOCATION: (12)..(809)
<223> OTHER INFORMATION: sc12B5, Single chain Fv

<400> SEQUENCE: 84
aagcttccac c atg gag ttt ggg ctg agc tgg gtt ttc ctc gtt gct ctt   50
            Met Glu Phe Gly Leu Ser Trp Val Phe Leu Val Ala Leu
             1               5                  10 tta aga ggt gtc cag tgt cag gtg cag ctg gtg cag tct ggg gga ggc   98
Leu Arg Gly Val Gln Cys Gln Val Gln Leu Val Gln Ser Gly Gly Gly
 15                  20                  25 ttg gtc cgg ccc ggg ggg tcc ctg agt ctc tcc tgt gca gtc tct gga  146
Leu Val Arg Pro Gly Gly Ser Leu Ser Leu Ser Cys Ala Val Ser Gly
 30                  35                  40                  45 atc acc ctc agg acc tac ggc atg cac tgg gtc cgc cag gct cca ggc  194
Ile Thr Leu Arg Thr Tyr Gly Met His Trp Val Arg Gln Ala Pro Gly
                 50                  55                  60 aag ggg ctg gag tgg gtg gca ggt ata tcc ttt gac gga aga agt gaa  242
Lys Gly Leu Glu Trp Val Ala Gly Ile Ser Phe Asp Gly Arg Ser Glu
 65                  70                  75 tac tat gca gac tcc gtg cag ggc cga ttc acc atc tcc aga gac agt  290
Tyr Tyr Ala Asp Ser Val Gln Gly Arg Phe Thr Ile Ser Arg Asp Ser
 80                  85                  90 tcc aag aac acc ctg tat ctg caa atg aac agc ctg aga gcc gag gac  338
Ser Lys Asn Thr Leu Tyr Leu Gln Met Asn Ser Leu Arg Ala Glu Asp
 95                 100                 105 acg gct gtg tat tac tgt gcg aga gga gca cat tat ggt ttc gat atc  386
Thr Ala Val Tyr Tyr Cys Ala Arg Gly Ala His Tyr Gly Phe Asp Ile
110                 115                 120                 125 tgg ggc caa ggg aca atg gtc acc gtc tcg agt ggt ggt ggt ggt tcg  434
Trp Gly Gln Gly Thr Met Val Thr Val Ser Ser Gly Gly Gly Gly Ser
                130                 135                 140 ggt ggt ggt ggt tcg ggt ggt ggc gga tcg gac atc cag atg acc cag  482
Gly Gly Gly Gly Ser Gly Gly Gly Gly Ser Asp Ile Gln Met Thr Gln
                145                 150                 155 tct cct tcc acc ctg tct gca tct att gga gac aga gtc acc atc acc  530
Ser Pro Ser Thr Leu Ser Ala Ser Ile Gly Asp Arg Val Thr Ile Thr
                160                 165                 170 tgc cgg gcc agc gag ggt att tat cac tgg ttg gcc tgg tat cag cag  578
Cys Arg Ala Ser Glu Gly Ile Tyr His Trp Leu Ala Trp Tyr Gln Gln
175                 180                 185 aag cca ggg aaa gcc cct aaa ctc ctg atc tat aag gcc tct agt tta  626
Lys Pro Gly Lys Ala Pro Lys Leu Leu Ile Tyr Lys Ala Ser Ser Leu
190                 195                 200                 205 gcc agt ggg gcc cca tca agg ttc agc ggc agt gga tct ggg aca gat  674
Ala Ser Gly Ala Pro Ser Arg Phe Ser Gly Ser Gly Ser Gly Thr Asp
                210                 215                 220 ttc act ctc acc atc agc agc ctg cag cct gat gat ttt gca act tat  722
Phe Thr Leu Thr Ile Ser Ser Leu Gln Pro Asp Asp Phe Ala Thr Tyr
                225                 230                 235 tac tgc caa caa tat agt aat tat ccg ctc act ttc ggc gga ggg acc  770
Tyr Cys Gln Gln Tyr Ser Asn Tyr Pro Leu Thr Phe Gly Gly Gly Thr
```

```
                    240                 245                 250
aag ctg gag atc aaa gac tac aag gat gac gac gat aag tgataagcgg         819
Lys Leu Glu Ile Lys Asp Tyr Lys Asp Asp Asp Asp Lys
    255                 260                 265 ccgc                                                                    823

<210> SEQ ID NO 85
<211> LENGTH: 114
<212> TYPE: PRT
<213> ORGANISM: Homo sapiens

<400> SEQUENCE: 85

Gln Val Gln Leu Gln Gln Ser Gly Pro Gly Leu Val Lys Pro Ser Glu
  1               5                  10                  15

Thr Leu Ser Leu Thr Cys Thr Val Ser Gly Asp Ser Ile Ser Ser Tyr
             20                  25                  30

Tyr Trp Ser Trp Ile Arg Gln Pro Pro Gly Lys Gly Leu Glu Trp Ile
         35                  40                  45

Gly Tyr Ile Tyr Tyr Ser Gly Ser Thr Asn Tyr Asn Pro Ser Leu Lys
     50                  55                  60

Ser Arg Val Thr Ile Ser Val Asp Thr Ser Lys Ser Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Arg Tyr Phe Asp Val Trp Gly Arg Gly Thr Met Val Thr Val
            100                 105                 110

Ser Ser

<210> SEQ ID NO 86
<211> LENGTH: 342
<212> TYPE: DNA
<213> ORGANISM: Homo sapiens

<400> SEQUENCE: 86
caggtgcagc tgcagcagtc gggcccagga ctggtgaagc cttcggagac cctgtccctc        60
acctgcactg tctctggtga ctccatcagt agttactact ggagctggat tcggcagccc       120
ccagggaagg gactggagtg gattgggtat atctattaca gtgggagcac caactacaac       180
ccctccctca gagtcgagt  caccatatca gtagacacgt ccaagagcca gttctccctg       240
aagctgagct ctgtgaccgc cgcagacacg gccgtgtatt actgtgcgag agggcggtac       300
ttcgatgtct ggggccgtgg caccatggtc actgtctcct ca                         342

<210> SEQ ID NO 87
<211> LENGTH: 57
<212> TYPE: DNA
<213> ORGANISM: Homo sapiens
<220> FEATURE:
<221> NAME/KEY: CDS
<222> LOCATION: (1)..(57)
<223> OTHER INFORMATION: reader sequence
<220> FEATURE:
<223> OTHER INFORMATION: Genbank Acc. No. AF062252

<400> SEQUENCE: 87 atg aaa cat ctg tgg ttc ttc ctt ctc ctg gtg gca gct ccc aga tgg       48
Met Lys His Leu Trp Phe Phe Leu Leu Leu Val Ala Ala Pro Arg Trp
  1               5                  10                  15 gtc ctg tcc                                                             57
Val Leu Ser
```

<210> SEQ ID NO 88
<211> LENGTH: 110
<212> TYPE: DNA
<213> ORGANISM: Artificial Sequence
<220> FEATURE:
<223> OTHER INFORMATION: Description of Artificial Sequence: 12E10VH15
      nucleotide sequence

<400> SEQUENCE: 88
atgaaacatc tgtggttctt ccttctcctg gtggcagctc ccagatgggt cctgtcccag        60
gtgcagctgc agcagtcggg cccaggactg gtgaagcctt cggagaccct                  110

<210> SEQ ID NO 89
<211> LENGTH: 110
<212> TYPE: DNA
<213> ORGANISM: Artificial Sequence
<220> FEATURE:
<223> OTHER INFORMATION: Description of Artificial Sequence: 12E10VH2
      nucleotide sequence

<400> SEQUENCE: 89
acccaatcca ctccagtccc ttccctgggg gctgccgaat ccagctccag tagtaactac        60
tgatggagtc accagagaca gtgcaggtga gggacagggt ctccgaaggc                  110

<210> SEQ ID NO 90
<211> LENGTH: 110
<212> TYPE: DNA
<213> ORGANISM: Artificial Sequence
<220> FEATURE:
<223> OTHER INFORMATION: Description of Artificial Sequence: 12E10VH3
      nucleotide sequence

<400> SEQUENCE: 90
tggagtggat tgggtatatc tattacagtg ggagcaccaa ctacaacccc tccctcaaga        60
gtcgagtcac catatcagta gacacgtcca agagccagtt ctccctgaag                  110

<210> SEQ ID NO 91
<211> LENGTH: 114
<212> TYPE: DNA
<213> ORGANISM: Artificial Sequence
<220> FEATURE:
<223> OTHER INFORMATION: Description of Artificial Sequence: 12E10VH4
      nucleotide sequence

<400> SEQUENCE: 91
tgaggagaca gtgaccatgg tgccacggcc ccagacatcg aagtaccgcc ctctcgcaca        60
gtaatacacg gccgtgtctg cggcggtcac agagctcagc ttcagggaga actg            114

<210> SEQ ID NO 92
<211> LENGTH: 32
<212> TYPE: DNA
<213> ORGANISM: Artificial Sequence
<220> FEATURE:
<223> OTHER INFORMATION: Description of Artificial Sequence: 12E10VHS,
      PCR primer

<400> SEQUENCE: 92
ttcaagcttc caccatgaaa catctgtggt tc                                      32

<210> SEQ ID NO 93
<211> LENGTH: 34
<212> TYPE: DNA
<213> ORGANISM: Artificial Sequence
<220> FEATURE:
<223> OTHER INFORMATION: Description of Artificial Sequence: 12E10VHA, PCR primer

<400> SEQUENCE: 93

```
ttgggatcca ctcacctgag gagacagtga ccat                              34
```

<210> SEQ ID NO 94
<211> LENGTH: 426
<212> TYPE: DNA
<213> ORGANISM: Mus sp.
<220> FEATURE:
<221> NAME/KEY: CDS
<222> LOCATION: (12)..(410)
<223> OTHER INFORMATION: 12E10H, H chain V region

<400> SEQUENCE: 94

```
aagcttccac c atg aaa cat ctg tgg ttc ttc ctt ctc ctg gtg gca gct      50
            Met Lys His Leu Trp Phe Phe Leu Leu Leu Val Ala Ala
            1               5                   10 ccc aga tgg gtc ctg tcc cag gtg cag ctg cag cag tcg ggc cca gga      98
Pro Arg Trp Val Leu Ser Gln Val Gln Leu Gln Gln Ser Gly Pro Gly
 15                  20                  25 ctg gtg aag cct tcg gag acc ctg tcc ctc acc tgc act gtc tct ggt     146
Leu Val Lys Pro Ser Glu Thr Leu Ser Leu Thr Cys Thr Val Ser Gly
 30                  35                  40                  45 gac tcc atc agt agt tac tac tgg agc tgg att cgg cag ccc cca ggg     194
Asp Ser Ile Ser Ser Tyr Tyr Trp Ser Trp Ile Arg Gln Pro Pro Gly
                 50                  55                  60 aag gga ctg gag tgg att ggg tat atc tat tac agt ggg agc acc aac     242
Lys Gly Leu Glu Trp Ile Gly Tyr Ile Tyr Tyr Ser Gly Ser Thr Asn
             65                  70                  75 tac aac ccc tcc ctc aag agt cga gtc acc ata tca gta gac acg tcc     290
Tyr Asn Pro Ser Leu Lys Ser Arg Val Thr Ile Ser Val Asp Thr Ser
         80                  85                  90 aag agc cag ttc tcc ctg aag ctg agc tct gtg acc gcc gca gac acg     338
Lys Ser Gln Phe Ser Leu Lys Leu Ser Ser Val Thr Ala Ala Asp Thr
     95                  100                 105 gcc gtg tat tac tgt gcg aga ggg cgg tac ttc gat gtc tgg ggc cgt     386
Ala Val Tyr Tyr Cys Ala Arg Gly Arg Tyr Phe Asp Val Trp Gly Arg
110                 115                 120                 125 ggc acc atg gtc act gtc tcc tca ggtgagtgga tcccaa                   426
Gly Thr Met Val Thr Val Ser Ser
                130
```

<210> SEQ ID NO 95
<211> LENGTH: 110
<212> TYPE: PRT
<213> ORGANISM: Mus sp.

<400> SEQUENCE: 95

```
Ser Tyr Val Leu Thr Gln Pro Pro Ser Val Ser Gly Ser Pro Gly Gln
 1               5                   10                  15

Ser Ile Thr Ile Ser Cys Thr Gly Thr Ser Ser Asp Val Gly Gly Tyr
             20                  25                  30

Asn Tyr Val Ser Trp Tyr Gln Gln His Pro Gly Lys Ala Pro Lys Leu
         35                  40                  45

Met Ile Tyr Glu Gly Ser Lys Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Thr Arg
             85                  90                  95
```

```
Ser Thr Arg Val Phe Gly Gly Gly Thr Lys Leu Thr Val Leu
            100                 105                 110
```

<210> SEQ ID NO 96
<211> LENGTH: 330
<212> TYPE: DNA
<213> ORGANISM: Mus sp.

<400> SEQUENCE: 96

```
tcctatgtgc tgactcagcc accctcggtg tcagggtctc ctggacagtc gatcaccatc    60
tcctgcactg gaaccagcag tgacgttggt ggttataact atgtctcctg gtaccaacag   120
cacccaggca aagcccccaa actcatgatt tatgagggca gtaaacggcc ctcaggggtt   180
tctaatcgct tctctggctc caagtctggc aacacggcct ccctgaccat ctctgggctc   240
caggctgagg acgaggctga ttattactgc agctcatata caaccagaag cactcgggtg   300
ttcggcggag ggaccaagct gaccgtccta                                    330
```

<210> SEQ ID NO 97
<211> LENGTH: 57
<212> TYPE: DNA
<213> ORGANISM: Homo sapiens
<220> FEATURE:
<221> NAME/KEY: CDS
<222> LOCATION: (1)..(57)
<223> OTHER INFORMATION: reader sequence

<400> SEQUENCE: 97

```
atg gcc tgg acc gtt ctc ctc ctc ggc ctc ctc tct cac tgc aca ggc      48
Met Ala Trp Thr Val Leu Leu Leu Gly Leu Leu Ser His Cys Thr Gly
  1               5                  10                  15 tct gtg acc                                                          57
Ser Val Thr
```

<210> SEQ ID NO 98
<211> LENGTH: 110
<212> TYPE: DNA
<213> ORGANISM: Artificial Sequence
<220> FEATURE:
<223> OTHER INFORMATION: Description of Artificial Sequence: 12E10VL1,
      PCR primer

<400> SEQUENCE: 98

```
atggcctgga ccgttctcct cctcggcctc ctctctcact gcacaggctc tgtgacctcc    60
tatgtgctga ctcagccacc ctcggtgtca gggtctcctg acagtcgat                110
```

<210> SEQ ID NO 99
<211> LENGTH: 110
<212> TYPE: DNA
<213> ORGANISM: Artificial Sequence
<220> FEATURE:
<223> OTHER INFORMATION: Description of Artificial Sequence: 12E10VL2,
      PCR primer

<400> SEQUENCE: 99

```
tcatgagttt gggggctttg cctggtgctg ttggtaccag gagacatag ttataaccac     60 caacgtcact gctggttcca gtgcaggaga tggtgatcga ctgtccagga               110
```

<210> SEQ ID NO 100
<211> LENGTH: 110
<212> TYPE: DNA
<213> ORGANISM: Artificial Sequence
<220> FEATURE:
<223> OTHER INFORMATION: Description of Artificial Sequence: 12E10VL3,
      PCR primer

<400> SEQUENCE: 100
cccccaaact catgatttat gagggcagta acggccctc aggggtttct aatcgcttct        60
ctggctccaa gtctggcaac acggcctccc tgaccatctc tgggctccag                 110

<210> SEQ ID NO 101
<211> LENGTH: 102
<212> TYPE: DNA
<213> ORGANISM: Artificial Sequence
<220> FEATURE:
<223> OTHER INFORMATION: Description of Artificial Sequence: 12E10VL4,
      PCR primer

<400> SEQUENCE: 101
taggacggtc agcttggtcc ctccgccgaa cacccgagtg cttctggttg tatatgagct      60
gcagtaataa tcagcctcgt cctcagcctg gagcccagag at                        102

<210> SEQ ID NO 102
<211> LENGTH: 31
<212> TYPE: DNA
<213> ORGANISM: Artificial Sequence
<220> FEATURE:
<223> OTHER INFORMATION: Description of Artificial Sequence: 12E10VLS,
      PCR primer

<400> SEQUENCE: 102
atcaagcttc caccatggcc tggaccgttc t                                     31

<210> SEQ ID NO 103
<211> LENGTH: 36
<212> TYPE: DNA
<213> ORGANISM: Artificial Sequence
<220> FEATURE:
<223> OTHER INFORMATION: Description of Artificial Sequence: 12E10VLA,
      PCR primer

<400> SEQUENCE: 103
ctaggatccg ggctgaccta ggacggtcag cttggt                                36

<210> SEQ ID NO 104
<211> LENGTH: 387
<212> TYPE: DNA
<213> ORGANISM: Mus sp.
<220> FEATURE:
<221> NAME/KEY: CDS
<222> LOCATION: (1)..(387)
<223> OTHER INFORMATION: 12E10L, L chain V region

<400> SEQUENCE: 104

```
atg gcc tgg acc gtt ctc ctc ctc ggc ctc ctc tct cac tgc aca ggc        48
Met Ala Trp Thr Val Leu Leu Leu Gly Leu Leu Ser His Cys Thr Gly
 1               5                  10                  15 tct gtg acc tcc tat gtg ctg act cag cca ccc tcg gtg tca ggg tct        96
Ser Val Thr Ser Tyr Val Leu Thr Gln Pro Pro Ser Val Ser Gly Ser
             20                  25                  30 cct gga cag tcg atc acc atc tcc tgc act gga acc agc agt gac gtt       144
Pro Gly Gln Ser Ile Thr Ile Ser Cys Thr Gly Thr Ser Ser Asp Val
         35                  40                  45 ggt ggt tat aac tat gtc tcc tgg tac caa cag cac cca ggc aaa gcc       192
Gly Gly Tyr Asn Tyr Val Ser Trp Tyr Gln Gln His Pro Gly Lys Ala
     50                  55                  60 ccc aaa ctc atg att tat gag ggc agt aaa cgg ccc tca ggg gtt tct       240
Pro Lys Leu Met Ile Tyr Glu Gly Ser Lys Arg Pro Ser Gly Val Ser
 65                  70                  75                  80
```

-continued

```
aat cgc ttc tct ggc tcc aag tct ggc aac acg gcc tcc ctg acc atc      288
Asn Arg Phe Ser Gly Ser Lys Ser Gly Asn Thr Ala Ser Leu Thr Ile
            85                  90                  95 tct ggg ctc cag gct gag gac gag gct gat tat tac tgc agc tca tat      336
Ser Gly Leu Gln Ala Glu Asp Glu Ala Asp Tyr Tyr Cys Ser Ser Tyr
100                 105                 110 aca acc aga agc act cgg gtg ttc ggc gga ggg acc aag ctg acc gtc      384
Thr Thr Arg Ser Thr Arg Val Phe Gly Gly Gly Thr Lys Leu Thr Val
        115                 120                 125 cta                                                                   387
Leu

<210> SEQ ID NO 105
<211> LENGTH: 24
<212> TYPE: DNA
<213> ORGANISM: Artificial Sequence
<220> FEATURE:
<223> OTHER INFORMATION: Description of Artificial Sequence: FLAG,
      reader sequence
<220> FEATURE:
<221> NAME/KEY: CDS
<222> LOCATION: (1)..(24)

<400> SEQUENCE: 105 gac tac aag gat gac gac gat aag                                       24
Asp Tyr Lys Asp Asp Asp Asp Lys
  1               5

<210> SEQ ID NO 106
<211> LENGTH: 30
<212> TYPE: DNA
<213> ORGANISM: Artificial Sequence
<220> FEATURE:
<223> OTHER INFORMATION: Description of Artificial Sequence: 12E10S, PCR
      primer

<400> SEQUENCE: 106
tatgaattcc accatgaaac atctgtggtt                                      30

<210> SEQ ID NO 107
<211> LENGTH: 38
<212> TYPE: DNA
<213> ORGANISM: Artificial Sequence
<220> FEATURE:
<223> OTHER INFORMATION: Description of Artificial Sequence: DB2, PCR
      primer

<400> SEQUENCE: 107
taggagctac cgcctccacc tgaggagaca gtgaccat                             38

<210> SEQ ID NO 108
<211> LENGTH: 44
<212> TYPE: DNA
<213> ORGANISM: Artificial Sequence
<220> FEATURE:
<223> OTHER INFORMATION: Description of Artificial Sequence: DB1, PCR
      primer

<400> SEQUENCE: 108
gtctcctcag gtggaggcgg tagctcctat gtgctgactc agcc                      44

<210> SEQ ID NO 109
<211> LENGTH: 59
<212> TYPE: DNA
<213> ORGANISM: Artificial Sequence
<220> FEATURE:
<223> OTHER INFORMATION: Description of Artificial Sequence: 12E10FA,
      PCR primer
```

-continued

```
<400> SEQUENCE: 109
attgcggccg cttatcactt atcgtcgtca tccttgtagt ctaggacggt cagcttggt      59

<210> SEQ ID NO 110
<211> LENGTH: 792
<212> TYPE: DNA
<213> ORGANISM: Artificial Sequence
<220> FEATURE:
<223> OTHER INFORMATION: Description of Artificial Sequence: 12E10,
      Single chain Fv
<220> FEATURE:
<221> NAME/KEY: CDS
<222> LOCATION: (11)..(778)

<400> SEQUENCE: 110
gaattccacc atg aaa cat ctg tgg ttc ttc ctt ctc ctg gtg gca gct        49
           Met Lys His Leu Trp Phe Phe Leu Leu Leu Val Ala Ala
             1               5                  10 ccc aga tgg gtc ctg tcc cag gtg cag ctg cag cag tcg ggc cca gga       97
Pro Arg Trp Val Leu Ser Gln Val Gln Leu Gln Gln Ser Gly Pro Gly
         15                  20                  25 ctg gtg aag cct tcg gag acc ctg tcc ctc acc tgc act gtc tct ggt      145
Leu Val Lys Pro Ser Glu Thr Leu Ser Leu Thr Cys Thr Val Ser Gly
 30                  35                  40                  45 gac tcc atc agt agt tac tac tgg agc tgg att cgg cag ccc cca ggg      193
Asp Ser Ile Ser Ser Tyr Tyr Trp Ser Trp Ile Arg Gln Pro Pro Gly
                 50                  55                  60 aag gga ctg gag tgg att ggg tat atc tat tac agt ggg agc acc aac      241
Lys Gly Leu Glu Trp Ile Gly Tyr Ile Tyr Tyr Ser Gly Ser Thr Asn
             65                  70                  75 tac aac ccc tcc ctc aag agt cga gtc acc ata tca gta gac acg tcc      289
Tyr Asn Pro Ser Leu Lys Ser Arg Val Thr Ile Ser Val Asp Thr Ser
         80                  85                  90 aag agc cag ttc tcc ctg aag ctg agc tct gtg acc gcc gca gac acg      337
Lys Ser Gln Phe Ser Leu Lys Leu Ser Ser Val Thr Ala Ala Asp Thr
     95                 100                 105 gcc gtg tat tac tgt gcg aga ggg cgg tac ttc gat gtc tgg ggc cgt      385
Ala Val Tyr Tyr Cys Ala Arg Gly Arg Tyr Phe Asp Val Trp Gly Arg
110                 115                 120                 125 ggc acc atg gtc act gtc tca gga gga ggc ggt agc tcc tat gtg           433
Gly Thr Met Val Thr Val Ser Ser Gly Gly Gly Gly Ser Ser Tyr Val
                130                 135                 140 ctg act cag cca ccc tcg gtg tca ggg tct cct gga cag tcg atc acc      481
Leu Thr Gln Pro Pro Ser Val Ser Gly Ser Pro Gly Gln Ser Ile Thr
            145                 150                 155 atc tcc tgc act gga acc agc agt gac gtt ggt ggt tat aac tat gtc      529
Ile Ser Cys Thr Gly Thr Ser Ser Asp Val Gly Gly Tyr Asn Tyr Val
        160                 165                 170 tcc tgg tac caa cag cac cca ggc aaa gcc ccc aaa ctc atg att tat      577
Ser Trp Tyr Gln Gln His Pro Gly Lys Ala Pro Lys Leu Met Ile Tyr
    175                 180                 185 gag ggc agt aaa cgg ccc tca ggg gtt tct aat cgc ttc tct ggc tcc      625
Glu Gly Ser Lys Arg Pro Ser Gly Val Ser Asn Arg Phe Ser Gly Ser
190                 195                 200                 205 aag tct ggc aac acg gcc tcc ctg acc atc tct ggg ctc cag gct gag      673
Lys Ser Gly Asn Thr Ala Ser Leu Thr Ile Ser Gly Leu Gln Ala Glu
                210                 215                 220 gac gag gct gat tat tac tgc agc tca tat aca acc aga agc act cgg      721
Asp Glu Ala Asp Tyr Tyr Cys Ser Ser Tyr Thr Thr Arg Ser Thr Arg
            225                 230                 235 gtg ttc ggc gga ggg acc aag ctg acc gtc cta gac tac aag gat gac      769
Val Phe Gly Gly Gly Thr Lys Leu Thr Val Leu Asp Tyr Lys Asp Asp
```

-continued

```
Val Phe Gly Gly Gly Thr Lys Leu Thr Val Leu Asp Tyr Lys Asp Asp
        240                 245                 250 gac gat aag tgataagcgg ccgc                                          792
Asp Asp Lys
    255

<210> SEQ ID NO 111
<211> LENGTH: 62
<212> TYPE: DNA
<213> ORGANISM: Artificial Sequence
<220> FEATURE:
<223> OTHER INFORMATION: Description of Artificial Sequence: sc4.3, PCR
      primer

<400> SEQUENCE: 111
ggtggctgag tcagcacata ggacgatccg ccaccacccg aaccaccacc acccgaacca    60
cc                                                                  62

<210> SEQ ID NO 112
<211> LENGTH: 61
<212> TYPE: DNA
<213> ORGANISM: Artificial Sequence
<220> FEATURE:
<223> OTHER INFORMATION: Description of Artificial Sequence: sc1.3, PCR
      primer

<400> SEQUENCE: 112
gcaccatggt cactgtctcc tcaggtggtg gtggttcggg tggtggtggt tcgggtggtg    60
g                                                                   61

<210> SEQ ID NO 113
<211> LENGTH: 822
<212> TYPE: DNA
<213> ORGANISM: Artificial Sequence
<220> FEATURE:
<223> OTHER INFORMATION: Description of Artificial Sequence: sc12E10,
      single chain Fv
<220> FEATURE:
<221> NAME/KEY: CDS
<222> LOCATION: (11)..(808)

<400> SEQUENCE: 113
gaattccacc atg aaa cat ctg tgg ttc ttc ctt ctc ctg gtg gca gct       49
            Met Lys His Leu Trp Phe Phe Leu Leu Leu Val Ala Ala
              1               5                  10 ccc aga tgg gtc ctg tcc cag gtg cag ctg cag cag tcg ggc cca gga      97
Pro Arg Trp Val Leu Ser Gln Val Gln Leu Gln Gln Ser Gly Pro Gly
         15                  20                  25 ctg gtg aag cct tcg gag acc ctg tcc ctc acc tgc act gtc tct ggt     145
Leu Val Lys Pro Ser Glu Thr Leu Ser Leu Thr Cys Thr Val Ser Gly
 30                  35                  40                  45 gac tcc atc agt agt tac tac tgg agc tgg att cgg cag ccc cca ggg     193
Asp Ser Ile Ser Ser Tyr Tyr Trp Ser Trp Ile Arg Gln Pro Pro Gly
                 50                  55                  60 aag gga ctg gag tgg att ggg tat atc tat tac agt ggg agc acc aac     241
Lys Gly Leu Glu Trp Ile Gly Tyr Ile Tyr Tyr Ser Gly Ser Thr Asn
             65                  70                  75 tac aac ccc tcc ctc aag agt cga gtc acc ata tca gta gac acg tcc     289
Tyr Asn Pro Ser Leu Lys Ser Arg Val Thr Ile Ser Val Asp Thr Ser
         80                  85                  90 aag agc cag ttc tcc ctg aag ctg agc tct gtg acc gcc gca gac acg     337
Lys Ser Gln Phe Ser Leu Lys Leu Ser Ser Val Thr Ala Ala Asp Thr
     95                 100                 105 gcc gtg tat tac tgt gcg aga ggg cgg tac ttc gat gtc tgg ggc cgt     385
```

```
                ggc acc atg gtc act gtc tcc tca ggt ggt ggt ggt tcg ggt ggt ggt        433
                Gly Thr Met Val Thr Val Ser Ser Gly Gly Gly Gly Ser Gly Gly Gly
                        130                 135                 140 ggt tcg ggt ggt ggc gga tcg tcc tat gtg ctg act cag cca ccc tcg        481
                Gly Ser Gly Gly Gly Gly Ser Ser Tyr Val Leu Thr Gln Pro Pro Ser
                        145                 150                 155 gtg tca ggg tct cct gga cag tcg atc acc atc tcc tgc act gga acc        529
                Val Ser Gly Ser Pro Gly Gln Ser Ile Thr Ile Ser Cys Thr Gly Thr
                        160                 165                 170 agc agt gac gtt ggt ggt tat aac tat gtc tcc tgg tac caa cag cac        577
                Ser Ser Asp Val Gly Gly Tyr Asn Tyr Val Ser Trp Tyr Gln Gln His
                        175                 180                 185 cca ggc aaa gcc ccc aaa ctc atg att tat gag ggc agt aaa cgg ccc        625
                Pro Gly Lys Ala Pro Lys Leu Met Ile Tyr Glu Gly Ser Lys Arg Pro
                190                 195                 200                 205 tca ggg gtt tct aat cgc ttc tct ggc tcc aag tct ggc aac acg gcc        673
                Ser Gly Val Ser Asn Arg Phe Ser Gly Ser Lys Ser Gly Asn Thr Ala
                                210                 215                 220 tcc ctg acc atc tct ggg ctc cag gct gag gac gag gct gat tat tac        721
                Ser Leu Thr Ile Ser Gly Leu Gln Ala Glu Asp Glu Ala Asp Tyr Tyr
                            225                 230                 235 tgc agc tca tat aca acc aga agc act cgg gtg ttc ggc gga ggg acc        769
                Cys Ser Ser Tyr Thr Thr Arg Ser Thr Arg Val Phe Gly Gly Gly Thr
                        240                 245                 250 aag ctg acc gtc cta gac tac aag gat gac gac gat aag tgataagcgg        818
                Lys Leu Thr Val Leu Asp Tyr Lys Asp Asp Asp Lys
                        255                 260                 265 ccgc                                                                    822

<210> SEQ ID NO 114
<211> LENGTH: 131
<212> TYPE: PRT
<213> ORGANISM: Mus sp.

<400> SEQUENCE: 114

Met Lys Leu Pro Val Arg Leu Leu Val Leu Met Phe Trp Ile Pro Ala
            -15                 -10                  -5

Ser Ser Ser Asp Val Val Met Thr Gln Thr Pro Leu Ser Leu Pro Val
        -1   1               5                  10

Ser Leu Gly Asp Gln Ala Ser Ile Ser Cys Arg Ser Ser Gln Ser Leu
            15                  20                  25

Leu His Ser Lys Gly Asn Thr Tyr Leu Gln Trp Tyr Leu Gln Lys Pro
    30                  35                  40                  45

Gly Gln Ser Pro Lys Leu Leu Ile Tyr Lys Val Ser Asn Arg Phe Ser
                50                  55                  60

Gly Val Pro Asp Arg Phe Ser Gly Ser Gly Ser Gly Thr Asp Phe Thr
            65                  70                  75

Leu Lys Ile Ser Arg Val Glu Ala Glu Asp Leu Gly Val Tyr Phe Cys
        80                  85                  90

Ser Gln Ser Thr His Val Pro Tyr Thr Ser Gly Gly Gly Thr Lys Leu
    95                  100                 105

Glu Ile Lys
110

<210> SEQ ID NO 115
<211> LENGTH: 136
<212> TYPE: PRT
```

Ala Val Tyr Tyr Cys Ala Arg Gly Arg Tyr Phe Asp Val Trp Gly Arg
110             115                 120                 125

<213> ORGANISM: Mus sp.

<400> SEQUENCE: 115

Met Glu Trp Ser Trp Ile Phe Leu Phe Leu Leu Ser Gly Thr Ala Gly
                -15                 -10                  -5

Val His Ser Gln Val Gln Leu Gln Gln Ser Gly Pro Asp Leu Val Lys
         -1   1               5                  10

Pro Gly Ala Ser Val Lys Met Ser Cys Lys Ala Ser Gly Tyr Thr Phe
         15                  20                  25

Val Asn His Val Met His Trp Val Lys Gln Lys Pro Gly Gln Gly Leu
 30               35                  40                      45

Glu Trp Ile Gly Tyr Ile Tyr Pro Tyr Asn Asp Gly Thr Lys Tyr Asn
                 50                  55                  60

Glu Lys Phe Lys Gly Lys Ala Thr Leu Thr Ser Glu Lys Ser Ser Ser
             65                  70                  75

Ala Ala Tyr Met Glu Leu Ser Ser Leu Ala Ser Glu Asp Ser Ala Val
             80                  85                  90

Tyr Tyr Cys Ala Arg Gly Gly Tyr Tyr Ser Asp Asp Trp Gly Gln
             95                 100                 105

Gly Thr Thr Leu Thr Val Ser Ser
110                 115

<210> SEQ ID NO 116
<211> LENGTH: 131
<212> TYPE: PRT
<213> ORGANISM: Mus sp.

<400> SEQUENCE: 116

Met Lys Leu Pro Val Arg Leu Leu Val Leu Met Phe Trp Ile Pro Gly
                -15                 -10                  -5

Ser Ser Ser Asp Val Val Met Thr Gln Ser Pro Leu Ser Leu Pro Val
         -1   1               5                  10

Ser Leu Gly Asp Gln Ala Ser Ile Ser Cys Arg Ser Ser Gln Ser Leu
         15                  20                  25

Val His Ser Asn Gly Lys Thr Tyr Leu His Trp Tyr Leu Gln Lys Pro
 30               35                  40                      45

Gly Gln Ser Pro Lys Leu Leu Ile Tyr Lys Val Ser Asn Arg Phe Ser
                 50                  55                  60

Gly Val Pro Asp Arg Phe Ser Gly Ser Gly Ser Val Thr Asp Phe Thr
             65                  70                  75

Leu Met Ile Ser Arg Val Glu Ala Glu Asp Leu Gly Val Tyr Phe Cys
             80                  85                  90

Ser Gln Ser Thr His Val Pro Tyr Thr Phe Gly Gly Gly Thr Lys Leu
             95                 100                 105

Glu Ile Lys
110

<210> SEQ ID NO 117
<211> LENGTH: 136
<212> TYPE: PRT
<213> ORGANISM: Mus sp.

<400> SEQUENCE: 117

Met Glu Trp Ser Trp Ile Phe Leu Phe Leu Leu Ser Gly Thr Ala Gly
                -15                 -10                  -5

Val His Ser Gln Val Gln Leu Gln Gln Ser Gly Pro Glu Leu Val Lys
         -1   1               5                  10

```
Pro Gly Ala Ser Val Lys Met Ser Cys Lys Ala Ser Gly Tyr Thr Phe
    15                  20                  25
Ala Asn His Val Ile His Trp Val Lys Gln Lys Pro Gly Gln Gly Leu
    30              35                  40                  45
Glu Trp Ile Gly Tyr Ile Tyr Pro Tyr Asn Asp Gly Thr Lys Tyr Asn
                50                  55                  60
Glu Lys Phe Lys Asp Lys Ala Thr Leu Thr Ser Asp Lys Ser Ser Thr
                65                  70                  75
Thr Ala Tyr Met Asp Leu Ser Ser Leu Ala Ser Glu Asp Ser Ala Val
            80                  85                  90
Tyr Tyr Cys Ala Arg Gly Gly Tyr Tyr Thr Tyr Asp Asp Trp Gly Gln
    95                  100                 105
Gly Thr Thr Leu Thr Val Ser Ser
110             115

<210> SEQ ID NO 118
<211> LENGTH: 15
<212> TYPE: PRT
<213> ORGANISM: Artificial Sequence
<220> FEATURE:
<223> OTHER INFORMATION: Description of Artificial Sequence: Linker
      peptide

<400> SEQUENCE: 118

Gly Gly Gly Gly Ser Gly Gly Gly Gly Ser Gly Gly Gly Gly Ser
1               5                   10                  15

<210> SEQ ID NO 119
<211> LENGTH: 274
<212> TYPE: PRT
<213> ORGANISM: Mus sp.

<400> SEQUENCE: 119

Met Lys Tyr Leu Leu Pro Thr Ala Ala Ala Gly Leu Leu Leu Leu Ala
1               5                   10                  15
Ala Gln Pro Ala Met Ala Gln Val Gln Leu Gln Gln Ser Gly Pro Asp
                20                  25                  30
Leu Val Lys Pro Gly Ala Ser Val Lys Met Ser Cys Lys Ala Ser Gly
            35                  40                  45
Tyr Thr Phe Val Asn His Val Met His Trp Val Lys Gln Lys Pro Gly
        50                  55                  60
Gln Gly Leu Glu Trp Ile Gly Tyr Ile Tyr Pro Tyr Asn Asp Gly Thr
65                  70                  75                  80
Lys Tyr Asn Glu Lys Phe Lys Gly Lys Ala Thr Leu Thr Ser Glu Lys
                85                  90                  95
Ser Ser Ser Ala Ala Tyr Met Glu Leu Ser Ser Leu Ala Ser Glu Asp
            100                 105                 110
Ser Ala Val Tyr Tyr Cys Ala Arg Gly Gly Tyr Tyr Ser Tyr Asp Asp
        115                 120                 125
Trp Gly Gln Gly Thr Thr Leu Thr Val Ser Ser Gly Gly Gly Gly Ser
130                 135                 140
Gly Gly Gly Gly Ser Gly Gly Gly Gly Ser Asp Val Val Met Thr Gln
145                 150                 155                 160
Thr Pro Leu Ser Leu Pro Val Ser Leu Gly Asp Gln Ala Ser Ile Ser
                165                 170                 175
Cys Arg Ser Ser Gln Ser Leu Leu His Ser Lys Gly Asn Thr Tyr Leu
            180                 185                 190
Gln Trp Tyr Leu Gln Lys Pro Gly Gln Ser Pro Lys Leu Leu Ile Tyr
```

```
                195                 200                 205
Lys Val Ser Asn Arg Phe Ser Gly Val Pro Asp Arg Phe Ser Gly Ser
    210                 215                 220

Gly Ser Gly Thr Asp Phe Thr Leu Lys Ile Ser Arg Val Glu Ala Glu
225                 230                 235                 240

Asp Leu Gly Val Tyr Phe Cys Ser Gln Ser Thr His Val Pro Tyr Thr
                245                 250                 255

Ser Gly Gly Gly Thr Lys Leu Glu Ile Lys Asp Tyr Lys Asp Asp Asp
    260                 265                 270

Asp Lys

<210> SEQ ID NO 120
<211> LENGTH: 271
<212> TYPE: PRT
<213> ORGANISM: Mus sp.

<400> SEQUENCE: 120

Met Gly Trp Ser Cys Ile Ile Leu Phe Leu Val Ala Thr Ala Thr Gly
1               5                   10                  15

Val Asp Ser Gln Val Gln Leu Gln Gln Ser Gly Pro Asp Leu Val Lys
            20                  25                  30

Pro Gly Ala Ser Val Lys Met Ser Cys Lys Ala Ser Gly Tyr Thr Phe
        35                  40                  45

Val Asn His Val Met His Trp Val Lys Gln Lys Pro Gly Gln Gly Leu
    50                  55                  60

Glu Trp Ile Gly Tyr Ile Tyr Pro Tyr Asn Asp Gly Thr Lys Tyr Asn
65                  70                  75                  80

Glu Lys Phe Lys Gly Lys Ala Thr Leu Thr Ser Glu Lys Ser Ser Ser
                85                  90                  95

Ala Ala Tyr Met Glu Leu Ser Ser Leu Ala Ser Glu Asp Ser Ala Val
            100                 105                 110

Tyr Tyr Cys Ala Arg Gly Gly Tyr Ser Tyr Asp Asp Trp Gly Gln
        115                 120                 125

Gly Thr Thr Leu Thr Val Ser Ser Gly Gly Gly Ser Gly Gly Gly
    130                 135                 140

Gly Ser Gly Gly Gly Ser Asp Val Val Met Thr Gln Thr Pro Leu
145                 150                 155                 160

Ser Leu Pro Val Ser Leu Gly Asp Gln Ala Ser Ile Ser Cys Arg Ser
                165                 170                 175

Ser Gln Ser Leu Leu His Ser Lys Gly Asn Thr Tyr Leu Gln Trp Tyr
            180                 185                 190

Leu Gln Lys Pro Gly Gln Ser Pro Lys Leu Leu Ile Tyr Lys Val Ser
        195                 200                 205

Asn Arg Phe Ser Gly Val Pro Asp Arg Phe Ser Gly Ser Gly Ser Gly
    210                 215                 220

Thr Asp Phe Thr Leu Lys Ile Ser Arg Val Glu Ala Glu Asp Leu Gly
225                 230                 235                 240

Val Tyr Phe Cys Ser Gln Ser Thr His Val Pro Tyr Thr Ser Gly Gly
                245                 250                 255

Gly Thr Lys Leu Glu Ile Lys Asp Tyr Lys Asp Asp Asp Asp Lys
            260                 265                 270

<210> SEQ ID NO 121
<211> LENGTH: 274
<212> TYPE: PRT
<213> ORGANISM: Mus sp.
```

```
<400> SEQUENCE: 121

Met Lys Tyr Leu Leu Pro Thr Ala Ala Ala Gly Leu Leu Leu Leu Ala
 1               5                  10                  15

Ala Gln Pro Ala Met Ala Gln Val Gln Leu Gln Gln Ser Gly Pro Glu
             20                  25                  30

Leu Val Lys Pro Gly Ala Ser Val Lys Met Ser Cys Lys Ala Ser Gly
         35                  40                  45

Tyr Thr Phe Ala Asn His Val Ile His Trp Val Lys Gln Lys Pro Gly
     50                  55                  60

Gln Gly Leu Glu Trp Ile Gly Tyr Ile Tyr Pro Tyr Asn Asp Gly Thr
 65                  70                  75                  80

Lys Tyr Asn Glu Lys Phe Lys Asp Lys Ala Thr Leu Thr Ser Asp Lys
                 85                  90                  95

Ser Ser Thr Thr Ala Tyr Met Asp Leu Ser Ser Leu Ala Ser Glu Asp
            100                 105                 110

Ser Ala Val Tyr Tyr Cys Ala Arg Gly Gly Tyr Tyr Thr Tyr Asp Asp
        115                 120                 125

Trp Gly Gln Gly Thr Thr Leu Thr Val Ser Ser Gly Gly Gly Gly Ser
    130                 135                 140

Gly Gly Gly Gly Ser Gly Gly Gly Ser Asp Val Val Met Thr Gln
145                 150                 155                 160

Ser Pro Leu Ser Leu Pro Val Ser Leu Gly Asp Gln Ala Ser Ile Ser
                165                 170                 175

Cys Arg Ser Ser Gln Ser Leu Val His Ser Asn Gly Lys Thr Tyr Leu
            180                 185                 190

His Trp Tyr Leu Gln Lys Pro Gly Gln Ser Pro Lys Leu Leu Ile Tyr
        195                 200                 205

Lys Val Ser Asn Arg Phe Ser Gly Val Pro Asp Arg Phe Ser Gly Ser
    210                 215                 220

Gly Ser Val Thr Asp Phe Thr Leu Met Ile Ser Arg Val Glu Ala Glu
225                 230                 235                 240

Asp Leu Gly Val Tyr Phe Cys Ser Gln Ser Thr His Val Pro Tyr Thr
                245                 250                 255

Phe Gly Gly Gly Thr Lys Leu Glu Ile Lys Asp Tyr Lys Asp Asp Asp
            260                 265                 270

Asp Lys

<210> SEQ ID NO 122
<211> LENGTH: 271
<212> TYPE: PRT
<213> ORGANISM: Mus sp.

<400> SEQUENCE: 122

Met Gly Trp Ser Cys Ile Ile Leu Phe Leu Val Ala Thr Ala Thr Gly
 1               5                  10                  15

Val Asp Ser Gln Val Gln Leu Gln Gln Ser Gly Pro Glu Leu Val Lys
             20                  25                  30

Pro Gly Ala Ser Val Lys Met Ser Cys Lys Ala Ser Gly Tyr Thr Phe
         35                  40                  45

Ala Asn His Val Ile His Trp Val Lys Gln Lys Pro Gly Gln Gly Leu
     50                  55                  60

Glu Trp Ile Gly Tyr Ile Tyr Pro Tyr Asn Asp Gly Thr Lys Tyr Asn
 65                  70                  75                  80

Glu Lys Phe Lys Asp Lys Ala Thr Leu Thr Ser Asp Lys Ser Ser Thr
```

```
                        85                  90                  95
Thr Ala Tyr Met Asp Leu Ser Ser Leu Ala Ser Glu Asp Ser Ala Val
                100                 105                 110
Tyr Tyr Cys Ala Arg Gly Gly Tyr Thr Tyr Asp Asp Trp Gly Gln
            115                 120                 125
Gly Thr Thr Leu Thr Val Ser Ser Gly Gly Gly Ser Gly Gly Gly
        130                 135                 140
Gly Ser Gly Gly Gly Gly Ser Asp Val Val Met Thr Gln Ser Pro Leu
145                 150                 155                 160
Ser Leu Pro Val Ser Leu Gly Asp Gln Ala Ser Ile Ser Cys Arg Ser
                165                 170                 175
Ser Gln Ser Leu Val His Ser Asn Gly Lys Thr Tyr Leu His Trp Tyr
                180                 185                 190
Leu Gln Lys Pro Gly Gln Ser Pro Lys Leu Leu Ile Tyr Lys Val Ser
            195                 200                 205
Asn Arg Phe Ser Gly Val Pro Asp Arg Phe Ser Gly Ser Gly Ser Val
        210                 215                 220
Thr Asp Phe Thr Leu Met Ile Ser Arg Val Glu Ala Glu Asp Leu Gly
225                 230                 235                 240
Val Tyr Phe Cys Ser Gln Ser Thr His Val Pro Tyr Thr Phe Gly Gly
                245                 250                 255
Gly Thr Lys Leu Glu Ile Lys Asp Tyr Lys Asp Asp Asp Lys
                260                 265                 270

<210> SEQ ID NO 123
<211> LENGTH: 150
<212> TYPE: PRT
<213> ORGANISM: Mus sp.

<400> SEQUENCE: 123

Met Trp Pro Leu Val Ala Ala Leu Leu Leu Gly Ser Ala Cys Cys Gly
1               5                   10                  15
Ser Ala Gln Leu Leu Phe Asn Lys Thr Lys Ser Val Glu Phe Thr Phe
                20                  25                  30
Cys Asn Asp Thr Val Val Ile Pro Cys Phe Val Thr Asn Met Glu Ala
            35                  40                  45
Gln Asn Thr Thr Glu Val Tyr Val Lys Trp Lys Phe Lys Gly Arg Asp
        50                  55                  60
Ile Tyr Thr Phe Asp Gly Ala Leu Asn Lys Ser Thr Val Pro Thr Asp
65                  70                  75                  80
Phe Ser Ser Ala Lys Ile Glu Val Ser Gln Leu Leu Lys Gly Asp Ala
                85                  90                  95
Ser Leu Lys Met Asp Lys Ser Asp Ala Val Ser His Thr Gly Asn Tyr
                100                 105                 110
Thr Cys Glu Val Thr Glu Leu Thr Arg Glu Gly Glu Thr Ile Ile Glu
            115                 120                 125
Leu Lys Tyr Arg Val Val Ser Trp Phe Ser Pro Asn Glu Asn Asp Tyr
        130                 135                 140
Lys Asp Asp Asp Asp Lys
145                 150

<210> SEQ ID NO 124
<211> LENGTH: 245
<212> TYPE: PRT
<213> ORGANISM: Mus sp.

<400> SEQUENCE: 124
```

-continued

Met Gln Val Gln Leu Gln Gln Ser Gly Pro Glu Leu Val Lys Pro Gly
1               5                   10                  15

Ala Ser Val Lys Met Ser Cys Lys Ala Ser Gly Tyr Thr Phe Ala Asn
            20                  25                  30

His Val Ile His Trp Val Lys Gln Lys Pro Gly Gln Gly Leu Glu Trp
        35                  40                  45

Ile Gly Tyr Ile Tyr Pro Tyr Asn Asp Gly Thr Lys Tyr Asn Glu Lys
    50                  55                  60

Phe Lys Asp Lys Ala Thr Leu Thr Ser Asp Lys Ser Ser Thr Thr Ala
65              70                  75                  80

Tyr Met Asp Leu Ser Ser Leu Ala Ser Glu Asp Ser Ala Val Tyr Tyr
            85                  90                  95

Cys Ala Arg Gly Gly Tyr Tyr Thr Tyr Asp Asp Trp Gly Gln Gly Thr
            100                 105                 110

Thr Leu Thr Val Ser Ser Gly Gly Gly Ser Gly Gly Gly Gly Ser
            115                 120                 125

Gly Gly Gly Gly Ser Asp Val Val Met Thr Gln Ser Pro Leu Ser Leu
130                 135                 140

Pro Val Ser Leu Gly Asp Gln Ala Ser Ile Ser Cys Arg Ser Ser Gln
145                 150                 155                 160

Ser Leu Val His Ser Asn Gly Lys Thr Tyr Leu His Trp Tyr Leu Gln
            165                 170                 175

Lys Pro Gly Gln Ser Pro Lys Leu Leu Ile Tyr Lys Val Ser Asn Arg
            180                 185                 190

Phe Ser Gly Val Pro Asp Arg Phe Ser Gly Ser Gly Ser Val Thr Asp
            195                 200                 205

Phe Thr Leu Met Ile Ser Arg Val Glu Ala Glu Asp Leu Gly Val Tyr
            210                 215                 220

Phe Cys Ser Gln Ser Thr His Val Pro Tyr Thr Phe Gly Gly Gly Thr
225                 230                 235                 240

Lys Leu Glu Ile Lys
                245

<210> SEQ ID NO 125
<211> LENGTH: 533
<212> TYPE: PRT
<213> ORGANISM: Mus sp.

<400> SEQUENCE: 125

Met Gly Trp Ser Cys Ile Ile Leu Phe Leu Val Ala Thr Ala Thr Gly
1               5                   10                  15

Val Asp Ser Gln Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Ala Asn His Val Ile His Trp Val Lys Gln Lys Pro Gly Gln Gly Leu
    50                  55                  60

Glu Trp Ile Gly Tyr Ile Tyr Pro Tyr Asn Asp Gly Thr Lys Tyr Asn
65              70                  75                  80

Glu Lys Phe Lys Asp Lys Ala Thr Leu Thr Ser Asp Lys Ser Ser Thr
            85                  90                  95

Thr Ala Tyr Met Asp Leu Ser Ser Leu Ala Ser Glu Asp Ser Ala Val
            100                 105                 110

Tyr Tyr Cys Ala Arg Gly Gly Tyr Tyr Thr Tyr Asp Asp Trp Gly Gln
            115                 120                 125

```
Gly Thr Thr Leu Thr Val Ser Ser Gly Gly Gly Ser Gly Gly
    130                 135                 140

Gly Ser Gly Gly Gly Ser Asp Val Val Met Thr Gln Ser Pro Leu
145                 150                 155                 160

Ser Leu Pro Val Ser Leu Gly Asp Gln Ala Ser Ile Ser Cys Arg Ser
                165                 170                 175

Ser Gln Ser Leu Val His Ser Asn Gly Lys Thr Tyr Leu His Trp Tyr
            180                 185                 190

Leu Gln Lys Pro Gly Gln Ser Pro Lys Leu Leu Ile Tyr Lys Val Ser
        195                 200                 205

Asn Arg Phe Ser Gly Val Pro Asp Arg Phe Ser Gly Ser Gly Ser Val
    210                 215                 220

Thr Asp Phe Thr Leu Met Ile Ser Arg Val Glu Ala Glu Asp Leu Gly
225                 230                 235                 240

Val Tyr Phe Cys Ser Gln Ser Thr His Val Pro Tyr Thr Phe Gly Gly
                245                 250                 255

Gly Thr Lys Leu Glu Ile Lys Gly Gly Gly Ser Gly Gly Gly Gly
            260                 265                 270

Ser Gly Gly Gly Gly Ser Val Asp Ser Gln Val Gln Leu Gln Gln Ser
        275                 280                 285

Gly Pro Glu Leu Val Lys Pro Gly Ala Ser Val Lys Met Ser Cys Lys
    290                 295                 300

Ala Ser Gly Tyr Thr Phe Ala Asn His Val Ile His Trp Val Lys Gln
305                 310                 315                 320

Lys Pro Gly Gln Gly Leu Glu Trp Ile Gly Tyr Ile Tyr Pro Tyr Asn
                325                 330                 335

Asp Gly Thr Lys Tyr Asn Glu Lys Phe Lys Asp Lys Ala Thr Leu Thr
            340                 345                 350

Ser Asp Lys Ser Ser Thr Thr Ala Tyr Met Asp Leu Ser Ser Leu Ala
        355                 360                 365

Ser Glu Asp Ser Ala Val Tyr Tyr Cys Ala Arg Gly Gly Tyr Tyr Thr
    370                 375                 380

Tyr Asp Asp Trp Gly Gln Gly Thr Thr Leu Thr Val Ser Ser Gly Gly
385                 390                 395                 400

Gly Gly Ser Gly Gly Gly Gly Ser Gly Gly Gly Gly Ser Asp Val Val
                405                 410                 415

Met Thr Gln Ser Pro Leu Ser Leu Pro Val Ser Leu Gly Asp Gln Ala
            420                 425                 430

Ser Ile Ser Cys Arg Ser Ser Gln Ser Leu Val His Ser Asn Gly Lys
        435                 440                 445

Thr Tyr Leu His Trp Tyr Leu Gln Lys Pro Gly Gln Ser Pro Lys Leu
    450                 455                 460

Leu Ile Tyr Lys Val Ser Asn Arg Phe Ser Gly Val Pro Asp Arg Phe
465                 470                 475                 480

Ser Gly Ser Gly Ser Val Thr Asp Phe Thr Leu Met Ile Ser Arg Val
                485                 490                 495

Glu Ala Glu Asp Leu Gly Val Tyr Phe Cys Ser Gln Ser Thr His Val
            500                 505                 510

Pro Tyr Thr Phe Gly Gly Gly Thr Lys Leu Glu Ile Lys Asp Tyr Lys
        515                 520                 525

Asp Asp Asp Asp Lys
530
```

-continued

```
<210> SEQ ID NO 126
<211> LENGTH: 256
<212> TYPE: PRT
<213> ORGANISM: Mus sp.

<400> SEQUENCE: 126

Met Gly Trp Ser Cys Ile Ile Leu Phe Leu Val Ala Thr Ala Thr Gly
  1               5                  10                  15

Val Asp Ser Gln Val Gln Leu Gln Gln Ser Gly Pro Glu Leu Val Lys
             20                  25                  30

Pro Gly Ala Ser Val Lys Met Ser Cys Lys Ala Ser Gly Tyr Thr Phe
         35                  40                  45

Ala Asn His Val Ile His Trp Val Lys Gln Lys Pro Gly Gln Gly Leu
     50                  55                  60

Glu Trp Ile Gly Tyr Ile Tyr Pro Tyr Asn Asp Gly Thr Lys Tyr Asn
 65                  70                  75                  80

Glu Lys Phe Lys Asp Lys Ala Thr Leu Thr Ser Asp Lys Ser Ser Thr
                 85                  90                  95

Thr Ala Tyr Met Asp Leu Ser Ser Leu Ala Ser Glu Asp Ser Ala Val
            100                 105                 110

Tyr Tyr Cys Ala Arg Gly Gly Tyr Thr Tyr Asp Trp Gly Gln
        115                 120                 125

Gly Thr Thr Leu Thr Val Ser Ser Asp Val Val Met Thr Gln Ser Pro
130                 135                 140

Leu Ser Leu Pro Val Ser Leu Gly Asp Gln Ala Ser Ile Ser Cys Arg
145                 150                 155                 160

Ser Ser Gln Ser Leu Val His Ser Asn Gly Lys Thr Tyr Leu His Trp
                165                 170                 175

Tyr Leu Gln Lys Pro Gly Gln Ser Pro Lys Leu Leu Ile Tyr Lys Val
            180                 185                 190

Ser Asn Arg Phe Ser Gly Val Pro Asp Arg Phe Ser Gly Ser Gly Ser
        195                 200                 205

Val Thr Asp Phe Thr Leu Met Ile Ser Arg Val Glu Ala Glu Asp Leu
    210                 215                 220

Gly Val Tyr Phe Cys Ser Gln Ser Thr His Val Pro Tyr Thr Phe Gly
225                 230                 235                 240

Gly Gly Thr Lys Leu Glu Ile Lys Asp Tyr Lys Asp Asp Asp Asp Lys
                245                 250                 255

<210> SEQ ID NO 127
<211> LENGTH: 256
<212> TYPE: PRT
<213> ORGANISM: Mus sp.

<400> SEQUENCE: 127

Met Lys Leu Pro Val Arg Leu Leu Val Leu Met Phe Trp Ile Pro Gly
  1               5                  10                  15

Ser Ser Ser Asp Val Val Met Thr Gln Ser Pro Leu Ser Leu Pro Val
             20                  25                  30

Ser Leu Gly Asp Gln Ala Ser Ile Ser Cys Arg Ser Ser Gln Ser Leu
         35                  40                  45

Val His Ser Asn Gly Lys Thr Tyr Leu His Trp Tyr Leu Gln Lys Pro
     50                  55                  60

Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Val Thr Asp Phe Thr
                 85                  90                  95
```

```
Leu Met Ile Ser Arg Val Glu Ala Glu Asp Leu Gly Val Tyr Phe Cys
            100                 105                 110

Ser Gln Ser Thr His Val Pro Tyr Thr Phe Gly Gly Gly Thr Lys Leu
        115                 120                 125

Glu Ile Lys Gln Val Gln Leu Gln Gln Ser Gly Pro Glu Leu Val Lys
    130                 135                 140

Pro Gly Ala Ser Val Lys Met Ser Cys Lys Ala Ser Gly Tyr Thr Phe
145                 150                 155                 160

Ala Asn His Val Ile His Trp Val Lys Gln Lys Pro Gly Gln Gly Leu
                165                 170                 175

Glu Trp Ile Gly Tyr Ile Tyr Pro Tyr Asn Asp Gly Thr Lys Tyr Asn
            180                 185                 190

Glu Lys Phe Lys Asp Lys Ala Thr Leu Thr Ser Asp Lys Ser Ser Thr
        195                 200                 205

Thr Ala Tyr Met Asp Leu Ser Ser Leu Ala Ser Glu Asp Ser Ala Val
    210                 215                 220

Tyr Tyr Cys Ala Arg Gly Gly Tyr Tyr Thr Tyr Asp Asp Trp Gly Gln
225                 230                 235                 240

Gly Thr Thr Leu Thr Val Ser Ser Asp Tyr Lys Asp Asp Asp Asp Lys
                245                 250                 255

<210> SEQ ID NO 128
<211> LENGTH: 117
<212> TYPE: PRT
<213> ORGANISM: Homo sapiens

<400> SEQUENCE: 128

Gln Val Gln Leu Val Gln Ser Gly Gly Gly Leu Val Arg Pro Gly Gly
  1               5                  10                  15

Ser Leu Ser Leu Ser Cys Ala Val Ser Gly Ile Thr Leu Arg Thr Tyr
             20                  25                  30

Gly Met His Trp Val Arg Gln Ala Pro Gly Lys Gly Leu Glu Trp Val
         35                  40                  45

Ala Gly Ile Ser Phe Asp Gly Arg Ser Glu Tyr Tyr Ala Asp Ser Val
     50                  55                  60

Gln Gly Arg Phe Thr Ile Ser Arg Asp Ser Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ala His Tyr Gly Phe Asp Ile Trp Gly Gln Gly Thr Met
            100                 105                 110

Val Thr Val Ser Ser
        115

<210> SEQ ID NO 129
<211> LENGTH: 19
<212> TYPE: PRT
<213> ORGANISM: Homo sapiens

<400> SEQUENCE: 129

Met Glu Phe Gly Leu Ser Trp Val Phe Leu Val Ala Leu Leu Arg Gly
  1               5                  10                  15

Val Gln Cys

<210> SEQ ID NO 130
<211> LENGTH: 108
<212> TYPE: PRT
```

<213> ORGANISM: Homo sapiens

<400> SEQUENCE: 130

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr
            100                 105

<210> SEQ ID NO 131
<211> LENGTH: 136
<212> TYPE: PRT
<213> ORGANISM: Homo sapiens

<400> SEQUENCE: 131

Met Glu Phe Gly Leu Ser Trp Val Phe Leu Val Ala Leu Leu Arg Gly
1               5                   10                  15

Val Gln Cys Gln Val Gln Leu Val Gln Ser Gly Gly Gly Leu Val Arg
            20                  25                  30

Pro Gly Gly Ser Leu Ser Leu Ser Cys Ala Val Ser Gly Ile Thr Leu
        35                  40                  45

Arg Thr Tyr Gly Met His Trp Val Arg Gln Ala Pro Gly Lys Gly Leu
    50                  55                  60

Glu Trp Val Ala Gly Ile Ser Phe Asp Gly Arg Ser Glu Tyr Tyr Ala
65                  70                  75                  80

Asp Ser Val Gln Gly Arg Phe Thr Ile Ser Arg Asp Ser Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gly Ala His Tyr Gly Phe Asp Ile Trp Gly Gln
        115                 120                 125

Gly Thr Met Val Thr Val Ser Ser
    130                 135

<210> SEQ ID NO 132
<211> LENGTH: 107
<212> TYPE: PRT
<213> ORGANISM: Homo sapiens

<400> SEQUENCE: 132

Asp Ile Gln Met Thr Gln Ser Pro Ser Thr Leu Ser Ala Ser Ile Gly
1               5                   10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
    50                  55                  60

```
Ser Gly Ser Gly Thr Asp Phe Thr Leu Thr Ile Ser Leu Gln Pro
 65                  70                  75                  80

Asp Asp Phe Ala Thr Tyr Tyr Cys Gln Gln Tyr Ser Asn Tyr Pro Leu
                 85                  90                  95

Thr Phe Gly Gly Gly Thr Lys Leu Glu Ile Lys
            100                 105

<210> SEQ ID NO 133
<211> LENGTH: 22
<212> TYPE: PRT
<213> ORGANISM: Homo sapiens

<400> SEQUENCE: 133

Met Asp Met Arg Val Pro Ala Gln Leu Leu Gly Leu Leu Leu Leu Trp
 1               5                  10                  15

Leu Pro Gly Ala Lys Cys
            20

<210> SEQ ID NO 134
<211> LENGTH: 129
<212> TYPE: PRT
<213> ORGANISM: Homo sapiens

<400> SEQUENCE: 134

Met Asp Met Arg Val Pro Ala Gln Leu Leu Gly Leu Leu Leu Leu Trp
 1               5                  10                  15

Leu Pro Gly Ala Lys Cys Asp Ile Gln Met Thr Gln Ser Pro Ser Thr
             20                  25                  30

Leu Ser Ala Ser Ile Gly Asp Arg Val Thr Ile Thr Cys Arg Ala Ser
         35                  40                  45

Glu Gly Ile Tyr His Trp Leu Ala Trp Tyr Gln Gln Lys Pro Gly Lys
     50                  55                  60

Ala Pro Lys Leu Leu Ile Tyr Lys Ala Ser Ser Leu Ala Ser Gly Ala
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Asp Asp Phe Ala Thr Tyr Tyr Cys Gln Gln
            100                 105                 110

Tyr Ser Asn Tyr Pro Leu Thr Phe Gly Gly Gly Thr Lys Leu Glu Ile
        115                 120                 125

Lys

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: FLAG
      peptide

<400> SEQUENCE: 135

Asp Tyr Lys Asp Asp Asp Asp Lys
 1               5

<210> SEQ ID NO 136
<211> LENGTH: 15
<212> TYPE: PRT
<213> ORGANISM: Artificial Sequence
<220> FEATURE:
<223> OTHER INFORMATION: Description of Artificial Sequence: Linker
      peptide
```

```
<400> SEQUENCE: 136

Gly Gly Gly Gly Ser Gly Gly Gly Ser Gly Gly Gly Gly Ser
 1               5                  10                  15

<210> SEQ ID NO 137
<211> LENGTH: 266
<212> TYPE: PRT
<213> ORGANISM: Homo sapiens

<400> SEQUENCE: 137

Met Glu Phe Gly Leu Ser Trp Val Phe Leu Val Ala Leu Leu Arg Gly
 1               5                  10                  15

Val Gln Cys Gln Val Gln Leu Val Gln Ser Gly Gly Gly Leu Val Arg
                20                  25                  30

Pro Gly Gly Ser Leu Ser Leu Ser Cys Ala Val Ser Gly Ile Thr Leu
            35                  40                  45

Arg Thr Tyr Gly Met His Trp Val Arg Gln Ala Pro Gly Lys Gly Leu
        50                  55                  60

Glu Trp Val Ala Gly Ile Ser Phe Asp Gly Arg Ser Glu Tyr Tyr Ala
 65                  70                  75                  80

Asp Ser Val Gln Gly Arg Phe Thr Ile Ser Arg Asp Ser Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gly Ala His Tyr Gly Phe Asp Ile Trp Gly Gln
        115                 120                 125

Gly Thr Met Val Thr Val Ser Ser Gly Gly Gly Ser Gly Gly Gly Gly
130                 135                 140

Gly Ser Gly Gly Gly Gly Ser Asp Ile Gln Met Thr Gln Ser Pro Ser
145                 150                 155                 160

Thr Leu Ser Ala Ser Ile Gly Asp Arg Val Thr Ile Thr Cys Arg Ala
                165                 170                 175

Ser Glu Gly Ile Tyr His Trp Leu Ala Trp Tyr Gln Gln Lys Pro Gly
            180                 185                 190

Lys Ala Pro Lys Leu Leu Ile Tyr Lys Ala Ser Ser Leu Ala Ser Gly
        195                 200                 205

Ala Pro Ser Arg Phe Ser Gly Ser Gly Thr Asp Phe Thr Leu
210                 215                 220

Thr Ile Ser Ser Leu Gln Pro Asp Asp Phe Ala Thr Tyr Tyr Cys Gln
225                 230                 235                 240

Gln Tyr Ser Asn Tyr Pro Leu Thr Phe Gly Gly Gly Thr Lys Leu Glu
                245                 250                 255

Ile Lys Asp Tyr Lys Asp Asp Asp Lys
        260                 265

<210> SEQ ID NO 138
<211> LENGTH: 19
<212> TYPE: PRT
<213> ORGANISM: Homo sapiens

<400> SEQUENCE: 138

Met Lys His Leu Trp Phe Phe Leu Leu Leu Val Ala Ala Pro Arg Trp
 1               5                  10                  15

Val Leu Ser

<210> SEQ ID NO 139
<211> LENGTH: 133
```

<212> TYPE: PRT
<213> ORGANISM: Mus sp.

<400> SEQUENCE: 139

Met Lys His Leu Trp Phe Phe Leu Leu Leu Val Ala Ala Pro Arg Trp
1               5                   10                  15

Val Leu Ser Gln Val Gln Leu Gln Gln Ser Gly Pro Gly Leu Val Lys
            20                  25                  30

Pro Ser Glu Thr Leu Ser Leu Thr Cys Thr Val Ser Gly Asp Ser Ile
        35                  40                  45

Ser Ser Tyr Tyr Trp Ser Trp Ile Arg Gln Pro Pro Gly Lys Gly Leu
    50                  55                  60

Glu Trp Ile Gly Tyr Ile Tyr Tyr Ser Gly Ser Thr Asn Tyr Asn Pro
65                  70                  75                  80

Ser Leu Lys Ser Arg Val Thr Ile Ser Val Asp Thr Ser Lys Ser Gln
                85                  90                  95

Phe Ser Leu Lys Leu Ser Ser Val Thr Ala Ala Asp Thr Ala Val Tyr
            100                 105                 110

Tyr Cys Ala Arg Gly Arg Tyr Phe Asp Val Trp Gly Arg Gly Thr Met
        115                 120                 125

Val Thr Val Ser Ser
    130

<210> SEQ ID NO 140
<211> LENGTH: 19
<212> TYPE: PRT
<213> ORGANISM: Homo sapiens

<400> SEQUENCE: 140

Met Ala Trp Thr Val Leu Leu Leu Gly Leu Leu Ser His Cys Thr Gly
1               5                   10                  15

Ser Val Thr

<210> SEQ ID NO 141
<211> LENGTH: 129
<212> TYPE: PRT
<213> ORGANISM: Mus sp.

<400> SEQUENCE: 141

Met Ala Trp Thr Val Leu Leu Leu Gly Leu Leu Ser His Cys Thr Gly
1               5                   10                  15

Ser Val Thr Ser Tyr Val Leu Thr Gln Pro Pro Ser Val Ser Gly Ser
            20                  25                  30

Pro Gly Gln Ser Ile Thr Ile Ser Cys Thr Gly Thr Ser Ser Asp Val
        35                  40                  45

Gly Gly Tyr Asn Tyr Val Ser Trp Tyr Gln Gln His Pro Gly Lys Ala
    50                  55                  60

Pro Lys Leu Met Ile Tyr Glu Gly Ser Lys Arg Pro Ser Gly Val Ser
65                  70                  75                  80

Asn Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Ser Ser Tyr
            100                 105                 110

Thr Thr Arg Ser Thr Arg Val Phe Gly Gly Gly Thr Lys Leu Thr Val
        115                 120                 125

Leu

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: FLAG reader
      sequence

<400> SEQUENCE: 142

Asp Tyr Lys Asp Asp Asp Asp Lys
1               5

<210> SEQ ID NO 143
<211> LENGTH: 256
<212> TYPE: PRT
<213> ORGANISM: Artificial Sequence
<220> FEATURE:
<223> OTHER INFORMATION: Description of Artificial Sequence: 12E10,
      single chain Fv

<400> SEQUENCE: 143

Met Lys His Leu Trp Phe Phe Leu Leu Val Ala Ala Pro Arg Trp
1               5                   10                  15

Val Leu Ser Gln Val Gln Leu Gln Gln Ser Gly Pro Gly Leu Val Lys
            20                  25                  30

Pro Ser Glu Thr Leu Ser Leu Thr Cys Thr Val Ser Gly Asp Ser Ile
        35                  40                  45

Ser Ser Tyr Tyr Trp Ser Trp Ile Arg Gln Pro Pro Gly Lys Gly Leu
    50                  55                  60

Glu Trp Ile Gly Tyr Ile Tyr Tyr Ser Gly Ser Thr Asn Tyr Asn Pro
65                  70                  75                  80

Ser Leu Lys Ser Arg Val Thr Ile Ser Val Asp Thr Ser Lys Ser Gln
                85                  90                  95

Phe Ser Leu Lys Leu Ser Ser Val Thr Ala Ala Asp Thr Ala Val Tyr
            100                 105                 110

Tyr Cys Ala Arg Gly Arg Tyr Phe Asp Val Trp Gly Arg Gly Thr Met
        115                 120                 125

Val Thr Val Ser Ser Gly Gly Gly Gly Ser Ser Tyr Val Leu Thr Gln
    130                 135                 140

Pro Pro Ser Val Ser Gly Ser Pro Gly Gln Ser Ile Thr Ile Ser Cys
145                 150                 155                 160

Thr Gly Thr Ser Ser Asp Val Gly Gly Tyr Asn Tyr Val Ser Trp Tyr
                165                 170                 175

Gln Gln His Pro Gly Lys Ala Pro Lys Leu Met Ile Tyr Glu Gly Ser
            180                 185                 190

Lys Arg Pro Ser Gly Val Ser Asn Arg Phe Ser Gly Ser Lys Ser Gly
        195                 200                 205

Asn Thr Ala Ser Leu Thr Ile Ser Gly Leu Gln Ala Glu Asp Glu Ala
    210                 215                 220

Asp Tyr Tyr Cys Ser Ser Tyr Thr Thr Arg Ser Thr Arg Val Phe Gly
225                 230                 235                 240

Gly Gly Thr Lys Leu Thr Val Leu Asp Tyr Lys Asp Asp Asp Asp Lys
                245                 250                 255

<210> SEQ ID NO 144
<211> LENGTH: 266
<212> TYPE: PRT
<213> ORGANISM: Artificial Sequence
<220> FEATURE:
<223> OTHER INFORMATION: Description of Artificial Sequence: sc12E10,
      single chain Fv

```
<400> SEQUENCE: 144

Met Lys His Leu Trp Phe Phe Leu Leu Val Ala Ala Pro Arg Trp
1               5                   10                  15

Val Leu Ser Gln Val Gln Leu Gln Gln Ser Gly Pro Gly Leu Val Lys
            20                  25                  30

Pro Ser Glu Thr Leu Ser Leu Thr Cys Thr Val Ser Gly Asp Ser Ile
            35                  40                  45

Ser Ser Tyr Tyr Trp Ser Trp Ile Arg Gln Pro Pro Gly Lys Gly Leu
        50                  55                  60

Glu Trp Ile Gly Tyr Ile Tyr Tyr Ser Gly Ser Thr Asn Tyr Asn Pro
65                  70                  75                  80

Ser Leu Lys Ser Arg Val Thr Ile Ser Val Asp Thr Ser Lys Ser Gln
                85                  90                  95

Phe Ser Leu Lys Leu Ser Ser Val Thr Ala Ala Asp Thr Ala Val Tyr
            100                 105                 110

Tyr Cys Ala Arg Gly Arg Tyr Phe Asp Val Trp Gly Arg Gly Thr Met
        115                 120                 125

Val Thr Val Ser Ser Gly Gly Gly Gly Ser Gly Gly Gly Gly Ser Gly
130                 135                 140

Gly Gly Ser Ser Tyr Val Leu Thr Gln Pro Pro Ser Val Ser Gly
145                 150                 155                 160

Ser Pro Gly Gln Ser Ile Thr Ile Ser Cys Thr Gly Thr Ser Ser Asp
                165                 170                 175

Val Gly Gly Tyr Asn Tyr Val Ser Trp Tyr Gln Gln His Pro Gly Lys
            180                 185                 190

Ala Pro Lys Leu Met Ile Tyr Glu Gly Ser Lys Arg Pro Ser Gly Val
        195                 200                 205

Ser Asn Arg Phe Ser Gly Ser Lys Ser Gly Asn Thr Ala Ser Leu Thr
    210                 215                 220

Ile Ser Gly Leu Gln Ala Glu Asp Glu Ala Asp Tyr Tyr Cys Ser Ser
225                 230                 235                 240

Tyr Thr Thr Arg Ser Thr Arg Val Phe Gly Gly Gly Thr Lys Leu Thr
                245                 250                 255

Val Leu Asp Tyr Lys Asp Asp Asp Lys
            260                 265

<210> SEQ ID NO 145
<211> LENGTH: 18
<212> TYPE: PRT
<213> ORGANISM: Artificial Sequence
<220> FEATURE:
<223> OTHER INFORMATION: Description of Artificial Sequence: Linker
      peptide

<400> SEQUENCE: 145

Gly Gly Gly Gly Ser Gly Gly Gly Gly Ser Gly Gly Gly Gly Ser Val
1               5                   10                  15

Asp Ser

<210> SEQ ID NO 146
<211> LENGTH: 18
<212> TYPE: DNA
<213> ORGANISM: Artificial Sequence
<220> FEATURE:
<223> OTHER INFORMATION: Description of Artificial Sequence: Plasmid/
      linker nucleotide sequence
<220> FEATURE:
<221> NAME/KEY: CDS
```

```
<222> LOCATION: (1)..(18)

<400> SEQUENCE: 146 gtc tcg agt gac gtc gtg                                            18
Val Ser Ser Asp Val Val
 1               5

<210> SEQ ID NO 147
<211> LENGTH: 6
<212> TYPE: PRT
<213> ORGANISM: Artificial Sequence
<220> FEATURE:
<223> OTHER INFORMATION: Description of Artificial Sequence: Plasmid/
      linker peptide sequence

<400> SEQUENCE: 147

Val Ser Ser Asp Val Val
 1               5

<210> SEQ ID NO 148
<211> LENGTH: 18
<212> TYPE: DNA
<213> ORGANISM: Artificial Sequence
<220> FEATURE:
<223> OTHER INFORMATION: Description of Artificial Sequence: Plasmid/
      linker nucleotide sequence
<220> FEATURE:
<221> NAME/KEY: CDS
<222> LOCATION: (1)..(18)

<400> SEQUENCE: 148 gtc tcg agt gac gtc gtg                                            18
Val Ser Ser Asp Val Val
 1               5

<210> SEQ ID NO 149
<211> LENGTH: 6
<212> TYPE: PRT
<213> ORGANISM: Artificial Sequence
<220> FEATURE:
<223> OTHER INFORMATION: Description of Artificial Sequence: Plasmid/
      linker peptide sequence

<400> SEQUENCE: 149

Val Ser Ser Asp Val Val
 1               5

<210> SEQ ID NO 150
<211> LENGTH: 27
<212> TYPE: DNA
<213> ORGANISM: Artificial Sequence
<220> FEATURE:
<223> OTHER INFORMATION: Description of Artificial Sequence: Plasmid/
      linker nucleotide sequence
<220> FEATURE:
<221> NAME/KEY: CDS
<222> LOCATION: (1)..(27)

<400> SEQUENCE: 150 gtc tcg agt ggt ggt tcc gac gtc gtg                                27
Val Ser Ser Gly Gly Ser Asp Val Val
 1               5

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Plasmid/
      linker peptide sequence
```

```
<400> SEQUENCE: 151

Val Ser Ser Gly Gly Ser Asp Val Val
  1               5

<210> SEQ ID NO 152
<211> LENGTH: 30
<212> TYPE: DNA
<213> ORGANISM: Artificial Sequence
<220> FEATURE:
<223> OTHER INFORMATION: Description of Artificial Sequence: Plasmid/
      linker nucleotide sequence
<220> FEATURE:
<221> NAME/KEY: CDS
<222> LOCATION: (1)..(30)

<400> SEQUENCE: 152 gtc tcg agt ggt ggt ggt tcc gac gtc gtg                              30
Val Ser Ser Gly Gly Gly Ser Asp Val Val
  1               5                  10

<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence: Plasmid/
      linker peptide sequence

<400> SEQUENCE: 153

Val Ser Ser Gly Gly Gly Ser Asp Val Val
  1               5                  10

<210> SEQ ID NO 154
<211> LENGTH: 33
<212> TYPE: DNA
<213> ORGANISM: Artificial Sequence
<220> FEATURE:
<223> OTHER INFORMATION: Description of Artificial Sequence: Plasmid/
      linker nucleotide sequence
<220> FEATURE:
<221> NAME/KEY: CDS
<222> LOCATION: (1)..(33)

<400> SEQUENCE: 154 gtc tcg agt ggt ggt ggt ggt tcc gac gtc gtg                          33
Val Ser Ser Gly Gly Gly Gly Ser Asp Val Val
  1               5                  10

<210> SEQ ID NO 155
<211> LENGTH: 11
<212> TYPE: PRT
<213> ORGANISM: Artificial Sequence
<220> FEATURE:
<223> OTHER INFORMATION: Description of Artificial Sequence: Plasmid/
      linker peptide sequence

<400> SEQUENCE: 155

Val Ser Ser Gly Gly Gly Gly Ser Asp Val Val
  1               5                  10

<210> SEQ ID NO 156
<211> LENGTH: 36
<212> TYPE: DNA
<213> ORGANISM: Artificial Sequence
<220> FEATURE:
<223> OTHER INFORMATION: Description of Artificial Sequence: Plasmid/
      linker nucleotide sequence
<220> FEATURE:
<221> NAME/KEY: CDS
```

<222> LOCATION: (1)..(36)

<400> SEQUENCE: 156

```
gtc tcg agt ggt ggt ggt ggt ggt tcc gac gtc gtg                     36
Val Ser Ser Gly Gly Gly Gly Gly Ser Asp Val Val
 1               5                  10
```

<210> SEQ ID NO 157
<211> LENGTH: 12
<212> TYPE: PRT
<213> ORGANISM: Artificial Sequence
<220> FEATURE:
<223> OTHER INFORMATION: Description of Artificial Sequence: Plasmid/
      linker peptide sequence

<400> SEQUENCE: 157

```
Val Ser Ser Gly Gly Gly Gly Ser Asp Val Val
 1               5                  10
```

<210> SEQ ID NO 158
<211> LENGTH: 39
<212> TYPE: DNA
<213> ORGANISM: Artificial Sequence
<220> FEATURE:
<223> OTHER INFORMATION: Description of Artificial Sequence: Plasmid/
      linker nucleotide sequence
<220> FEATURE:
<221> NAME/KEY: CDS
<222> LOCATION: (1)..(39)

<400> SEQUENCE: 158

```
gtc tcg agt ggt ggt ggt ggt ggt tcc gac gtc gtg                     39
Val Ser Ser Gly Gly Gly Gly Gly Ser Asp Val Val
 1               5                  10
```

<210> SEQ ID NO 159
<211> LENGTH: 13
<212> TYPE: PRT
<213> ORGANISM: Artificial Sequence
<220> FEATURE:
<223> OTHER INFORMATION: Description of Artificial Sequence: Plasmid/
      linker peptide sequence

<400> SEQUENCE: 159

```
Val Ser Ser Gly Gly Gly Gly Gly Ser Asp Val Val
 1               5                  10
```

<210> SEQ ID NO 160
<211> LENGTH: 18
<212> TYPE: DNA
<213> ORGANISM: Artificial Sequence
<220> FEATURE:
<223> OTHER INFORMATION: Description of Artificial Sequence: Plasmid/
      linker nucleotide sequence
<220> FEATURE:
<221> NAME/KEY: CDS
<222> LOCATION: (1)..(18)

<400> SEQUENCE: 160

```
gag ata aaa cag gtc caa                                             18
Glu Ile Lys Gln Val Gln
 1               5
```

<210> SEQ ID NO 161
<211> LENGTH: 6
<212> TYPE: PRT
<213> ORGANISM: Artificial Sequence
<220> FEATURE:
<223> OTHER INFORMATION: Description of Artificial Sequence: Plasmid/
      linker peptide sequence

<400> SEQUENCE: 161

Glu Ile Lys Gln Val Gln
 1               5

<210> SEQ ID NO 162
<211> LENGTH: 18
<212> TYPE: DNA
<213> ORGANISM: Artificial Sequence
<220> FEATURE:
<223> OTHER INFORMATION: Description of Artificial Sequence: Plasmid/
      linker nucleotide sequence
<220> FEATURE:
<221> NAME/KEY: CDS
<222> LOCATION: (1)..(18)

<400> SEQUENCE: 162 gag ata aaa cag gtc caa                                           18
Glu Ile Lys Gln Val Gln
 1               5

<210> SEQ ID NO 163
<211> LENGTH: 6
<212> TYPE: PRT
<213> ORGANISM: Artificial Sequence
<220> FEATURE:
<223> OTHER INFORMATION: Description of Artificial Sequence: Plasmid/
      linker peptide sequence

<400> SEQUENCE: 163

Glu Ile Lys Gln Val Gln
 1               5

<210> SEQ ID NO 164
<211> LENGTH: 27
<212> TYPE: DNA
<213> ORGANISM: Artificial Sequence
<220> FEATURE:
<223> OTHER INFORMATION: Description of Artificial Sequence: Plasmid/
      linker nucleotide sequence
<220> FEATURE:
<221> NAME/KEY: CDS
<222> LOCATION: (1)..(27)

<400> SEQUENCE: 164 gag ata aaa tcc gga ggc cag gtc caa                               27
Glu Ile Lys Ser Gly Gly Gln Val Gln
 1               5

<210> SEQ ID NO 165
<211> LENGTH: 9
<212> TYPE: PRT
<213> ORGANISM: Artificial Sequence
<220> FEATURE:
<223> OTHER INFORMATION: Description of Artificial Sequence: Plasmid/
      linker peptide sequence

<400> SEQUENCE: 165

Glu Ile Lys Ser Gly Gly Gln Val Gln
 1               5

<210> SEQ ID NO 166
<211> LENGTH: 30
<212> TYPE: DNA
<213> ORGANISM: Artificial Sequence
<220> FEATURE:
<223> OTHER INFORMATION: Description of Artificial Sequence: Plasmid/
      linker nucleotide sequence
<220> FEATURE:
<221> NAME/KEY: CDS

```
<222> LOCATION: (1)..(30)

<400> SEQUENCE: 166 gag ata aaa tcc gga ggt ggc cag gtc caa                              30
Glu Ile Lys Ser Gly Gly Gly Gln Val Gln
 1               5                  10

<210> SEQ ID NO 167
<211> LENGTH: 10
<212> TYPE: PRT
<213> ORGANISM: Artificial Sequence
<220> FEATURE:
<223> OTHER INFORMATION: Description of Artificial Sequence: Plasmid/
      linker peptide sequence

<400> SEQUENCE: 167

Glu Ile Lys Ser Gly Gly Gly Gln Val Gln
 1               5                  10

<210> SEQ ID NO 168
<211> LENGTH: 33
<212> TYPE: DNA
<213> ORGANISM: Artificial Sequence
<220> FEATURE:
<223> OTHER INFORMATION: Description of Artificial Sequence: Plasmid/
      linker nucleotide sequence
<220> FEATURE:
<221> NAME/KEY: CDS
<222> LOCATION: (1)..(33)

<400> SEQUENCE: 168 gag ata aaa tcc gga ggt ggt ggc cag gtc caa                          33
Glu Ile Lys Ser Gly Gly Gly Gly Gln Val Gln
 1               5                  10

<210> SEQ ID NO 169
<211> LENGTH: 11
<212> TYPE: PRT
<213> ORGANISM: Artificial Sequence
<220> FEATURE:
<223> OTHER INFORMATION: Description of Artificial Sequence: Plasmid/
      linker peptide sequence

<400> SEQUENCE: 169

Glu Ile Lys Ser Gly Gly Gly Gly Gln Val Gln
 1               5                  10

<210> SEQ ID NO 170
<211> LENGTH: 36
<212> TYPE: DNA
<213> ORGANISM: Artificial Sequence
<220> FEATURE:
<223> OTHER INFORMATION: Description of Artificial Sequence: Plasmid/
      linker nucleotide sequence
<220> FEATURE:
<221> NAME/KEY: CDS
<222> LOCATION: (1)..(36)

<400> SEQUENCE: 170 gag ata aaa tcc gga ggt ggt ggt ggc cag gtc caa                      36
Glu Ile Lys Ser Gly Gly Gly Gly Gly Gln Val Gln
 1               5                  10

<210> SEQ ID NO 171
<211> LENGTH: 12
<212> TYPE: PRT
<213> ORGANISM: Artificial Sequence
<220> FEATURE:
<223> OTHER INFORMATION: Description of Artificial Sequence: Plasmid/
      linker peptide sequence
```

```
<400> SEQUENCE: 171

Glu Ile Lys Ser Gly Gly Gly Gly Gly Gln Val Gln
 1               5                  10

<210> SEQ ID NO 172
<211> LENGTH: 39
<212> TYPE: DNA
<213> ORGANISM: Artificial Sequence
<220> FEATURE:
<223> OTHER INFORMATION: Description of Artificial Sequence: Plasmid/
      linker nucleotide sequence
<220> FEATURE:
<221> NAME/KEY: CDS
<222> LOCATION: (1)..(39)

<400> SEQUENCE: 172 gag ata aaa tcc gga ggt ggt ggt ggt ggc cag gtc caa              39
Glu Ile Lys Ser Gly Gly Gly Gly Gly Gln Val Gln
 1               5                  10

<210> SEQ ID NO 173
<211> LENGTH: 13
<212> TYPE: PRT
<213> ORGANISM: Artificial Sequence
<220> FEATURE:
<223> OTHER INFORMATION: Description of Artificial Sequence: Plasmid/
      linker peptide sequence

<400> SEQUENCE: 173

Glu Ile Lys Ser Gly Gly Gly Gly Gly Gln Val Gln
 1               5                  10

<210> SEQ ID NO 174
<211> LENGTH: 4
<212> TYPE: PRT
<213> ORGANISM: Artificial Sequence
<220> FEATURE:
<223> OTHER INFORMATION: Description of Artificial Sequence: Linker
      peptide

<400> SEQUENCE: 174

Gly Gly Gly Ser
 1

<210> SEQ ID NO 175
<211> LENGTH: 4
<212> TYPE: PRT
<213> ORGANISM: Artificial Sequence
<220> FEATURE:
<223> OTHER INFORMATION: Description of Artificial Sequence: Linker
      peptide

<400> SEQUENCE: 175

Ser Gly Gly Gly
 1

<210> SEQ ID NO 176
<211> LENGTH: 5
<212> TYPE: PRT
<213> ORGANISM: Artificial Sequence
<220> FEATURE:
<223> OTHER INFORMATION: Description of Artificial Sequence: Linker
      peptide

<400> SEQUENCE: 176

Gly Gly Gly Gly Ser
 1               5
```

-continued

<210> SEQ ID NO 177
<211> LENGTH: 5
<212> TYPE: PRT
<213> ORGANISM: Artificial Sequence
<220> FEATURE:
<223> OTHER INFORMATION: Description of Artificial Sequence: Linker
      peptide

<400> SEQUENCE: 177

Ser Gly Gly Gly Gly
  1               5

<210> SEQ ID NO 178
<211> LENGTH: 6
<212> TYPE: PRT
<213> ORGANISM: Artificial Sequence
<220> FEATURE:
<223> OTHER INFORMATION: Description of Artificial Sequence: Linker
      peptide

<400> SEQUENCE: 178

Gly Gly Gly Gly Gly Ser
  1               5

<210> SEQ ID NO 179
<211> LENGTH: 6
<212> TYPE: PRT
<213> ORGANISM: Artificial Sequence
<220> FEATURE:
<223> OTHER INFORMATION: Description of Artificial Sequence: Linker
      peptide

<400> SEQUENCE: 179

Ser Gly Gly Gly Gly Gly
  1               5

<210> SEQ ID NO 180
<211> LENGTH: 7
<212> TYPE: PRT
<213> ORGANISM: Artificial Sequence
<220> FEATURE:
<223> OTHER INFORMATION: Description of Artificial Sequence: Linker
      peptide

<400> SEQUENCE: 180

Gly Gly Gly Gly Gly Gly Ser
  1               5

<210> SEQ ID NO 181
<211> LENGTH: 7
<212> TYPE: PRT
<213> ORGANISM: Artificial Sequence
<220> FEATURE:
<223> OTHER INFORMATION: Description of Artificial Sequence: Linker
      peptide

<400> SEQUENCE: 181

Ser Gly Gly Gly Gly Gly Gly
  1               5

<210> SEQ ID NO 182
<211> LENGTH: 20
<212> TYPE: PRT
<213> ORGANISM: Artificial Sequence
<220> FEATURE:
<223> OTHER INFORMATION: Description of Artificial Sequence: Linker
      peptide
<220> FEATURE:
<223> OTHER INFORMATION: this sequence may encompass 1-20 residues; for

```
preferred embodiments see specification as filed

<400> SEQUENCE: 182

Gly Gly Gly Gly Ser Gly Gly Gly Ser Gly Gly Gly Ser Gly
 1               5                  10                  15

Gly Gly Gly Gly
            20

<210> SEQ ID NO 183
<211> LENGTH: 20
<212> TYPE: PRT
<213> ORGANISM: Artificial Sequence
<220> FEATURE:
<223> OTHER INFORMATION: Description of Artificial Sequence: Linker
      peptide
<220> FEATURE:
<223> OTHER INFORMATION: this sequence may encompass 1-20 residues; for
      preferred embodiments see specification as filed

<400> SEQUENCE: 183

Ser Gly Gly Gly Gly Ser Gly Gly Gly Gly Ser Gly Gly Gly Ser
 1               5                  10                  15

Gly Gly Gly Gly
            20
```